United States Patent
LaVoie et al.

(10) Patent No.: US 11,458,121 B2
(45) Date of Patent: Oct. 4, 2022

(54) THERAPEUTIC COMPOUNDS AND METHODS TO TREAT INFECTION

(71) Applicants: RUTGERS, THE STATE UNIVERSITY OF NEW JERSEY, New Brunswick, NJ (US); TAXIS PHARMACEUTICALS, INC., Monmouth Junction, NJ (US); Edmond J. LaVoie, New Brunswick, NJ (US); Ajit Parhi, New Brunswick, NJ (US); Hye Yeon Sagong, Monmouth Junction, NJ (US)

(72) Inventors: Edmond J. LaVoie, New Brunswick, NJ (US); Ajit Parhi, New Brunswick, NJ (US); Hye Yeon Sagong, Monmouth Junction, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/626,249

(22) PCT Filed: Jun. 26, 2018

(86) PCT No.: PCT/US2018/039567
§ 371 (c)(1),
(2) Date: Dec. 23, 2019

(87) PCT Pub. No.: WO2019/005841
PCT Pub. Date: Jan. 3, 2019

(65) Prior Publication Data
US 2020/0155507 A1 May 21, 2020

Related U.S. Application Data

(60) Provisional application No. 62/525,079, filed on Jun. 26, 2017.

(51) Int. Cl.
| | |
|---|---|
| A61K 31/404 | (2006.01) |
| A61P 31/04 | (2006.01) |
| A61K 31/5377 | (2006.01) |
| A61K 45/06 | (2006.01) |
| C07D 209/88 | (2006.01) |
| C07D 413/08 | (2006.01) |

(52) U.S. Cl.
CPC ........ *A61K 31/404* (2013.01); *A61K 31/5377* (2013.01); *A61K 45/06* (2013.01); *A61P 31/04* (2018.01); *C07D 209/88* (2013.01); *C07D 413/08* (2013.01)

(58) Field of Classification Search
CPC ... C07D 209/88; C07D 413/08; A61K 31/404
See application file for complete search history.

(56) References Cited

U.S. PATENT DOCUMENTS

| | | | |
|---|---|---|---|
| 3,978,224 A | 8/1976 | Steinman et al. | |
| 4,938,949 A | 7/1990 | Borch et al. | |
| 5,663,152 A | 9/1997 | Hayano et al. | |
| 6,204,279 B1 | 3/2001 | Leger et al. | |
| 6,326,391 B1 | 12/2001 | Markham et al. | |
| 6,555,569 B2 | 4/2003 | Sutcliffe et al. | |
| 6,730,684 B1 | 5/2004 | Miller et al. | |
| 7,419,997 B2* | 9/2008 | Boggs | C07D 403/12 514/411 |
| 7,855,228 B2 | 12/2010 | Gitai et al. | |
| 7,893,020 B2 | 2/2011 | Glinka et al. | |
| 8,642,076 B2 | 2/2014 | Manoharan et al. | |
| 9,271,960 B2* | 3/2016 | Lennox | A61P 5/00 |
| 9,926,261 B2 | 3/2018 | Lavoie et al. | |

(Continued)

FOREIGN PATENT DOCUMENTS

| | | |
|---|---|---|
| WO | 1992004017 A1 | 3/1992 |
| WO | 2005113579 A1 | 12/2005 |

(Continued)

OTHER PUBLICATIONS

Astolfi, A, et al., "Pharmacophore-Based Repositioning of Approved Drugs as Novel *Staphylococcus aureus* NorA Efflux Pump Inhibitors", J Med Chem 60(4), 1598-1604 (2017).

Awuni, E, et al., "Effect of A22 on the Conformation of Bacterial Actin MreB", International Journal of Molecular Sciences 20, 1304 (2019).

Awuni, Y, et al., "Exploring the A22-Bacterial Actin MreB Interaction through Molecular Dynamics Simulations", J. Phys. Chem, B 120(37), 4867-4874 (2016).

Barker, C, et al., "Degradation of MAC13243 and studies of the interaction of resulting thiourea compounds with the lipoprotein targeting chaperone LoIA", Bioorganic & Medicinal Chemistry Letters 23, 2426-2431 (2013).

(Continued)

*Primary Examiner* — Kamal A Saeed
(74) *Attorney, Agent, or Firm* — Viksnins Harris Padys Malen LLP

(57) ABSTRACT

Disclosed herein are compounds of formula I: or a salt thereof and compositions comprising a compound of formula I or a pharmaceutically acceptable salt thereof. Also disclosed herein are methods for treating or preventing a bacterial infection in an animal comprising administering to the animal a compound of formula I or a pharmaceutically acceptable salt thereof, alone or in combination with a bacterial efflux pump inhibitor.

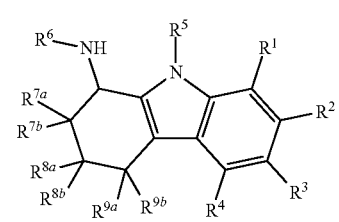

I

20 Claims, No Drawings

(56) References Cited

U.S. PATENT DOCUMENTS

| | | | |
|---|---|---|---|
| 9,950,993 | B2 | 4/2018 | Lavoie et al. |
| 2004/0204378 | A1 | 10/2004 | Nelson et al. |
| 2008/0132457 | A1 | 6/2008 | Bostian et al. |
| 2009/0042866 | A1 | 2/2009 | Lennox et al. |
| 2010/0256112 | A1 | 10/2010 | Bradbury et al. |
| 2013/0296228 | A1 | 11/2013 | Patel et al. |
| 2014/0323532 | A1 | 10/2014 | Wei et al. |
| 2015/0175539 | A1 | 6/2015 | Jiricek et al. |
| 2015/0291565 | A1 | 10/2015 | Djaballah et al. |
| 2016/0271081 | A1 | 9/2016 | Lavoie et al. |
| 2016/0271082 | A1 | 9/2016 | Lavoie et al. |
| 2018/0179158 | A1 | 6/2018 | Dreier et al. |
| 2019/0031624 | A1 | 1/2019 | Lavoie et al. |
| 2019/0055188 | A1 | 2/2019 | Lavoie et al. |
| 2019/0084919 | A1 | 3/2019 | Lavoie et al. |

FOREIGN PATENT DOCUMENTS

| | | | |
|---|---|---|---|
| WO | 2009110002 | A1 | 9/2009 |
| WO | 2012084971 | A1 | 6/2012 |
| WO | 2014078294 | A1 | 5/2014 |
| WO | 2015164482 | A1 | 10/2015 |
| WO | 2018165611 | A1 | 9/2018 |
| WO | 2018165612 | A1 | 9/2018 |
| WO | 2018165614 | A1 | 9/2018 |
| WO | 2018218192 | A1 | 11/2018 |
| WO | 2019005841 | A1 | 1/2019 |

OTHER PUBLICATIONS

Bean, G, et al., "A22 disrupts the bacterial actin cytoskeleton by directly binding and inducing a low-affinity state in MreB", Biochemistry 48 (22), 4852-7 (2009).

Bohnert, J, et al., "Efflux inhibition by selective serotonin reuptake inhibitors in *Escherichia coli*", J Antimicrob Chemother 66, 2057-2060 (2011).

Bonez, P, et al., "Antibacterial, cyto and genotoxic activities of A22 compound ((S-3,4-dichlorobenzyl) Isothiourea hydrochloride)", Microbial Pathogenesis 99, 14-18 (2016).

Bonez, P, et al., "Anti-biofilm activity of A22 ((S-3,4-dichlorobenzyl) isothiourea hydrochloride) against Pseudomonas aeruginosa: Influence on biofilm formation, motility and bioadhesion", Microbial Pathogenesis 111, 6-13 (2017).

Buonerba, F, et al., "Improved Potency of Indole-Based NorA Efflux Pump Inhibitors: From Serendipity toward Rational Design and Development", J. Med. Chem DOI:10.1021/acs.jmedchem. 6b01281, 8 pages (Dec. 2, 2016).

Charles, E, "Inhibition of MreB and ftsZ proteins to minimize *E. coli* biofilms formation", doi: https://doi.org/10.1101/523167, 20 pages (2019).

Fleeman, R, et al., "Identification of a Novel Polyamine Scaffold With Potent Efflux Pump Inhibition Activity Toward Multi-Drug Resistant Bacterial Pathogens", Frontiers in Microbiology 9, 1301, 16 pages (2018).

Grossman, T., et al., "The Efflux Pump Inhibitor Timcodar Improves the Potency of Antimycobacterial Agents", Antimicrobial Agents and Chemotherapy 59(3), 1534-1541 (2015).

Gupta, S, et al., "Acceleration of Tuberculosis Treatment by Adjunctive Therapy with Verapamil as an Efflux Inhibitor", American Journal of respiratory and Critical Care Medicince 188, 600-607 (2013).

Handzlik, J, et al., "Recent Advances in Multi-Drug Resistance (MDR) Efflux Pump Inhibitors of Gram-Positive Bacteria *S. aureus*", Antibiotics 2, 28-45 (2013).

Iwai, N, et al., "Novel S-Benzylisothiourea Compound That Induces Spherical Cells in *Escherichia coli* Probably by Acting on a Rod-shape-determining Protein(s) Other Than Penicillin-binding Protein 2", Biosci Biotechnol Biochem 66 (12), 2658-2662 (2002).

Iwai, N, et al., "Structure-Activity Relationship of S-Benzylisothiourea Derivatives to Induce Spherical Cells in *Escherichia coli*", Biosci Biotechnol Biochem 68(11), 2265-2269 (2004).

Iwai, N, et al., "Structure-Activity Relationship Study of the Bacterial Actin-Like Protein MreB Inhibitors: Effects of Substitution of Benzyl Group in S-Benzylisothiourea", Biosci. Biotechnol. Biochem 71 (1), 246-248 (2007).

Lee, J, et al., "Roles of Indole as an Interspecies and Interkingdom Signaling Molecule", Trends in Microbiology 23 (11), 707-718 (2015).

Noguchi, N, et al., "Anti-infectious Effect of S-Benzylisothiourea Compound A22, Which Inhibits the Actin-Like Protein, MreB, in Shigella flexneri", Biol. Pharm. Bull 31 (7), 1327-1332 (2008).

Patent Cooperation Treaty, International Searching Authority, Search Report and Written Opinion for PCT/US2018/039567, 13 pages, dated Aug. 28, 2018.

Perry, J, et al., "In vitro activity of S-(3,4-dichlorobenzyl)isothiourea hydrochloride and novel structurally related compounds against multidrug-resistant bacteria, including Pseudomonas aeruginosa and Burkholderia cepacian complex". International Journal of Antimicrobial Agents, 39 (1), 27-32 (2012).

PubChem, "101437777", CID 101437777, 9 pages, Create Date Dec. 18, 2015.

PubChem, "10954401", CID 10954401, 14 pages, Create Date Oct. 26, 2006.

PubChem, "67894517", CID 67894517, 10 pages, Create Date Nov. 30, 2012.

PubChem, "6-Chloro-2,3,4,9-tetrahydro-1H-carbazol-1-amine", Compound Summary for CID 17743497, 15 pages (Create Date Nov. 13, 2007).

PubChem, "LLVYCKNUAXLGFC-UHFFFAOYSA-N", Compound Summary for CID 67376113, 11 pages (create date Nov. 30, 2012).

PubChem, "SCHEMBL9670581", Substance Record for SID 235049721, 7 pages, Feb. 13, 2015.

PubChem Database, "Acetamide, N-cyclohexyl-2-phenyl-", Compound Summary for CID 82500, 16 pages (Create Date: Mar. 26, 2005).

PubChem Database, "Cyclohexyloxybenzene", CID 137492, 17 pages (Create date: Mar. 27, 2005).

PubChem Database, "N-Cyclohexyl-3-methylbenzamide", Compound Summary for CID 236099,14 pages (create date: Mar. 26, 2005).

Robertson, GT, et al., "A Novel Indole Compound That Inhibits Pseudomonas aeruginosa Growth by Targeting MreB is a Substrate for MexAB-OprM", Journal of Bacteriology 189 (19), 6870-6881 (2007).

Samosorn, S, et al., "Synthesis of functionalised 2-aryl-5-nitro-1H-indoles and their activity as bacterial NorA efflux pump inhibitors", Bioorganic & Medicinal Chemistry 14, 857-865 (2006).

Shi, H, et al., "Chiral twisting in a bacterial cytoskeletal polymer affects filament size and orientation", Nature Communications 11, 1408, 1-12 (2020).

STN CAS Registry No. Registry File No. 1026060-58-1, 1 page (2008).

STN CAS Registry No. Registry File No. 788216-67-0, 1 page (2004).

STN CAS Registry No. Registry File No. 860554-34-3, 1 page (2005).

Tambat, R, et al., "Microbe-Derived Indole Metabolite Demonstrates Potent Multidrug Efflux Pump Inhibition in *Staphylococcus aureus*", Frontiers in Microbiology 10, 2153, 13 pages (2019).

Taylor, P, et al., "A Forward Chemical Screen Identifies Antibiotic Adjuvants in *Escherichia coli*", ACS Chem Biol 7, 1547-1555 (2012).

Yamachika, S, et al., "Anti-Pseudomonas aeruginosa Compound, 1,2,3,4-Tetrahydro-1,3,5-triazine Derivative, Exerts Its Action by Primarily Targeting MreB", Biol Pharm Bull 35(10), 1740-1744 (2012).

Yang, X, et al., "A tobramycin vector enhances synergy and efficacy of efflux pump inhibitors against multidrug-resistant Gram-negative bacteria", J. Med. Chem 60, 3913-1932 (2017).

Yaqub, G, et al., "Conventional-Microwave Mediated Synthesis and In Vitro Antimicrobial Activity of Novel Carbazole-Efflux Pump

(56) References Cited

OTHER PUBLICATIONS

Inhibitor Hybrid Antibacterials", Hindawi J. Chemistry, doi: 10.1155/2017/7243279, Article ID 724329, 5 pages (2017).

\* cited by examiner

THERAPEUTIC COMPOUNDS AND METHODS TO TREAT INFECTION

RELATED APPLICATION

This application claims priority to U.S. Provisional Application No. 62/525,079 that was filed on Jun. 26, 2017. The entire content of this application is hereby incorporated by reference herein.

BACKGROUND OF THE INVENTION

Antibiotics have been effective tools in the treatment of infectious diseases. However, bacteria have developed several different mechanisms to overcome the action of antibiotics. The emergence of Multidrug Resistant (MDR) bacterial pathogens has increased concerns as to the adequacy of current antimicrobials and pathogen treatment methods. The lethality of pathogens, such as Pseudomonas aeruginosa, has often led to treatment methods that are experimental or would otherwise normally be avoided in standard clinical practice. The growing threat from MDR pathogens highlights a critical need for additional antimicrobials. Thus, there is a pressing need for new antibiotics that exhibit novel mechanisms of action or circumvent conventional mechanisms of resistance.

Mechanisms of resistance can be specific such as for a molecule or a family of antibiotics, or the mechanisms can be non-specific. Several mechanisms of resistance can exist in a single bacterial strain, and those mechanisms may act independently or they may act synergistically to overcome the action of an antibiotic or a combination of antibiotics. Specific mechanisms include, for example, degradation of the drug, inactivation of the drug by enzymatic modification, and alteration of the drug target. Additional mechanisms of drug resistance include mechanisms in which access of the antibiotic to the target is prevented or reduced by decreasing the transport of the antibiotic into the cell or by increasing the efflux of the drug from the cell to the outside medium. Both of these mechanisms can lower the concentration of drug at the target site and allow bacterial survival in the presence of one or more antibiotics that would otherwise inhibit or kill the bacterial cells. Some bacteria utilize both mechanisms, combining low permeability of the cell wall (including membranes) with an active efflux of antibiotics. It has been shown that efflux of antibiotics can be mediated by more than one pump in a single organism and that almost all antibiotics are subject to resistance by this mechanism. For example, Pseudomonas aeruginosa expresses numerous efflux pumps including MexAB-OprM, MexCD-OprJ, MexEF-OprN, and MexXY-OprA(OprM) which actively efflux various antibacterial agents.

These multiple resistance mechanisms have become widespread and threaten the clinical utility of antibacterial therapy. The increase in antibiotic resistant strains has been particularly noted in major hospitals and care centers. The consequences of the increase in resistant strains include, for example higher morbidity and mortality, longer patient hospitalization, and an increase in treatment costs. Accordingly, there is a need for novel antibiotics and agents that can be used in combination to inhibit or mitigate one or more of these mechanisms of bacterial resistance. There is also a need for new methods of treatment for overcoming or mitigating these mechanisms of bacterial resistance.

MreB is a well conserved and essential cytoskeleton-like protein, which represents a bacterial homolog of actin. Studies with various MreB homnologs have established that this protein forms dynamic, actin-like helical filaments in an ATP- or GTP-dependent fashion. The filaments are localized within the bacterial cell on the inner surface of the cytoplasmic membrane. MreB protein provides a critical role in the maintenance of cell shape, polar protein localization, and/or chromosome segregation. Because of its essential role in bacterial growth and function, MreB inhibitors represent a novel class of antibacterial agents.

The MreB homolog of P. aeruginosa is essential for cell viability as well as maintenance of rod-like cell morphology. CBR-4830 was identified as an effective MreB inhibitor in P. aeruginosa while screening libraries of compounds against a P. aeruginosa strains with defective efflux transporters.

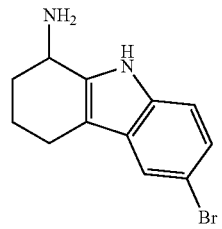

CBR-4830

CBR-4830 is a substrate for the MexAB-OprM efflux transporter present in wild-type P. aeruginosa, which limited its efficacy and clinical promise. Thus, there is an ongoing need for antibacterial agents with novel mechanisms of action (e.g., MreB inhibitors). There is also a need for antibacterial agents (e.g., MreB inhibitors) that have improved properties such as improved formulation characteristics and/or lowered toxicity.

SUMMARY OF THE INVENTION

Compounds disclose herein, when tested alone or in combination with a bacterial efflux pump inhibitor, exhibit antibacterial activities.

Accordingly, one embodiment provides a method of treating or preventing a bacterial infection in an animal (e.g., a mammal such as a human) comprising administering to the animal a bacterial efflux pump inhibitor and a compound of formula I:

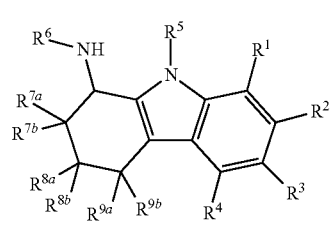

I or a pharmaceutically acceptable salt thereof, wherein:
$R^1$ is hydrogen, halo, cyano, nitro, $(C_1-C_6)$alkyl, $(C_1-C_4)$alkoxy, phenyl or heteroaryl, wherein the $(C_1-C_6)$alkyl, $(C_1-C_4)$alkoxy, phenyl or heteroaryl is optionally substituted with one or more groups selected from halo, hydroxy, $(C_1-C_4)$alkyl, $(C_1-C_4)$haloalkyl, $(C_1-C_4)$alkoxy, $(C_1-C_4)$haloalkoxy, nitro or cyano;
$R^2$ is hydrogen, halo, cyano, nitro, $(C_1-C_6)$alkyl, $(C_1-C_4)$alkoxy, phenyl or heteroaryl, wherein the $(C_1-C_6)$alkyl, ($C_1$-$C_4$)alkoxy, phenyl or heteroaryl is optionally substituted with one or more groups selected from halo, hydroxy, ($C_1$-$C_4$)alkyl, ($C_1$-$C_4$)haloalkyl, ($C_1$-$C_4$)alkoxy, ($C_1$-$C_4$)haloalkoxy, nitro or cyano;

$R^3$ is hydrogen, halo, cyano, nitro, ($C_1$-$C_6$)alkyl, ($C_1$-$C_4$) alkoxy, phenyl or heteroaryl, wherein the ($C_1$-$C_6$)alkyl, ($C_1$-$C_4$)alkoxy, phenyl or heteroaryl is optionally substituted with one or more groups selected from halo, hydroxy, ($C_1$-$C_4$)alkyl, ($C_1$-$C_4$)haloalkyl, ($C_1$-$C_4$)alkoxy, ($C_1$-$C_4$)haloalkoxy, nitro or cyano;

$R^4$ is hydrogen, halo, cyano, nitro, ($C_1$-$C_6$)alkyl, ($C_1$-$C_4$) alkoxy, phenyl or heteroaryl, wherein the ($C_1$-$C_6$)alkyl, ($C_1$-$C_4$)alkoxy, phenyl or heteroaryl is optionally substituted with one or more groups selected from halo, hydroxy, ($C_1$-$C_4$)alkyl, ($C_1$-$C_4$)haloalkyl, ($C_1$-$C_4$)alkoxy, ($C_1$-$C_4$)haloalkoxy, nitro or cyano;

$R^5$ is hydrogen or ($C_1$-$C_4$)alkyl; $R^6$ is hydrogen, ($C_1$-$C_6$) alkyl, ($C_3$-$C_6$)cycloalkyl, —C(=O)$R^X$, or —C(=O)O$R^X$, wherein the ($C_1$-$C_6$)alkyl or ($C_3$-$C_6$)cycloalkyl is optionally substituted with one or more groups selected from halo, O$R^a$ or N$R^a R^b$;

$R^{7a}$ is hydrogen, halo, ($C_1$-$C_6$)alkyl, —C(=O)O$R^c$, —C(=O)N$R^d R^e$, —N$R^f R^g$, or phenyl, wherein the ($C_1$-$C_6$) alkyl or phenyl is optionally substituted with one or more halogen, O$R^h$, ($C_1$-$C_6$)alkyl, or —N$R^f R^g$;

$R^{7b}$ is hydrogen, halo, or ($C_1$-$C_6$)alkyl;

$R^{8a}$ is hydrogen, halo, ($C_1$-$C_6$)alkyl, —C(=O)O$R^c$, —C(=O)N$R^d R^e$, —N$R^f R^g$, or phenyl, wherein the ($C_1$-$C_6$) alkyl or phenyl is optionally substituted with one or more halogen, O$R^h$, ($C_1$-$C_6$)alkyl, or —N$R^f R^g$;

$R^{8b}$ is hydrogen, halo, or ($C_1$-$C_6$)alkyl;

$R^{9a}$ is hydrogen, halo, ($C_1$-$C_6$)alkyl, —C(=O)O$R^c$, —C(=O)N$R^d R^e$, —N$R^f R^g$, or phenyl, wherein the ($C_1$-$C_6$) alkyl or phenyl is optionally substituted with one or more halogen, O$R^h$, ($C_1$-$C_6$)alkyl, or —N$R^f R^g$;

$R^{9b}$ is hydrogen, halo, or ($C_1$-$C_6$)alkyl;

each $R^X$ is independently ($C_1$-$C_6$)alkyl, ($C_3$-$C_6$)cycloalkyl, or phenyl, wherein the ($C_1$-$C_6$) alkyl, ($C_3$-$C_6$) cycloalkyl, or phenyl is optionally substituted with one or more groups selected from halo, O$R^a$ or N$R^a R^b$;

each $R^a$ is independently hydrogen or ($C_1$-$C_4$)alkyl;

each $R^b$ is independently hydrogen or ($C_1$-$C_4$)alkyl; or $R^a$ and $R^b$ taken together with the nitrogen to which they are attached form pyrrolidinyl, piperidinyl, piperazinyl or morpholinyl;

$R^c$ is hydrogen or ($C_1$-$C_4$)alkyl;

$R^d$ is hydrogen or ($C_1$-$C_4$)alkyl;

$R^e$ is hydrogen or ($C_1$-$C_4$)alkyl wherein the ($C_1$-$C_4$)alkyl is optionally substituted with one or more halo, ($C_1$-$C_4$) alkoxy, —NH$_2$, —NH($C_1$-$C_4$) alkyl or —N(($C_1$-$C_4$)alkyl)$_2$; or $R^d$ and $R^e$ taken together with the nitrogen to which they are attached form pyrrolidinyl, piperidinyl, piperazinyl or morpholinyl;

$R^f$ is hydrogen or ($C_1$-$C_4$)alkyl;

$R^g$ is hydrogen or ($C_1$-$C_4$)alkyl; or $R^f$ and $R^g$ taken together with the nitrogen to which they are attached form pyrrolidinyl, piperidinyl, piperazinyl or morpholinyl; and $R^h$ is hydrogen or ($C_1$-$C_4$)alkyl.

One embodiment provides a method of treating or preventing a bacterial infection in an animal (e.g., a mammal such as a human) comprising administering to the animal a bacterial efflux pump inhibitor and a compound of formula Ia (sub-formula of formula I):

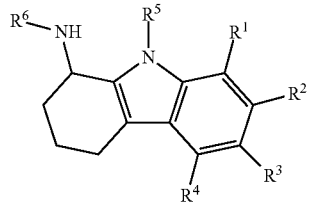

or a pharmaceutically acceptable salt thereof, wherein:

$R^1$ is hydrogen, halo, cyano, nitro, ($C_1$-$C_6$)alkyl, phenyl or heteroaryl, wherein the ($C_1$-$C_6$)alkyl, phenyl or heteroaryl is optionally substituted with one or more groups selected from halo, hydroxy, ($C_1$-$C_4$)alkyl, ($C_1$-$C_4$)haloalkyl, ($C_1$-$C_4$) alkoxy, nitro or cyano;

$R^2$ is hydrogen, halo, cyano, nitro, ($C_1$-$C_6$)alkyl, phenyl or heteroaryl, wherein the ($C_1$-$C_6$)alkyl, phenyl or heteroaryl is optionally substituted with one or more groups selected from halo, hydroxy, ($C_1$-$C_4$)alkyl, ($C_1$-$C_4$)haloalkyl, ($C_1$-$C_4$) alkoxy, nitro or cyano;

$R^3$ is hydrogen, halo, cyano, nitro, ($C_1$-$C_6$)alkyl, phenyl or heteroaryl, wherein the ($C_1$-$C_6$)alkyl, phenyl or heteroaryl is optionally substituted with one or more groups selected from halo, hydroxy, ($C_1$-$C_4$)alkyl, ($C_1$-$C_4$)haloalkyl, ($C_1$-$C_4$) alkoxy, nitro or cyano;

$R^4$ is hydrogen, halo, cyano, nitro, ($C_1$-$C_6$)alkyl, phenyl or heteroaryl, wherein the ($C_1$-$C_6$)alkyl, phenyl or heteroaryl is optionally substituted with one or more groups selected from halo, hydroxy, ($C_1$-$C_4$)alkyl, ($C_1$-$C_4$)haloalkyl, ($C_1$-$C_4$) alkoxy, nitro or cyano;

$R^5$ is hydrogen or ($C_1$-$C_4$)alkyl;

$R^6$ is hydrogen, ($C_1$-$C_6$)alkyl, ($C_3$-$C_6$)cycloalkyl, —C(=O)$R^X$, or —C(=O)O$R^X$, wherein the ($C_1$-$C_6$) alkyl or ($C_3$-$C_6$) cycloalkyl is optionally substituted with one or more groups selected from halo, —O$R^a$ or —N$R^a R^b$;

each $R^X$ is independently ($C_1$-$C_6$)alkyl, ($C_3$-$C_6$)cycloalkyl, or phenyl, wherein the ($C_1$-$C_6$)alkyl, ($C_3$-$C_6$)cycloalkyl, or phenyl is optionally substituted with one or more groups selected from halo, —O$R^a$ or —N$R^a R^b$;

each $R^a$ is independently hydrogen or ($C_1$-$C_4$)alkyl; and each $R^b$ is independently hydrogen or ($C_1$-$C_4$)alkyl; or $R^a$ and $R^b$ taken together with the nitrogen to which they are attached form pyrrolidinyl, piperidinyl, piperazinyl or morpholinyl.

One embodiment provides a method of treating or preventing a bacterial infection in an animal (e.g., a mammal such as a human) comprising administering to the animal in need thereof a compound of formula I (or Ia) or a pharmaceutically acceptable salt thereof as described herein.

One embodiment provides a method of treating or preventing a bacterial infection in an animal (e.g., a mammal such as a human) comprising administering to the animal in need thereof a bacterial efflux pump inhibitor and a compound of formula I (or Ia) or a pharmaceutically acceptable salt thereof as described herein.

One embodiment provides a method of treating or preventing a bacterial infection in an animal (e.g., a mammal such as a human) comprising administering to the animal in need thereof a compound of formula I (or Ia) or a pharmaceutically acceptable salt thereof as described herein.

One embodiment provides a method of treating or preventing a bacterial infection in an animal (e.g., a mammal such as a human) infected with bacteria comprising administering to the animal a bacterial efflux pump inhibitor and a compound of formula I (or Ia) or a pharmaceutically acceptable salt thereof as described herein and one or more antibacterial agents.

One embodiment provides a method of treating or preventing a bacterial infection in an animal (e.g., a mammal such as a human) infected with bacteria comprising administering to the animal a compound of formula I (or Ia) or a pharmaceutically acceptable salt thereof as described herein and one or more antibacterial agents.

One embodiment provides a compound of formula I or a salt thereof as described herein; provided that the compound of formula I is not

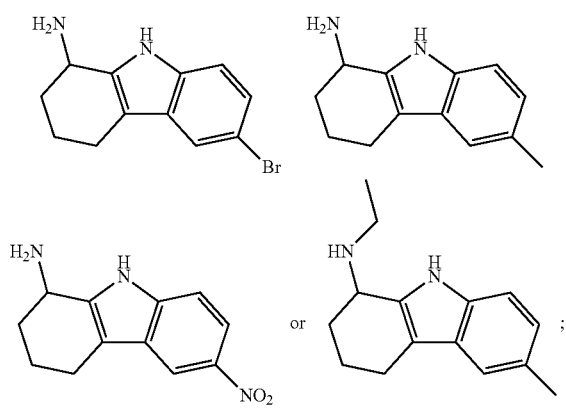

or a salt thereof.

One embodiment provides a pharmaceutical composition comprising a compound of formula I (or Ia) or a pharmaceutically acceptable salt thereof as described herein, and a pharmaceutically acceptable vehicle.

One embodiment provides pharmaceutical composition comprising a compound of formula I (or Ia) or a pharmaceutically acceptable salt thereof as described herein, a bacterial efflux pump inhibitor and a pharmaceutically acceptable vehicle.

One embodiment provides a compound of formula I (or Ia) or a pharmaceutically acceptable salt thereof as described herein, combined with a bacterial efflux pump inhibitor, for use in medical therapy.

One embodiment provides a compound of formula I (or Ia) or a pharmaceutically acceptable salt thereof as described herein, for use in medical therapy.

One embodiment provides a compound of formula I (or Ia) or a pharmaceutically acceptable salt thereof as described herein, combined with a bacterial efflux pump inhibitor, for the prophylactic or therapeutic treatment of a bacterial infection.

One embodiment provides a compound of formula I (or Ia) or a pharmaceutically acceptable salt thereof as described herein, for the prophylactic or therapeutic treatment of a bacterial infection.

One embodiment provides the use of a compound of formula I (or Ia) or a pharmaceutically acceptable salt thereof as described herein, combined with a bacterial efflux pump inhibitor, for the preparation of a medicament for treating a bacterial infection in an animal (e.g., a mammal such as a human).

One embodiment provides the use of a compound of formula I (or Ia) or a pharmaceutically acceptable salt thereof as described herein, for the preparation of a medicament for treating a bacterial infection in an animal (e.g., a mammal such as a human).

One embodiment provides processes and intermediates disclosed herein that are useful for preparing compounds of formula I or salts thereof.

DETAILED DESCRIPTION

The following definitions are used, unless otherwise described: halo or halogen is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to).

As used herein, the term "$(C_a\text{-}C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "aryl" as used herein refers to a single aromatic ring or a multiple condensed ring system wherein the ring atoms are carbon. For example, an aryl group can have 6 to 10 carbon atoms, or 6 to 12 carbon atoms. Aryl includes a phenyl radical. Aryl also includes multiple condensed ring systems (e.g., ring systems comprising 2 rings) having about 9 to 12 carbon atoms or 9 to 10 carbon atoms in which at least one ring is aromatic. Such multiple condensed ring systems may be optionally substituted with one or more (e.g., 1 or 2) oxo groups on any cycloalkyl portion of the multiple condensed ring system. It is to be understood that the point of attachment of a multiple condensed ring system, as defined above, can be at any position of the ring system including an aryl or a cycloalkyl portion of the ring. Typical aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 rings) wherein a heteroaryl group, as defined above, can be condensed with one or more heteroaryls (e.g., naphthyridinyl), heterocycles, (e.g., 1, 2, 3, 4-tetrahydronaphthyridinyl), cycloalkyls (e.g., 5,6,7,8-tetrahydroquinolyl) or aryls (e.g. indazolyl) to form a multiple condensed ring system. Such multiple condensed ring systems may be optionally substituted with one or more (e.g., 1 or 2) oxo groups on the cycloalkyl or heterocycle portions of the condensed ring. In one embodiment a monocyclic or bicyclic heteroaryl has 5 to 10 ring atoms comprising 1 to 9 carbon atoms and 1 to 4 heteroatoms. It is to be understood that the point of attachment of a multiple condensed ring system (as defined above for a heteroaryl) can be at any position of the multiple condensed ring system including a heteroaryl, heterocycle, aryl or cycloalkyl portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl and thianaphthenyl.

The term cycloalkyl, carbocycle, or carbocyclyl includes saturated and partially unsaturated carbocyclic ring systems. In one embodiment the cycloalkyl is a monocyclic carbocyclic ring. Such cycloalkyls include "$(C_3-C_7)$carbocyclyl" and "$(C_3-C_8)$cycloalkyl".

The term "heterocyclyl" or "heterocycle" as used herein refers to a single saturated or partially unsaturated ring or a multiple condensed ring system. The term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. It is to be understood that the point of attachment for a heterocycle can be at any suitable atom of the heterocycle Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl and tetrahydrothiopyranyl.

The term "haloalkyl" includes an alkyl group as defined herein that is substituted with one or more (e.g., 1, 2, 3, or 4) halo groups. One specific halo alkyl is a "$(C_1-C_6)$ haloalkyl".

The term "alkoxy" refers to —O(alkyl) and the term "haloalkoxy" refers to an alkoxy that is substituted with one or more (e.g., 1, 2, 3, or 4) halo.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_3-C_8)$cycloalkyl can be cyclopropyl, cyclobutyl, cyclopentyl, or cyclohexyl; and heteroaryl can be furyl, imidazolyl, triazolyl, triazinyl, oxazolyl, isoxazolyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In one embodiment, the bacterial efflux pump inhibitor is a compound of formula II:

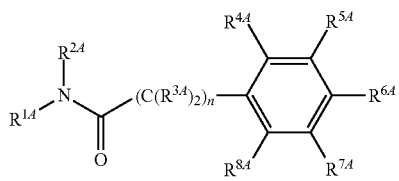

II or a pharmaceutically acceptable salt thereof, wherein:
$R^{1A}$ is $(C_3-C_8)$alkyl substituted with two or more groups selected from —$NR^{b1}R^{c1}$, —$NHNH_2$, —$C(=NR^{a1})(NR^{b1}R^{c1})$, —$NR^{a1}C(=NR^{a1})(R^{d1})$ and —$NR^{a1}C(=NR^{a1})(NR^{b1}R^{c1})$;
$R^{2A}$ is hydrogen or $(C_1-C_3)$alkyl;

each $R^{3A}$ is independently hydrogen, halo or $(C_1-C_4)$ alkyl;
$R^{4A}$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$ haloalkoxy;
$R^{5A}$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$ haloalkoxy;
$R^{6A}$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$ haloalkoxy;
$R^{7A}$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$ haloalkoxy;
$R^{8A}$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$ haloalkoxy;
each $R^{a1}$ is independently hydrogen or $(C_1-C_4)$alkyl;
each $R^{b1}$ and $R^{c1}$ is independently hydrogen or $(C_1-C_4)$ alkyl;
$R^{d1}$ is $(C_1-C_3)$alkyl and
n is 0 or 1.

It is to be understood that the embodiments provided below are for compounds of formula II and all sub-formulas thereof (e.g., formulas IIa, IIb, IIc, IId, IIe, IIf, IIg). It is to be understood the two or more embodiments may be combined.

In one embodiment $R^{2A}$ is hydrogen.
In one embodiment $R^{3A}$ is hydrogen.
One embodiment provides a bacterial efflux pump inhibitor which is a compound of formula IIa:

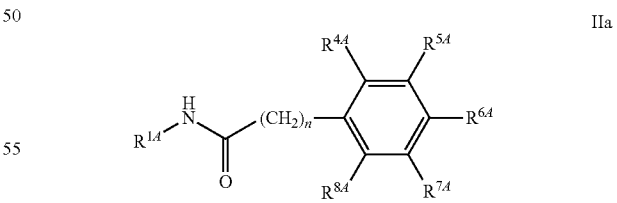

IIa or a pharmaceutically acceptable salt thereof.
In one embodiment $R^{8A}$ is hydrogen.
In one embodiment $R^{4A}$ is hydrogen, $(C_1-C_6)$haloalkyl or aryl wherein the aryl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy.
In one embodiment $R^{4A}$ is hydrogen, —$CF_3$ or phenyl.
In one embodiment $R^{4A}$ is hydrogen.

One embodiment provides a bacterial efflux pump inhibitor which is a compound of formula IIb:

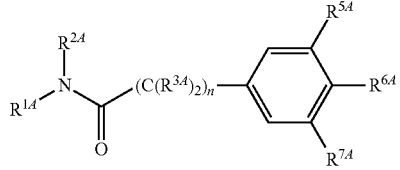

or a pharmaceutically acceptable salt thereof.

In one embodiment $R^{7A}$ is hydrogen.

One embodiment provides a bacterial efflux pump inhibitor which is a compound of formula IIc:

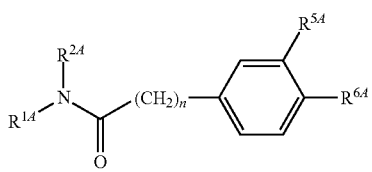

or a pharmaceutically acceptable salt thereof.

In one embodiment $R^{5A}$ is halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

In one embodiment $R^{5A}$ is $(C_1\text{-}C_6)$haloalkyl.

In one embodiment $R^{5A}$—$CF_3$.

In one embodiment $R^{6A}$ is halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy;

In one embodiment $R^{6A}$ is $(C_1\text{-}C_6)$haloalkyl.

In one embodiment $R^{6A}$—$CF_3$.

In one embodiment $R^{6A}$ is hydrogen.

One embodiment provides a bacterial efflux pump inhibitor which is a compound formula IId:

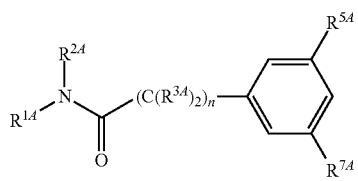

or a pharmaceutically acceptable salt thereof.

One embodiment provides a bacterial efflux pump inhibitor which is a compound of formula IIe:

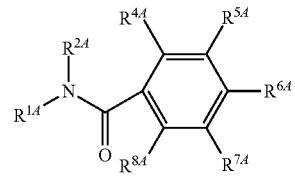

or a pharmaceutically acceptable salt thereof.

One embodiment provides a bacterial efflux pump inhibitor which is a compound of formula IIf:

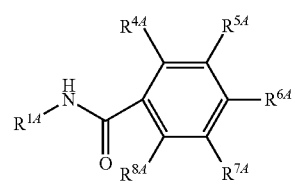

or a pharmaceutically acceptable salt thereof.

One embodiment provides a bacterial efflux pump inhibitor which is a compound of formula IIg:

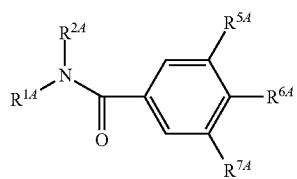

or a pharmaceutically acceptable salt thereof.

In one embodiment $R^{5A}$ is halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^{5A}$ is $(C_1\text{-}C_6)$alkyl, $(C_1\text{-}C_6)$haloalkyl, or aryl wherein the aryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^{5A}$ is $(C_1\text{-}C_6)$alkyl, $(C_1\text{-}C_6)$haloalkyl, or phenyl wherein phenyl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^{5A}$ is tert-butyl, —$CF_3$, phenyl or 4-fluorophenyl.

In one embodiment $R^{7A}$ is halo, $(C_1\text{-}C_6)$alkyl, $(C_1\text{-}C_6)$haloalkyl, $(C_1\text{-}C_6)$alkoxy, $(C_1\text{-}C_4)$haloalkoxy, aryl or heteroaryl wherein the aryl or heteroaryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^{7A}$ is $(C_1\text{-}C_6)$alkyl, $(C_1\text{-}C_6)$haloalkyl or aryl wherein the aryl is optionally substituted with one or more (e.g., 1, 2, 3, 4 or 5) groups independently selected from halo, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^{7A}$ is $(C_1-C_6)$alkyl, $(C_1-C_6)$haloalkyl, or phenyl wherein phenyl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^{7A}$ is tert-butyl, —$CF_3$, phenyl or 4-fluorophenyl.

In one embodiment the moiety:

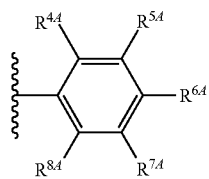

of the compound of formula II is:

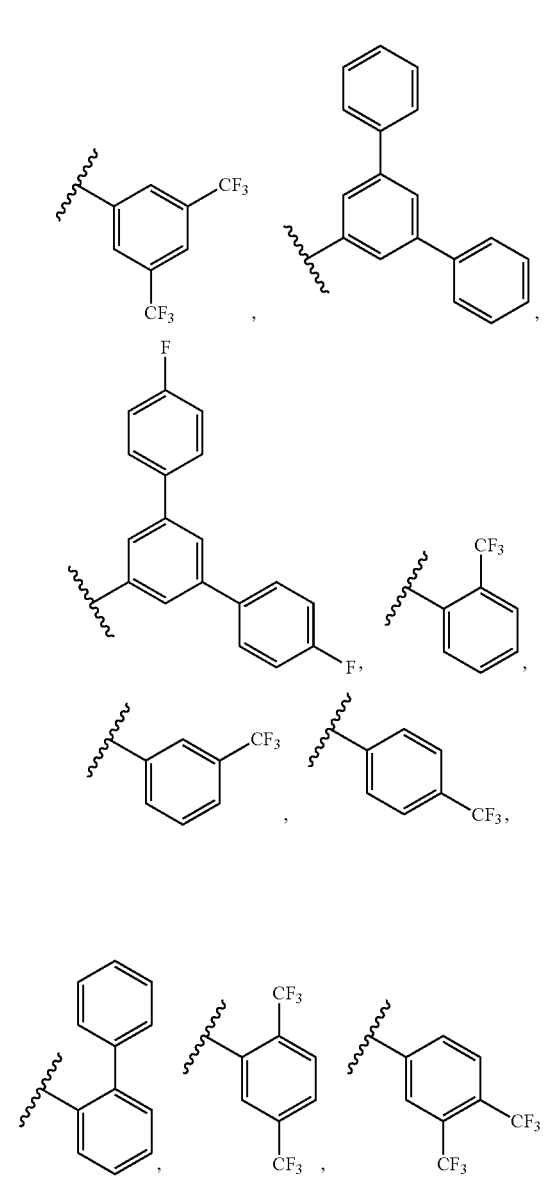

-continued

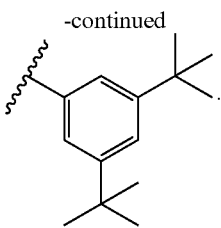

In one embodiment $R^{1A}$ is $(C_3-C_8)$alkyl substituted with two or more groups independently selected from —$NR^{b1}R^{c1}$.

In one embodiment $R^{1A}$ is $(C_3-C_8)$alkyl substituted with two groups independently selected from —$NR^{b1}R^{c1}$.

In one embodiment $R^{1A}$ is $(C_4-C_5)$alkyl substituted with two groups independently selected from —$NR^{b1}R^{c1}$.

In one embodiment $R^{b1}$ and $R^{c1}$ are each hydrogen.

In one embodiment $R^{1A}$ is:

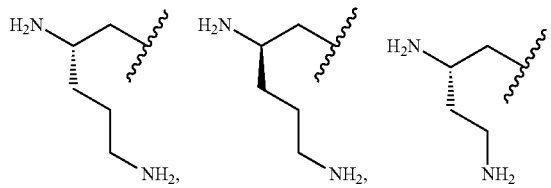

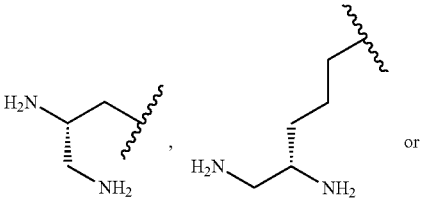

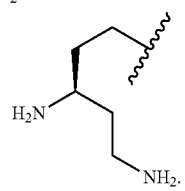

In one embodiment $R^{1A}$ is:

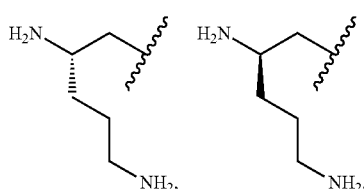

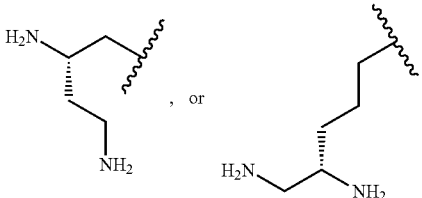

In one embodiment n is 0.

In one embodiment, the bacterial efflux pump inhibitor is a compound of formula III:

III

[Chemical structure: benzene ring with substituents A, R^6B, R^5B, R^4B, R^3B, R^2B]

or a pharmaceutically acceptable salt thereof, wherein:

A is —C(=O)N($R^{a1}$)—$R^{1B}$, —($C_1$-$C_3$)alkyl-C(=O)N($R^{a1}$)—$R^{1B}$, —($C_1$-$C_3$)alkyl-O—$R^{1B}$, —O—$R^{1B}$, —($C_1$-$C_3$)alkyl-N($R^{a1}$)—$R^{1B}$, or —N($R^{a1}$)—$R^{1B}$;

each $R^{1B}$ is independently a ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, wherein each ($C_3$-$C_7$)carbocyclyl or ($C_3$-$C_7$)carbocyclyl-($C_1$-$C_4$)alkyl- is independently substituted with one or more groups selected from the group consisting of Z and —($C_1$-$C_6$)alkyl substituted with one or more Z, and wherein each 4-7 membered monocyclic heterocyclyl or 4-7 membered monocyclic heterocyclyl-($C_1$-$C_4$)alkyl- is independently optionally substituted with one or more groups selected from the group consisting of Z and —($C_1$-$C_6$)alkyl substituted with one or more Z, wherein each Z is independently selected from the group consisting of $NR^{b2}R^{c2}$, —$NHNH_2$, —C(=$NR^{a2}$)($NR^{b2}R^{c2}$), —$NR^{a2}$C(=$NR^{a2}$)($R^{d2}$), and —$NR^{a2}$C(=$NR^{a2}$)($NR^{b2}R^{c2}$) and wherein each ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, is independently optionally substituted independently with one or more ($C_1$-$C_4$)alkyl;

$R^{2B}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_4$)alkyl, ($C_1$-$C_4$)haloalkyl, ($C_1$-$C_4$)alkoxy and ($C_1$-$C_4$)haloalkoxy;

$R^{3B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy;

$R^{4B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy;

$R^{5B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy;

$R^{6B}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_4$)alkyl, ($C_1$-$C_4$)haloalkyl, ($C_1$-$C_4$)alkoxy and ($C_1$-$C_4$)haloalkoxy;

each $R^{a1}$ is independently hydrogen, ($C_1$-$C_6$)alkyl or ($C_3$-$C_7$)carbocyclyl;

each $R^{a2}$ is independently hydrogen, ($C_1$-$C_6$)alkyl or ($C_3$-$C_7$)carbocyclyl;

each $R^{b2}$ and $R^{c2}$ is independently hydrogen, ($C_1$-$C_6$)alkyl or ($C_3$-$C_7$)carbocyclyl; and $R^{d2}$ is ($C_1$-$C_6$)alkyl or ($C_3$-$C_7$)carbocyclyl.

It is to understood that the embodiments provided below are for compounds of formula III and all sub-formulas thereof. It is to be understood the two or more embodiments may be combined.

In one embodiment A is —C(=O)N($R^{a1}$)—$R^{1B}$, —($C_1$-$C_3$)alkyl-C(=O)N($R^{a1}$)$R^{1B}$, —($C_1$-$C_3$)alkyl-O—$R^{1B}$, or —O—$R^{1B}$.

In one embodiment A is —C(=O)N($R^{a1}$)—$R^{1B}$.

In one embodiment A is —($C_1$-$C_3$)alkyl-C(=O)N($R^{a1}$)$R^{1B}$.

In one embodiment $R^{a1}$ is hydrogen.

In one embodiment A is —O—$R^{1B}$.

In one embodiment $R^{2B}$ is hydrogen, halo, ($C_1$-$C_4$)alkyl, ($C_1$-$C_4$)haloalkyl, ($C_1$-$C_4$)alkoxy, or ($C_1$-$C_4$)haloalkoxy.

In one embodiment $R^{2B}$ is hydrogen.

In one embodiment $R^{3B}$ is aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy.

In one embodiment $R^{3B}$ is phenyl wherein the phenyl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy.

In one embodiment $R^{3B}$ is 4-fluorophenyl.

In one embodiment $R^{4B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy.

In one embodiment $R^{4B}$ is hydrogen.

In one embodiment $R^{5B}$ is aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy.

In one embodiment $R^{5B}$ is phenyl wherein the phenyl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy.

In one embodiment $R^{5B}$ is 4-fluorophenyl.

In one embodiment $R^{6B}$ is hydrogen, halo, ($C_1$-$C_4$)alkyl, ($C_1$-$C_4$)haloalkyl, ($C_1$-$C_4$)alkoxy, or ($C_1$-$C_4$)haloalkoxy.

In one embodiment $R^{6B}$ is hydrogen.

In one embodiment the moiety:

[Chemical structure: benzene ring with wavy bond on left and substituents $R^{6B}$, $R^{5B}$, $R^{4B}$, $R^{3B}$, $R^{2B}$]

of the compound of formula III is:

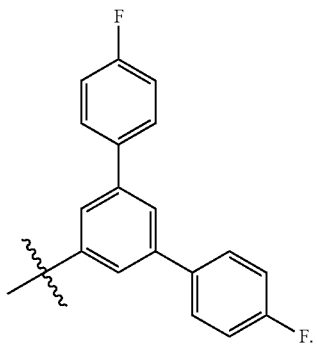 [SMILES: *c1cc(-c2ccc(F)cc2)cc(-c2ccc(F)cc2)c1]

In one embodiment $R^{1B}$ is a 4-7 membered monocyclic heterocyclyl or 4-7 membered monocyclic heterocyclyl-($C_1$-$C_4$)alkyl-, wherein the 4-7 membered monocyclic heterocyclyl or 4-7 membered monocyclic heterocyclyl-($C_1$-$C_4$)alkyl- is optionally substituted independently with one or more groups selected from the group consisting of Z and —($C_1$-$C_6$)alkyl substituted with one or more Z, wherein each Z is $NR^{b2}R^{c2}$ and wherein the 4-7 membered monocyclic heterocyclyl or 4-7 membered monocyclic heterocyclyl-($C_1$-$C_4$)alkyl- is optionally substituted with one or more ($C_1$-$C_4$)alkyl.

In one embodiment $R^{1B}$ is a 4-7 membered monocyclic N-heterocyclyl or 4-7 membered monocyclic N-heterocyclyl-($C_1$-$C_4$)alkyl-, wherein the 4-7 membered monocyclic N-heterocyclyl or 4-7 membered monocyclic N-heterocyclyl-($C_1$-$C_4$)alkyl- is optionally substituted independently with one or more groups selected from the group consisting of Z and —($C_1$-$C_6$)alkyl substituted with one or more Z, wherein each Z is $NR^{b2}R^{c2}$ and wherein the 4-7 membered monocyclic N-heterocyclyl or 4-7 membered monocyclic N-heterocyclyl-($C_1$-$C_4$)alkyl- is optionally substituted with one or more ($C_1$-$C_4$)alkyl.

In one embodiment $R^{1B}$ is a pyrrolidinyl or pyrrolidinyl-($C_1$-$C_4$)alkyl-, wherein the pyrrolidinyl or pyrrolidinyl-($C_1$-$C_4$)alkyl- is optionally substituted independently with one or more groups selected from the group consisting of Z and —($C_1$-$C_6$)alkyl substituted with one or more Z, wherein each Z is $NR^{b2}R^{c2}$ and wherein the pyrrolidinyl or pyrrolidinyl-($C_1$-$C_4$)alkyl- is optionally substituted with one or more ($C_1$-$C_4$)alkyl.

In one embodiment $R^{1B}$ is a pyrrolidinyl or pyrrolidinyl-($CH_2$)—, wherein the pyrrolidinyl-($CH_2$)— is optionally substituted independently with one or more groups selected from the group consisting of Z and —($C_1$-$C_6$)alkyl substituted with one or more Z, wherein each Z is $NR^{b2}R^{c2}$ and wherein the pyrrolidinyl or pyrrolidinyl-($C_1$-$C_4$)alkyl- is optionally substituted with one or more ($C_1$-$C_4$)alkyl.

In one embodiment $R^{1B}$ is a pyrrolidinyl or pyrrolidinyl-($CH_2$)—, wherein the pyrrolidinyl-($CH_2$)— is optionally substituted independently with one or more groups selected from the group consisting of Z and —($C_1$-$C_6$)alkyl substituted with one or more Z, wherein each Z is $NR^{b2}R^{c2}$.

In one embodiment each $R^{b2}$ and $R^{c2}$ is hydrogen.

In one embodiment $R^{1B}$ is:

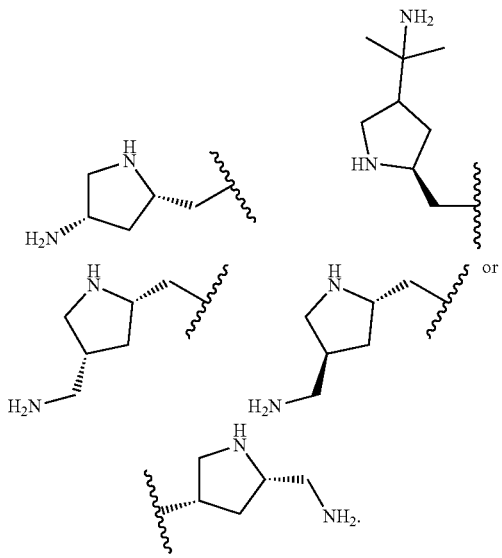

In one embodiment A is:

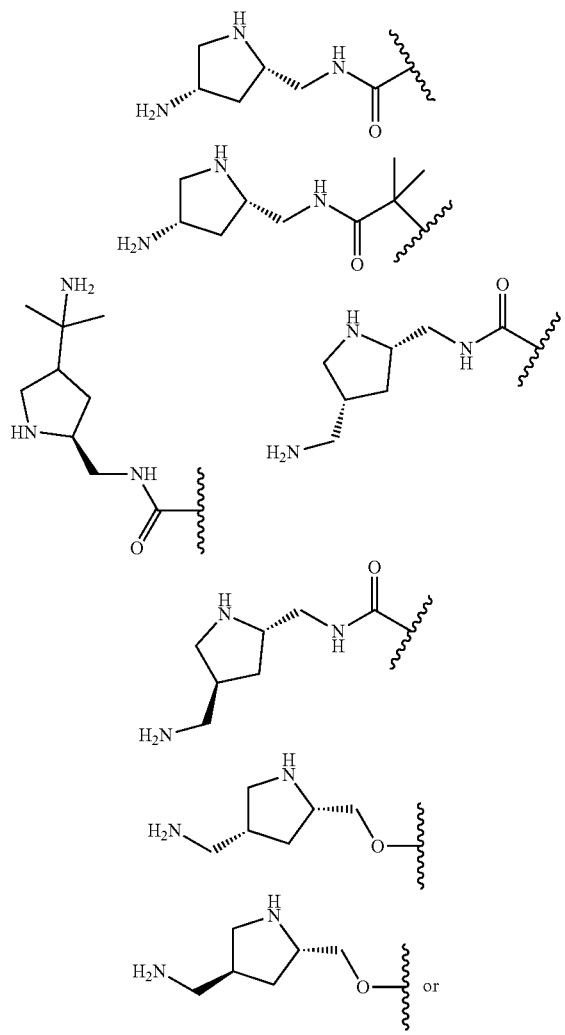

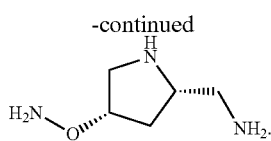

In one embodiment, the bacterial efflux pump inhibitor is a compound of formula IV:

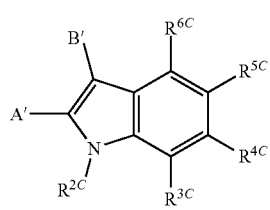

or a pharmaceutically acceptable salt thereof, wherein:

one of A' or B' is —C(=O)N($R^{a1}$)—$R^{1C}$, —($C_1$-$C_3$)alkyl-C(=O)N($R^{a1}$)$R^{1C}$, —($C_1$-$C_3$)alkyl-O—$R^{1C}$, —O—$R^{1C}$, —($C_1$-$C_3$)alkyl-N($R^{a1}$)—$R^{1C}$, —N($R^{a1}$)—$R^{1C}$, or $R^{1C}$ and the other of A' or B' is H, halogen, or ($C_1$-$C_4$)alkyl;

each $R^{1C}$ is independently:

(a) ($C_1$-$C_{14}$)alkyl substituted with one or more groups selected from the group consisting of —$NR^{b2}R^{c2}$, —$NHNH_2$, —C(=$NR^{a2}$)($NR^{b2}R^{c2}$), —$NR^{a2}$C(=$NR^{a2}$)($R^{d2}$), and —$NR^{a2}$C(=$NR^{a2}$)($NR^{b2}R^{c2}$); and wherein ($C_1$-$C_{14}$)alkyl is optionally substituted independently with one or more halo, ($C_1$-$C_4$)alkyl or ($C_3$-$C_7$)carbocyclyl; or (b) ($C_3$-$C_7$)carbocyclyl, ($C_3$-$C_7$)carbocyclyl-($C_1$-$C_4$)alkyl-, 4-7 membered monocyclic heterocyclyl, 4-7 membered monocyclic heterocyclyl-($C_1$-$C_4$)alkyl-, ($C_3$-$C_7$)carbocyclyl-$NR^e$—($C_1$-$C_4$)alkyl- or 4-7 membered monocyclic heterocyclyl-$NR^e$—($C_1$-$C_4$)alkyl- wherein each ($C_3$-$C_7$)carbocyclyl, ($C_3$-$C_7$)carbocyclyl-($C_1$-$C_4$)alkyl- or -, ($C_3$-$C_7$)carbocyclyl-$NR^e$—($C_1$-$C_4$)alkyl- is independently substituted with one or more $Z^1$ or $Z^2$, and wherein each 4-7 membered monocyclic heterocyclyl, 4-7 membered monocyclic heterocyclyl-($C_1$-$C_4$)alkyl- or 4-7 membered monocyclic heterocyclyl-$NR^e$—($C_1$-$C_4$)alkyl- is independently optionally substituted with one or more $Z^1$ or $Z^2$, and wherein any ($C_3$-$C_7$)carbocyclyl, ($C_3$-$C_7$)carbocyclyl-($C_1$-$C_4$)alkyl-, 4-7 membered monocyclic heterocyclyl, 4-7 membered monocyclic heterocyclyl-($C_1$-$C_4$)alkyl-, ($C_3$-$C_7$)carbocyclyl $NR^e$—($C_1$-$C_4$)alkyl- or 4-7 membered monocyclic heterocyclyl-$NR^e$—($C_1$-$C_4$)alkyl- of $R^1$ is independently optionally substituted with one or more halo, ($C_1$-$C_4$)alkyl, ($C_3$-$C_7$)carbocyclyl, —C(=O)$NH_2$, —C(=O)NH($C_1$-$C_4$)alkyl, —C(=O)N(($C_1$-$C_4$)alkyl)$_2$, —NHC(=O)($C_1$-$C_4$)alkyl-$NH_2$, or 3-7 membered monocyclic heterocyclyl wherein ($C_1$-$C_4$)alkyl, ($C_3$-$C_7$)carbocyclyl or 3-7 membered monocyclic heterocyclyl is optionally substituted with one or more halogen, ($C_1$-$C_4$)alkyl, —$NH_2$, —NH($C_1$-$C_4$)alkyl or —N(($C_1$-$C_4$)alkyl)$_2$;

$R^{2C}$ is hydrogen, ($C_1$-$C_4$)alkyl or phenyl($C_1$-$C_3$)alkyl-, wherein the phenyl is optionally substituted with one or more ($C_1$-$C_4$)alkyl, —O($C_1$-$C_4$)alkyl, halogen, or —$NO_2$;

$R^{3C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^{4C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, heteroaryl, aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)alkynyl-, phenoxy or heteroaryloxy, wherein the aryl, heteroaryl, aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)alkynyl-, phenoxy or heteroaryloxy, is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, ($C_1$-$C_4$)haloalkoxy, methylenedioxy (—$OCH_2O$—), and ($C_3$-$C_7$)carbocyclyl;

$R^{5C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, heteroaryl aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)alkynyl-, phenoxy or heteroaryloxy, wherein the aryl, heteroaryl, aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)alkynyl-, phenoxy or heteroaryloxy, is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, ($C_1$-$C_4$)haloalkoxy, methylenedioxy (—$OCH_2O$—), and ($C_3$-$C_7$)carbocyclyl;

$R^{6C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

each $Z^1$ is independently selected from the group consisting of —$NR^{b3}R^{c3}$, —$NHNH_2$, —C(=$NR^{a3}$)($NR^{b3}R^{c3}$), —$NR^{a3}$C(=$NR^{a3}$)($R^{d3}$), and —$NR^{a3}$C(=$NR^{a3}$)($NR^{b3}R^{c3}$);

each $Z^2$ is independently —($C_1$-$C_6$)alkyl substituted with one or more $Z^1$ and optionally substituted with one or more $Z^3$;

each $Z^3$ is independently halo or ($C_3$-$C_7$)carbocyclyl;

each $R^{a1}$ is independently hydrogen, ($C_1$-$C_4$)alkyl, ($C_3$-$C_7$)carbocyclyl or 3-7 membered monocyclic heterocycly optionally substituted with one or more halogen or ($C_1$-$C_4$)alkyl;

each $R^{a2}$ is independently hydrogen, ($C_1$-$C_4$)alkyl or ($C_3$-$C_7$)carbocyclyl;

each $R^{b2}$ and $R^{c2}$ is independently hydrogen, ($C_1$-$C_4$)alkyl or ($C_3$-$C_7$)carbocyclyl;

$R^{d2}$ is ($C_1$-$C_4$)alkyl or ($C_3$-$C_7$)carbocyclyl;

each $R^{a3}$ is independently hydrogen ($C_1$-$C_4$)alkyl or ($C_3$-$C_7$)carbocyclyl;

each $R^{b3}$ and $R^3$ is independently hydrogen ($C_1$-$C_4$)alkyl or ($C_3$-$C_7$)carbocyclyl;

$R^{d3}$ is ($C_1$-$C_4$)alkyl or ($C_3$-$C_7$)carbocyclyl; and each $R^e$ is independently hydrogen, ($C_1$-$C_4$)alkyl or ($C_3$-$C_7$)carbocyclyl;

In one embodiment, the bacterial efflux pump inhibitor is a compound of formula IV:

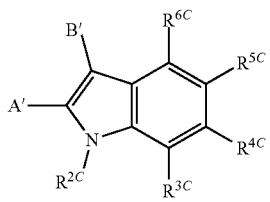

IV or a pharmaceutically acceptable salt thereof, wherein:
one of A' or B' is —C(=O)N($R^{a1}$)—$R^{1C}$, —($C_1$-$C_3$)alkyl-C(=O)N($R^{a1}$)$R^{1C}$, —($C_1$-$C_3$)alkyl-O—$R^{1C}$, —O—$R^{1C}$, —($C_1$-$C_3$)alkyl-N($R^{a1}$)—$R^{1C}$, —N($R^{a1}$)—$R^{1C}$, or $R^{1C}$ and the other of A' or B' is H, halogen, or ($C_1$-$C_4$)alkyl;

each $R^{1C}$ is independently:
(a) ($C_1$-$C_{14}$)alkyl substituted with one or more groups selected from the group consisting of —NR$^{b2}$R$^{c2}$, —NHNH$_2$, —C(=NR$^{a2}$)(NR$^{b2}$R$^{c2}$), —NR$^{a2}$C(=NR$^{a2}$)(R$^{a2}$), and —NR$^{a2}$C(=NR$^{a2}$)(NR$^{b2}$R$^{c2}$); and wherein ($C_1$-$C_4$)alkyl is optionally substituted independently with one or more halo, ($C_1$-$C_4$)alkyl or ($C_3$-$C_7$)carbocyclyl; or (b) ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, wherein each ($C_3$-$C_7$)carbocyclyl or ($C_3$-$C_7$)carbocyclyl-($C_1$-$C_4$)alkyl- is independently substituted with one or more $Z^1$ or $Z^2$, and wherein each 4-7 membered monocyclic heterocyclyl or 4-7 membered monocyclic heterocyclyl-($C_1$-$C_4$)alkyl- is independently optionally substituted with one or more $Z^1$ or $Z^2$, and wherein any ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl- of $R^1$ is independently optionally substituted independently with one or more halo, ($C_1$-$C_4$)alkyl or ($C_3$-$C_7$)carbocyclyl;

$R^{2C}$ is hydrogen, ($C_1$-$C_4$)alkyl or phenyl($C_1$-$C_3$)alkyl-, wherein the phenyl is optionally substituted with one or more ($C_1$-$C_4$)alkyl, —O($C_1$-$C_4$)alkyl, halogen, or —NO$_2$;

$R^{3C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —NO$_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^{4C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —NO$_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^{5C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —NO$_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^{6C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —NO$_2$, —CN, ($C_1$-$C_4$)alkyl, ($C_1$-$C_4$)haloalkyl, ($C_1$-$C_4$)alkoxy, and ($C_1$-$C_4$)haloalkoxy;

each $Z^1$ is independently selected from the group consisting of —NR$^{b3}$R$^{c3}$, —NHNH$_2$, —C(=NR$^{a3}$)(NR$^{b3}$R$^{c3}$), —NR$^{a3}$C(=NR$^{a3}$)(R$^{a3}$) and —NR$^{a3}$C(=NR$^{a3}$)(NR$^{b3}$R$^{c3}$);

each $Z^2$ is independently —($C_1$-$C_6$)alkyl substituted with one or more $Z^1$ and optionally substituted with one or more $Z^3$;

each $Z^3$ is independently halo or ($C_3$-$C_7$)carbocyclyl;
each $R^{a1}$ is independently hydrogen, ($C_1$-$C_4$)alkyl or ($C_3$-$C_7$)carbocyclyl;
each $R^{a2}$ is independently hydrogen, ($C_1$-$C_4$)alkyl or ($C_3$-$C_7$)carbocyclyl;
each $R^{b2}$ and $R^{c2}$ is independently hydrogen, ($C_1$-$C_4$)alkyl or ($C_3$-$C_7$)carbocyclyl;
$R^{d2}$ is ($C_1$-$C_4$)alkyl or ($C_3$-$C_7$)carbocyclyl;
each $R^{a3}$ is independently hydrogen ($C_1$-$C_4$)alkyl or ($C_3$-$C_7$)carbocyclyl;
each $R^{b3}$ and $R^3$ is independently hydrogen ($C_1$-$C_4$)alkyl or ($C_3$-$C_7$)carbocyclyl; and
$R^{d3}$ is ($C_1$-$C_4$)alkyl or ($C_3$-$C_7$)carbocyclyl.

It is to understood that the embodiments provided below are for compounds of formula IV and all sub-formulas thereof (e.g., formulas IVa, IVb). It is to be understood the two or more embodiments may be combined.

In one embodiment one of A' or B' is —C(=O)N($R^{a1}$)—$R^{1C}$ or —($C_1$-$C_3$)alkyl-C(=O)N($R^{a1}$)$R^{1C}$, and the other of A' or B' is H, halogen, or ($C_1$-$C_6$)alkyl.

In one embodiment one of A' or B' is —C(=O)N($R^{a1}$)—$R^{1C}$, and the other of A' or B' is H, halogen, or ($C_1$-$C_6$)alkyl.

In one embodiment A' is —C(=O)N($R^{a1}$)—$R^{1C}$, and B' is H.

In one embodiment B' is —C(=O)N($R^{a1}$)—$R^{1C}$, and A' is H.

In one embodiment one of A' or B' is —C(=O)N($R^{a1}$)—$R^{1C}$ or —($C_1$-$C_3$)alkyl-C(=O)N($R^{a1}$)$R^{1C}$, and the other of A' or B' is H.

In one embodiment one of A' or B' is —C(=O)N($R^{a1}$)—$R^{1C}$, and the other of A' or B' is H.

In one embodiment $R^{2C}$ is hydrogen, ($C_1$-$C_4$)alkyl or benzyl, wherein benzyl is optionally substituted with one or more ($C_1$-$C_4$)alkyl, —O($C_1$-$C_4$)alkyl, halogen or —NO$_2$.

In one embodiment $R^{a1}$ is hydrogen.
In one embodiment $R^{2C}$ is hydrogen or ($C_1$-$C_4$)alkyl.
In one embodiment $R^{2C}$ is hydrogen.
In one embodiment $R^{2C}$ is hydrogen, methyl, or 4-fluorobenzyl.

In one embodiment a compound of formula IV is a compound formula IVa or IVb:

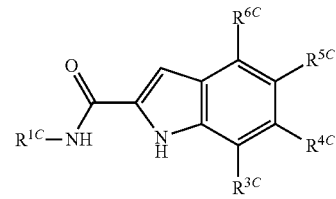

IVa

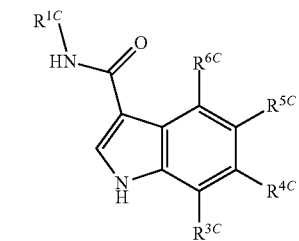

IVb or a pharmaceutically acceptable salt thereof.

In one embodiment $R^{3C}$ is hydrogen or aryl wherein the aryl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment $R^{3C}$ is hydrogen or phenyl wherein the phenyl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment $R^{3C}$ is hydrogen or 4-fluorophenyl.

In one embodiment $R^{4C}$ is hydrogen, aryl, or heteroaryl wherein the aryl or heteroaryl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy.

In one embodiment $R^{4C}$ is hydrogen, phenyl, or pyridinyl wherein the phenyl or pyridinyl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy.

In one embodiment $R^{4C}$ is hydrogen, 4-nitrophenyl, 4-fluorophenyl, 3,4-difluorophenyl, 4-t-butylphenyl, 4-methoxyphenyl, pyridin-4-yl, 4-hydroxyphenyl, 4-chlorophenyl, or 4-cyanophenyl.

In one embodiment $R^{5C}$ is hydrogen or aryl wherein the aryl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment $R^{5C}$ is hydrogen or phenyl wherein the phenyl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment $R^{5C}$ is hydrogen or 4-fluorophenyl.

In one embodiment $R^{6C}$ is hydrogen or aryl wherein the aryl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment $R^{6C}$ is hydrogen or phenyl wherein the phenyl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment $R^{6C}$ is hydrogen or 4-fluorophenyl.

In one embodiment $R^{1C}$ is (C$_1$-C$_{14}$)alkyl substituted with one or more groups independently selected from —NR$^{b2}$R$^{c2}$.

In one embodiment $R^{1C}$ is (C$_2$-C$_{10}$)alkyl substituted with one or more groups independently selected from —NR$^{b2}$R$^{c2}$.

In one embodiment $R^{1C}$ is (C$_1$-C$_{14}$)alkyl substituted with one or more groups independently selected from —NR$^{b2}$R$^{c2}$.

In one embodiment $R^{1C}$ is (C$_2$-C$_8$)alkyl substituted with two or more groups independently selected from —NR$^{b2}$R$^{c2}$.

In one embodiment $R^{1C}$ is (C$_4$-C$_8$)alkyl substituted with two or more groups independently selected from —NR$^{b2}$R$^{c2}$.

In one embodiment $R^{b2}$ and $R^{c2}$ are each hydrogen.

In one embodiment $R^{1C}$ is a 4-7 membered monocyclic heterocyclyl-(C$_1$-C$_4$)alkyl-, wherein the 4-7 membered monocyclic heterocyclyl-(C$_1$-C$_4$)alkyl- is substituted with one or more groups independently selected from the group consisting of Z and —(C$_1$-C$_6$)alkyl substituted with one or more Z, wherein each Z is independently selected from the group consisting of —NR$^{b3}$R$^{c3}$, —NHNH$_2$, —C(=NR$^{a3}$)(NR$^{b3}$R$^{c3}$), —NR$^{a3}$C(=NR$^{a3}$)(R$^{d3}$), and NR$^{a3}$C(=NR$^{a3}$)(NR$^{b3}$R$^{c3}$) and wherein the 4-7 membered monocyclic heterocyclyl-(C$_1$-C$_4$)alkyl- is optionally substituted with one or more (C$_1$-C$_6$)alkyl.

In one embodiment $R^{1C}$ is a 4-7 membered monocyclic heterocyclyl-(C$_1$-C$_4$)alkyl-, wherein the 4-7 membered monocyclic heterocyclyl-(C$_1$-C$_4$)alkyl- is substituted with one or more groups independently selected from the group consisting of Z and (C$_1$-C$_6$)alkyl substituted with one or more Z, wherein each Z is independently —NR$^{b3}$R$^{c3}$ and wherein the 4-7 membered monocyclic heterocyclyl-(C$_1$-C$_4$)alkyl- is optionally substituted with one or more (C$_1$-C$_6$) alkyl.

In one embodiment $R^{1C}$ is pyrrolidinyl-(C$_1$-C$_4$)alkyl-, wherein the pyrrolidinyl-(C$_1$-C$_4$)alkyl- is substituted with one or more groups independently selected from the group consisting of Z and —(C$_1$-C$_6$)alkyl substituted with one or more Z, wherein each Z is independently —NR$^{b3}$R$^{c3}$ and wherein is pyrrolidinyl-(C$_1$-C$_4$)alkyl- is optionally substituted independently with one or more (C$_1$-C$_6$)alkyl In one embodiment $R^{1C}$ is pyrrolidinyl-(CH$_2$)—, wherein the pyrrolidinyl-(CH$_2$)— is substituted with one or more groups independently selected from the group consisting of Z and —(C$_1$-C$_6$)alkyl substituted with one or more Z, wherein each Z is independently —NR$^{b3}$R$^{c3}$ and wherein the pyrrolidinyl-(CH$_2$)— is optionally substituted independently with one or more (C$_1$-C$_6$)alkyl.

In one embodiment $R^{1C}$ is pyrrolidinyl-(CH$_2$)—, wherein the pyrrolidinyl-(CH$_2$)— is substituted on the pyrrolidinyl with an —(C$_1$-C$_6$)alkyl substituted with one or more —NR$^{b3}$R$^{c3}$.

In one embodiment $R^{b3}$ and $R^{c3}$ are each hydrogen.

In one embodiment $R^{1C}$ is:

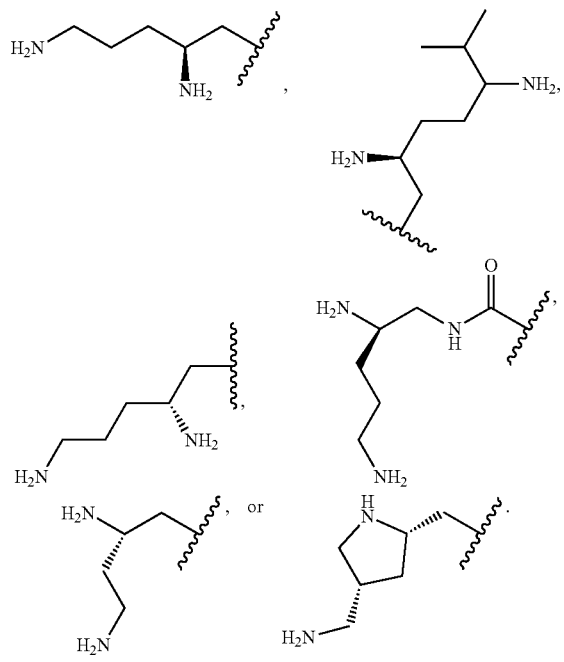

In one embodiment one of A' or B' is:

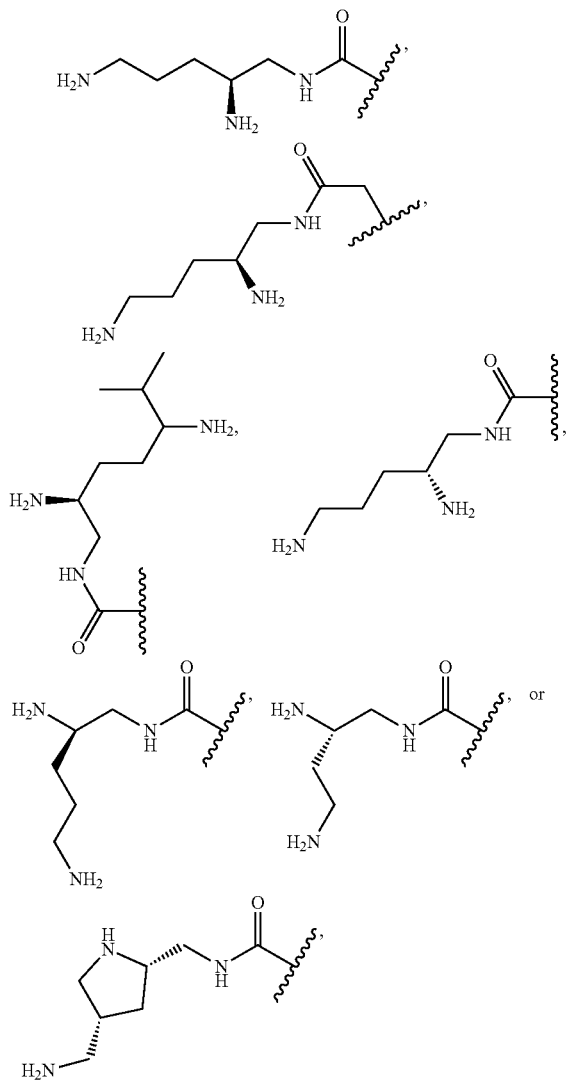

and the other of A' or B' is H.

In one embodiment, the bacterial efflux pump inhibitor is a compound of formula V:

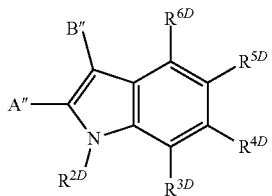

or a pharmaceutically acceptable salt thereof, wherein:
A" is —C(═O)N($R^{a1}$)—$R^{1D}$, —($C_1$-$C_3$)alkyl-C(═O)N($R^{a1}$)$R^{1D}$, —($C_1$-$C_3$)alkyl-O—$R^{1D}$, —O—$R^{1D}$, —($C_1$-$C_3$)alkyl-N($R^{a1}$)—$R^{1D}$, —N($R^{a1}$)—$R^{1D}$, or $R^{1D}$;
B" is ($C_2$-$C_8$)alkenyl, ($C_2$-$C_8$)alkynyl, ($C_1$-$C_4$)haloalkyl, ($C_1$-$C_4$)alkoxy, ($C_1$-$C_4$)haloalkoxy, ($C_3$-$C_7$)carbocyclyl, ($C_3$-$C_7$)carbocyclyl-($C_1$-$C_4$)alkyl-, aryl, aryl-($C_1$-$C_4$)alkyl-, heteroaryl, heteroaryl-($C_1$-$C_4$)alkyl-, 3-7 membered-monocyclic-heterocycle, or 3-7 membered-monocyclic-heterocycle-($C_1$-$C_4$)alkyl- wherein any ($C_3$-$C_7$)carbocyclyl, ($C_3$-$C_7$)carbocyclyl-($C_1$-$C_4$)alkyl-, aryl, aryl-($C_1$-$C_4$)alkyl-, heteroaryl, heteroaryl-($C_1$-$C_4$)alkyl-, 3-7 membered-monocyclic-heterocycle, or 3-7 membered-monocyclic-heterocycle-($C_1$-$C_4$)alkyl- of B" is optionally substituted with one or more $Z^1$ groups;
each $R^{1D}$ is independently:
(a) ($C_1$-$C_{14}$)alkyl substituted with one or more groups selected from the group consisting of —$NR^{b2}R^{c2}$, —$NHNH_2$, —C(═$NR^{a2}$)($NR^{b2}R^{c2}$), —$NR^{a2}$C(═$NR^{a2}$)($R^{d2}$), and —$NR^{a2}$C(═$NR^{a2}$)($NR^{b2}R^{c2}$) and wherein ($C_1$-$C_{14}$)alkyl is optionally substituted independently with one or more halo, ($C_1$-$C_4$)alkyl or ($C_3$-$C_7$)carbocyclyl; or
(b) ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, wherein each ($C_3$-$C_7$)carbocyclyl or ($C_3$-$C_7$)carbocyclyl-($C_1$-$C_4$)alkyl- is independently substituted with one or more $Z^2$ or $Z^3$, and wherein each 4-7 membered monocyclic heterocyclyl or 4-7 membered monocyclic heterocyclyl-($C_1$-$C_4$)alkyl- is independently optionally substituted with one or more $Z^2$ or $Z^3$, and wherein any ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl- of $R^1$ is optionally substituted independently with one or more halo, ($C_1$-$C_4$)alkyl or ($C_3$-$C_7$)carbocyclyl;
$R^{2D}$ is hydrogen, ($C_1$-$C_4$)alkyl or phenyl($C_1$-$C_3$)alkyl-, wherein the phenyl is optionally substituted with one or more ($C_1$-$C_4$)alkyl, —O($C_1$-$C_4$)alkyl, halogen, or —$NO_2$;
$R^{3D}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;
$R^{4D}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;
$R^{5D}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;
$R^{6D}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;
each $Z^1$ is independently halo, —OH, —$NO_2$, —CN, ($C_1$-$C_4$)alkyl, ($C_1$-$C_4$)haloalkyl, ($C_1$-$C_4$)alkoxy, or ($C_1$-$C_4$)haloalkoxy;
each $Z^2$ is independently selected from the group consisting of —$NR^{b3}R^{c3}$, —$NHNH_2$, —C(═$NR^{a3}$)($NR^{b3}R^{c3}$), —$NR^{a3}$C(═$NR^{a3}$)($R^{d3}$), and —$NR^{a3}$C(═$NR^{a3}$)($NR^{b3}R^{c3}$)
each $Z^3$ is independently —($C_1$-$C_6$)alkyl substituted with one or more $Z^2$ and optionally substituted with one or more $Z^4$;
each $Z^4$ is independently halo or ($C_3$-$C_7$)carbocyclyl;
each $R^{a1}$ is independently hydrogen, ($C_1$-$C_4$)alkyl or ($C_3$-$C_7$)carbocyclyl;

each $R^{a2}$ is independently hydrogen, $(C_1-C_4)$alkyl or $(C_3-C_7)$carbocyclyl;

each $R^{b2}$ and $R^{c2}$ is independently hydrogen, $(C_1-C_4)$alkyl or $(C_3-C_7)$carbocyclyl;

$R^{a2}$ is $(C_1-C_4)$alkyl or $(C_3-C_7)$carbocyclyl;

each $R^{a3}$ is independently hydrogen $(C_1-C_4)$alkyl or $(C_3-C_7)$carbocyclyl;

each $R^{b3}$ and $R^3$ is independently hydrogen $(C_1-C_4)$alkyl or $(C_3-C_7)$carbocyclyl; and $R^{a3}$ is $(C_1-C_4)$alkyl or $(C_3-C_7)$carbocyclyl.

It is understood that the embodiments provided below are for compounds of formula V and all sub-formulas thereof (e.g., formulas Va). It is to be understood the two or more embodiments may be combined.

In one embodiment A" is —C(=O)N($R^{a1}$)—$R^{1D}$.

In one embodiment $R^{a1}$ is hydrogen.

In one embodiment $R^{2D}$ is hydrogen or $(C_1-C_6)$alkyl.

In one embodiment $R^{2D}$ is hydrogen.

In one embodiment a compound of formula I is a compound of formula Va:

Va or a pharmaceutically acceptable salt thereof.

In one embodiment $R^{3D}$ is hydrogen, halo, $(C_1-C_4)$alkyl, $(C_1-C_4)$haloalkyl, $(C_1-C_4)$alkoxy, or $(C_1-C_4)$haloalkoxy.

In one embodiment $R^{3D}$ is hydrogen.

In one embodiment $R^{4D}$ is hydrogen, aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy.

In one embodiment $R^{4D}$ is phenyl wherein the phenyl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy.

In one embodiment $R^{4D}$ is phenyl wherein the phenyl is optionally substituted with one or more halo.

In one embodiment $R^{4D}$ is 4-fluorophenyl.

In one embodiment $R^{5D}$ is hydrogen, halo, $(C_1-C_4)$alkyl, $(C_1-C_4)$haloalkyl, $(C_1-C_4)$alkoxy, or $(C_1-C_4)$haloalkoxy.

In one embodiment $R^{5D}$ is hydrogen.

In one embodiment $R^{6D}$ is hydrogen, halo, $(C_1-C_4)$alkyl, $(C_1-C_4)$haloalkyl, $(C_1-C_4)$alkoxy, or $(C_1-C_4)$haloalkoxy.

In one embodiment $R^{6D}$ is hydrogen.

In one embodiment B" is $(C_3-C_7)$carbocyclyl, $(C_3-C_7)$carbocyclyl-$(C_1-C_4)$alkyl-, aryl, aryl-$(C_1-C_4)$alkyl-, heteroaryl, or heteroaryl-$(C_1-C_4)$alkyl-, wherein any $C_3-C_7$ carbocyclyl, $(C_3-C_7)$carbocyclyl-$(C_1-C_4)$alkyl-, aryl, aryl-$(C_1-C_4)$alkyl-, heteroaryl, or heteroaryl-$(C_1-C_4)$alkyl- of B" is optionally substituted with one or more $Z^1$ groups.

In one embodiment B" is $(C_3-C_7)$carbocyclyl, aryl, aryl-$(C_1-C_4)$alkyl-, or heteroaryl wherein any $(C_3-C_7)$carbocyclyl, aryl, aryl-$(C_1-C_4)$alkyl-, or heteroaryl, of B" is optionally substituted with one or more $Z^1$ groups.

In one embodiment B" is $(C_3-C_7)$carbocyclyl, phenyl, phenyl-$(C_1-C_4)$alkyl-, or 5-6 membered heteroaryl wherein any $(C_3-C_7)$carbocyclyl, phenyl, phenyl-$(C_1-C_4)$alkyl-, or 5-6 membered heteroaryl of B" is optionally substituted with one or more $Z^1$ groups.

In one embodiment B" is $(C_3-C_7)$carbocyclyl, phenyl, phenyl-$(C_1-C_4)$alkyl-, or 5-6 membered heteroaryl wherein any $(C_3-C_7)$carbocyclyl, phenyl, phenyl-$(C_1-C_4)$alkyl-, or 5-6 membered heteroaryl of B" is optionally substituted with one or more $Z^1$ groups.

In one embodiment B" is $(C_3-C_7)$carbocyclyl, phenyl, phenyl-$(C_1-C_4)$alkyl-, or 6 membered heteroaryl wherein any $(C_3-C_7)$carbocyclyl, phenyl, phenyl-$(C_1-C_4)$alkyl-, or 6 membered heteroaryl of B" is optionally substituted with one or more $Z^1$ groups.

In one embodiment B" is $(C_3-C_7)$carbocyclyl, phenyl, phenyl-$(CH_2)$—, or pyridinyl wherein any phenyl, phenyl-$(CH_2)$—, or pyridinyl of B" is optionally substituted with one or more $Z^1$ groups.

In one embodiment each $Z^1$ is independently halo, —OH, or $(C_1-C_4)$haloalkyl.

In one embodiment B" is 4-fluorophenyl, cyclopropyl, benzyl, pyrdin-4-yl, 4-hydroxyphenyl, or 4-trifluoromethylphenyl.

In one embodiment $R^{1D}$ is $(C_1-C_{14})$alkyl substituted with one or more groups independently selected from —$NR^{b2}R^{c2}$ and wherein the $(C_1-C_{14})$alkyl is optionally substituted with one or more $(C_3-C_7)$carbocyclyl.

In one embodiment $R^{1D}$ is $(C_2-C_{10})$alkyl substituted with one or more groups independently selected from —$NR^{b2}R^{c2}$ and wherein the $(C_2-C_{10})$alkyl is optionally substituted with one or more $(C_3-C_7)$carbocyclyl.

In one embodiment $R^{1D}$ is $(C_4-C_8)$alkyl substituted with two or more groups independently selected from —$NR^{b2}R^{c2}$.

In one embodiment $R^{b2}$ and $R^{c2}$ are each hydrogen.

In one embodiment $R^{1D}$ is a 4-7 membered monocyclic heterocyclyl-$(C_1-C_4)$alkyl-, wherein the 4-7 membered monocyclic heterocyclyl-$(C_1-C_4)$alkyl- is substituted with one or more groups independently selected from the group consisting of Z and —$(C_1-C_6)$alkyl substituted with one or more Z, wherein each Z is independently selected from the group consisting of —$NR^{b3}R^{c3}$, —$NHNH_2$, —$C(=NR^{a3})(NR^{b3}R^{c3})$, —$NR^{a3}C(=NR^{a3})(R^{a3})$, and —$NR^{a3}C(=NR^{a3})(NR^{b3}R^{c3})$ and wherein the 4-7 membered monocyclic heterocyclyl-$(C_1-C_4)$alkyl- is optionally substituted with one or more $(C_1-C_6)$alkyl.

In one embodiment $R^{1D}$ is a 4-7 membered monocyclic heterocyclyl-$(C_1-C_4)$alkyl-, wherein the 4-7 membered monocyclic heterocyclyl-$(C_1-C_4)$alkyl- is substituted with one or more groups independently selected from the group consisting of Z and $(C_1-C_6)$alkyl substituted with one or more Z, wherein each Z is independently —$NR^{b3}R^{c3}$ and wherein the 4-7 membered monocyclic heterocyclyl-$(C_1-C_4)$alkyl- is optionally substituted with one or more $(C_1-C_6)$alkyl.

In one embodiment $R^{1D}$ is pyrrolidinyl-$(C_1-C_4)$alkyl-, wherein the pyrrolidinyl-$(C_1-C_4)$alkyl- is substituted with one or more groups independently selected from the group consisting of Z and —$(C_1-C_6)$alkyl substituted with one or more Z, wherein each Z is independently —$NR^{b3}R^{c3}$ and wherein is pyrrolidinyl-$(C_1-C_4)$alkyl- is optionally substituted independently with one or more $(C_1-C_6)$alkyl In one embodiment $R^{1D}$ is pyrrolidinyl-$(CH_2)$—, wherein the pyrrolidinyl-$(CH_2)$— is substituted with one or more groups independently selected from the group consisting of Z and —$(C_1-C_6)$alkyl substituted with one or more Z, wherein each Z is independently —$NR^{b3}R^{c3}$ and wherein the pyrrolidinyl-(CH$_2$)— is optionally substituted independently with one or more (C$_1$-C$_6$)alkyl.

In one embodiment R$^{1D}$ is pyrrolidinyl-(CH$_2$)—, wherein the pyrrolidinyl-(CH$_2$)— is substituted on the pyrrolidinyl with —(C$_1$-C$_6$)alkyl substituted with one or more —NR$^{b3}$R$^{c3}$.

In one embodiment R$^{b3}$ and R$^3$ are each hydrogen.

In one embodiment R$^{1D}$ is:

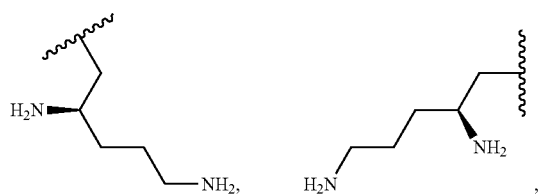

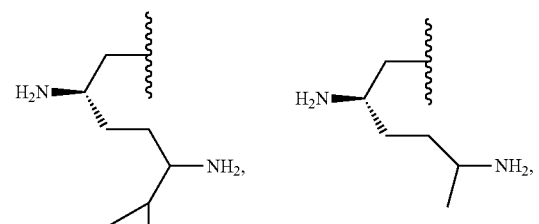

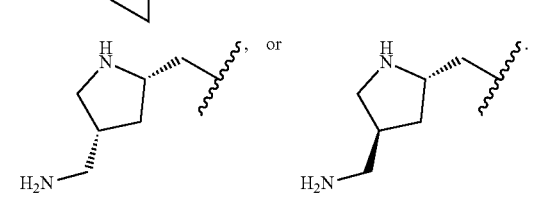

, or 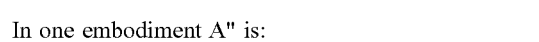.

In one embodiment A″ is:

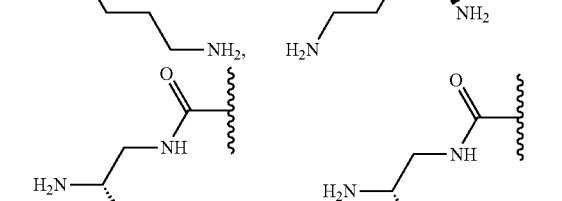

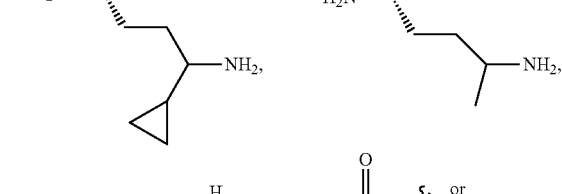, or

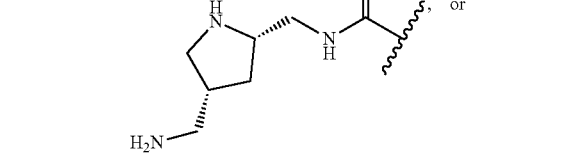

In one embodiment, the bacterial efflux pump inhibitor is selected from the group consisting of:

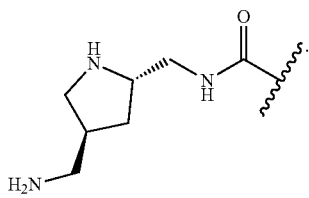,

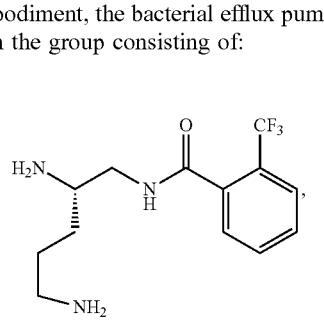,

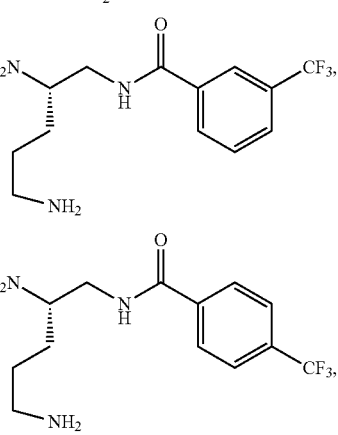,

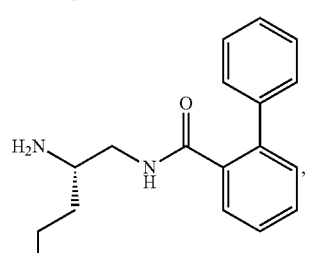,

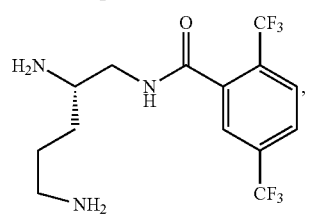,

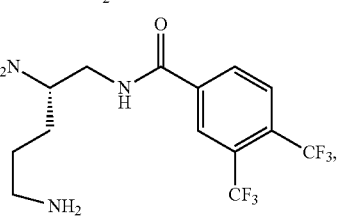,

-continued
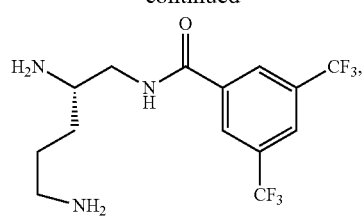
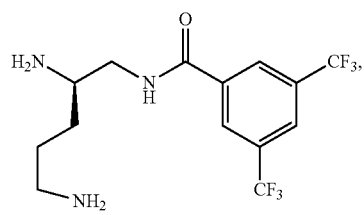
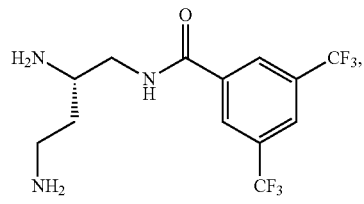
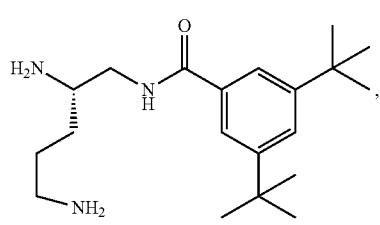
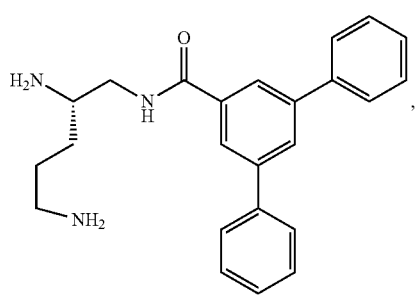
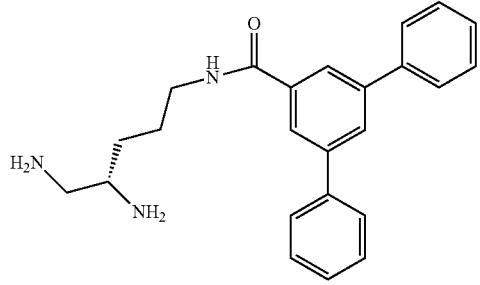
-continued
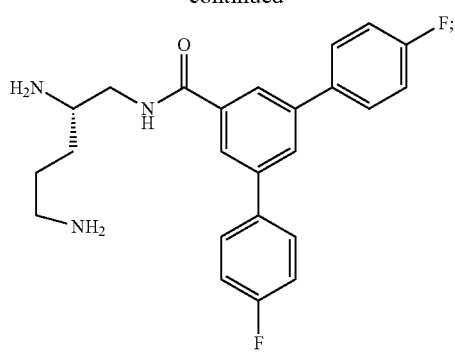
or a pharmaceutically acceptable salt thereof.
In one embodiment, the bacterial efflux pump inhibitor is selected from the group consisting of:
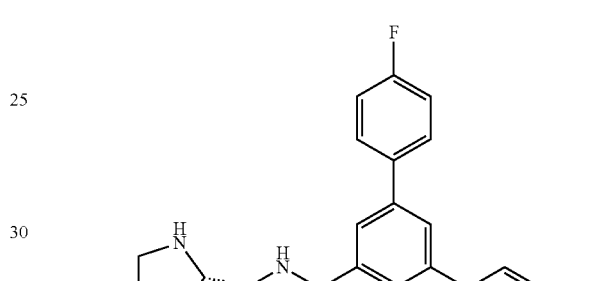
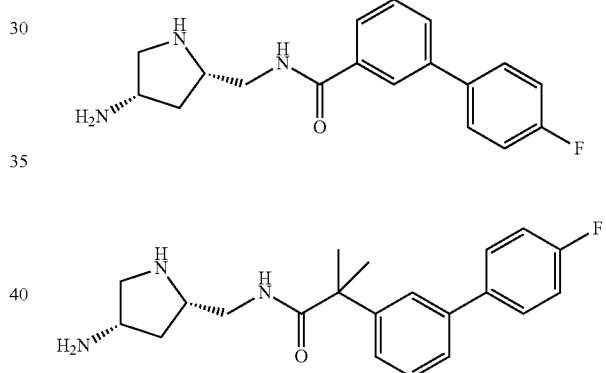
and
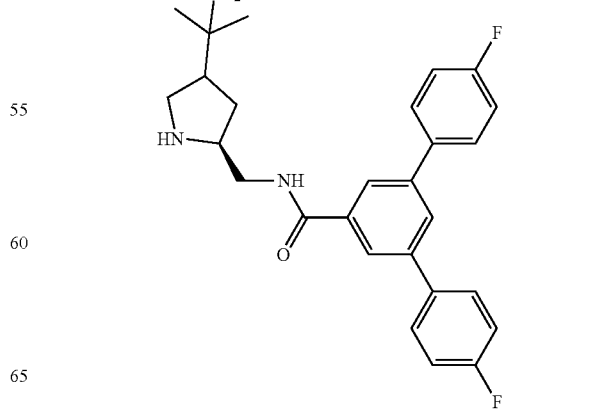

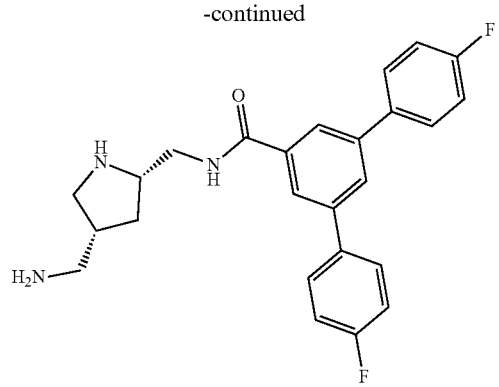
or a pharmaceutically acceptable salt thereof.
In one embodiment, the bacterial efflux pump inhibitor is selected from the group consisting of:
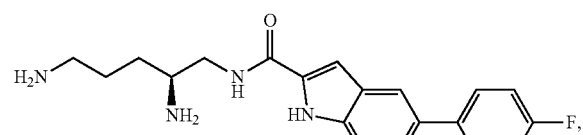
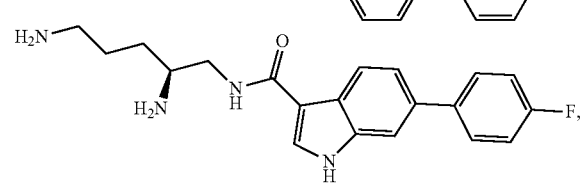
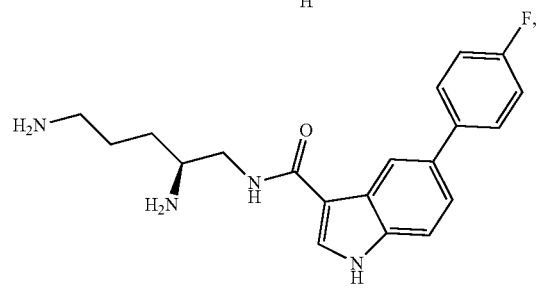
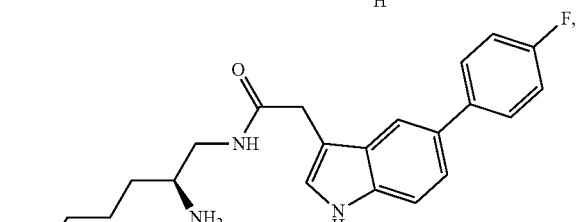
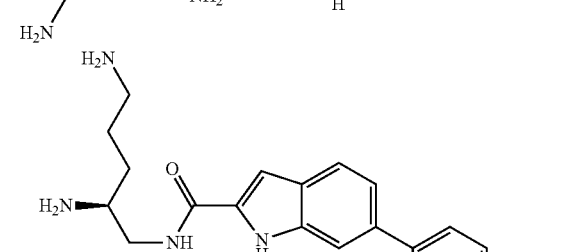
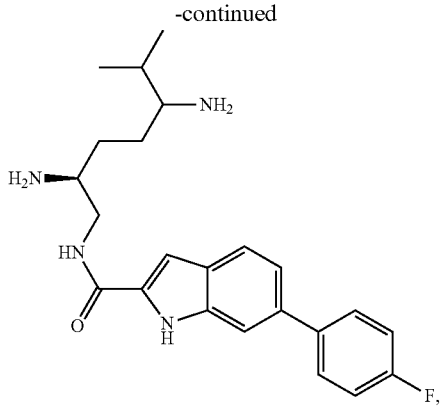
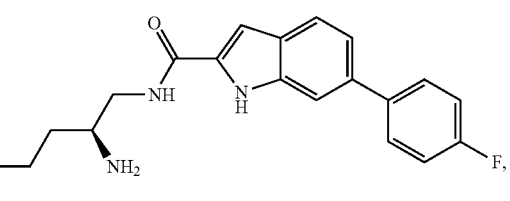
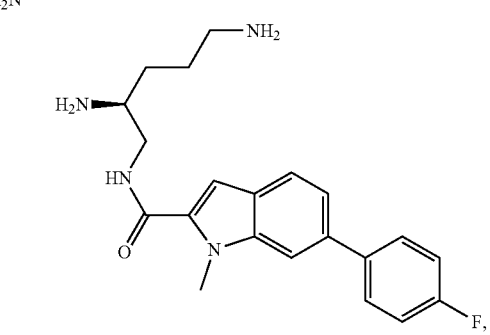
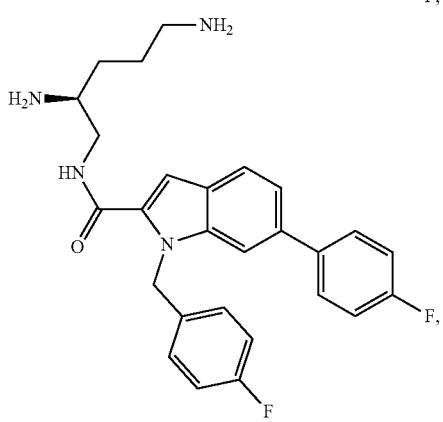
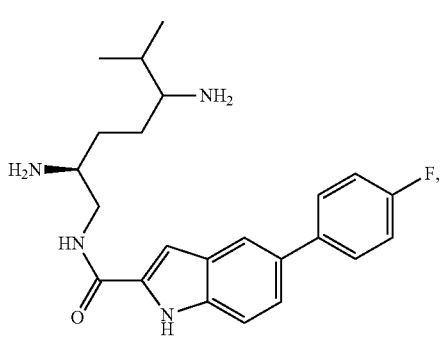

33
-continued
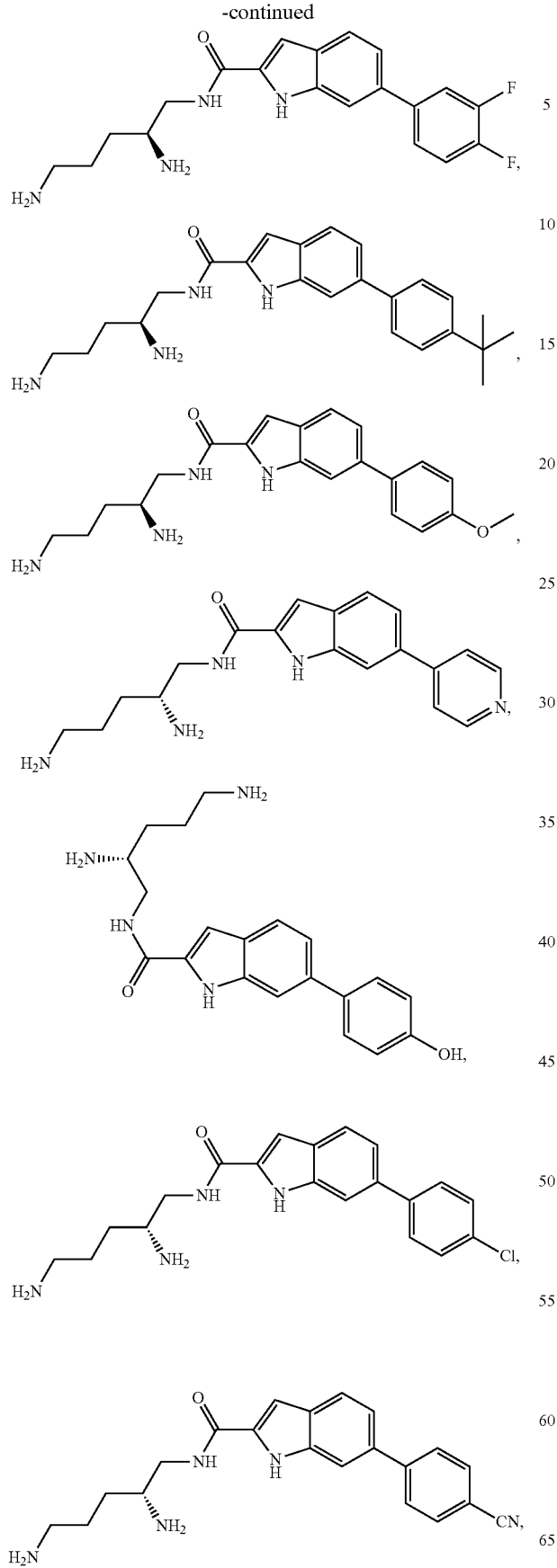
34
-continued
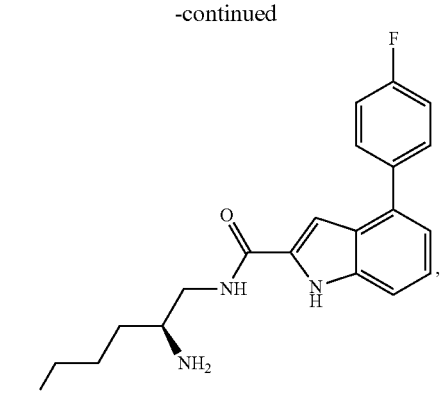
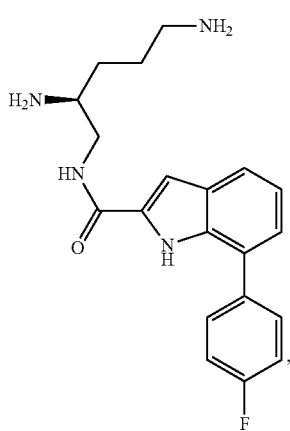
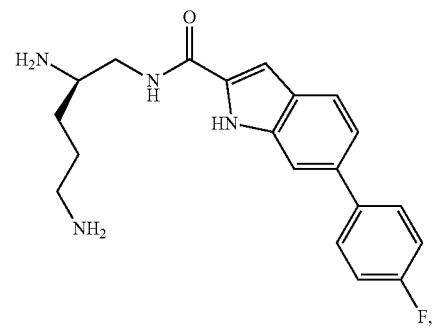
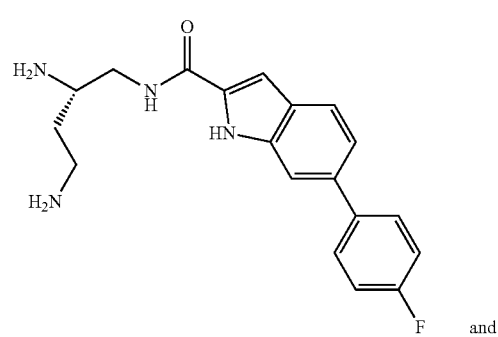
and -continued
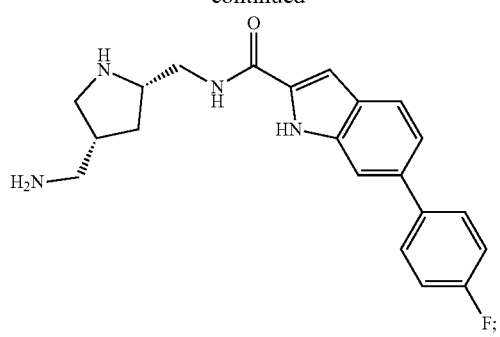
or a pharmaceutically acceptable salt thereof.
In one embodiment, the bacterial efflux pump inhibitor is selected from the group consisting of:
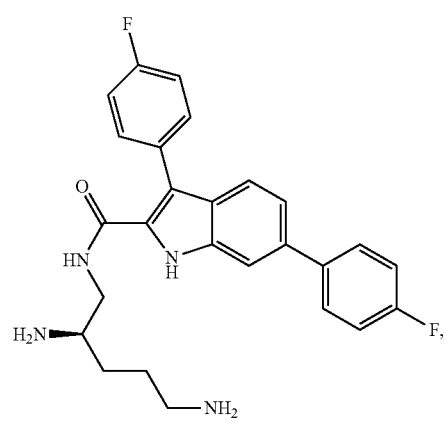
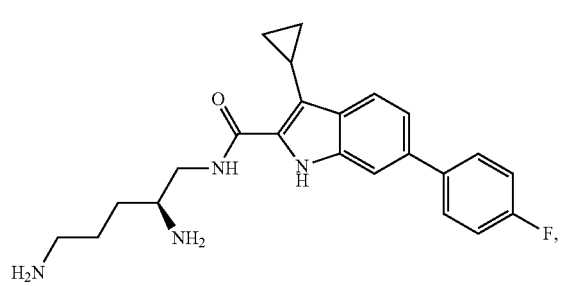
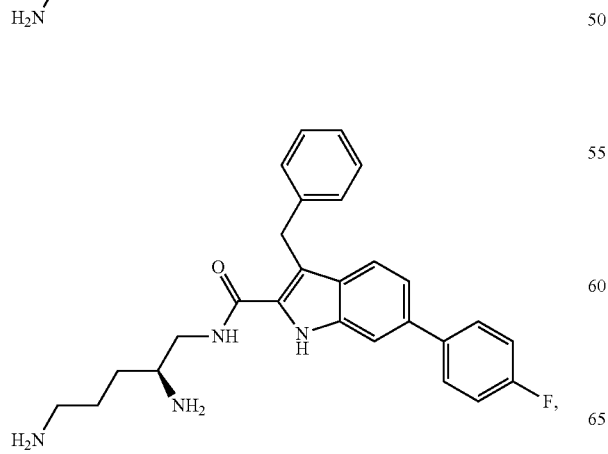
-continued
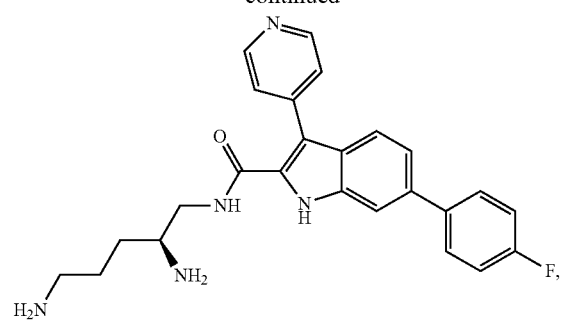
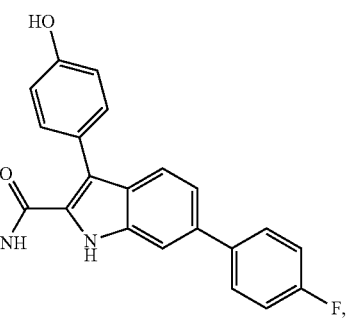
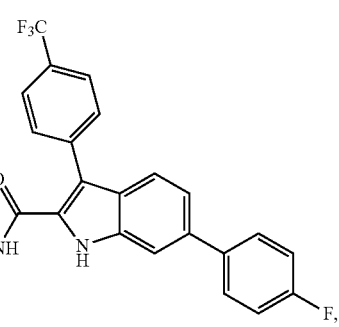
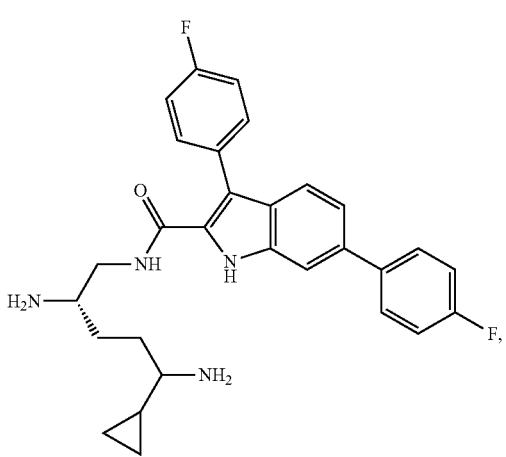

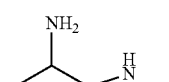

or a pharmaceutically acceptable salt thereof.

In one embodiment, the bacterial efflux pump inhibitor is

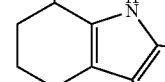

or a pharmaceutically acceptable salt thereof.

It is to be understood that the embodiments provided below are for compounds of formula I and all sub-formulas thereof (e.g., formula Ia). It is to be understood the two or more embodiments may be combined.

In one embodiment, $R^1$ is hydrogen, halo, cyano, nitro, $(C_1-C_6)$alkyl, phenyl or heteroaryl, wherein the $(C_1-C_6)$ alkyl, phenyl or heteroaryl is optionally substituted with one or more groups selected from halo, hydroxy, $(C_1-C_4)$alkyl, $(C_1-C_4)$haloalkyl, $(C_1-C_4)$alkoxy, nitro or cyano;

$R^2$ is hydrogen, halo, cyano, nitro, $(C_1-C_6)$alkyl, phenyl or heteroaryl, wherein the $(C_1-C_6)$alkyl, phenyl or heteroaryl is optionally substituted with one or more groups selected from halo, hydroxy, $(C_1-C_4)$alkyl, $(C_1-C_4)$haloalkyl, $(C_1-C_4)$ alkoxy, nitro or cyano;

$R^3$ is hydrogen, halo, cyano, nitro, $(C_1-C_6)$alkyl, phenyl or heteroaryl, wherein the $(C_1-C_6)$alkyl, phenyl or heteroaryl is optionally substituted with one or more groups selected from halo, hydroxy, $(C_1-C_4)$alkyl, $(C_1-C_4)$haloalkyl, $(C_1-C_4)$ alkoxy, nitro or cyano;

$R^4$ is hydrogen, halo, cyano, nitro, $(C_1-C_6)$alkyl, phenyl or heteroaryl, wherein the $(C_1-C_6)$alkyl, phenyl or heteroaryl is optionally substituted with one or more groups selected from halo, hydroxy, $(C_1-C_4)$alkyl, $(C_1-C_4)$haloalkyl, $(C_1-C_4)$ alkoxy, nitro or cyano;

$R^5$ is hydrogen or $(C_1-C_4)$alkyl;

$R^6$ is hydrogen, $(C_1-C_6)$alkyl, or $(C_3-C_6)$cycloalkyl, wherein the $(C_1-C_6)$alkyl or $(C_3-C_6)$cycloalkyl is optionally substituted with one or more groups selected from halo, $-OR^a$ or $-NR^aR^b$;

each $R^a$ is independently hydrogen or $(C_1-C_4)$alkyl; and each $R^b$ is independently hydrogen or $(C_1-C_4)$alkyl; or $R^a$ and $R^b$ taken together with the nitrogen to which they are attached form pyrrolidinyl, piperidinyl, piperazinyl or morpholinyl.

In one embodiment, at least one of $R^1$, $R^2$, $R^3$, and $R^4$ is not hydrogen.

In one embodiment, at least one of $R^1$, $R^2$, $R^3$, and $R^4$ is halo or phenyl which is optionally substituted with one or more groups selected from halo, hydroxy, $(C_1-C_4)$ alkyl, $(C_1-C_4)$ haloalkyl, $(C_1-C_4)$ alkoxy, nitro or cyano.

In one embodiment, at least one of $R^1$, $R^2$, $R^3$, and $R^4$ is halo.

In one embodiment, $R^3$ is Br; and $R^1$, $R^2$, and $R^4$ are hydrogen.

In one embodiment, at least one of $R^1$, $R^2$, $R^3$, and $R^4$ is phenyl which is optionally substituted with one or more groups selected from halo, $(C_1-C_4)$ haloalkyl, or $(C_1-C_4)$ alkoxy.

In one embodiment, $R^3$ is 4-fluorophenyl, 4-methoxyphenyl, or 4-trifluoromethylphenyl; and $R^1$, $R^2$, and $R^4$ are hydrogen.

In one embodiment, $R^5$ is hydrogen.

In one embodiment, $R^6$ is hydrogen or $(C_1-C_6)$ alkyl.

In one embodiment, $R^6$ is hydrogen or methyl.

In one embodiment, the compound of formula I is:

-continued
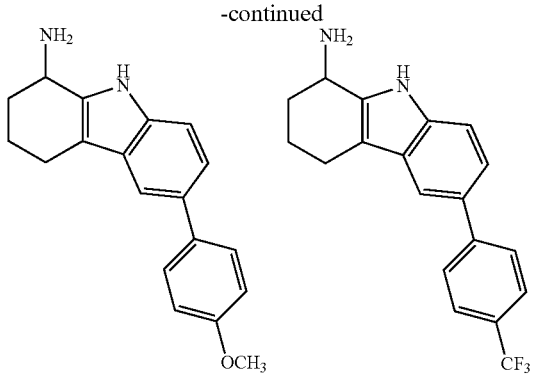
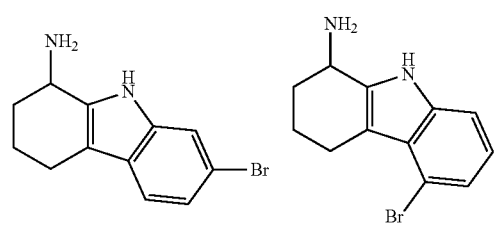
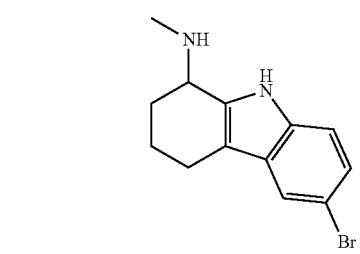
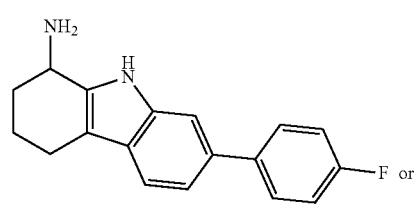
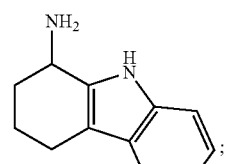
or a salt thereof.
In one embodiment, compound of claim 1 is:
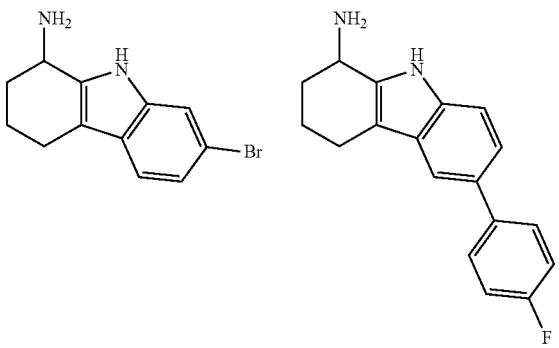
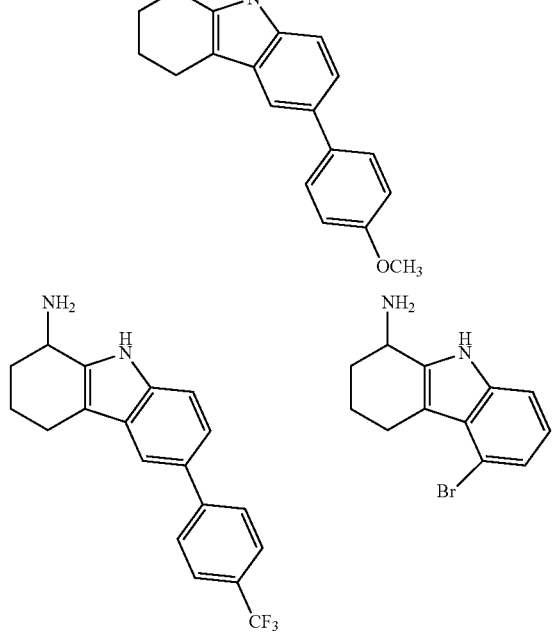
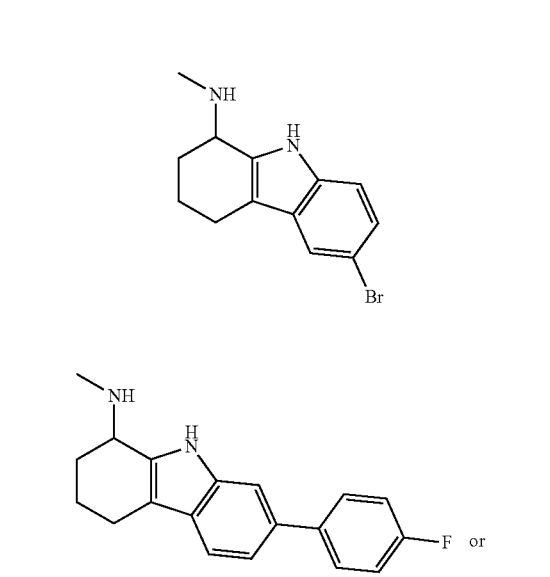

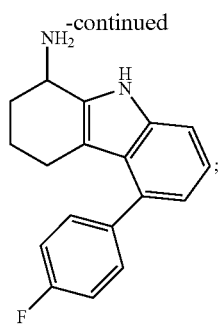
or a salt thereof.
In one embodiment, the compound of formula I is:
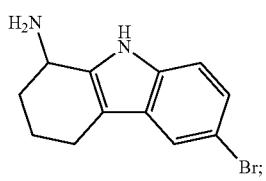
or a salt thereof.
In one embodiment, the compound of formula I is not
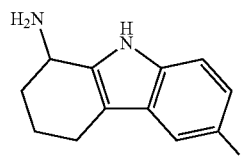 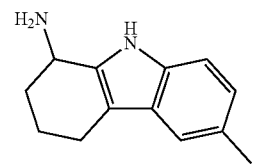
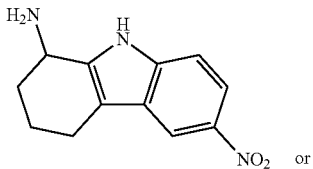 or
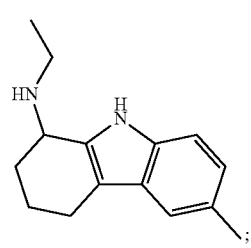
or a salt thereof.
In one embodiment, the compound of formula I is not:
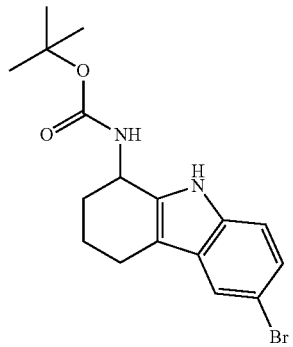
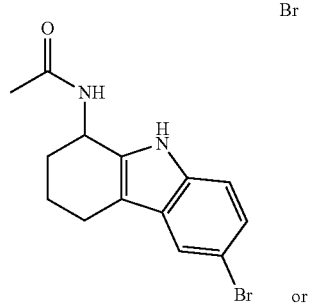
or
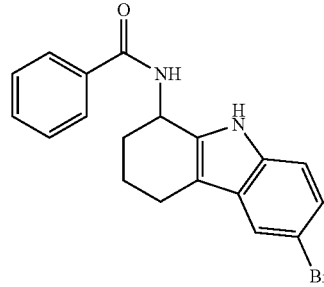
or a salt thereof.
In one embodiment, the compound of formula I is not:
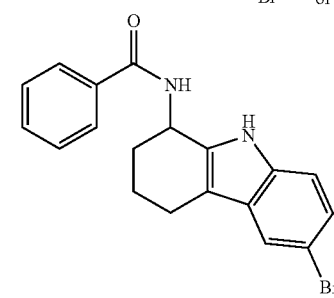
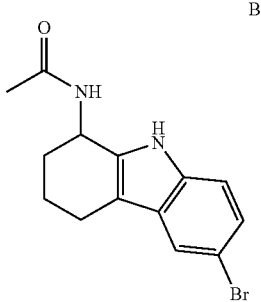

-continued

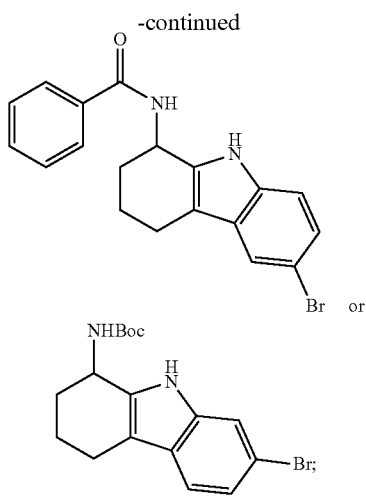

or a salt thereof.

In one embodiment, the compound of formula I is:

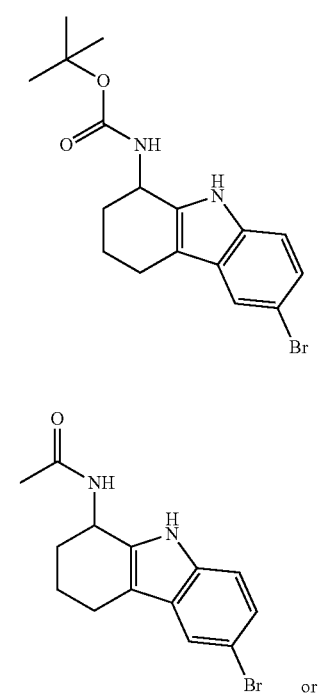

or a salt thereof.

In one embodiment, the compound of formula I is:

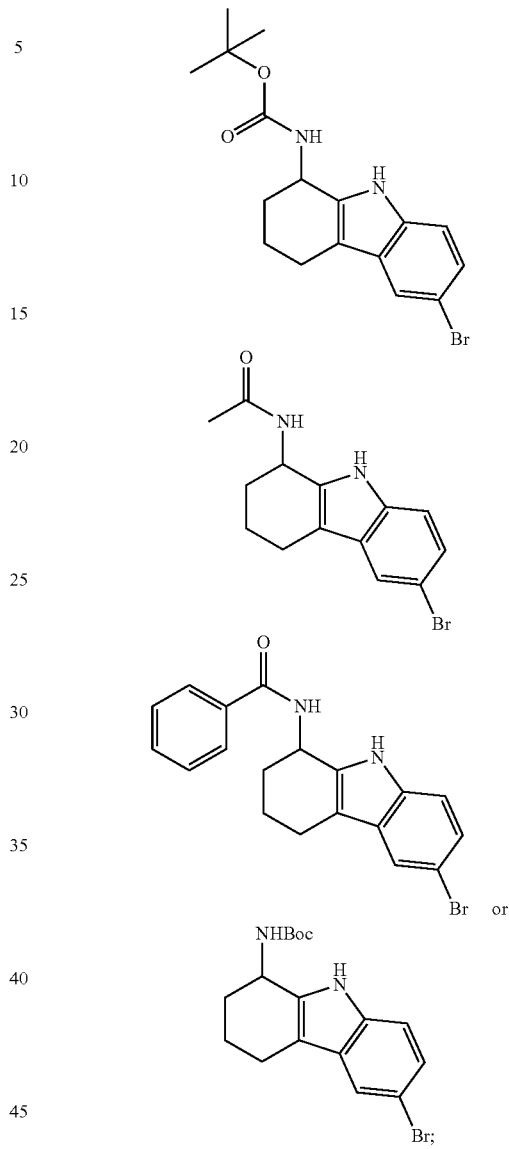

or a salt thereof.

In one embodiment, $R^1$ is hydrogen.

In one embodiment, $R^2$ is hydrogen, halo or phenyl, wherein the phenyl is optionally substituted with one or more groups selected from halo, hydroxy, $(C_1-C_4)$alkyl, $(C_1-C_4)$haloalkyl, $(C_1-C_4)$alkoxy, nitro or cyano.

In one embodiment, $R^2$ is hydrogen, bromo, chloro or phenyl, wherein the phenyl is optionally substituted with one or more groups selected from halo.

In one embodiment, $R^2$ is hydrogen, bromo, chloro or 4-fluorophenyl.

In one embodiment, $R^2$ is hydrogen.

In one embodiment, $R^3$ is hydrogen, halo, cyano, $(C_1-C_6)$alkyl, $(C_1-C_4)$alkoxy, or phenyl, wherein the $(C_1-C_6)$alkyl, $(C_1-C_4)$alkoxy, or phenyl is optionally substituted with one or more groups selected from halo, hydroxy, $(C_1-C_4)$alkyl, $(C_1-C_4)$haloalkyl, $(C_1-C_4)$alkoxy, nitro or cyano.

In one embodiment, $R^3$ is hydrogen, halo, cyano, nitro, $(C_1-C_6)$alkyl, $(C_1-C_4)$alkoxy, or phenyl, wherein the $(C_1-C_6)$alkyl, $(C_1-C_4)$alkoxy, or phenyl is optionally substituted with one or more groups selected from halo, $(C_1-C_4)$haloalkyl, or $(C_1-C_4)$alkoxy.

In one embodiment, $R^3$ is hydrogen, fluoro, bromo, chloro, —$CF_3$, —$OCF_3$, CN, —$OCH_3$, or phenyl, wherein the phenyl is optionally substituted with one or more groups selected from fluoro, —$OCH_3$, or —$CF_3$.

In one embodiment, $R^3$ is hydrogen, fluoro, bromo, chloro, —$CF_3$, —$OCF_3$, CN, —$OCH_3$, 4-fluorophenyl, 4-methoxyphenyl, or 4-trifluoromethylphenyl.

In one embodiment, $R^3$ is halo, cyano, ($C_1$-$C_6$)alkyl, ($C_1$-$C_4$)alkoxy, or phenyl, wherein the ($C_1$-$C_6$)alkyl, ($C_1$-$C_4$)alkoxy, or phenyl is optionally substituted with one or more groups selected from halo, hydroxy, ($C_1$-$C_4$)alkyl, ($C_1$-$C_4$)haloalkyl, ($C_1$-$C_4$)alkoxy, nitro or cyano.

In one embodiment, $R^3$ is halo, cyano, nitro, ($C_1$-$C_6$)alkyl, ($C_1$-$C_4$)alkoxy, or phenyl, wherein the ($C_1$-$C_6$)alkyl, ($C_1$-$C_4$)alkoxy, or phenyl is optionally substituted with one or more groups selected from halo, ($C_1$-$C_4$)haloalkyl, or ($C_1$-$C_4$)alkoxy.

In one embodiment, $R^3$ fluoro, bromo, chloro, —$CF_3$, —$OCF_3$, CN, —$OCH_3$, or phenyl, wherein the phenyl is optionally substituted with one or more groups selected from fluoro, —$OCH_3$, or —$CF_3$.

In one embodiment, $R^3$ is fluoro, bromo, chloro, —$CF_3$, —$OCF_3$, CN, —$OCH_3$, 4-fluorophenyl, 4-methoxyphenyl, or 4-trifluoromethylphenyl.

In one embodiment, $R^3$ is hydrogen.

In one embodiment, $R^4$ is hydrogen or halo.

In one embodiment, $R^4$ is hydrogen, bromo, or chloro.

In one embodiment, $R^4$ is hydrogen.

In one embodiment, at least one of $R^1$, $R^2$, $R^3$, and $R^4$ is halo, cyano, nitro, ($C_1$-$C_6$)alkyl, ($C_1$-$C_4$)alkoxy, or phenyl, wherein the ($C_1$-$C_6$)alkyl, ($C_1$-$C_4$)alkoxy, or phenyl is optionally substituted with one or more groups selected from halo, hydroxy, ($C_1$-$C_4$)alkyl, ($C_1$-$C_4$)haloalkyl, ($C_1$-$C_4$)alkoxy, nitro or cyano.

In one embodiment, at least one of $R^1$, $R^2$, $R^3$, and $R^4$ is halo, cyano, nitro, ($C_1$-$C_6$)alkyl, ($C_1$-$C_4$)alkoxy, or phenyl, wherein the ($C_1$-$C_6$)alkyl, ($C_1$-$C_4$)alkoxy, or phenyl is optionally substituted with one or more groups selected from halo, ($C_1$-$C_4$)haloalkyl, or ($C_1$-$C_4$)alkoxy.

In one embodiment, at least one of $R^1$, $R^2$, $R^3$, and $R^4$ is fluoro, bromo, chloro, —$CF_3$, —$OCF_3$, CN, —$OCH_3$, or phenyl, wherein the phenyl is optionally substituted with one or more groups selected from fluoro, —$OCH_3$, of —$CF_3$.

In one embodiment, at least one of $R^1$, $R^2$, $R^3$, and $R^4$ is fluoro, bromo, chloro, —$CF_3$, —$OCF_3$, CN, —$OCH_3$, 4-fluorophenyl, 4-methoxyphenyl, or 4-trifluoromethylphenyl.

In one embodiment, $R^6$ is hydrogen or ($C_1$-$C_6$) alkyl.

In one embodiment, $R^6$ is hydrogen, or ($C_1$-$C_6$)alkyl, wherein the ($C_1$-$C_6$)alkyl is optionally substituted with one or more groups selected from halo, —$OR^a$ or —$NR^aR^b$.

In one embodiment, $R^6$ is hydrogen, or ($C_1$-$C_6$)alkyl, wherein the ($C_1$-$C_6$)alkyl is optionally substituted with one or more —$NR^aR^b$.

In one embodiment, each $R^a$ is hydrogen or ($C_1$-$C_4$)alkyl.

In one embodiment, each $R^a$ is hydrogen.

In one embodiment, $R^6$ is hydrogen, methyl, —$(CH_2)_2$$NH_2$, or —$(CH_2)_3NH_2$.

In one embodiment, $R^{7a}$ is hydrogen, ($C_1$-$C_6$)alkyl, or halo.

In one embodiment, $R^{7a}$ is hydrogen, methyl, or fluoro.

In one embodiment, $R^{7b}$ is hydrogen.

In one embodiment, $R^{8a}$ is hydrogen, ($C_1$-$C_6$)alkyl, —C(=O)$OR^c$, —C(=O)$NR^dR^e$, or phenyl, wherein the ($C_1$-$C_6$)alkyl or phenyl is optionally substituted with one or more halogen, —$OR^h$, ($C_1$-$C_6$)alkyl, or —$NR^fR^g$.

In one embodiment, $R^{8a}$ is hydrogen, ($C_1$-$C_6$)alkyl, —C(=O)$OR^c$, —C(=O)$NR^dR^e$, or phenyl, wherein the ($C_1$-$C_6$)alkyl is optionally substituted with one or more —$NR^fR^g$.

In one embodiment, $R^c$ is hydrogen or ethyl.

In one embodiment, $R^d$ is hydrogen or methyl; and $R^e$ is hydrogen or ($C_1$-$C_4$)alkyl wherein the ($C_1$-$C_4$)alkyl is optionally substituted with one or more —$NH_2$, —NH($C_1$-$C_4$) alkyl or —N(($C_1$-$C_4$)alkyl)$_2$.

In one embodiment, $R^f$ is hydrogen and $R^g$ is methyl; or $R^f$ and $R^g$ taken together with the nitrogen to which they are attached form morpholinyl.

In one embodiment, $R^{8a}$ is hydrogen, methyl, isopropyl, t-butyl, —C(=O)$OCH_2CH_3$, —C(=O)OH, —$CH_2OH$, —$CH_2NHCH_3$, —C(=O)$NH_2$, —C(=O)$N(CH_3)_2$, or 4-morpholinomethyl, ($C_1$—$C_6$)alkyl, —C(=O)$OR^c$, —C(=O)$NR^dR^e$, or phenyl, wherein the ($C_1$-$C_6$)alkyl or phenyl is optionally substituted with one or more halogen, —$OR^h$, ($C_1$-$C_6$)alkyl, or —$NR^fR^g$.

In one embodiment, $R^{8b}$ is hydrogen or ($C_1$-$C_6$)alkyl.

In one embodiment, $R^{8b}$ is hydrogen or methyl.

In one embodiment, $R^{8b}$ is hydrogen.

In one embodiment, $R^{9a}$ is hydrogen or ($C_1$-$C_6$)alkyl.

In one embodiment, $R^{9a}$ is methyl or isopropyl.

In one embodiment, $R^{9b}$ is hydrogen.

In one embodiment, $R^{9b}$ is hydrogen or ($C_1$-$C_6$)alkyl.

In one embodiment, $R^{9b}$ is hydrogen or methyl.

In one embodiment, compound of claim I is:

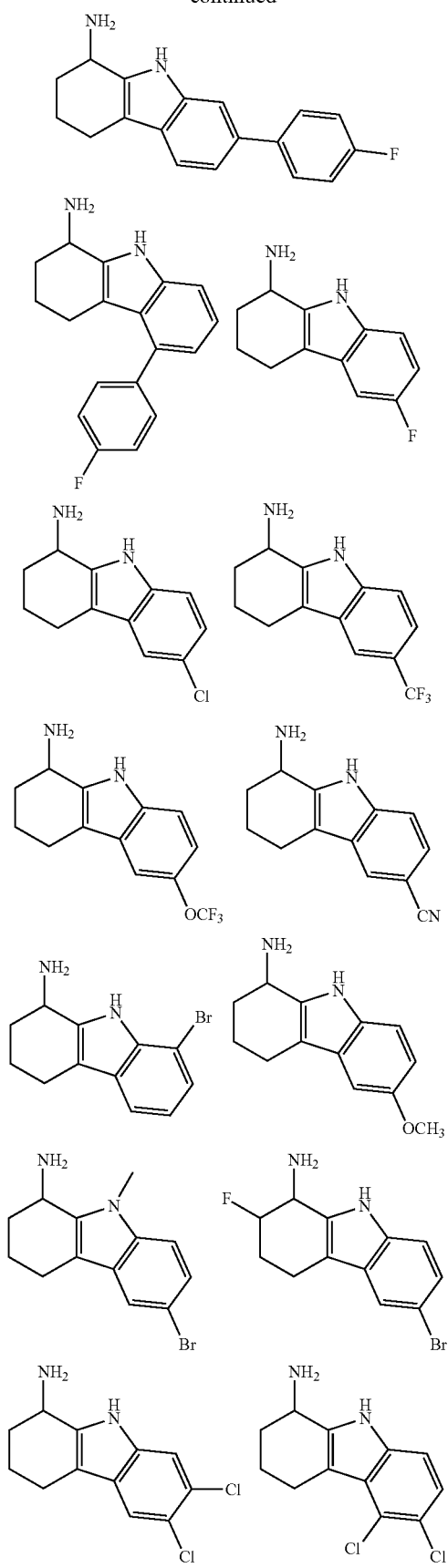
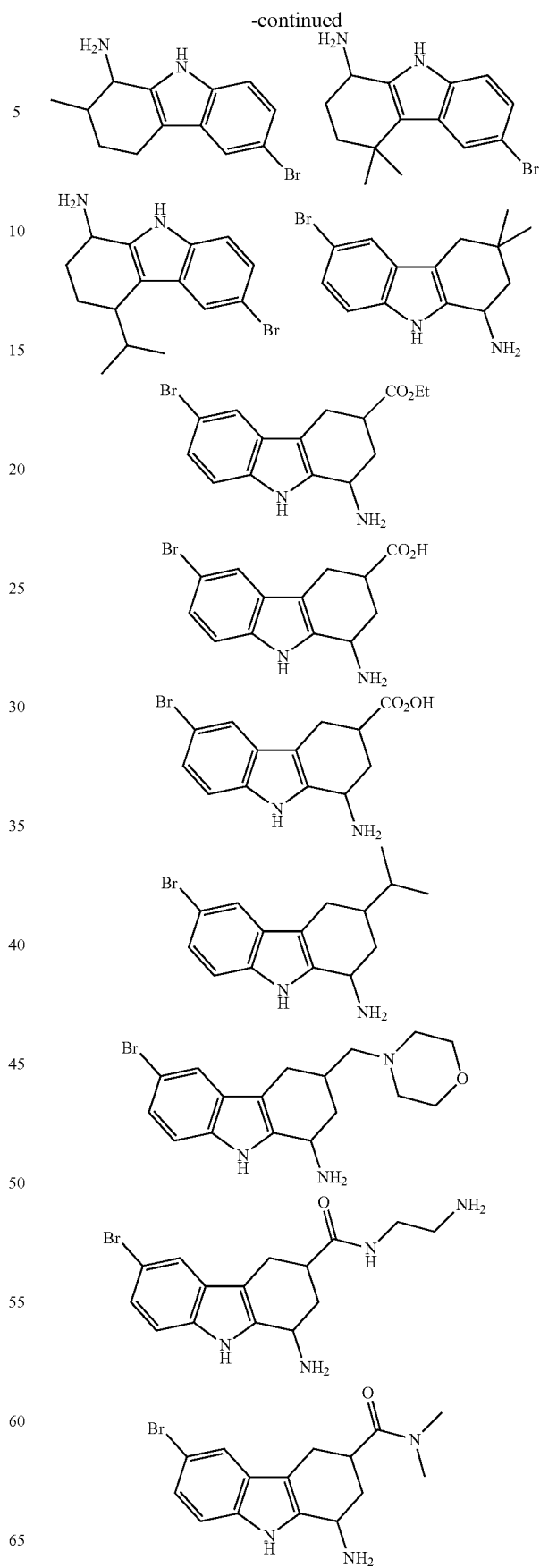

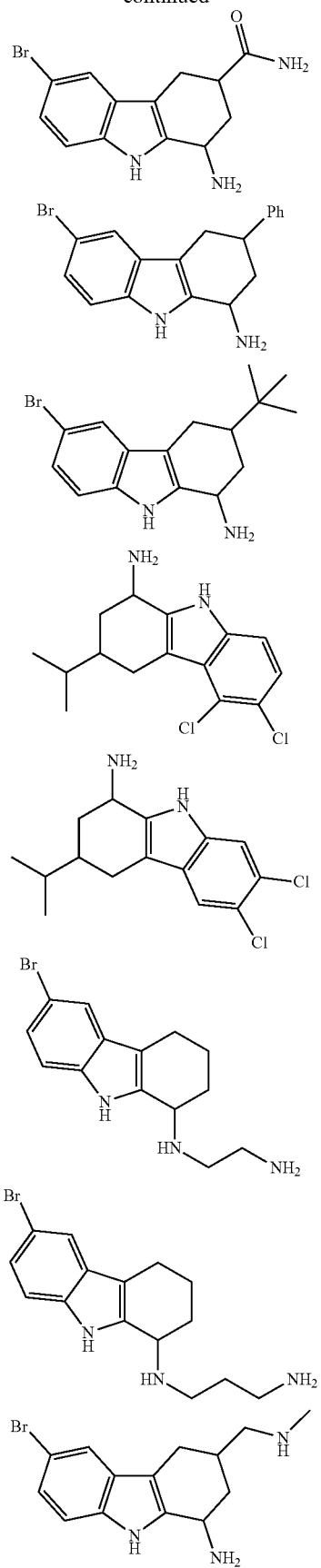
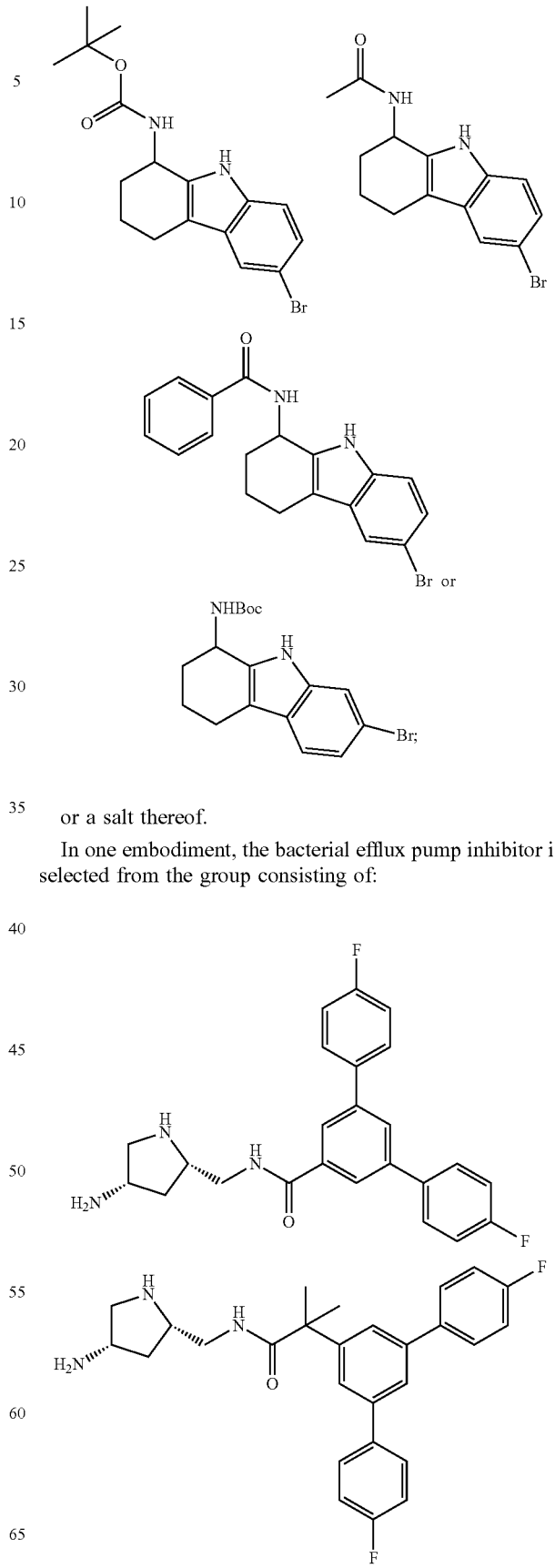
or a salt thereof.
In one embodiment, the bacterial efflux pump inhibitor is selected from the group consisting of:

51
-continued
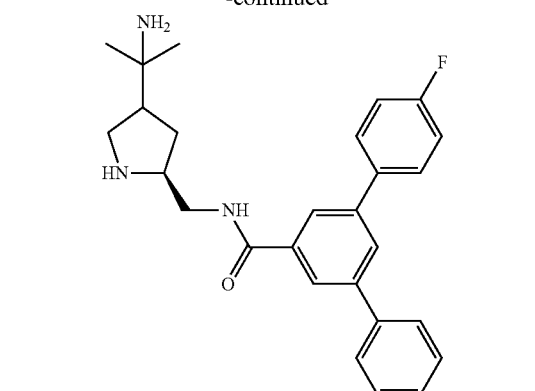
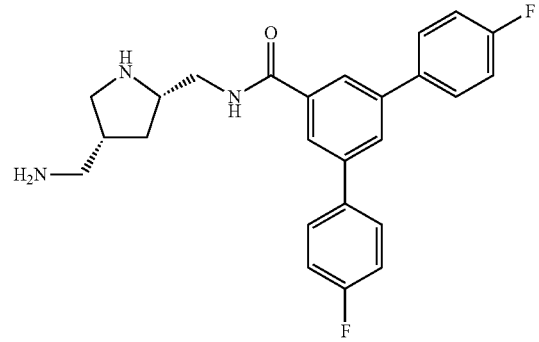
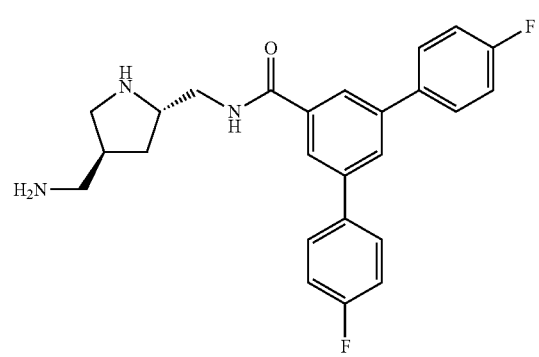
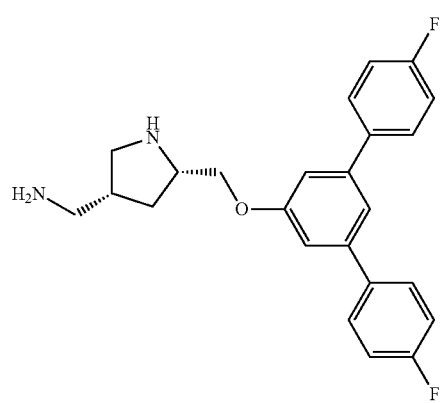
52
-continued
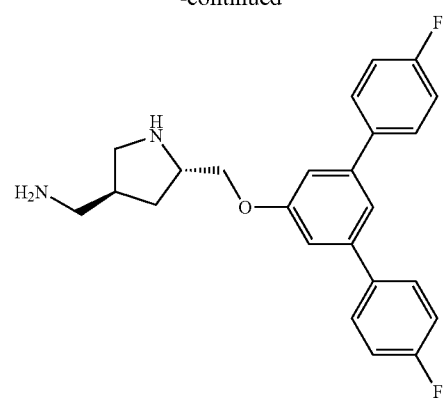
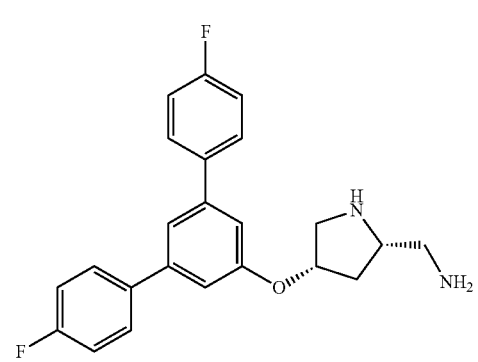
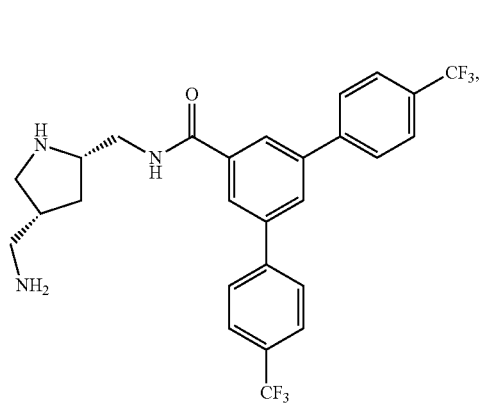
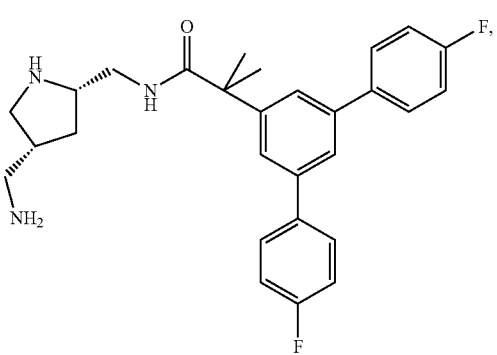

53
-continued
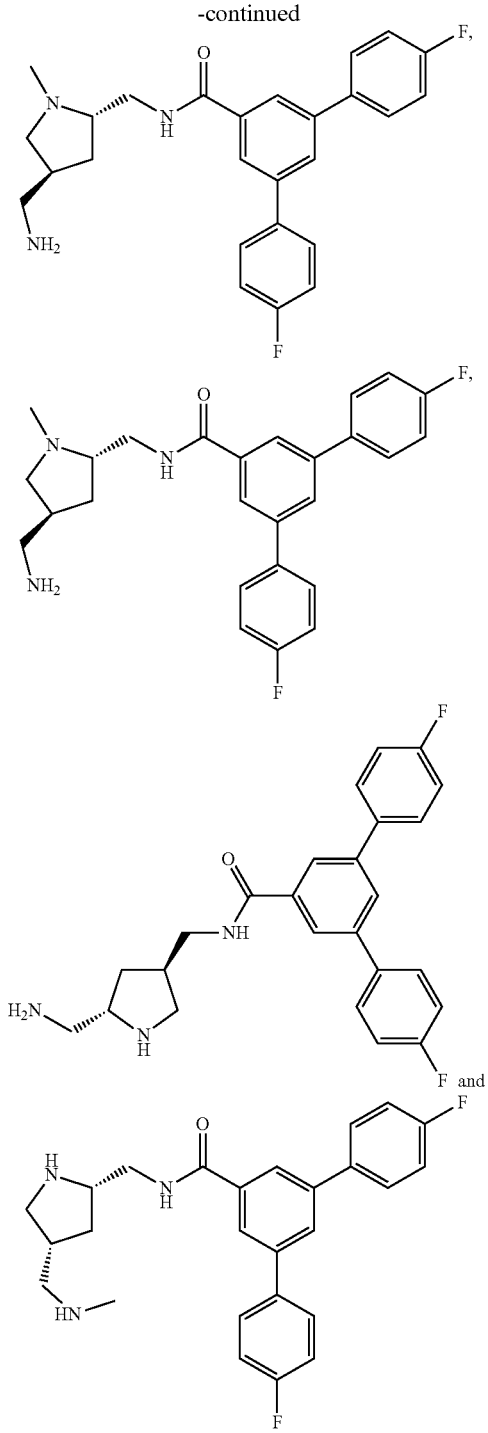
or a pharmaceutically acceptable salt thereof.
In one embodiment, the bacterial efflux pump inhibitor is selected from the group consisting of:
54
-continued
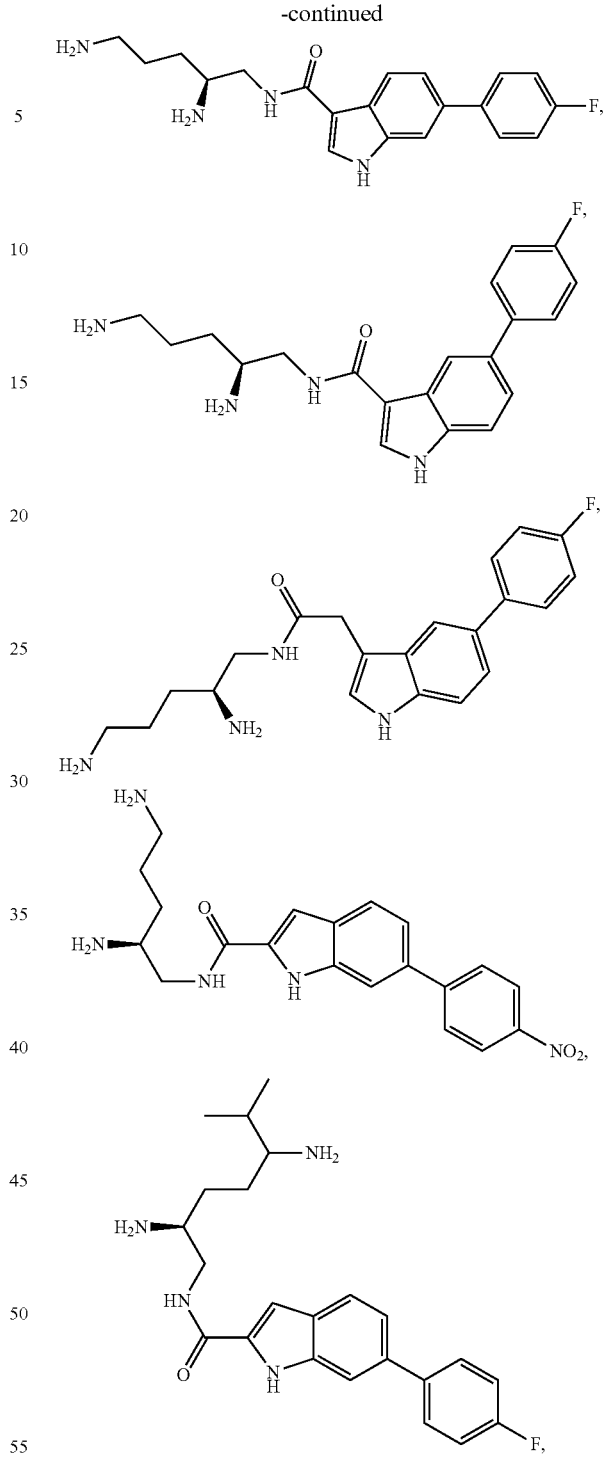

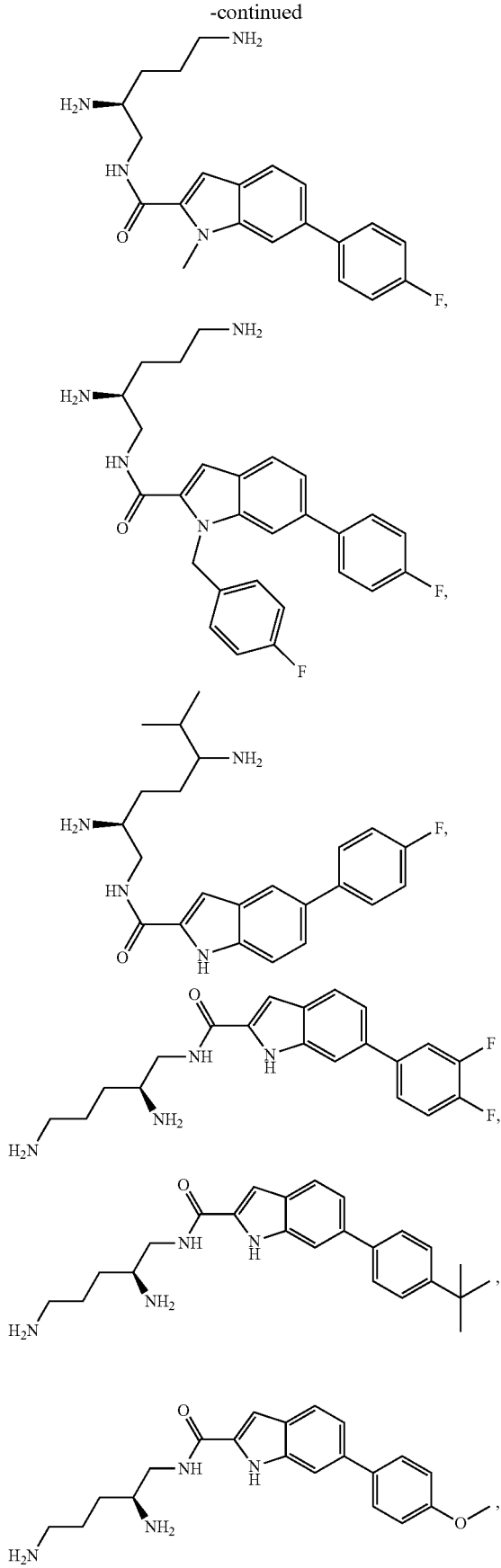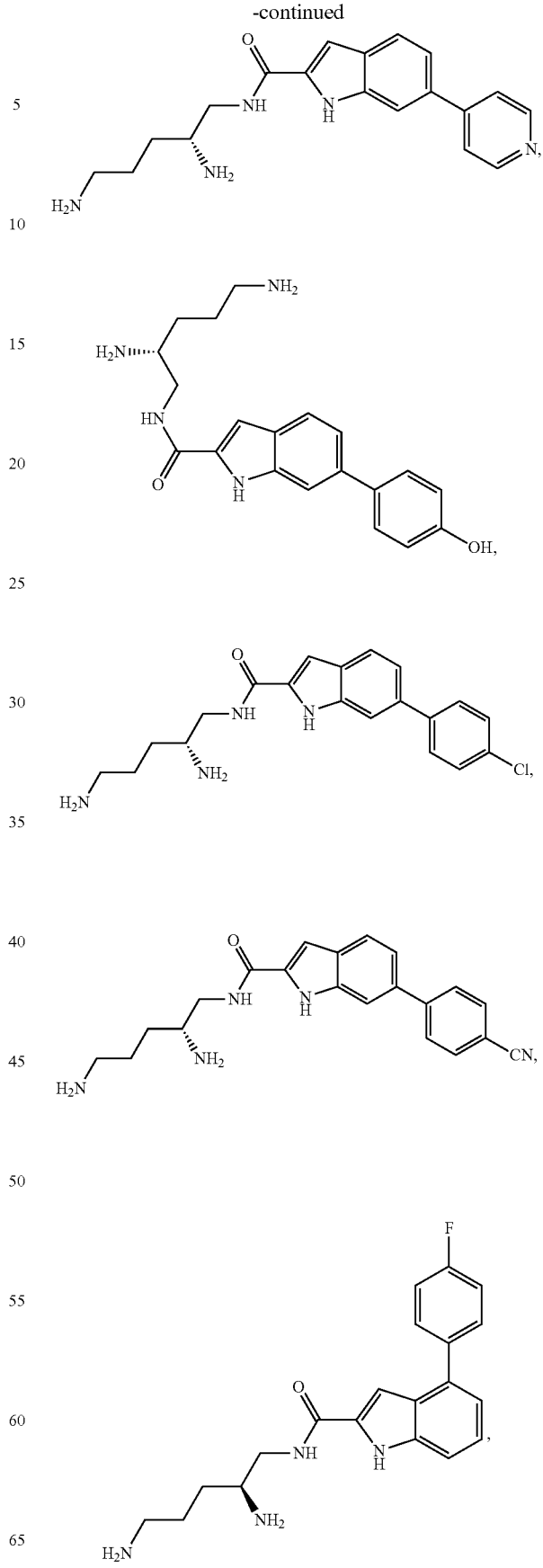

57
-continued
58
-continued
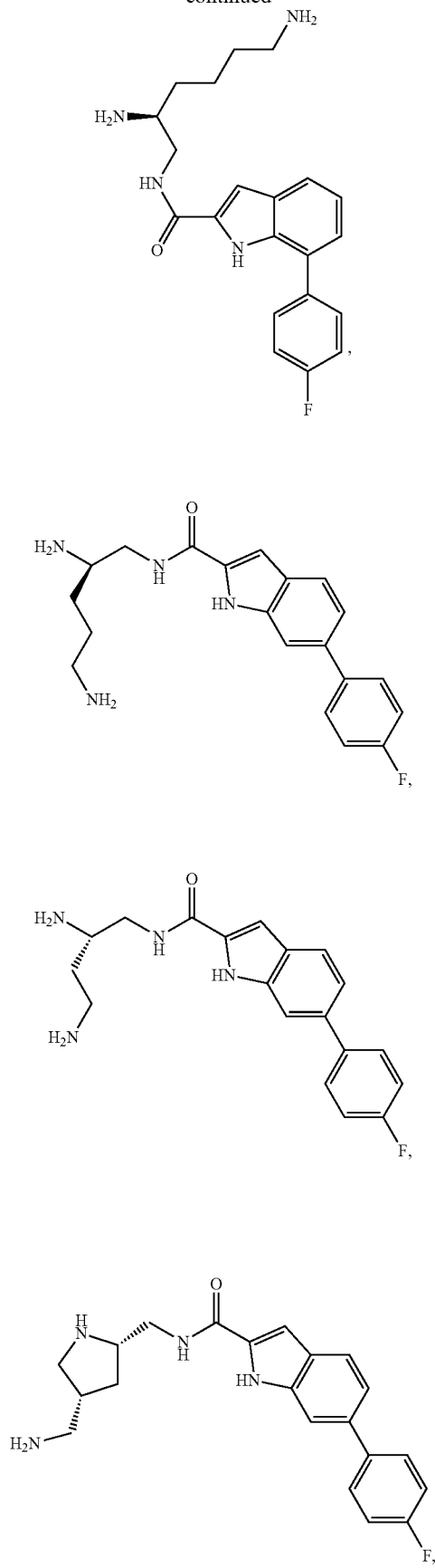
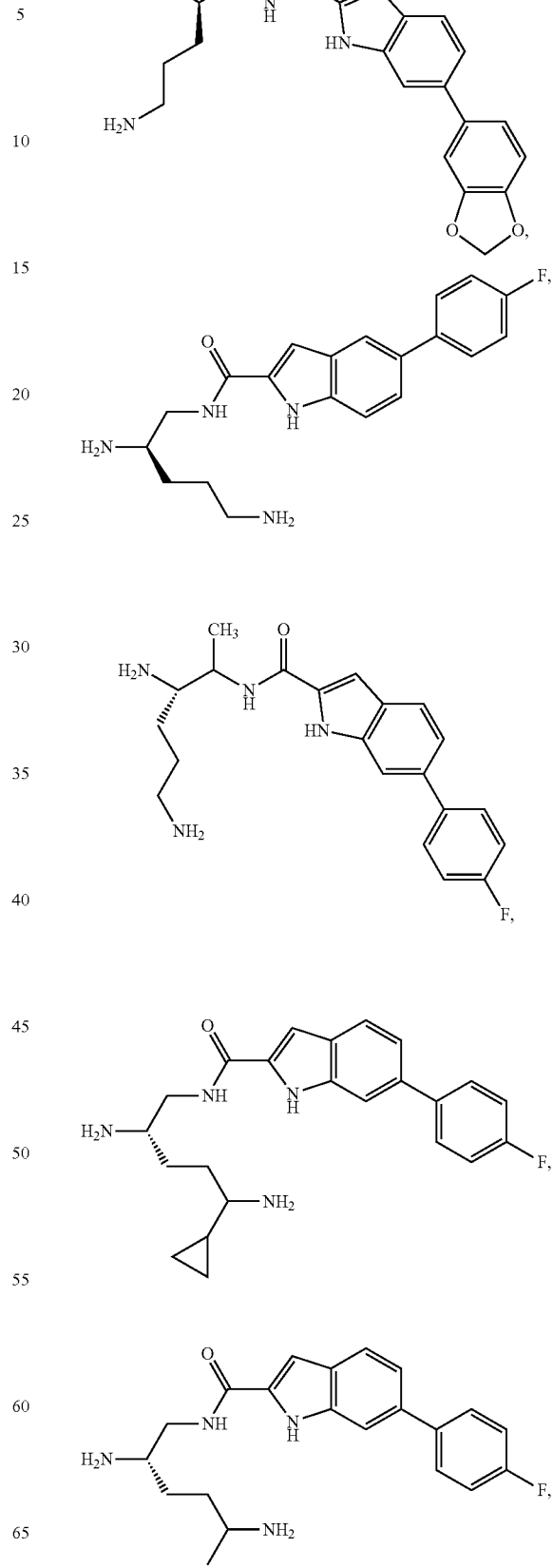

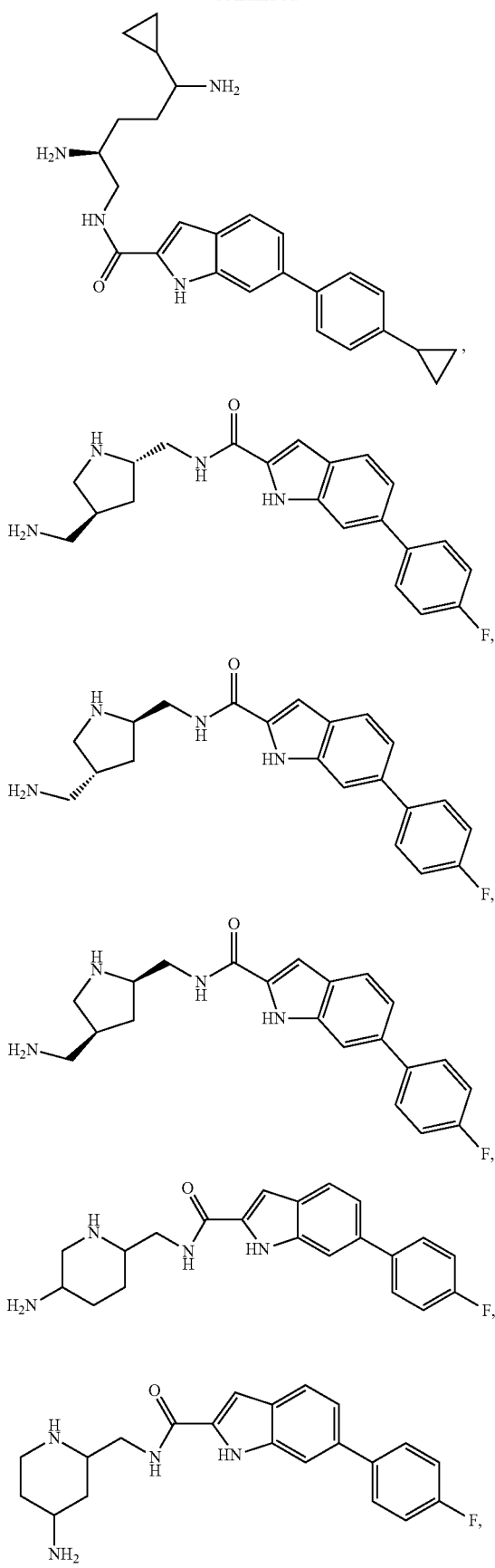

-continued
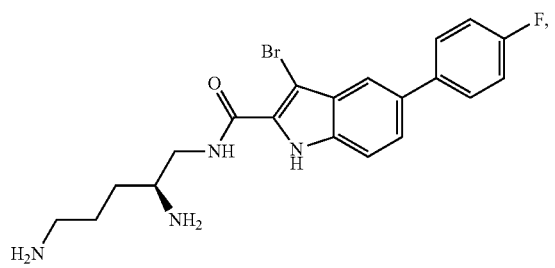
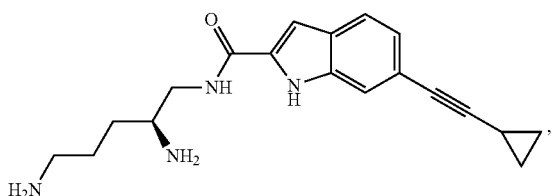
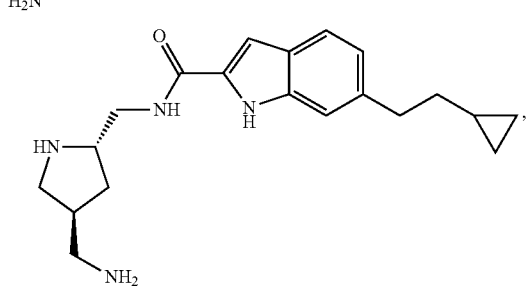
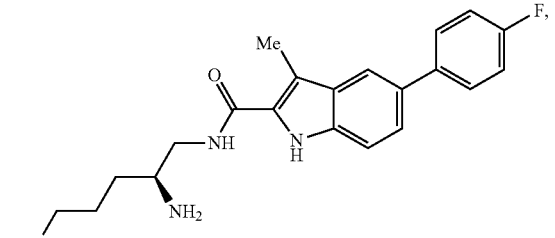
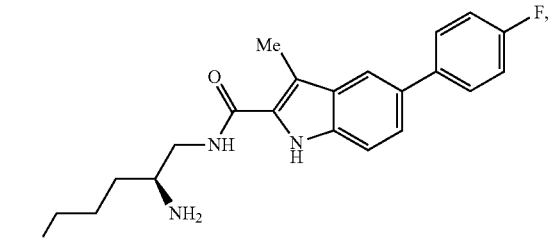
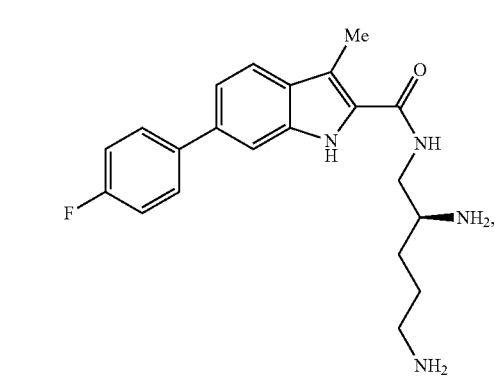
-continued
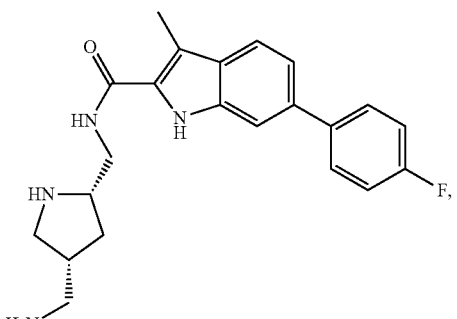
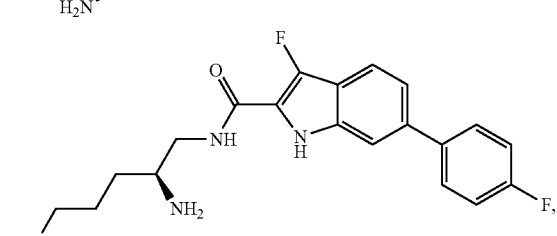
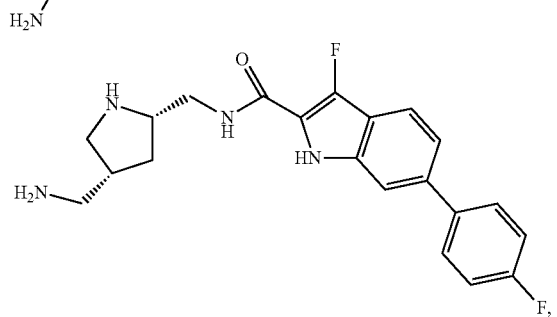
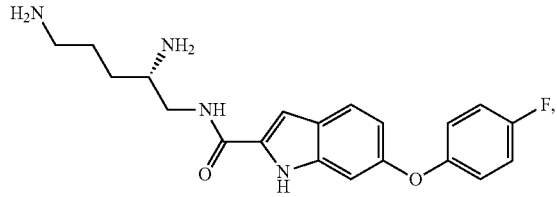
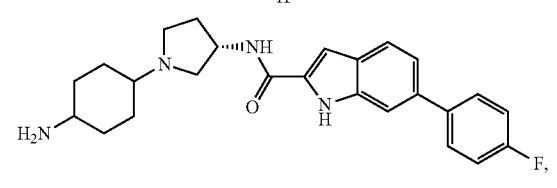
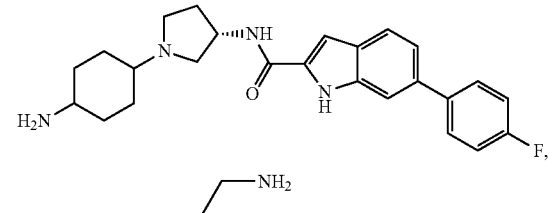
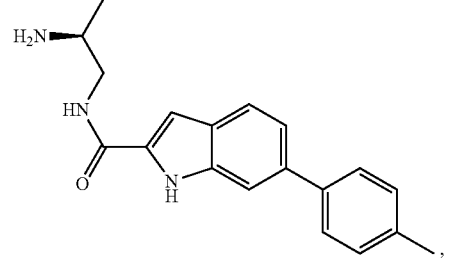

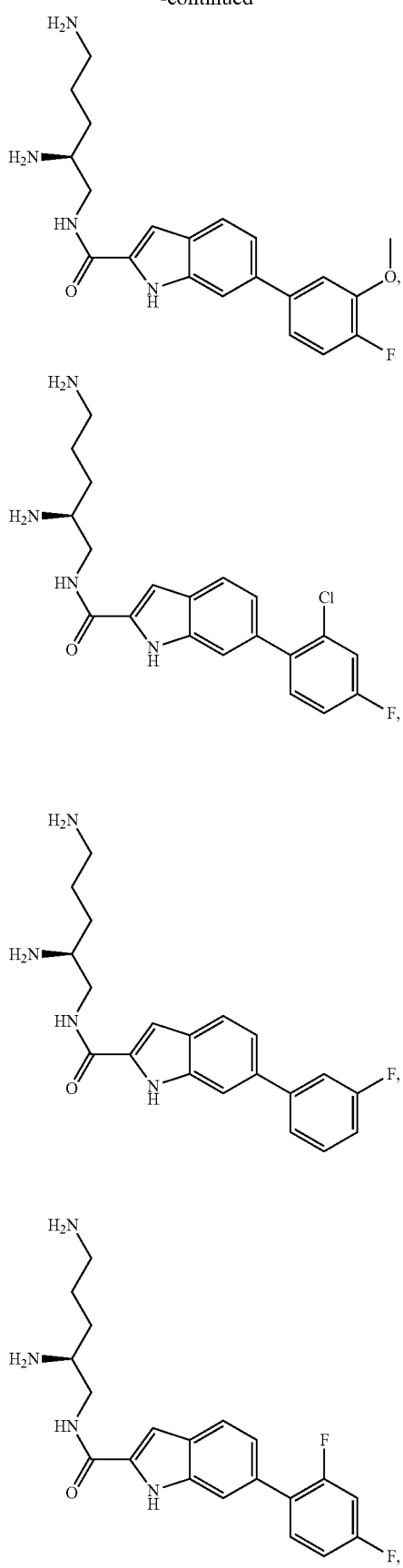
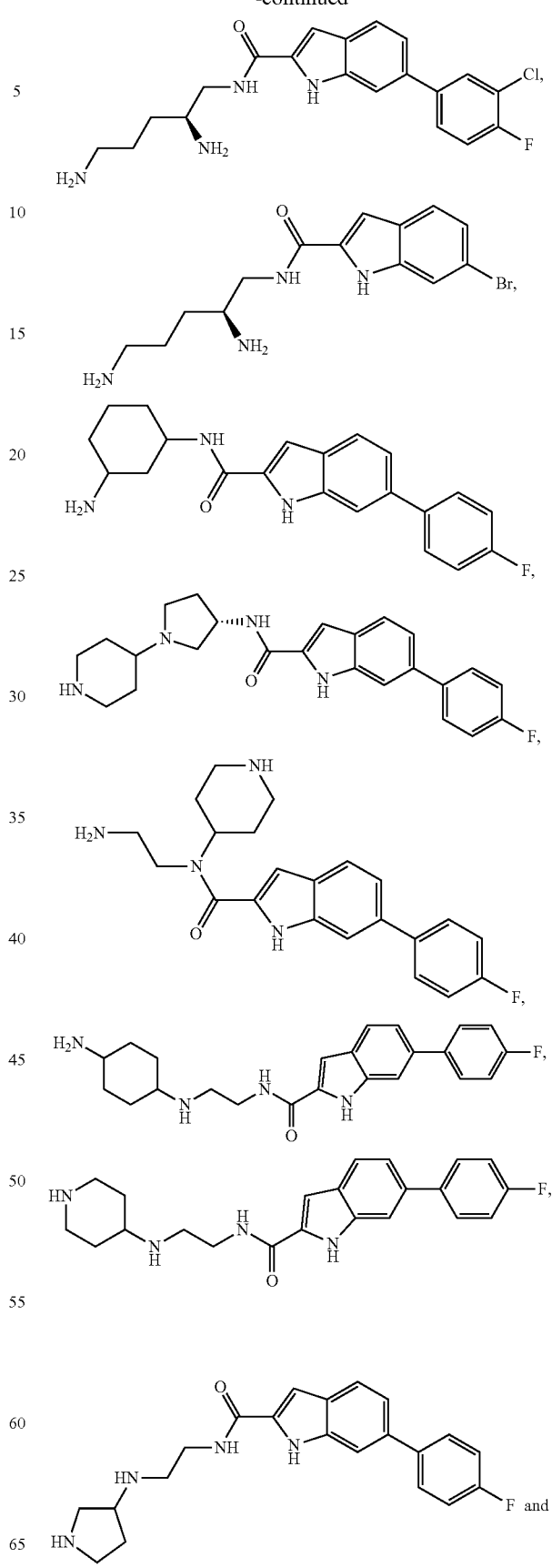

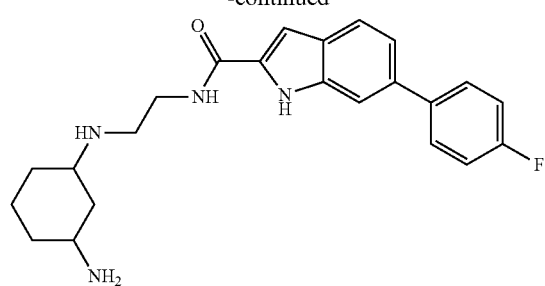
or a pharmaceutically acceptable salt thereof.
In one embodiment, the bacterial efflux pump inhibitor is selected from the group consisting of:
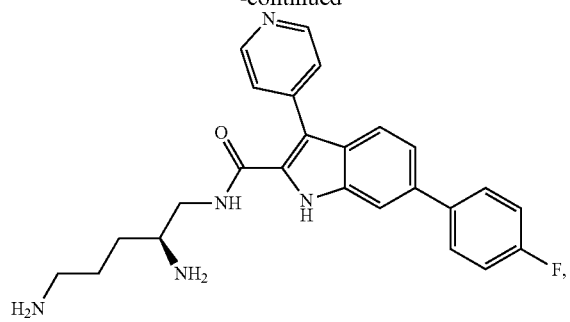
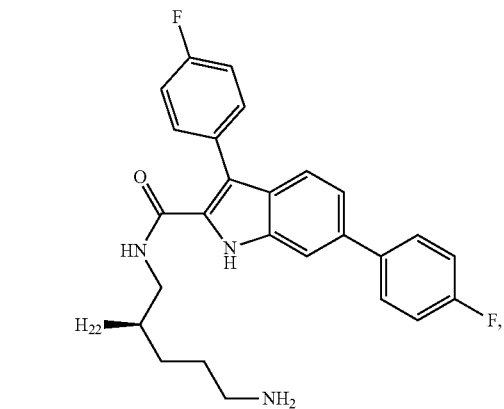
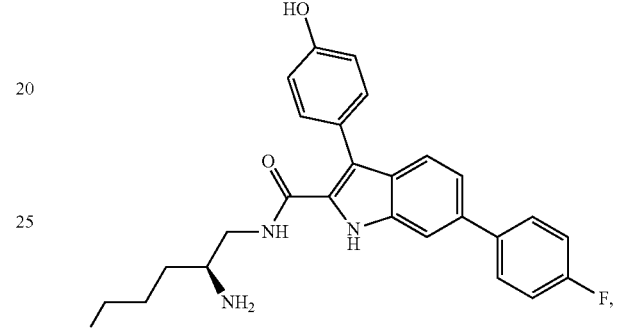
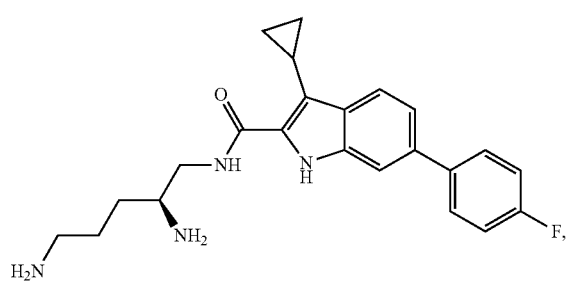
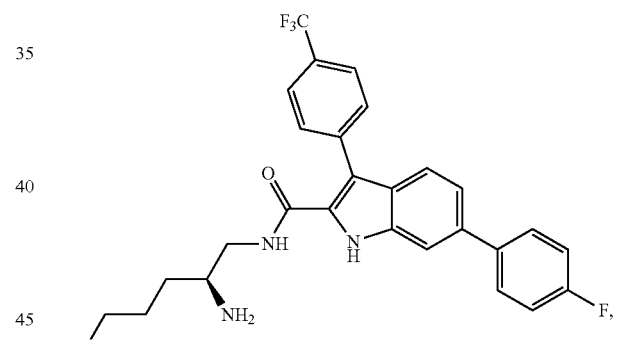
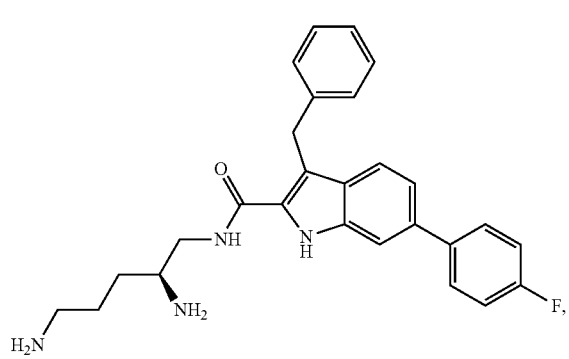
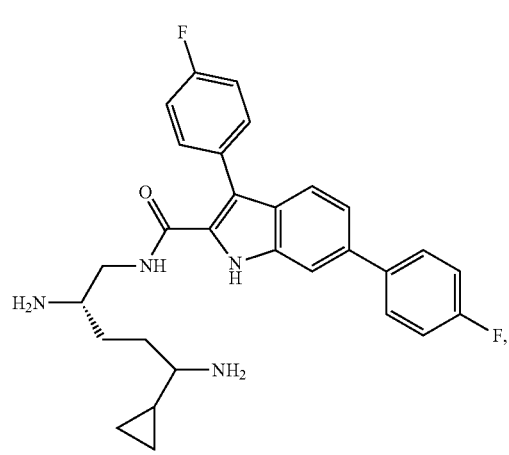

67
-continued
68
-continued
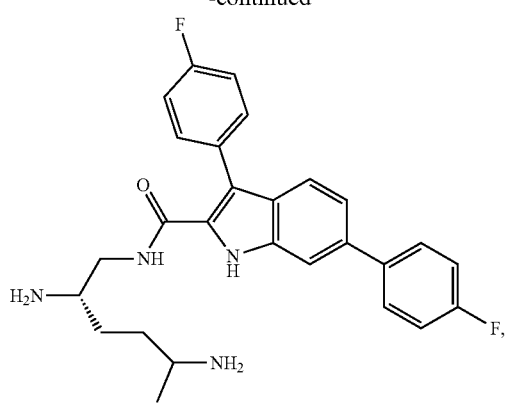
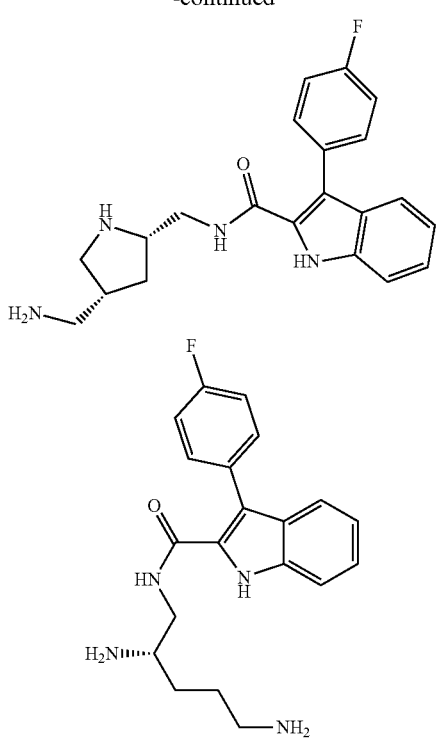
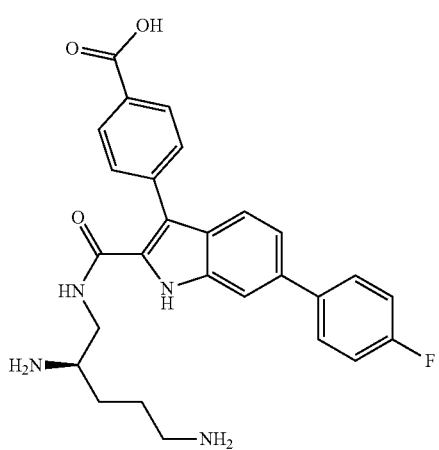
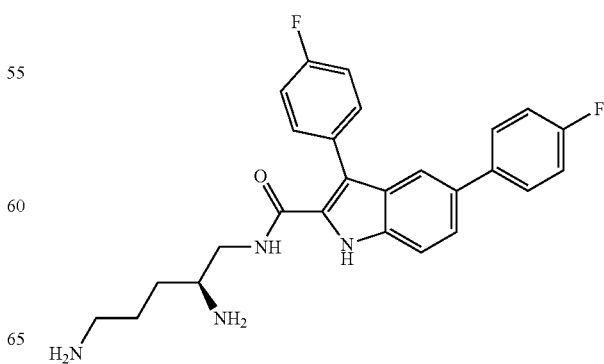

69
-continued
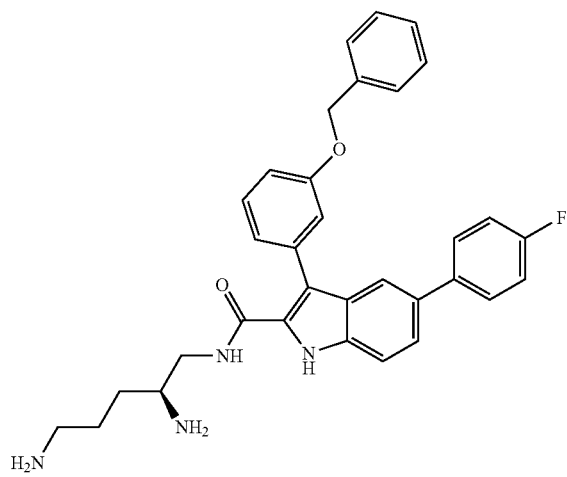
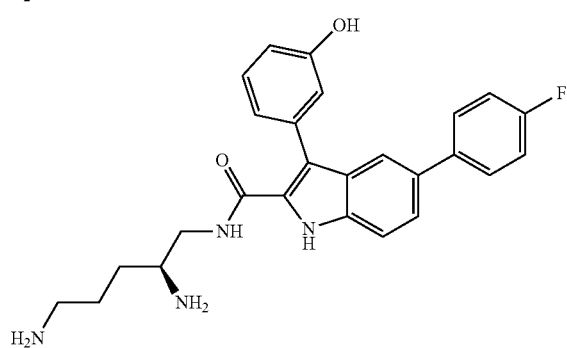
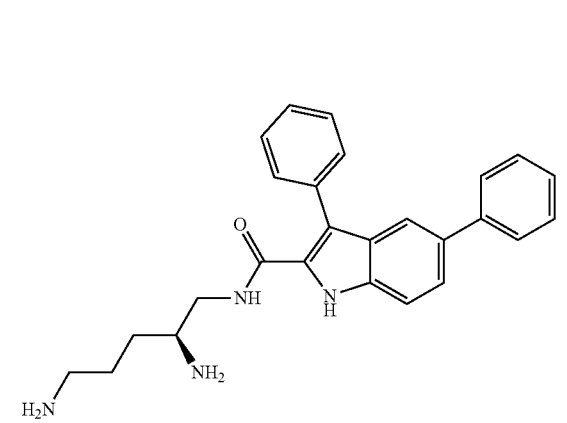
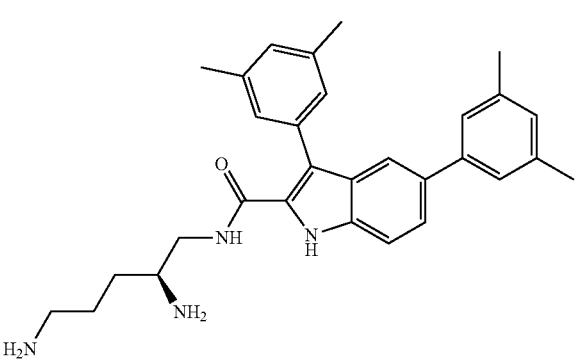
70
-continued
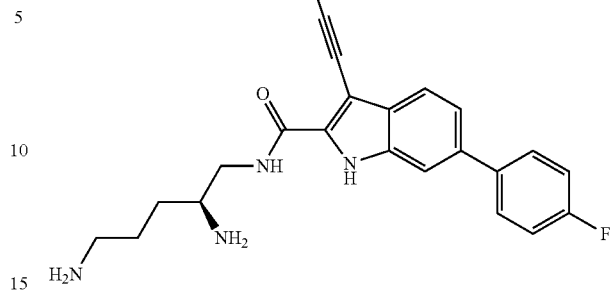
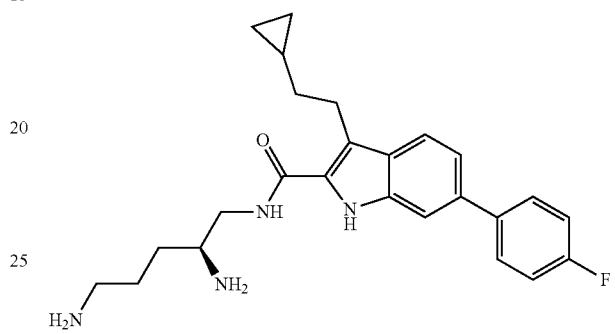
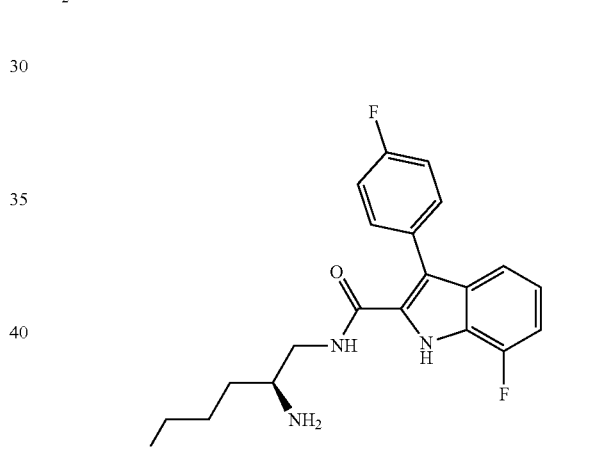
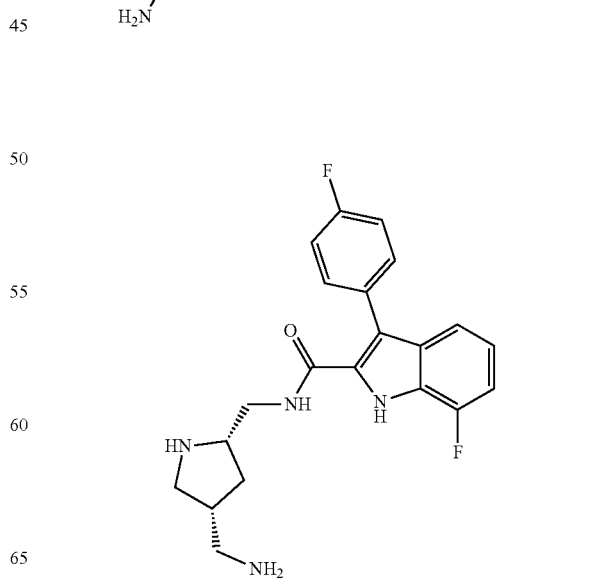

-continued

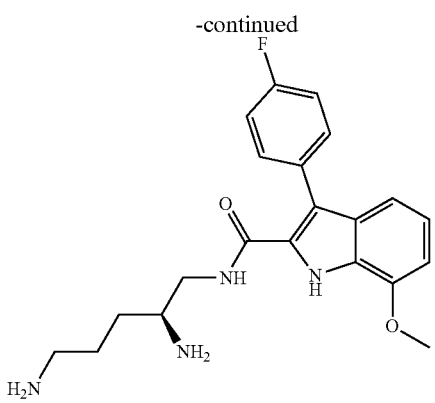

and

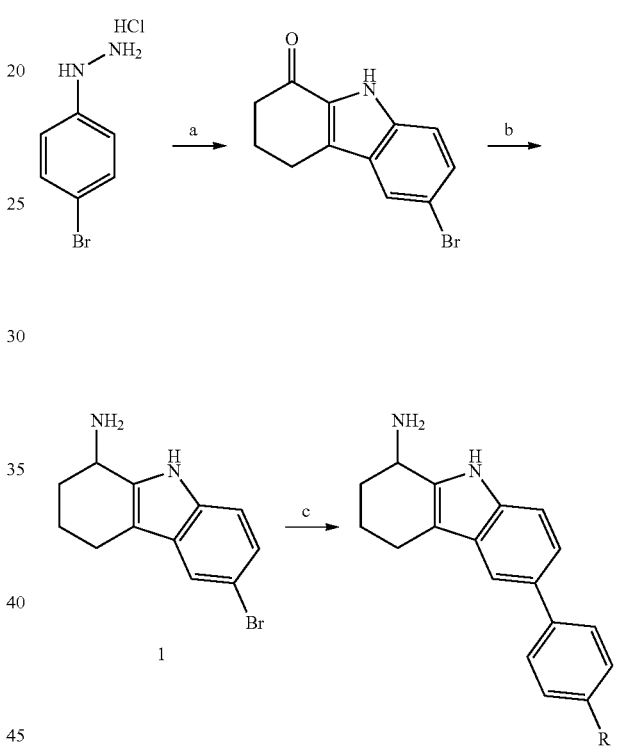

or a pharmaceutically acceptable salt thereof.

As used herein, the term "minimum inhibitory concentration (MIC)" refers to the lowest concentration of a compound (e.g., an antibiotic) that prevents visible growth of a bacterium. Assays for measuring the MIC of a compound are known in the art, for example, as described herein. As used herein, the term "intrinsic MIC" refers the MIC of a compound (e.g., an antibiotic) for the particular bacterial species that has not been pre-exposed to the compound.

As used herein, the term "sub-inhibitory concentration" refers to a concentration of the antibiotic that does not reduce the visible growth of the bacteria. In certain embodiments, the sub-inhibitory concentration is ½×MIC of the antibiotic. In certain embodiments, the sub-inhibitory concentration of the antibiotic is a concentration that is capable of inducing the expression of one or more efflux pumps in the bacteria.

As used herein, the term "inhibitory concentration" refers to a concentration of the antibiotic that reduces the visible growth of the bacteria. In certain embodiments, this concentration is the intrinsic MIC of the antibiotic.

In certain embodiments, the combination of the compound of formula I and a bacterial efflux pump inhibitor is a synergistic combination.

In certain embodiments, the animal is a non-human animal. For example, in certain embodiments, the animal is a mouse.

Generally, compounds of formula I as well as synthetic intermediates that can be used for preparing compounds of formula I can be prepared as illustrated in the following General Methods and Schemes. It is understood that variable groups shown below (e.g., R) can represent the final corresponding groups present in a compound of formula I or that these groups can represent groups that can be converted to the final corresponding groups present in a compound of formula I at a convenient point in a synthetic sequence. For example, the variable groups can contain one or more protecting groups that can be removed at a convenient point in a synthetic sequence to provide the final corresponding groups in the compound of formula I.

Scheme 1.

(a) 1,2-cyclohexadione, AcOH, conc. HCl, MeOH, 60° C.; (b) NH₄OAc, NaBH₃CN, MeOH, 60° C.; (c) 4-fluorophenylboronic acid (for 2), 4-methoxyphenylboronic acid (for 3), 4-trifluoromethylphenylboronic acid (for 4), Pd(PPh₃)₄, K₂CO₃, dioxane: H₂O (3:1), 100° C.

Scheme 2.

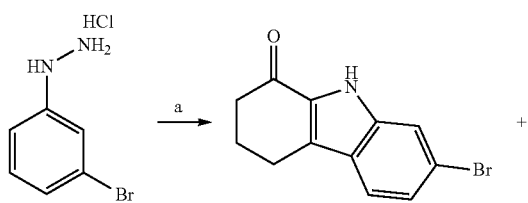

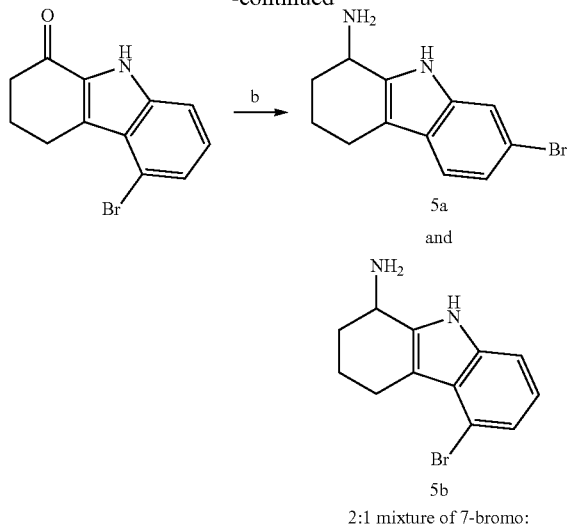

5a and

5b

2:1 mixture of 7-bromo: 5-bromo (a) 1,2-cyclohexadione AcOH, con. HCl, MeOH, 60° C.; (b) NH$_4$OAc, NaBH$_3$CN, MeOH, 60° C.

Scheme 3.

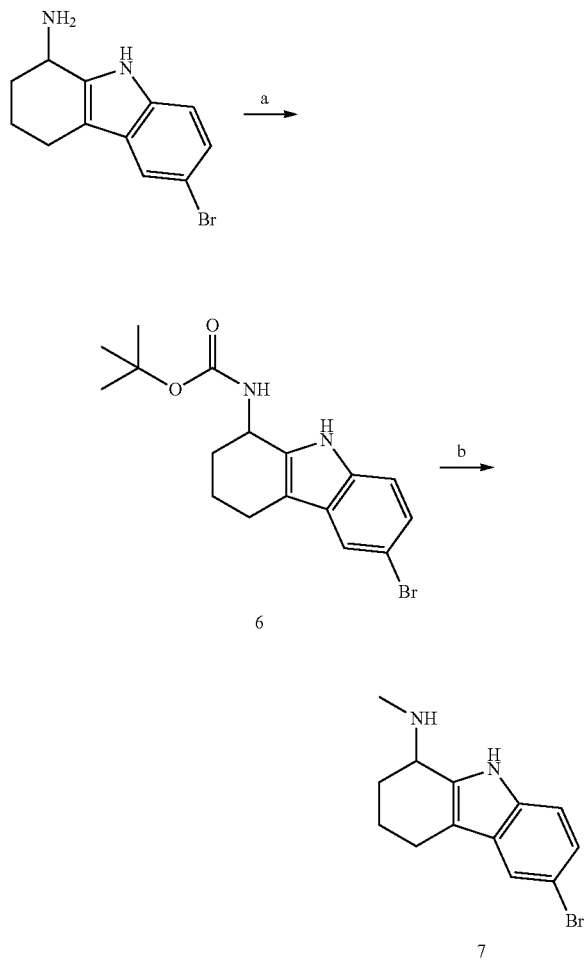

6

7

(a) Boc$_2$O, THF; (b) LAH, THF, 50° C.

Scheme 4.

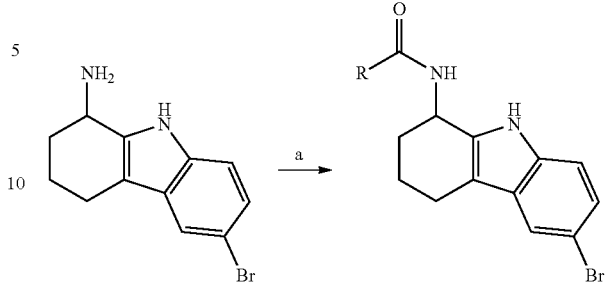

8, R = CH$_3$
9, R = Ph (a) acetyl chloride (for 8), benzoyl chloride (for 9), EtN(Pr-i)$_2$, CH$_2$Cl$_2$.

An efflux pump inhibitor is a compound that interferes with the ability of an efflux pump to export a substrate. The inhibitor may have intrinsic antibacterial properties of its own. The compounds disclosed herein may be useful for treating bacterial infections (e.g., gram negative and gram positive) when administered with an bacterial efflux pump inhibitor.

In one embodiment the bacterial infection being treated is a Gram-negative bacterial strain infection. In one embodiment the Gram-negative bacterial strain is selected from the group consisting of *Acinetobacter baumannii, Acinetobacter calcoaceticus, Acinetobacter haemolyticus, Acinetobacter lwoffi, Actinobacillus actinomycetemcomitans, Aeromonas hydrophilia, Aggregatibacter actinomycetemcomitans, Agrobacterium tumefaciens, Bacteroides distasonis, Bacteroides eggerthii, Bacteroides forsythus, Bacteroides fagilis, Bacteroides ovalus, Bacteroides splanchnicus, Bacteroides thetaiotaomicron, Bacteroides uniformis, Bacteroides vulgatus, Bordetella bronchiseptica, Bordetella parapertussis, Bordetella pertussis, Borrelia burgdorferi, Branhamella catarrhalis, Burkholderia cepacia, Campylobacter coli, Campylobacter fetus, Campylobacterjejuni, Caulobacter crescentus, Chlamydia trachomatis, Citrobacter diversus, Citrobacter freundii, Enterobacter aerogenes, Enterobacter asburiae, Enterobacter cloacae, Enterobacter sakazakii, Escherchia coli, Francisella tularensis, Fusobacterium nucleatum, Gardnerella vaginalis, Haemophilus ducreyi, Haemophilus haemolyticus, Haemophilus influenzae, Haemophilus parahaemolyticus, Haemophilus parainfluenzae, Helicobacter pylori, Kingella denitrificans, Kingella indologenes, Kingella kingae, Kingella oralis, Klebsiella oxytoca, Klebsiella pneumoniae, Klebsiella rhinoscleromatis, Legionella pneumophila, Listeria monocytogenes, Moraxella bovis, Moraxella catarrhalis, Moraxella lacunata, Morganella morganii, Neisseria gonorrhoeae, Neisseria meningitidis, Pantoea agglomerans, Pasteurella canis, Pasteurella haemolytica, Pasteurella multocida, Pasteurella tularensis, Porphyromonas gingivalis, Proteus mirabilis, Proteus vulgaris, Providencia alcalifaciens, Providencia rettgeri, Providencia stuartii, Pseudomonas acidovorans, Pseudomonas aeruginosa, Pseudomonas alcaligenes, Pseudomonas fluorescens, Pseudomonas putida, Salmonella enteriditis, Salmonella paratyphi, Salmonella typhi, Salmonella typhimurium, Serratia marcescens, Shigella dysenteriae, Shigella jlexneri, Shigella sonnei, Stenotrophomonas maltophilla, Veillonella parvula, Vibrio cholerae, Vibrio parahaemolyticus, Yersinia enterocolitica, Yersinia intermedia, Yersinia pestis* and *Yersinia pseudotuberculosis.*

In one embodiment the bacterial infection being treated is a Gram-positive bacterial strain infection. In one embodiment the Gram-positive bacterial strain is selected from the group consisting of *Actinomyces naeslundii, Actinomyces viscosus, Bacillus anthracis, Bacillus cereus, Bacillus subtilis, Clostridium difficile, Corynebacterium diphtheriae, Corynebacterium ulcerans, Enterococcusfaecalis, Enterococcus faecium, Micrococcus luteus, Mycobacterium avium, Mycobacterium intracellulare, Mycobacterium leprae, Mycobacterium tuberculosis, Propionibacterium acnes, Staphylococcus aureus, Staphylococcus epidermidis, Staphylococcus haemolyticus, Staphylococcus hominis, Staphylococcus hyicus, Staphylococcus intermedius, Staphylococcus saccharolyticus, Staphylococcus saprophyticus, Streptococcus agalactiae, Streptococcus mutans, Streptococcus pneumoniae, Streptococcus pyogenes, Streptococcus salivarius* and *Streptococcus sanguis.*

In one embodiment, the animal is infected with *P. aeruginosa.*

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, an antimicrobial (for example, an aminoglycoside, an antifungal, an antiparasitic, an antiviral, a carbapenem, a cephalosporin (e.g., cefepime), a fluoroquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropoietin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

It will also be appreciated by those skilled in the art that certain compounds of the invention can exist in more than one tautomeric form. For example, a substituent of formula —NH—C(=O)H in a compound of formula (I) could exist in tautomeric form as —N=C(OH)H. The present invention encompasses all tautomeric forms of a compound of formula I as well as mixtures thereof that can exist in equilibrium with non-charged and charged entities depending upon pH, which possess the useful properties described herein In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, fumarate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $H_2PO_4^-$, $CF_3SO_3^-$, $p\text{-}CH_3C_6H_4SO_3^-$, citrate, tartrate, phosphate, malate, fumarate, formate, or acetate.

It will be appreciated by those skilled in the art that a compound of the invention comprising a counterion can be converted to a compound of the invention comprising a different counterion. Such a conversion can be accomplished using a variety of well-known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For oral administration the compounds can be formulated as a solid dosage form with or without an enteric coating.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 500 mg/kg, e.g., from about 5 to about 400 mg/kg of body weight per day, such as 1 to about 250 mg per kilogram body weight of the recipient per day. The compound is conveniently formulated in unit dosage form; for example, containing 5 to 500 mg, 10 to 400 mg, or 5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Co-administration of a compound disclosed herein with one or more other active therapeutic agents (e.g., antibacterial agents) generally refers to simultaneous or sequential administration of a compound disclosed herein and one or more other active therapeutic agents, such that therapeutically effective amounts of disclosed herein and one or more other active therapeutic agents are both present in the body of the patient.

The ability of a compound to produce an antibiotic effect can be determined using a method as described in Example 42. Data for representative compounds used in combination with the efflux pump inhibitor (2S,4R)-4-(ammoniomethyl)-2-((6-(4-fluorophenyl)-1H-indole-2-carboxamido)methyl)pyrrolidin-1-ium is shown in Table 1.

TABLE 1

| Example | Structure | Antibiotic Activity Against *P. aeruginosa*[a] | | Antibiotic Activity Against *E. coli*[b] Intrinsic MIC μg/ml |
|---|---|---|---|---|
| | | Intrinsic MIC μg/ml | MIC with EPI* μg/ml (Enhancement) | |
| 1 | 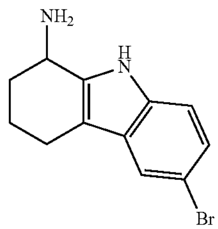 [SMILES: NC1CCCc2c1[nH]c1ccc(Br)cc21] | 32 | 0.5 (64x) | 8 |
| 2 | 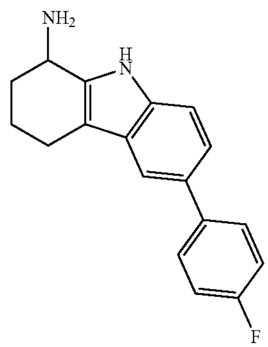 [SMILES: NC1CCCc2c1[nH]c1ccc(-c3ccc(F)cc3)cc21] | 256 | 4 (64x) | 16 |
| 3 | 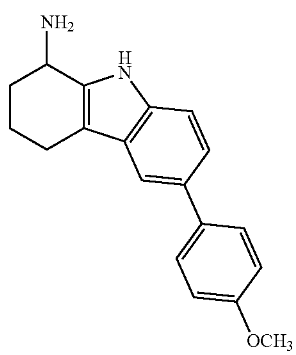 [SMILES: COc1ccc(-c2ccc3[nH]c4c(c3c2)CCCC4N)cc1] | >256 | 16 (>16x) | 32 |
| 4 | 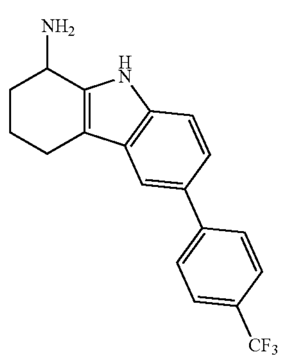 [SMILES: NC1CCCc2c1[nH]c1ccc(-c3ccc(C(F)(F)F)cc3)cc21] | >256 | 4 (>64x) | 16 |

TABLE 1-continued

| Example | Structure | Antibiotic Activity Against *P. aeruginosa*[a] | | Antibiotic Activity Against *E. coli*[b] Intrinsic MIC μg/ml |
|---|---|---|---|---|
| | | Intrinsic MIC μg/ml | MIC with EPI* μg/ml (Enhancement) | |
| 5a and 5b | (two structures: 7-Br and 5-Br 1-amino-tetrahydrocarbazoles) | 64 | 2 (32x) | 32 |
| 5a | (7-Br 1-amino-tetrahydrocarbazole) | 64 | 1 (64x) | 32 |
| 5b | (5-Br 1-amino-tetrahydrocarbazole) | 128 | 2 (64x) | 16 |
| 6 | (Boc-NH tetrahydrocarbazole with Br) | >256 | >64 (4x) | >256 |
| 7 | (methylamino tetrahydrocarbazole with Br) | 256 | 8 (32x) | 32 |

TABLE 1-continued

| Example | Structure | Antibiotic Activity Against *P. aeruginosa*[a] | | Antibiotic Activity Against *E. coli*[b] |
|---|---|---|---|---|
| | | Intrinsic MIC μg/ml | MIC with EPI* μg/ml (Enhancement) | Intrinsic MIC μg/ml |
| 8 | 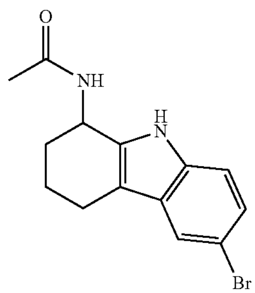 [SMILES: CC(=O)NC1CCCc2c1[nH]c1ccc(Br)cc21] | >256 | >64 (4x) | >256 |
| 9 | 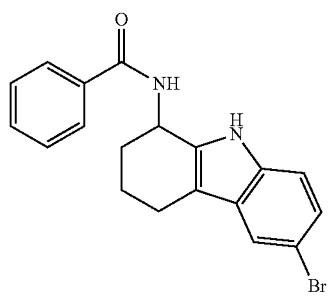 [SMILES: O=C(NC1CCCc2c1[nH]c1ccc(Br)cc21)c1ccccc1] | >256 | >64 (4x) | >256 |
| 10a and 10b | | >256 | 32 (>8x) | 32 |
| 11 | 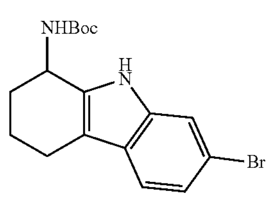 [SMILES: CC(C)(C)OC(=O)NC1CCCc2c1[nH]c1cc(Br)ccc21] | >256 | >64 (4x) | >256 |

TABLE 1-continued

| Example | Structure | Antibiotic Activity Against *P. aeruginosa*[a] | | Antibiotic Activity Against *E. coli*[b] Intrinsic MIC μg/ml |
| --- | --- | --- | --- | --- |
| | | Intrinsic MIC μg/ml | MIC with EPI* μg/ml (Enhancement) | |
| 12 | [structure: 1-amino-tetrahydrocarbazole with F substituent] | 128 | 2 (64x) | 64 |
| 13 | [structure: 1-amino-tetrahydrocarbazole with Cl substituent] | 128 | 1 (16x) | 16 |
| 14 | [structure: 1-amino-tetrahydrocarbazole with CF₃ substituent] | 64 | 2 (32x) | 64 |
| 15 | [structure: 1-amino-tetrahydrocarbazole with OCF₃ substituent] | 128 | 16 (8x) | 64 |
| 16 | [structure: 1-amino-tetrahydrocarbazole with CN substituent] | >256 | 32 (>8x) | 256 |
| 17 | [structure: 1-amino-tetrahydrocarbazole with Br substituent] | >256 | 128 (>2x) | 64 |

TABLE 1-continued

| Example | Structure | Antibiotic Activity Against *P. aeruginosa*[a] | | Antibiotic Activity Against *E. coli*[b] Intrinsic MIC µg/ml |
|---|---|---|---|---|
| | | Intrinsic MIC µg/ml | MIC with EPI* µg/ml (Enhancement) | |
| 18 | [structure: 1-amino-6-methoxy-2,3,4,9-tetrahydro-1H-carbazole hydrochloride] | >256 | 32 (>8x) | >256 |
| 19 | [structure: 1-amino-6-bromo-9-methyl-2,3,4,9-tetrahydro-1H-carbazole] | 256 | 64 (4x) | 64 |
| 20 | [structure: 1-amino-6-bromo-3-fluoro-2,3,4,9-tetrahydro-1H-carbazole hydrochloride] | >256 | 32 (>8x) | 64 |
| 21 | [structure: 1-amino-6,7-dichloro-2,3,4,9-tetrahydro-1H-carbazole] | 64 | 4 (16x) | 8 |
| 22 | [structure: 1-amino-5,6-dichloro-2,3,4,9-tetrahydro-1H-carbazole] | 32 | <0.125 (>256x) | 4 |
| 23 | [structure: 1-amino-7-bromo-3-methyl-2,3,4,9-tetrahydro-1H-carbazole] | 256 | 16 (16x) | 16 |

TABLE 1-continued

| Example | Structure | Antibiotic Activity Against *P. aeruginosa*[a] | | Antibiotic Activity Against *E. coli*[b] Intrinsic MIC μg/ml |
|---|---|---|---|---|
| | | Intrinsic MIC μg/ml | MIC with EPI* μg/ml (Enhancement) | |
| 24 | [structure: 6-bromo-4,4-dimethyl-tetrahydrocarbazole with NH₂] | 64 | 16 (4x) | 16 |
| 25 | [structure: 6-bromo-4-isopropyl-tetrahydrocarbazole with NH₂, HCl] | 64 | 16 (4x) | 8 |
| 26 | [structure: bromo-dimethyl-tetrahydrocarbazole with NH₂] | 64 | 4 (16x) | 32 |
| 27 | [structure: bromo-tetrahydrocarbazole with CO₂Et and NH₂] | >256 | 32 (>8x) | 16 |
| 28 | [structure: bromo-tetrahydrocarbazole with CO₂H and NH₂] | >256 | 256 (>1x) | >256 |
| 29 | [structure: bromo-tetrahydrocarbazole with CH₂OH and NH₂] | 256 | 32 (8x) | 64 |
| 30 | [structure: bromo-isopropyl-tetrahydrocarbazole with NH₂] | 64 | 8 (8x) | 4 |

TABLE 1-continued

| Example | Structure | Antibiotic Activity Against *P. aeruginosa*[a] | | Antibiotic Activity Against *E. coli*[b] Intrinsic MIC μg/ml |
|---|---|---|---|---|
| | | Intrinsic MIC μg/ml | MIC with EPI* μg/ml (Enhancement) | |
| 31 | 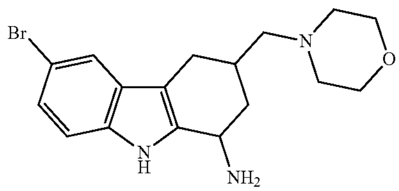 [SMILES: NC1CC(CN2CCOCC2)Cc2c1[nH]c1ccc(Br)cc21] | 256 | 64 (4x) | 64 |
| 32 | 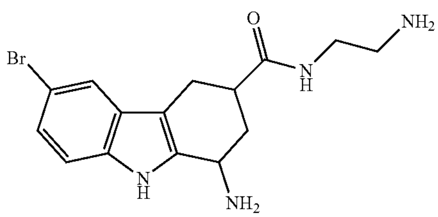 [SMILES: NCCNC(=O)C1Cc2c([nH]c3ccc(Br)cc23)C(N)C1] | >256 | >256 (1x) | >256 |
| 33 | 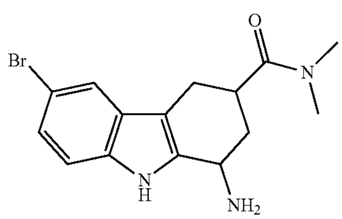 [SMILES: CN(C)C(=O)C1Cc2c([nH]c3ccc(Br)cc23)C(N)C1] | >256 | 128 (>2x) | 128 |
| 34 | 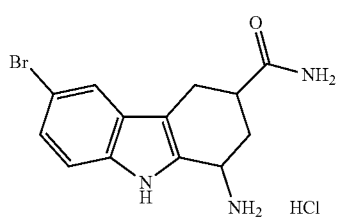 [SMILES: NC(=O)C1Cc2c([nH]c3ccc(Br)cc23)C(N)C1 ; Cl] | 256 | 256 | 128 |
| 35 | 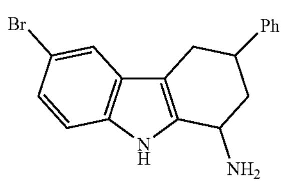 [SMILES: NC1CC(c2ccccc2)Cc2c1[nH]c1ccc(Br)cc21] | >256 | 8 (>32x) | 8 |
| 36 | 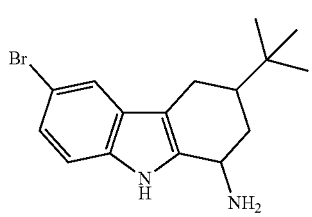 [SMILES: CC(C)(C)C1Cc2c([nH]c3ccc(Br)cc23)C(N)C1] | >256 | 8 (>32x) | 8 |
| 37 | 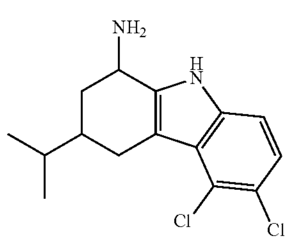 [SMILES: CC(C)C1Cc2c([nH]c3ccc(Cl)c(Cl)c23)C(N)C1] | 128 | 4 (32x) | 4 |

TABLE 1-continued

| Example | Structure | Antibiotic Activity Against *P. aeruginosa*[a] | | Antibiotic Activity Against *E. coli*[b] |
|---|---|---|---|---|
| | | Intrinsic MIC μg/ml | MIC with EPI* μg/ml (Enhancement) | Intrinsic MIC μg/ml |
| 38 | 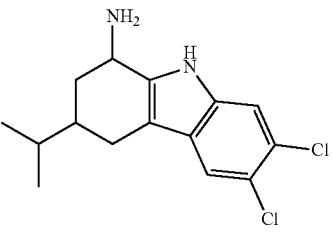 [SMILES: CC(C)C1Cc2c([nH]c3cc(Cl)c(Cl)cc23)C(N)C1] | >256 | 4 (>64x) | 4 |
| 39 | 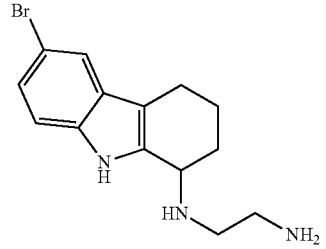 [SMILES: NCCNC1CCCc2c1[nH]c1ccc(Br)cc21] | 32 | 16 | 16 |
| 40 | 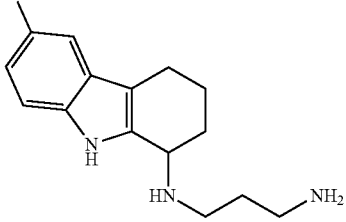 | 32 | N/A | 32 |
| 41 | 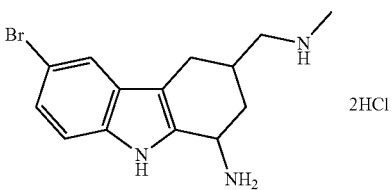 [SMILES: CNCC1Cc2c([nH]c3ccc(Br)cc23)C(N)C1] | 128 | 64 (4x) | 256 |

[a] *P. aeruginosa* PAO1

[b] *E. coli* 25922

*The EPI that was used in these assay was (2S,4R)-4-(ammoniomethyl)-2-((6-(4-fluorophenyl)-1H-indole-2-carboxamido)methyl)pyrrolidin-1-ium. The MIC$_{90}$ was determined by using varying concentration of each test compounds with and without 12.5 ug/ml of bacterial efflux pump inhibitor.

The invention will now be illustrated by the following non-limiting examples.

EXAMPLES

Example 1

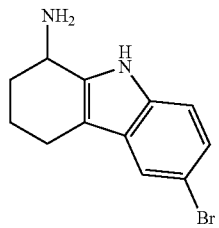 [SMILES: NC1CCCc2c1[nH]c1ccc(Br)cc21]

6-Bromo-2,3,4,9-tetrahydro-1H-carbazol-1-amine

6-Bromo-2,3,4,9-tetrahydro-1H-carbazol-1-one (250 mg, 0.95 mmol), ammonium acetate (732 mg, 9.5 mmol) and sodium cyanoborohydride (298 mg, 4.75 mmol) were dissolved in methanol (5 mL). The reaction mixture was stirred for overnight at 60° C. After removal of the solvent, the reaction mixture was diluted with ethyl acetate. The organic layer was washed with 10% NaOH and brine, and it was dried over $Na_2SO_4$. The organic layer was concentrated under reduced pressure. The residue was purified on an ISCO chromatograph (0-10% methanol/dichloromethane+ 0.1% $NH_4OH$) to give the product as a white solid (127 mg, 50%); $^1$H NMR (300 MHz) ($CD_3OD$) δ 7.49 (s, 1H), 7.19 (d, J=9 Hz, 1H), 7.12 (dd, J=9 Hz, J=2 Hz, 1H), 4.05 (t, J=6 Hz, 1H), 2.62 (t, J=6 Hz, 2H), 2.19-1.99 (m, 2H), 1.82-1.66 (m, 2H); LC/MS RT=2.62 (M−H$^-$: 263/265).

a. Preparation of Compound

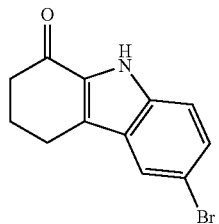 [SMILES: O=C1CCCc2c1[nH]c1ccc(Br)cc21]

6-Bromo-2,3,4,9-tetrahydro-1H-carbazol-1-one

A solution of 4-bromophenyl hydrazine hydrochloride (2.0 g, 8.92 mmol) in methanol (20 mL) was added slowly at 60° C. to a mixture of 1,2-cyclohexanedione in acetic acid (44 mL) and concentrated hydrochloric acid (16 mL). The reaction mixture was stirred for 3 hours at 60° C. The reaction mixture was cooled in the refrigerator overnight. The crystallized solid was filtered to give a product as a brown solid (1.03 g, 44%); $^1$H NMR (300 MHz) ($CDCl_3$) δ 8.95 (s, 1H), 7.80 (s, 1H), 7.44 (dd, J=8 Hz, J=2 Hz, 1H), 7.31 (d, J=9 Hz, 1H), 2.97 (t, J=6 Hz, 2H), 2.66 (t, J=6 Hz, 2H), 2.31-2.23 (m, 2H); LC/MS RT=3.87 (M+H$^+$: 264/266).

Example 2

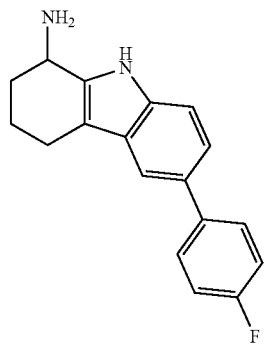 [SMILES: NC1CCCc2c1[nH]c1ccc(-c3ccc(F)cc3)cc21]

6-(4-Fluorophenyl)-2,3,4,9-tetrahydro-1H-carbazol-1-amine

6-Bromo-2,3,4,9-tetrahydro-1H-carbazol-1-amine (70 mg, 0.26 mmol), (4-fluorophenyl)boronic acid (109 mg, 0.78 mmol), $Pd(PPh_3)_4$ (35 mg, 0.03 mmol) and $K_2CO_3$ (108 mg, 0.78 mmol) were dissolved in a mixture of dioxane (3 mL) and water (1 mL). The air was evacuated from the reaction flask and replaced with $N_2$. The reaction mixture was then refluxed overnight. Reaction was monitored by TLC and stopped once the starting material was consumed. The reaction mixture was diluted with ethyl acetate, and it was washed with water followed by brine. The organic layer was dried over $Na_2SO_4$ and was concentrated under reduced pressure. The residue was purified on an ISCO chromatograph (0-10% methanol/dichloromethane+0.1% $NH_4OH$) to give the product as a white solid (14 mg, 19%); $^1$H NMR (300 MHz) ($CDCl_3$) δ; 8.54 (s, 1H), 7.61-7.56 (m, 3H), 7.35-7.34 (m, 2H), 7.11 (t, J=9 Hz, 2H), 4.09 (t, J=6 Hz, 1H), 2.75-2.71 (m, 2H), 2.23-2.19 (m, 1H), 2.05-1.84 (m, 2H), 1.67-1.60 (m, 1H); LC/MS RT=3.60 (M−H$^-$: 279).

Example 3

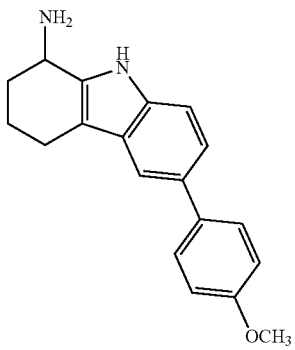 [SMILES: COc1ccc(-c2ccc3[nH]c4c(c3c2)CCCC4N)cc1]

6-(4-Methoxyphenyl)-2,3,4,9-tetrahydro-1H-carbazol-1-amine

6-Bromo-2,3,4,9-tetrahydro-1H-carbazol-1-amine (75 mg, 0.28 mmol), (4-methoxyphenyl)boronic acid (128 mg, 0.84 mmol), $Pd(PPh_3)_4$ (35 mg, 0.03 mmol) and $K_2CO_3$ (116 mg, 0.84 mmol) were dissolved in a mixture of dioxane (3 mL) and water (1 mL). The air was evacuated from the reaction flask and replaced with N$_2$. The reaction mixture was then refluxed overnight. Reaction was monitored by TLC and stopped once the starting material was consumed. The reaction mixture was diluted with ethyl acetate, and it was washed with water followed by brine. The organic layer was dried over Na$_2$SO$_4$ and was concentrated under reduced pressure. The residue was purified on an ISCO chromatograph (0-10% methanol/dichloromethane+0.1% NH$_4$OH) to give the product as a white solid (53 mg, 63%); $^1$H NMR (300 MHz) (CDCl$_3$) δ 8.58 (s, 1H), 7.62-7.56 (m, 3H), 7.35 (m, 2H), 6.98 (d, J=9 Hz, 2H), 4.10 (t, J=6 Hz, 1H), 3.85 (s, 3H), 2.75-2.69 (m, 2H), 2.22-2.16 (m, 1H), 2.05-1.78 (m, 2H), 1.68-1.60 (m, 1H); LC/MS RT=2.72 (M–H$^-$: 291).

Example 4

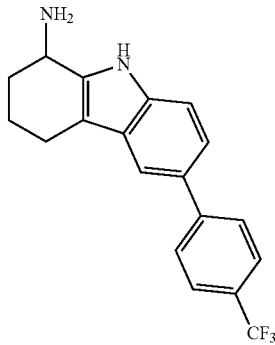 [SMILES: NC1CCCc2c1[nH]c1ccc(-c3ccc(C(F)(F)F)cc3)cc21]

6-(4-(Trifluoromethyl)phenyl)-2,3,4,9-tetrahydro-1H-carbazol-1-amine

6-Bromo-2,3,4,9-tetrahydro-1H-carbazol-1-amine (75 mg, 0.28 mmol), (4-trifluoromethylphenyl)boronic acid (160 mg, 0.84 mmol), Pd(PPh$_3$)$_4$ (35 mg, 0.03 mmol) and K$_2$CO$_3$ (116 mg, 0.84 mmol) were dissolved in a mixture of dioxane (3 mL) and water (1 mL). The air was evacuated from the reaction flask and replaced with N$_2$. The reaction mixture was then refluxed overnight. Reaction was monitored by TLC and stopped once the starting material was consumed. The reaction mixture was diluted with ethyl acetate, and it was washed with water followed by brine. The organic layer was dried over Na$_2$SO$_4$ and was concentrated under reduced pressure. The residue was purified on an ISCO chromatograph (0-10% methanol/dichloromethane+ 0.1% NH$_4$OH) to give the product as a yellow oil (24 mg, 26%); $^1$H NMR (300 MHz) (CDCl$_3$) δ 8.85 (s, 1H), 7.81-7.60 (m, 3H), 7.39 (s, 1H), 7.36-7.31 (m, 3H), 4.12-4.10 (m, 1H), 2.78-2.72 (m, 2H), 2.25-2.18 (m, 1H), 2.03-1.79 (m, 2H), 1.66-1.61 (m, 1H); LC/MS RT=2.89 (M–H$^-$: 329).

Example 5a and Example 5b

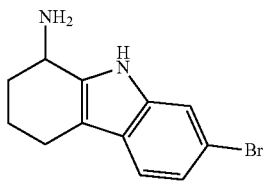 [SMILES: NC1CCCc2c1[nH]c1cc(Br)ccc21]

7-Bromo-2,3,4,9-tetrahydro-1H-carbazol-1-amine (Example 5a) and

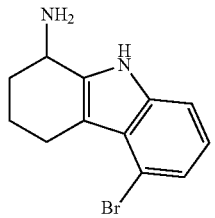 [SMILES: NC1CCCc2c1[nH]c1cccc(Br)c21]

5-Bromo-2,3,4,9-tetrahydro-1H-carbazol-1-amine (Example 5b)

A mixture of 7-bromo-2,3,4,9-tetrahydro-1H-carbazol-1-one and 5-bromo-2,3,4,9-tetrahydro-1H-carbazol-1-one (250 mg, 0.95 mmol), ammonium acetate (732 mg, 9.5 mmol) and sodium cyanoborohydride (298 mg, 4.75 mmol) were dissolved in methanol (5 mL). The reaction mixture was stirred for overnight at 60° C. After removal of the solvent, the reaction mixture was diluted with ethyl acetate. The organic layer was washed with 10% NaOH and brine, and it was dried over Na$_2$SO$_4$. The organic layer was concentrated under reduced pressure. The residue was purified on an ISCO chromatograph (0-10% methanol/dichloromethane+0.1% NH$_4$OH) to give 7-bromo-2,3,4,9-tetrahydro-1H-carbazol-1-amine as a white solid (120 mg, 48%). $^1$H NMR (300 MHz) (CDCl$_3$) δ 8.49 (s, 1H), 7.43 (d, J=1 Hz, 1H), 7.31 (d, J=8 Hz, 1H), 7.15 (dd, J=8 Hz, J=2 Hz, 1H), 3.98-3.94 (m, 1H), 2.69-2.64 (m, 2H), 2.31-2.24 (m, 1H), 2.05-1.99 (m, 1H), 1.81-1.71 (m, 1H), 1.58-1.47 (m, 1H); LC/MS RT=2.66 (M–H$^-$: 263/265), along with a mixture of 7-bromo-2,3,4,9-tetrahydro-1H-carbazol-1-amine and 5-bromo-2,3,4,9-tetrahydro-1H-carbazol-1-amine as a white solid (90 mg, 36%). LC/MS RT=2.57 (M–H$^-$: 263/265).

a. Preparation of Compound

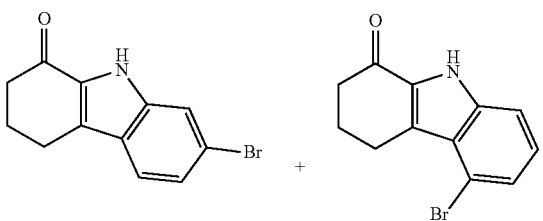 [SMILES: O=C1CCCc2c1[nH]c1cc(Br)ccc21 ; O=C1CCCc2c1[nH]c1cccc(Br)c21]

A Mixture of 7-bromo-2,3,4,9-tetrahydro-1H-carbazol-1-one and 5-bromo-2,3,4,9-tetrahydro-1H-carbazol-1-one A solution of 3-bromophenyl hydrazine hydrochloride (2.0 g, 8.92 mmol) in methanol (20 mL) was added slowly at 60° C. to a mixture of 1,2-cyclohexanedione in acetic acid (44 mL) and concentrated hydrochloric acid (16 mL). The reaction mixture was stirred for 3 hours at 60° C. The reaction mixture was cooled in the refrigerator overnight. The crystallized solid was filtered to give a mixture of 7-bromo-2,3,4,9-tetrahydro-1H-carbazol-1-one and 5-bromo-2,3,4,9-tetrahydro-1H-carbazol-1-one as a brown solid (447 mg, 19%); LC/MS RT=3.84 (M+H⁺: 264/266).

Example 5a. Preparation of 7-bromo-2,3,4,9-tetrahydro-1H-carbazol-1-amine

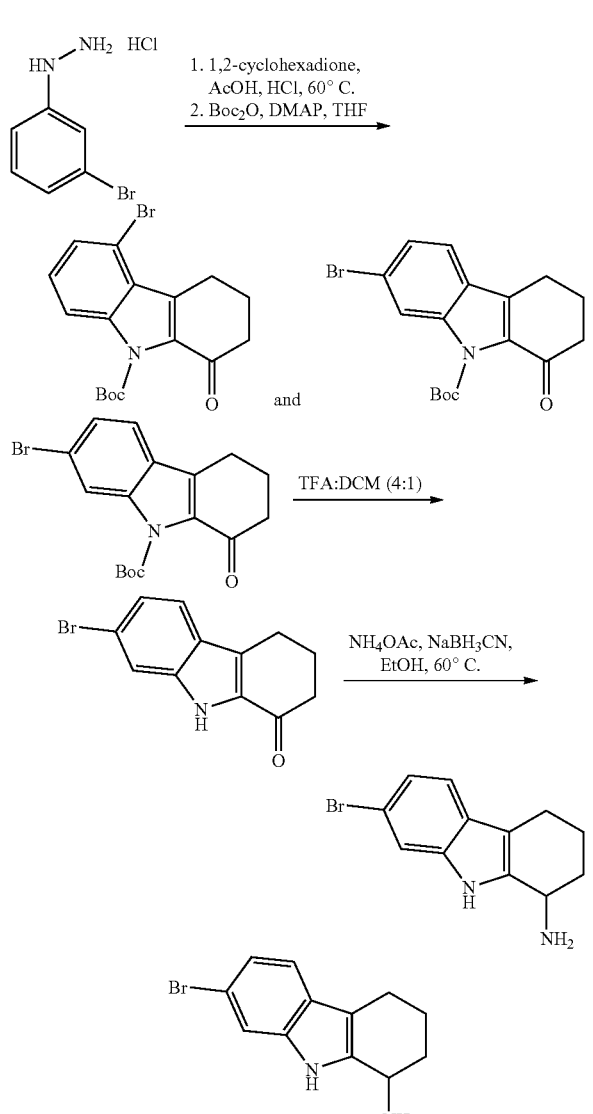

7-Bromo-2,3,4,9-tetrahydro-1H-carbazol-1-amine

7-Bromo-2,3,4,9-tetrahydro-1H-carbazol-1-one (100 mg, 0.38 mmol), ammonium acetate (293 mg, 3.80 mmol) and sodium cyanoborohydride (119 mg, 1.90 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH₄OH) to give the product as a white solid (58 mg, 57%); $^1$H NMR (300 MHz) (DMSO-d$_6$) δ 10.86 (bs, 1H), 7.44-7.27 (m, 3H), 7.03 (m, 1H), 6.67 (m, 1H), 3.90 (m, 1H), 2.48 (m, 2H), 1.97 (m, 2H), 1.74 (m, 1H), 1.52 (m, 1H); LC/MS RT=2.76 (M−H⁻: 263/265).

The requisite intermediates were prepared as follows:
Step 1)

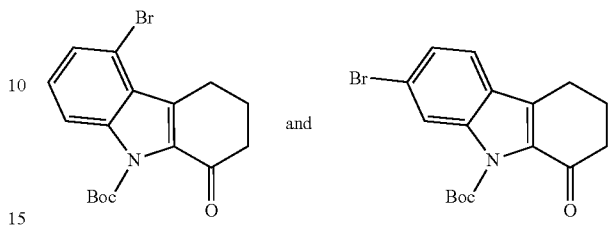

Tert-Butyl 5-bromo-1-oxo-1,2,3,4-tetrahydro-9H-carbazole-9-carboxylate and tert-Butyl 7-bromo-1-oxo-1,2,3,4-tetrahydro-9H-carbazole-9-carboxylate A solution of (3-bromophenyl)hydrazine hydrochloride (2.00 g, 8.92 mmol) in methanol (20 mL) was added slowly at 60° C. to a mixture of 1,2-cyclohexanedione (2.0 g, 17.84 mmol) in acetic acid (44 mL) and concentrated hydrochloric acid (16 mL). The reaction mixture was stirred for 3 hours at 60° C. The reaction mixture was diluted with ethyl acetate, and it was washed with water followed by brine. The organic layer was dried over sodium sulfate, and it was concentrated under reduced pressure. The residue was purified on an ISCO chromatograph (0-20% ethyl acetate/hexane) to give a mixture of two regioisomers, 5-bromo-2,3,4,9-tetrahydro-1H-carbazol-1-one and 7-bromo-2,3,4,9-tetrahydro-1H-carbazol-1-one, as a white solid (1.11 g, 47%).

To a solution of a mixture of two regioisomers (1.10 g, 4.16 mmol) in tetrahydrofuran (25 mL), boc anhydride (1.82 g, 8.32 mmol) and DAMP (508 mg, 4.16 mmol) were added. The reaction mixture was stirred for 5 hours. The reaction mixture was diluted with ethyl acetate, and it was washed with saturated ammonium chloride followed by brine. The organic layer was dried over sodium sulfate, and it was concentrated under reduced pressure. The residue was purified on an ISCO chromatograph (0-5% ethyl acetate/hexane) to give tert-butyl 5-bromo-1-oxo-1,2,3,4-tetrahydro-9H-carbazole-9-carboxylate as a white solid (220 mg, 14%). $^1$H NMR (300 MHz) (CDCl$_3$) δ 8.00 (d, J=9 Hz, 1H), 7.41 (d, J=8 Hz, 1H), 7.29-7.24 (m, 1H), 3.38 (t, J=6 Hz, 2H), 2.64 (t, J=7 Hz, 2H), 2.26-2.20 (m, 2H), 1.62 (s, 9H), along with tert-butyl 7-bromo-1-oxo-1,2,3,4-tetrahydro-9H-carbazole-9-carboxylate as a white solid (655 mg, 44%). $^1$H NMR (300 MHz) (CDCl$_3$) δ 8.23 (d, J=2 Hz, 1H), 7.40 (d, J=8 Hz, 1H), 7.33 (d, J=8 Hz, 1H), 4.58 (bs, 1H), 2.90 (t, J=6 Hz, 2H), 2.64 (t, J=6 Hz, 2H), 2.26-2.17 (m, 2H), 1.60 (s, 9H).

Step 2)

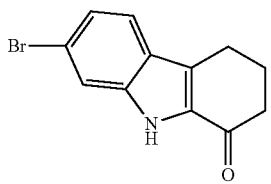 [SMILES: O=C1CCCc2c1[nH]c1cc(Br)ccc21]

7-Bromo-2,3,4,9-tetrahydro-1H-carbazol-1-one

To a solution of tert-butyl 7-bromo-1-oxo-1,2,3,4-tetrahydro-9H-carbazole-9-carboxylate (655 mg, 0.82 mmol) in dichloromethane (20 mL), trifluoroacetic acid (5 mL) was added. The reaction mixture was stirred for an hour at room temperature. After removal of solvent, the mixture was diluted with ethyl acetate, and it was washed with 10% sodium hydroxide and brine. The organic layer was dried over sodium sulfate, and it was concentrated under reduced pressure to product as a white solid (219 mg, 45%); $^1$H NMR (300 MHz) (CDCl$_3$) δ 8.83 (bs, 1H), 7.59 (d, J=2 Hz, 1H), 7.52 (d, J=9 Hz, 1H), 7.33-7.24 (m, 1H), 2.99 (t, J=6 Hz, 2H), 2.65 (t, J=6 Hz, 2H), 2.31-2.23 (m, 2H).

Example 5b. Preparation of 5-bromo-2,3,4,9-tetrahydro-1H-carbazol-1-amine

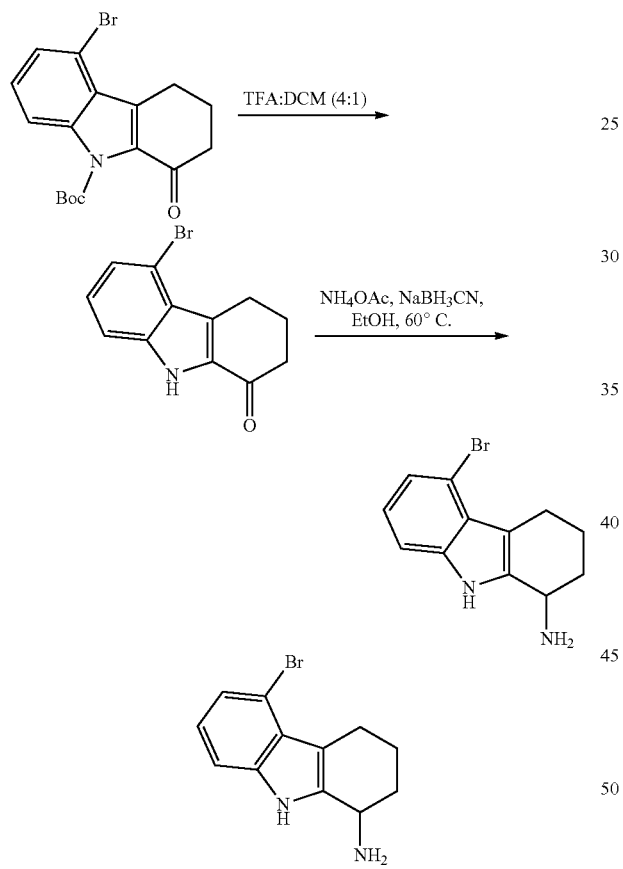

5-Bromo-2,3,4,9-tetrahydro-1H-carbazol-1-amine

5-Bromo-2,3,4,9-tetrahydro-1H-carbazol-1-one (100 mg, 0.38 mmol), ammonium acetate (293 mg, 3.80 mmol) and sodium cyanoborohydride (119 mg, 1.90 mmol) were dissolved in ethanol (5 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (57 mg, 56%); $^1$H NMR (300 MHz) (DMSO-d$_6$) δ 11.06 (bs, 1H), 7.28-7.26 (m, 1H), 7.06-7.03 (m, 1H), 6.88-6.86 (m, 1H), 3.89 (m, 1H), 2.94 (m, 2H), 1.96 (m, 2H), 1.66 (m, 1H), 1.50 (m, 1H); LC/MS RT=2.78 (M−H$^−$: 263/265).

The requisite intermediate was prepared as follows:
Step 1)

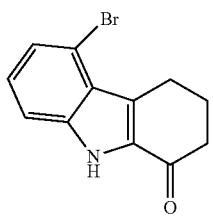 [SMILES: O=C1CCCc2c1[nH]c1cccc(Br)c21]

5-Bromo-2,3,4,9-tetrahydro-1H-carbazol-1-one

To a solution of tert-butyl 5-bromo-1-oxo-1,2,3,4-tetrahydro-9H-carbazole-9-carboxylate (317 mg, 0.87 mmol) in dichloromethane (10 mL), trifluoroacetic acid (2.5 mL) was added. The reaction mixture was stirred for an hour at room temperature. After removal of solvent, the mixture was diluted with ethyl acetate, and it was washed with 10% sodium hydroxide and brine. The organic layer was dried over sodium sulfate, and it was concentrated under reduced pressure to product as a white solid (144 mg, 63%); $^1$H NMR (300 MHz) (CDCl$_3$) δ 8.92 (bs, 1H), 7.36-7.29 (m, 2H), 7.16 (t, J=8 Hz, 1H), 3.40 (t, J=6 Hz, 2H), 2.64 (t, J=7 Hz, 2H), 2.31-2.23 (m, 2H).

Example 6

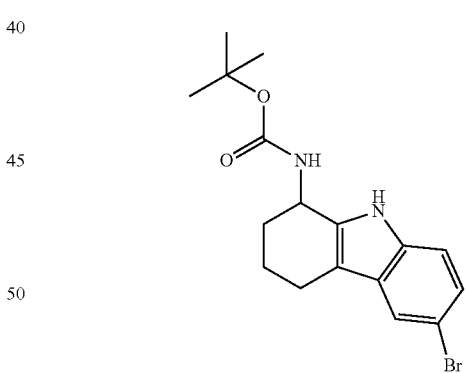

Tert-Butyl (6-bromo-2,3,4,9-tetrahydro-1H-carbazol-1-yl)carbamate

6-Bromo-2,3,4,9-tetrahydro-1H-carbazol-1-amine (150 mg, 0.57 mmol) and boc anhydride (249 mg, 1.14 mmol) were dissolved in THF (10 mL). The reaction mixture was stirred for 3 hours at room temperature. After removal of the solvent, the reaction mixture was diluted with ethyl acetate. The organic layer was washed with water and brine, and it was dried over Na$_2$SO$_4$. The organic layer was concentrated under reduced pressure. The residue was purified on an ISCO chromatograph (0-50% ethyl acetate/hexane) to give the product as a colorless oil (192 mg, 92%); ¹H NMR (300 MHz) (CDCl₃) δ 8.83 (s, 1H), 7.59 (s, 1H), 7.26-7.16 (m, 2H), 4.85 (t, J=6 Hz, 1H), 2.68-2.62 (m, 2H), 2.19-2.15 (m, 1H), 1.92-1.73 (m, 3H), 1.49 (s, 9H); LC/MS RT=4.32 (M+H⁺: 365/367).

Example 7

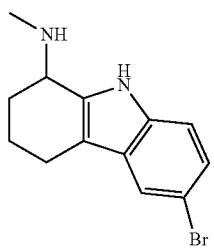 [SMILES: CNC1CCCc2c1[nH]c1ccc(Br)cc21]

6-Bromo-N-methyl-2,3,4,9-tetrahydro-1H-carbazol-1-amine tert-Butyl (6-bromo-2,3,4,9-tetrahydro-1H-carbazol-1-yl) carbamate (90 mg, 0.25 mmol) and lithium aluminum hydride (38 mg, 1.00 mmol) were dissolved in THF (5 mL). The reaction mixture was stirred for an hour at 50° C. The reaction was stopped by adding 0.5 mL water, and it was dried over Na₂SO₄. It was filtered through a celite, pad, and the filtrate was concentrated under reduced pressure. The residue was purified on an ISCO chromatograph (0-10% methanol/dichloromethane+0.1% NH₄OH) to give the product as a colorless oil (44 mg, 64%); ¹H NMR (300 MHz) (CDCl₃) δ 8.64 (s, 1H), 7.58 (s, 1H), 7.26-7.13 (m, 2H), 3.87 (t, J=6 Hz, 1H), 2.67-2.63 (m, 2H), 2.51 (s, 3H), 2.28-2.19 (m, 1H), 2.06-1.99 (m, 1H), 1.82-1.62 (m, 2H); LC/MS RT=2.68 (M−H⁻: 277/279).

Example 8

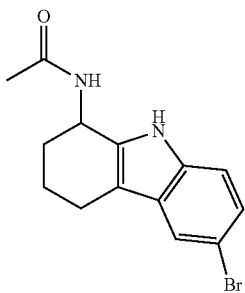 [SMILES: CC(=O)NC1CCCc2c1[nH]c1ccc(Br)cc21]

N-(6-Bromo-2,3,4,9-tetrahydro-1H-carbazol-1-yl) acetamide

6-Bromo-2,3,4,9-tetrahydro-1H-carbazol-1-amine (75 mg, 0.28 mmol) and acetyl chloride (30 μL, 0.42 mmol), and DIPEA (98 μL, 0.56 mmol) were dissolved in dichloromethane (5 mL). The reaction mixture was stirred for 5 hours at room temperature. The reaction mixture was diluted with ethyl acetate. The organic layer was washed with water and brine, and it was dried over Na₂SO₄. The organic layer was concentrated under reduced pressure. The residue was purified on an ISCO chromatograph (0-100% ethyl acetate/hexane) to give the product as a colorless oil (86 mg, 100%); ¹H NMR (300 MHz) (CDCl₃) δ 8.89 (s, 1H), 7.59 (s, 1H), 7.26-7.15 (m, 2H), 5.82 (bs, 1H), 5.13-5.07 (m, 1H), 2.70-2.61 (m, 2H), 2.26-2.20 (m, 1H), 2.04 (s, 3H), 1.95-1.84 (m, 2H), 1.83-1.76 (m, 1H); LC/MS RT=3.63 (M+H⁺: 307/309).

Example 9

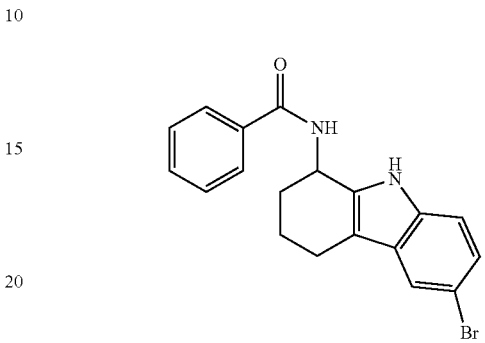

N-(6-Bromo-2,3,4,9-tetrahydro-1H-carbazol-1-yl) benzamide

6-Bromo-2,3,4,9-tetrahydro-1H-carbazol-1-amine (75 mg, 0.28 mmol) and benzoyl chloride (48 μL, 0.42 mmol), and DIPEA (98 μL, 0.56 mmol) were dissolved in dichloromethane (5 mL). The reaction mixture was stirred for 5 hours at room temperature. The reaction mixture was diluted with ethyl acetate. The organic layer was washed with water and brine, and it was dried over Na₂SO₄. The organic layer was concentrated under reduced pressure. The residue was purified on an ISCO chromatograph (0-30% ethyl acetate/hexane) to give the product as a white solid (43 mg, 42%); ¹H NMR (300 MHz) (CDCl₃) δ 9.01 (s, 1H), 7.77 (d, J=8 Hz, 2H), 7.61 (s, 1H), 7.54-7.49 (m, 1H), 7.43 (t, J=7 Hz, 2H), 7.26-7.16 (m, 2H), 6.44 (d, J=6 Hz, 1H), 5.34-5.32 (m, 1H), 2.72-2.70 (m, 2H), 2.31-2.26 (m, 1H), 1.97 (m, 2H), 1.66 (m, 1H); LC/MS RT=4.08 (M+H⁺: 369/371).

Example 10a and Example 10b

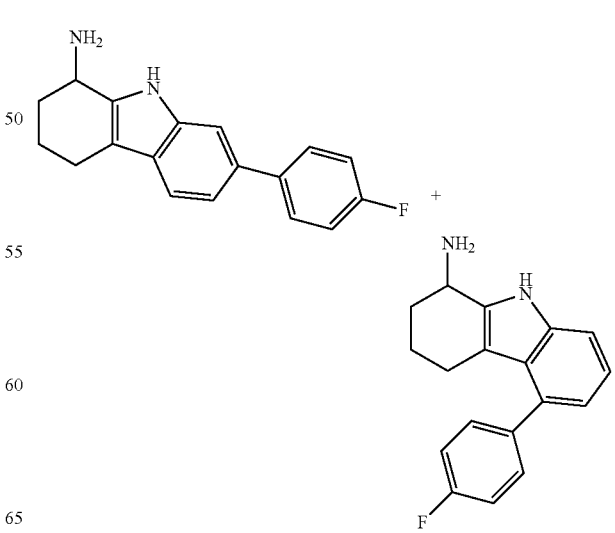

7-(4-fluorophenyl)-2,3,4,9-tetrahydro-1H-carbazol-1-amine (10a) and 5-(4-fluorophenyl)-2,3,4,9-tetrahydro-1H-carbazol-1-amine (10b)

A mixture of 7-bromo-2,3,4,9-tetrahydro-1H-carbazol-1-amine and 5-bromo-2,3,4,9-tetrahydro-1H-carbazol-1-amine (90 mg, 0.34 mmol), (4-fluorophenyl)boronic acid (143 mg, 1.02 mmol), Pd(PPh$_3$)$_4$ (35 mg, 0.03 mmol) and K$_2$CO$_3$ (141 mg, 1.02 mmol) were dissolved in a mixture of dioxane (3 mL) and water (1 mL). The air was evacuated from the reaction flask and replaced with N$_2$. The reaction mixture was then refluxed overnight. Reaction was monitored by TLC and stopped once the starting material was consumed. The reaction mixture was diluted with ethyl acetate, and it was washed with water followed by brine. The organic layer was dried over Na$_2$SO$_4$ and was concentrated under reduced pressure. The residue was purified on an ISCO chromatograph (0-10% methanol/dichloromethane+0.1% NH$_4$OH) to give a mixture of 7-(4-fluorophenyl)-2,3,4,9-tetrahydro-1H-carbazol-1-amine and 5-(4-fluorophenyl)-2,3,4,9-tetrahydro-1H-carbazol-1-amine as a white solid (24 mg, 25%); LC/MS RT=2.79 (M−H$^-$: 279).

Example 11

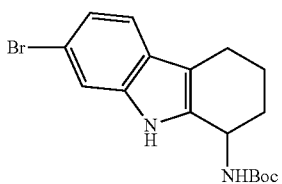

Tert-Butyl (7-bromo-2,3,4,9-tetrahydro-1H-carbazol-1-yl)carbamate

7-Bromo-2,3,4,9-tetrahydro-1H-carbazol-1-amine (25 mg, 0.09 mmol) and boc anhydride (39 mg, 0.18 mmol) were dissolved in THF (1 mL). The reaction mixture was stirred for 3 hours at room temperature. After removal of solvent, the reaction mixture was diluted with ethyl acetate. The organic layer was washed with water and brine, and it was dried over sodium sulfate. The organic layer was concentrated under reduced pressure. The residue was purified on an ISCO chromatograph (0-50% ethyl acetate/hexane) to give the product as colorless oil (32 mg, 97%); $^1$H NMR (300 MHz) (CDCl$_3$) δ 8.78 (bs, 1H), 7.46 (s, 1H), 7.33 (d, J=9 Hz, 1H), 7.17 (d, J=8 Hz, 1H), 4.85-4.84 (m, 2H), 2.70-2.64 (m, 2H), 2.20-2.16 (m, 1H), 1.91-1.85 (m, 2H), 1.81-1.77 (m, 1H), 1.48 (s, 9H); LC/MS RT=4.45 (M+H$^+$: 365/367).

Example 12

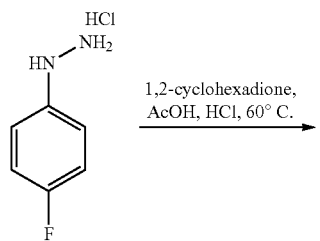

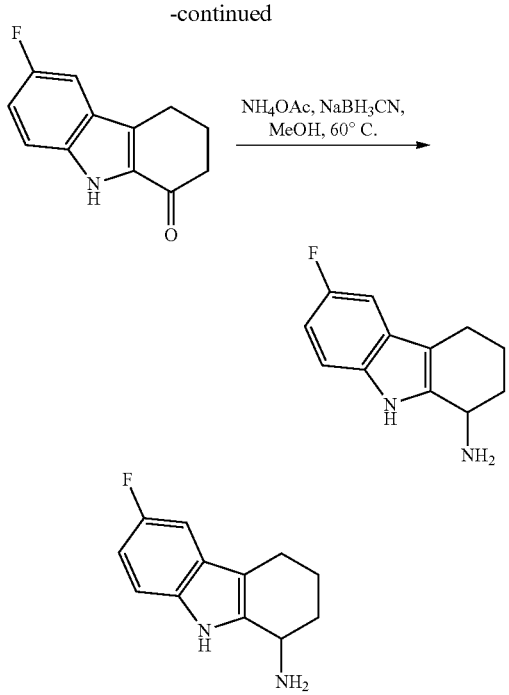

6-Fluoro-2,3,4,9-tetrahydro-1H-carbazol-1-amine

6-Fluoro-2,3,4,9-tetrahydro-1H-carbazol-1-one (400 mg, 1.97 mmol), ammonium acetate (1.52 g, 19.7 mmol) and sodium cyanoborohydride (619 mg, 9.85 mmol) were dissolved in methanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (120 mg, 30%); $^1$H NMR (300 MHz) (DMSO-d$_6$) δ 10.76 (bs, 1H), 7.24 (dd, J=9 Hz, J=5 Hz, 1H), 7.06 (d, J=10 Hz, 1H), 6.83-6.77 (m, 1H), 3.90 (m, 1H), 1.97 (m, 4H), 1.73-1.46 (m, 2H); LC/MS RT=2.46 (M−H$^-$: 203).

The requisite intermediate was prepared as follows:
Step 1)

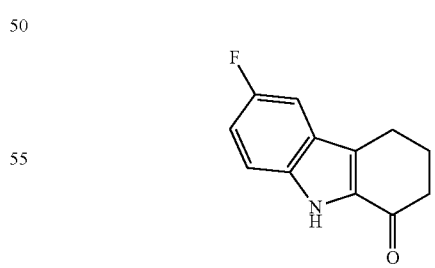

6-Fluoro-2,3,4,9-tetrahydro-1H-carbazol-1-one

A solution of 4-fluorophenylhydrazine hydrochloride (1.45 g, 8.92 mmol) in methanol (20 mL) was added slowly at 60° C. to a mixture of 1,2-cyclohexanedione (2.0 g, 17.84 mmol) in acetic acid (44 mL) and concentrated hydrochloric acid (16 mL). The reaction mixture was stirred for 3 hours at 60° C. The reaction mixture was diluted with ethyl acetate, and it was washed with water followed by brine. The organic layer was dried over sodium sulfate, and it was concentrated under reduced pressure. The residue was purified on an ISCO chromatograph (0-50% ethyl acetate/hexane) to give the product as a beige solid (700 mg, 39%); $^1$H NMR (300 MHz) (CDCl$_3$) δ 9.33 (bs, 1H), 7.39 (dd, J=9 Hz, J=4 Hz, 1H), 7.28 (dd, J=9 Hz, J=2 Hz, 1H), 7.13 (td, J=9 Hz, J=2 Hz, 1H), 2.97 (t, J=6 Hz, 2H), 2.67 (t, J=6 Hz, 2H), 2.31-2.25 (m, 2H).

Example 13

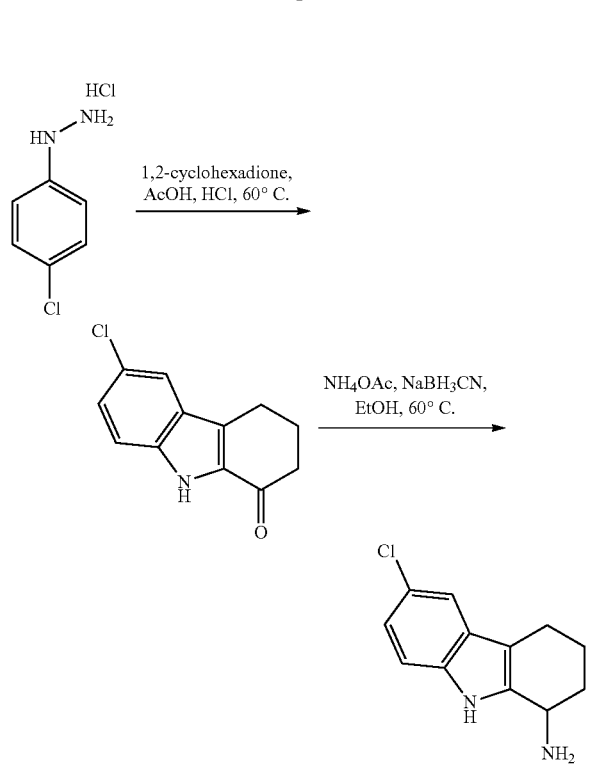

6-Chloro-2,3,4,9-tetrahydro-1H-carbazol-1-amine

6-Chloro-2,3,4,9-tetrahydro-1H-carbazol-1-one (100 mg, 0.45 mmol), ammonium acetate (347 mg, 4.50 mmol) and sodium cyanoborohydride (141 mg, 2.25 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (57 mg, 58%); (DMSO-d$_6$) δ 10.89 (bs, 1H), 7.34 (d, J=2 Hz, 1H), 7.27 (d, J=9 Hz, 1H), 6.97 (dd, J=9 Hz, J=2 Hz, 1H), 6.68 (bs, 2H), 3.93-3.87 (m, 1H), 2.61-2.54 (m, 2H), 2.03-1.90 (m, 2H), 1.73-1.66 (m, 1H), 1.55-1.46 (m, 1H); LC/MS RT=2.55 (M−H$^−$: 219/221).

The requisite intermediate was prepared as follows:

Step 1)

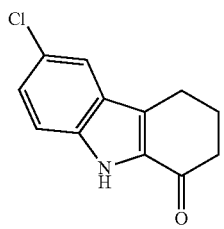 [SMILES: O=C1CCCc2c1[nH]c1ccc(Cl)cc21]

6-Chloro-2,3,4,9-tetrahydro-1H-carbazol-1-one

A solution of 4-chlorophenylhydrazine hydrochloride (1.60 g, 8.92 mmol) in methanol (30 mL) was added slowly at 60° C. to a mixture of 1,2-cyclohexanedione (2.0 g, 17.84 mmol) in acetic acid (44 mL) and concentrated hydrochloric acid (16 mL). The reaction mixture was stirred for 3 hours at 60° C. The reaction mixture was diluted with ethyl acetate, and it was washed with water followed by brine. The organic layer was dried over sodium sulfate, and it was concentrated under reduced pressure. The residue was purified on an ISCO chromatograph (0-50% ethyl acetate/hexane) to give the product as a beige solid (700 mg, 39%); $^1$H NMR (300 MHz) (CDCl$_3$) δ 8.89 (bs, 1H), 7.63 (s, 1H), 7.37-7.30 (m, 2H), 2.97 (t, J=6 Hz, 2H), 2.67 (t, J=6 Hz, 2H), 2.32-2.23 (m, 2H).

Example 14

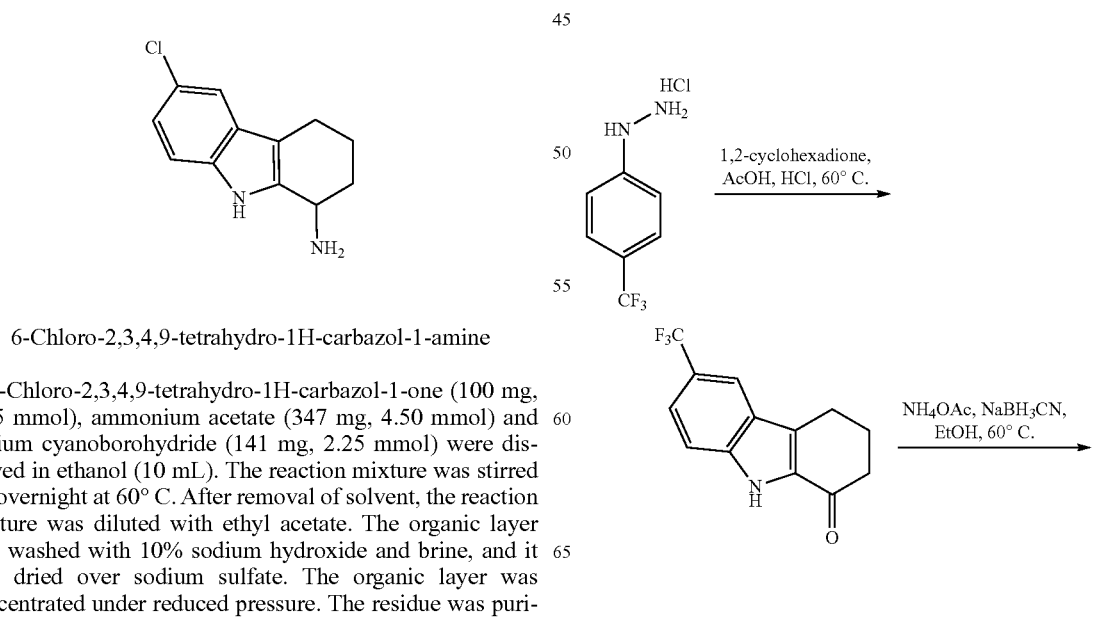

-continued

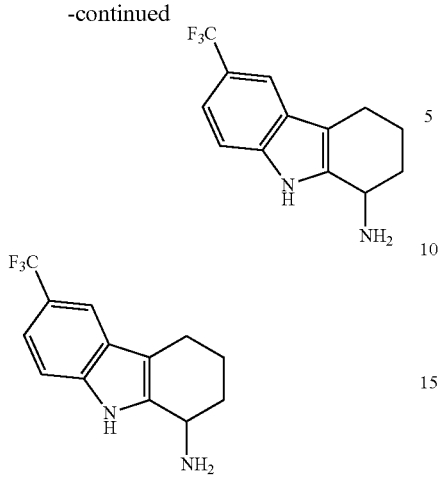

6-(Trifluoromethyl)-2,3,4,9-tetrahydro-1H-carbazol-1-amine

6-Trifluoromethyl-2,3,4,9-tetrahydro-1H-carbazol-1-one (125 mg, 0.49 mmol), ammonium acetate (378 mg, 4.50 mmol) and sodium cyanoborohydride (154 mg, 2.45 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (53 mg, 42%); $^1$H NMR (300 MHz) (DMSO-d$_6$) δ 11.19 (bs, 1H), 7.69 (s, 1H), 7.45 (d, J=9 Hz, 1H), 7.28 (d, J=8 Hz, 1H), 3.94 (m, 1H), 2.62 (m, 2H), 2.04-2.00 (m, 2H), 1.68 (m, 1H), 1.55 (m, 1H); LC/MS RT=2.65 (M−H$^-$: 253). The requisite intermediate was prepared as follows:
Step 1)

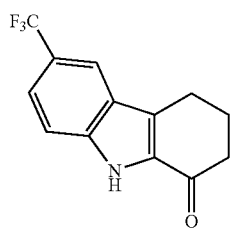 [SMILES: O=C1CCCc2c1[nH]c1ccc(C(F)(F)F)cc21]

6-(Trifluoromethyl)-2,3,4,9-tetrahydro-1H-carbazol-1-one

A solution of 4-trifluoromethylphenylhydrazine hydrochloride (1.90 g, 8.92 mmol) in methanol (20 mL) was added slowly at 60° C. to a mixture of 1,2-cyclohexanedione (2.0 g, 17.84 mmol) in acetic acid (44 mL) and concentrated hydrochloric acid (16 mL). The reaction mixture was stirred for 3 hours at 60° C. The reaction mixture was diluted with ethyl acetate, and it was washed with water followed by brine. The organic layer was dried over sodium sulfate, and it was concentrated under reduced pressure. The residue was purified on an ISCO chromatograph (0-20% ethyl acetate/hexane) to give the product as a white solid (197 mg, 9%); $^1$H NMR (300 MHz) (CDCl$_3$) δ 10.02 (bs, 1H), 7.97 (s, 1H), 7.57 (m, 2H), 3.05 (m, 2H), 2.72 (m, 2H), 2.33-2.29 (m, 2H).

Example 15

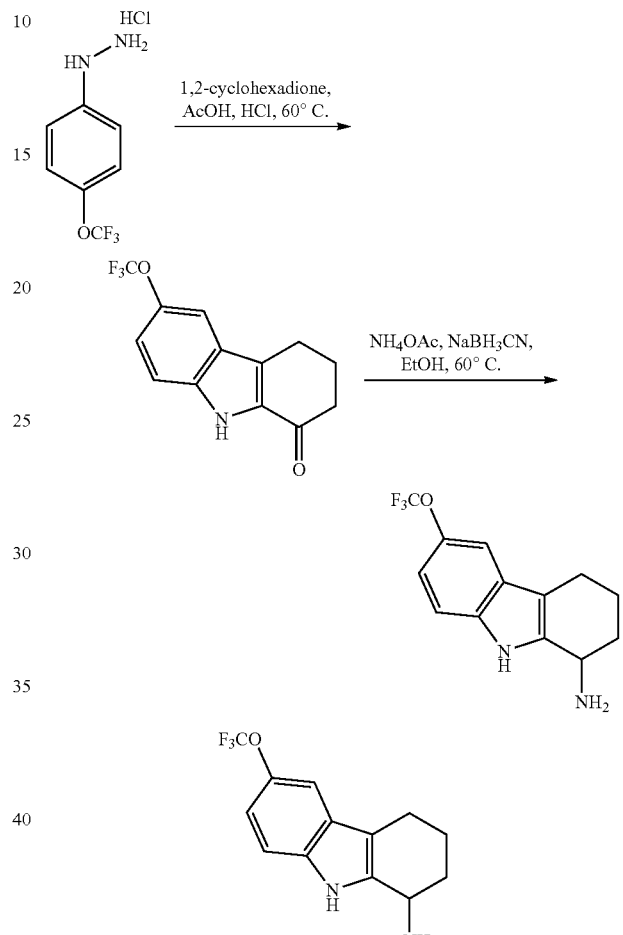

6-(Trifluoromethoxy)-2,3,4,9-tetrahydro-1H-carbazol-1-amine

6-Trifluoromethoxy-2,3,4,9-tetrahydro-1H-carbazol-1-one (135 mg, 0.50 mmol), ammonium acetate (385 mg, 5.00 mmol) and sodium cyanoborohydride (157 mg, 2.50 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (65 mg, 48%); $^1$H NMR (300 MHz) (CDCl$_3$) δ 8.66 (bs, 1H), 7.31-7.26 (m, 2H), 7.01 (d, J=8 Hz, 1H), 4.08 (m, 1H), 2.68 (m, 2H), 2.21-2.19 (m, 1H), 2.02 (m, 1H), 1.83 (m, 1H), 1.66-1.59 (m, 1H); LC/MS RT=2.67 (M−H$^-$: 269).

111

The requisite intermediate was prepared as follows:

Step 1)

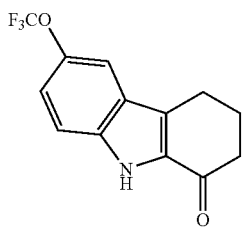 [SMILES: O=C1CCCc2c1[nH]c1ccc(OC(F)(F)F)cc21]

6-(Trifluoromethoxy)-2,3,4,9-tetrahydro-1H-carbazol-1-one

A solution of 4-trifluoromethoxyphenylhydrazine hydrochloride (2.04 g, 8.92 mmol) in methanol (20 mL) was added slowly at 60° C. to a mixture of 1,2-cyclohexanedione (2.0 g, 17.84 mmol) in acetic acid (44 mL) and concentrated hydrochloric acid (16 mL). The reaction mixture was stirred for 3 hours at 60° C. The reaction mixture was diluted with ethyl acetate, and it was washed with water followed by brine. The organic layer was dried over sodium sulfate, and it was concentrated under reduced pressure. The residue was purified on an ISCO chromatograph (0-20% ethyl acetate/hexane) to give the product as a white solid (135 mg, 6%); $^1$H NMR (300 MHz) (CDCl$_3$) δ 8.80 (bs, 1H), 7.51 (s, 1H), 7.40 (d, J=9 Hz, 1H), 7.26-7.23 (m, 1H), 3.00 (t, J=6 Hz, 2H), 2.67 (t, J=6 Hz, 2H), 2.30-2.26 (m, 2H).

Example 16

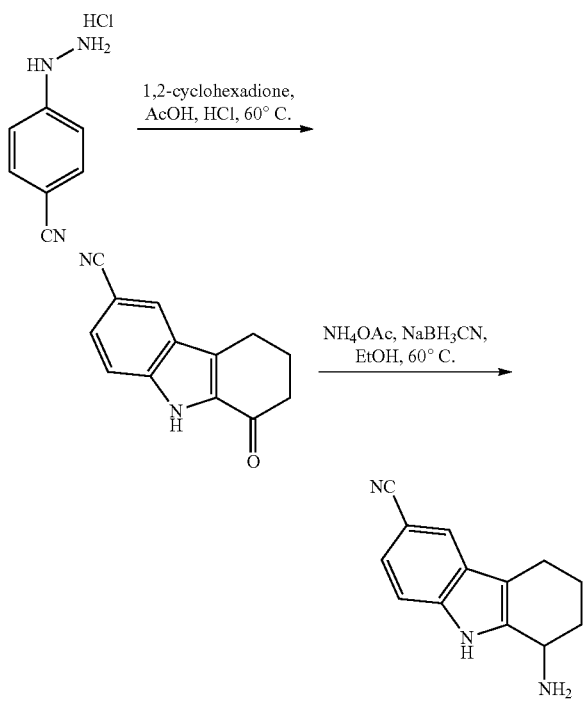

112

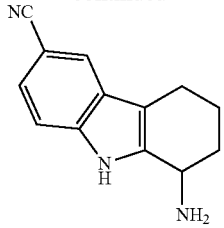

1-Amino-2,3,4,9-tetrahydro-1H-carbazole-6-carbonitrile

1-Oxo-2,3,4,9-tetrahydro-1H-carbazole-6-carbonitrile (105 mg, 0.50 mmol), ammonium acetate (385 mg, 5.00 mmol) and sodium cyanoborohydride (157 mg, 2.50 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (75 mg, 71%); $^1$H NMR (300 MHz) (CDCl$_3$) δ 7.79 (s, 1H), 7.35-7.26 (m, 2H), 4.07 (m, 1H), 2.67 (m, 2H), 2.18-1.63 (m, 4H); LC/MS RT=2.37 (M−H$^-$: 210).

The requisite intermediate was prepared as follows:

Step 1)

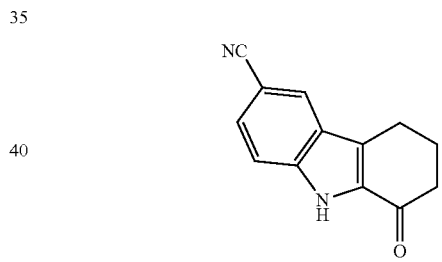

1-Oxo-2,3,4,9-tetrahydro-1H-carbazole-6-carbonitrile

A solution of 4-hydrazineylbenzonitrile hydrochloride (2.04 g, 8.92 mmol) in methanol (20 mL) was added slowly at 60° C. to a mixture of 1,2-cyclohexanedione (2.0 g, 17.84 mmol) in acetic acid (44 mL) and concentrated hydrochloric acid (16 mL). The reaction mixture was stirred for 3 hours at 60° C. The reaction mixture was diluted with ethyl acetate, and it was washed with water followed by brine. The organic layer was dried over sodium sulfate, and it was concentrated under reduced pressure. The residue was purified on an ISCO chromatograph (0-20% ethyl acetate/hexane) to give the product as a brown solid (130 mg, 7%); $^1$H NMR (300 MHz) (CDCl$_3$) δ 9.15 (bs, 1H), 8.05 (s, 1H), 7.58 (dd, J=9 Hz, J=2 Hz, 1H), 7.49 (d, J=8 Hz, 1H), 3.03 (t, J=6 Hz, 2H), 2.70 (t, J=6 Hz, 2H), 2.35-2.29 (m, 2H).

Example 17

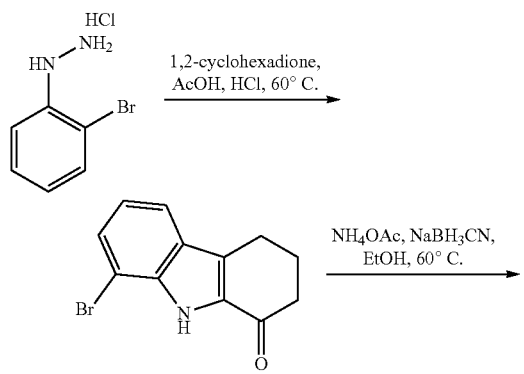

8-Bromo-2,3,4,9-tetrahydro-1H-carbazol-1-amine

8-Bromo-2,3,4,9-tetrahydro-1H-carbazol-1-one (100 mg, 0.38 mmol), ammonium acetate (293 mg, 3.80 mmol) and sodium cyanoborohydride (119 mg, 1.90 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (59 mg, 58%); $^1$H NMR (300 MHz) (DMSO-d$_6$) δ 10.78 (bs, 1H), 7.35 (d, J=8 Hz, 1H), 7.20 (d, J=8 Hz, 1H), 6.87 (t, J=8 Hz, 1H), 3.94 (m, 1H), 2.55-2.48 (m, 2H), 1.97-1.91 (m, 2H), 1.73-1.66 (m, 1H), 1.54-1.51 (m, 1H); LC/MS RT=2.56 (M-NH$_3$$^+$: 248/250).

The requisite intermediate was prepared as follows:
Step 1)

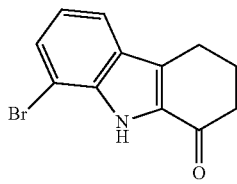 [SMILES: O=C1CCCc2c1[nH]c1c(Br)cccc21]

8-Bromo-2,3,4,9-tetrahydro-1H-carbazol-1-one

A solution of (2-bromophenyl)hydrazine hydrochloride (2.00 g, 8.92 mmol) in methanol (20 mL) was added slowly at 60° C. to a mixture of 1,2-cyclohexanedione (2.0 g, 17.84 mmol) in acetic acid (44 mL) and concentrated hydrochloric acid (16 mL). The reaction mixture was stirred for 3 hours at 60° C. The reaction mixture was diluted with ethyl acetate, and it was washed with water followed by brine. The organic layer was dried over sodium sulfate, and it was concentrated under reduced pressure. The residue was purified on an ISCO chromatograph (0-30% ethyl acetate/hexane) to give the product as a white solid (739 mg, 31%); $^1$H NMR (300 MHz) (CDCl$_3$) δ 8.84 (bs, 1H), 7.61 (d, J=8 Hz, 1H), 7.52 (d, J=7 Hz, 1H), 7.05 (t, J=8 Hz, 1H), 3.00 (t, J=6 Hz, 2H), 2.67 (t, J=6 Hz, 2H), 2.32-2.26 (m, 2H).

Example 18

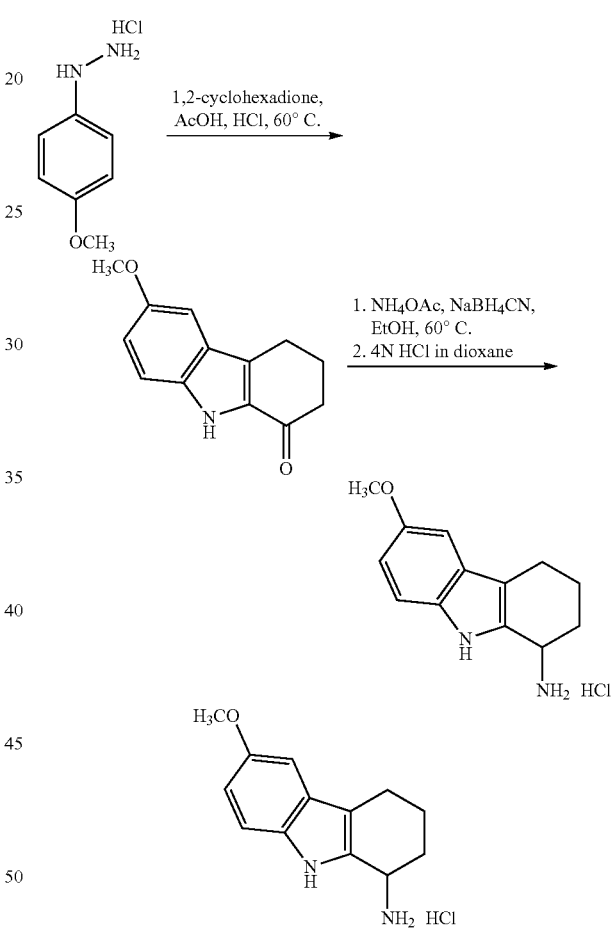

6-Methoxy-2,3,4,9-tetrahydro-1H-carbazol-1-amine Hydrogen Chloride Salt

6-Methoxy-2,3,4,9-tetrahydro-1H-carbazol-1-one (150 mg, 0.70 mmol), ammonium acetate (540 mg, 7.00 mmol) and sodium cyanoborohydride (220 mg, 3.50 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH₄OH) to give the product as a white solid. The product was suspended in 4N hydrochloric acid in dioxane, and the resulted suspension was stirred for 15 minutes at room temperature. After removal of solvent, the resulted residue was suspended in ethyl acetate. The resulted suspension was then filtered to give product of hydrochloric salt as a white solid (75 mg, 42%); ¹H NMR (300 MHz) (DMSO-d₆) δ 10.60 (bs, 1H), 8.41 (bs, 3H), 7.28 (d, J=9 Hz, 1H), 6.92 (s, 1H), 6.75 (d, J=9 Hz, 1H), 4.49 (m, 1H), 3.73 (s, 3H), 2.60 (m, 2H), 2.17-2.12 (m, 1H), 1.99-1.90 (m, 2H), 1.80-1.75 (m, 1H), LC/MS RT=2.36 (M-NH₃⁺: 200).

The requisite intermediate was prepared as follows:

Step 1)

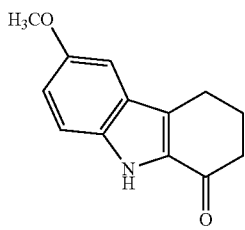

6-Methoxy-2,3,4,9-tetrahydro-1H-carbazol-1-one

A solution of (4-methoxyphenyl)hydrazine hydrochloride (1.56 g, 8.92 mmol) in methanol (20 mL) was added slowly at 60° C. to a mixture of 1,2-cyclohexanedione (2.0 g, 17.84 mmol) in acetic acid (44 mL) and concentrated hydrochloric acid (16 mL). The reaction mixture was stirred for 3 hours at 60° C. The reaction mixture was diluted with ethyl acetate, and it was washed with water followed by brine. The organic layer was dried over sodium sulfate, and it was concentrated under reduced pressure. The residue was purified on an ISCO chromatograph (0-20% ethyl acetate/hexane) to give the product as a brown solid (273 mg, 14%); ¹H NMR (300 MHz) (CDCl₃) δ 8.90 (bs, 1H), 7.34-7.29 (m, 1H), 7.07-6.99 (m, 2H), 3.87 (s, 3H), 3.00-2.96 (m, 2H), 2.65-2.63 (m, 2H), 2.29-2.24 (m, 2H).

Example 19

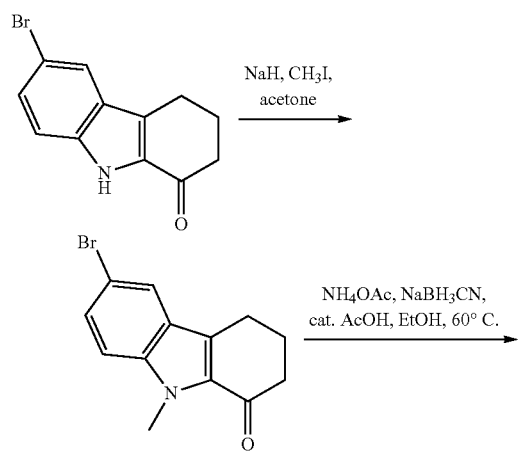

-continued

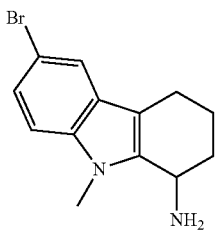

6-Bromo-9-methyl-2,3,4,9-tetrahydro-1H-carbazol-1-amine

The 6-bromo-9-methyl-2,3,4,9-tetrahydro-1H-carbazol-1-one (170 mg, 0.61 mmol), ammonium acetate (470 mg, 6.10 mmol) and sodium cyanoborohydride (192 mg, 3.05 mmol) were dissolved in ethanol (10 mL). Catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH₄OH) to give the product as a white solid (29 mg, 17%); ¹H NMR (300 MHz) (CDCl₃) δ 7.51 (s, 1H), 7.17 (d, J=9 Hz, 1H), 7.07 (d, J=9 Hz, 1H), 4.08 (m, 1H), 3.70 (s, 3H), 2.71 (m, 2H), 1.94-1.86 (m, 4H); LC/MS RT=2.67 (M-NH₃⁺: 262/264).

The requisite intermediate was prepared as follows:

Step 1)

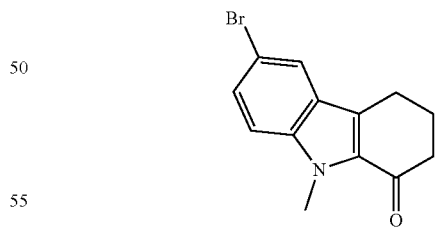

6-Bromo-9-methyl-2,3,4,9-tetrahydro-1H-carbazol-1-one

To a solution of 6-bromo-2,3,4,9-tetrahydro-1H-carbazol-1-one (200 mg, 0.76 mmol) in acetone (10 mL), sodium hydride (60% dispersed in oil, 91 mg, 2.28 mmol) was added at 0° C. After it was stirred for 15 minutes, methyl iodide (0.14 mL, 2.28 mmol) was added. The reaction mixture was stirred for 2 hours. The reaction mixture was diluted with ethyl acetate, and it was washed with water followed by brine. The organic layer was dried over sodium sulfate, and it was concentrated under reduced pressure. The residue was purified on an ISCO chromatograph (0-10% ethyl acetate/hexane) to give the product as a white solid (174 mg, 82%); $^1$H NMR (300 MHz) (CDCl$_3$) δ 7.78 (d, J=2 Hz, 1H), 7.46 (dd, J=9 Hz, J=2 Hz), 7.25-7.22 (m, 1H), 4.05 (s, 3H), 2.97 (t, J=6 Hz, 2H), 2.65 (t, J=6 Hz, 2H), 2.23-2.17 (m, 2H).

Example 20

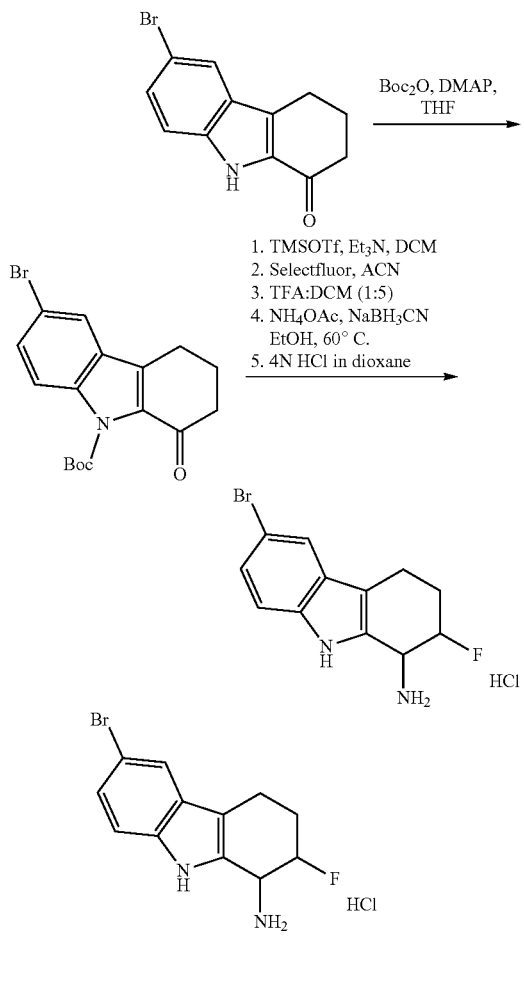 [SMILES: O=C1CCCc2c1[nH]c1ccc(Br)cc21 ; CC(C)(C)OC(=O)n1c2c(c3cc(Br)ccc31)CCCC2=O ; NC1c2[nH]c3ccc(Br)cc3c2CCC1F ; Cl ; NC1c2[nH]c3ccc(Br)cc3c2CCC1F ; Cl]

6-Bromo-2-fluoro-2,3,4,9-tetrahydro-1H-carbazol-1-amine Hydrogen Chloride Salt

To a solution of tert-butyl 6-bromo-1-oxo-1,2,3,4-tetrahydro-9H-carbazole-9-carboxylate (300 mg, 0.82 mmol) in dichloromethane (20 mL), triethylamine (0.57 mL, 4.12 mmol) followed by trimethylsilyl trifluoromethanesulfonate (0.30 mL, 1.64 mmol) were added at 0° C. The reaction mixture was stirred for 0.5 hour at the temperature, and it was then diluted with ethyl acetate. The organic layer was washed with saturated sodium bicarbonate and brine, and it was dried over sodium sulfate. The organic layer was concentrated under reduced pressure, and the crude material was diluted in acetonitrile (20 mL). To the solution, Selectfluor (290 mg, 0.82 mmol) was added, and the reaction mixture was stirred for an hour at room temperature, and it was then diluted with ethyl acetate. The organic layer was washed with saturated sodium bicarbonate and brine, and it was dried over sodium sulfate. The organic layer was concentrated under reduced pressure to provide tert-butyl 6-bromo-2-fluoro-1-oxo-1,2,3,4-tetrahydro-9H-carbazole-9-carboxylate as a crude material.

The crude material was diluted with dichloromethane (20 mL), and trifluoroacetic acid (4 mL) was added. The reaction mixture was stirred for an hour at room temperature. After removal of solvent, the mixture was diluted with ethyl acetate, and it was washed with 10% sodium hydroxide and brine. The organic layer was dried over sodium sulfate, and it was concentrated under reduced pressure to provide 6-bromo-2-fluoro-2,3,4,9-tetrahydro-1H-carbazol-1-one as a crude material.

The crude material (200 mg, 0.71 mmol), ammonium acetate (547 mg, 7.10 mmol) and sodium cyanoborohydride (223 mg, 3.55 mmol) were dissolved in ethanol (20 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid. The product was suspended in 4N hydrochloric acid in dioxane, and the resulted suspension was stirred for 15 minutes at room temperature. After removal of solvent, the resulted residue was suspended in ethyl acetate. The resulted suspension was then filtered to give product of hydrochloric salt as a white solid (38 mg, 17%); (DMSO-d$_6$) δ 11.03 (bs, 1H), 8.78 (bs, 3H), 7.69 (s, 1H), 7.43 (d, J=9 Hz, 1H), 7.26 (d, J=8 Hz, 1H), 5.20-4.74 (m, 1H), 3.55 (m, 1H), 2.76-2.72 (m, 2H), 2.25-2.17 (m, 2H). LC/MS RT=2.63 (M-NH$_3$$^+$: 266/268).

The requisite intermediate was prepared as follows:
Step 1)

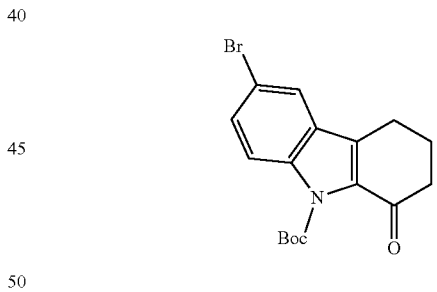

Tert-Butyl 6-bromo-1-oxo-1,2,3,4-tetrahydro-9H-carbazole-9-carboxylate

To a solution of 6-bromo-2,3,4,9-tetrahydro-1H-carbazol-1-one (500 mg, 1.89 mmol) in tetrahydrofuran (20 mL), boc anhydride (825 mg, 3.78 mmol) and DAMP (231 mg, 1.89 mmol) were added. The reaction mixture was stirred for 3 hours. The reaction mixture was diluted with ethyl acetate, and it was washed with saturated ammonium chloride followed by brine. The organic layer was dried over sodium sulfate, and it was concentrated under reduced pressure. The residue was purified on an ISCO chromatograph (0-50% ethyl acetate/hexane) to give the product as a white solid (570 mg, 83%); $^1$H NMR (300 MHz) (CDCl$_3$) δ 7.93 (d, J=9 Hz, 1H), 7.73 (s, 1H), 7.54 (d, J=9 Hz, 1H), 2.92 (t, J=6 Hz, 2H), 2.67 (t, J=6 Hz, 2H), 2.29-2.21 (m, 2H). 1.62 (s, 9H).

Example 21

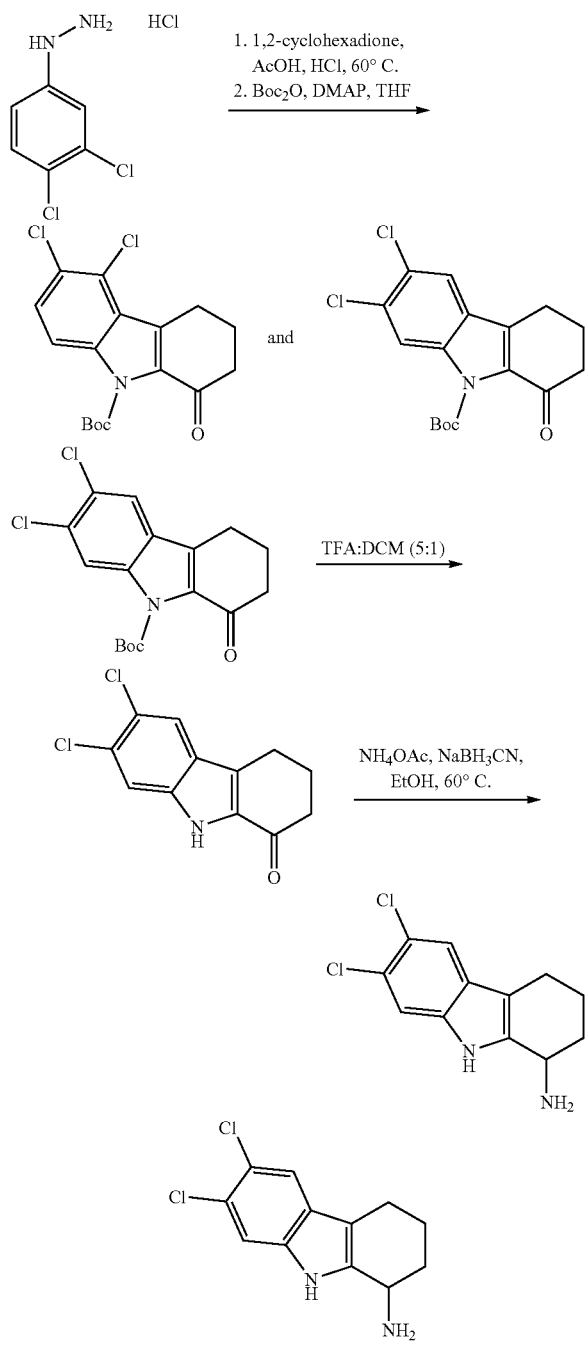

6,7-Dichloro-2,3,4,9-tetrahydro-1H-carbazol-1-amine 6,7-Dichloro-2,3,4,9-tetrahydro-1H-carbazol-1-one (100 mg, 0.39 mmol), ammonium acetate (301 mg, 3.90 mmol) and sodium cyanoborohydride (123 mg, 1.90 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (58 mg, 58%); $^1$H NMR (300 MHz) (DMSO-d$_6$) δ 11.02 (bs, 1H), 7.56 (s, 1H), 7.49 (s, 1H), 3.92-3.88 (m, 1H), 2.55-2.52 (m, 2H), 2.06-1.89 (m, 2H), 1.65-1.61 (m, 1H), 1.55-1.49 (m, 1H); LC/MS RT=2.74 (M–H$^-$: 253/255).

The requisite intermediate was prepared as follows:

Step 1)

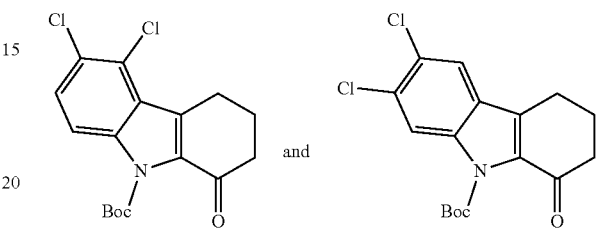

Tert-Butyl 5,6-dichloro-1-oxo-1,2,3,4-tetrahydro-9H-carbazole-9-carboxylate and tert-Butyl 6,7-dichloro-1-oxo-1,2,3,4-tetrahydro-9H-carbazole-9-carboxylate A solution of (3,4-dichlorophenyl)hydrazine hydrochloride (1.90 g, 8.92 mmol) in methanol (20 mL) was added slowly at 60° C. to a mixture of 1,2-cyclohexanedione (2.0 g, 17.84 mmol) in acetic acid (44 mL) and concentrated hydrochloric acid (16 mL). The reaction mixture was stirred for 3 hours at 60° C. The reaction mixture was diluted with ethyl acetate, and it was washed with water followed by brine. The organic layer was dried over sodium sulfate, and it was concentrated under reduced pressure. The residue was purified on an ISCO chromatograph (0-20% ethyl acetate/hexane) to give a mixture of two regioisomers, 5,6-dichloro-2,3,4,9-tetrahydro-1H-carbazol-1-one and 6,7-dichloro-2,3,4,9-tetrahydro-1H-carbazol-1-one, as a white solid (797 mg, 18%).

To a solution of a mixture of two regioisomers (797 mg, 3.14 mmol) in tetrahydrofuran (20 mL), boc anhydride (1.37 g, 6.28 mmol) and DAMP (384 mg, 3.14 mmol) were added. The reaction mixture was stirred for 3 hours. The reaction mixture was diluted with ethyl acetate, and it was washed with saturated ammonium chloride followed by brine. The organic layer was dried over sodium sulfate, and it was concentrated under reduced pressure. The residue was purified on an ISCO chromatograph (0-10% ethyl acetate/hexane) to give tert-butyl 5,6-dichloro-1-oxo-1,2,3,4-tetrahydro-9H-carbazole-9-carboxylate as a white solid (467 mg, 42%). $^1$H NMR (300 MHz) (CDCl$_3$) δ 7.90 (d, J=9 Hz, 1H), 7.47 (d, J=9 Hz, 1H), 3.33 (t, J=6 Hz, 2H), 2.64 (t, J=7 Hz, 2H), 2.29-2.00 (m, 2H), 1.56 (s, 9H), along with tert-butyl 6,7-dichloro-1-oxo-1,2,3,4-tetrahydro-9H-carbazole-9-carboxylate as a white solid (503 mg, 45%). $^1$H NMR (300 MHz) (CDCl$_3$) δ 8.23 (s, 1H), 7.68 (s, 1H), 2.91 (t, J=6 Hz, 2H), 2.67 (t, J=7 Hz, 2H), 2.29-2.21 (m, 2H), 1.62 (s, 9H).

Step 2)

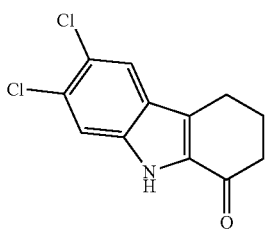 [SMILES: O=C1CCCc2c1[nH]c1cc(Cl)c(Cl)cc21]

6,7-Dichloro-2,3,4,9-tetrahydro-1H-carbazol-1-one

To a solution of tert-butyl 6,7-dichloro-1-oxo-1,2,3,4-tetrahydro-9H-carbazole-9-carboxylate (500 mg, 1.41 mmol) in dichloromethane (20 mL), trifluoroacetic acid (4 mL) was added. The reaction mixture was stirred for an hour at room temperature. After removal of solvent, the mixture was diluted with ethyl acetate, and it was washed with 10% sodium hydroxide and brine. The organic layer was dried over sodium sulfate, and it was concentrated under reduced pressure to product as a white solid (328 mg, 92%); $^1$H NMR (300 MHz) (DMSO-$d_6$) δ 11.89 (bs, 1H), 8.00 (s, 1H), 7.56 (s, 1H), 2.92 (t, J=6 Hz, 2H), 2.55 (t, J=6 Hz, 2H), 2.16-2.06 (m, 2H).

Example 22

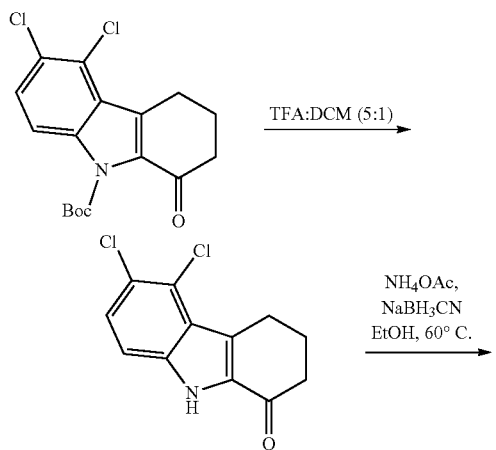

5,6-Dichloro-2,3,4,9-tetrahydro-1H-carbazol-1-amine 5,6-Dichloro-2,3,4,9-tetrahydro-1H-carbazol-1-one (100 mg, 0.39 mmol), ammonium acetate (301 mg, 3.90 mmol) and sodium cyanoborohydride (123 mg, 1.90 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (45 mg, 45%); $^1$H NMR (300 MHz) (CD$_3$OD) δ 7.18 (d, J=8 Hz, 1H), 7.09 (d, J=9 Hz, 1H), 4.08-4.03 (m, 1H), 3.04-2.98 (m, 2H), 2.15-1.99 (m, 2H), 1.83-1.75 (m, 1H), 1.72-1.65 (m, 1H); LC/MS RT=2.72 (M−H⁻: 253/255).

The requisite intermediate was prepared as follows:

Step 1)

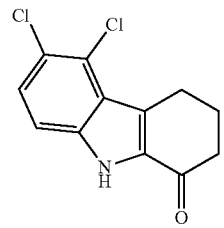 [SMILES: O=C1CCCc2c1[nH]c1ccc(Cl)c(Cl)c21]

5,6-Dichloro-2,3,4,9-tetrahydro-1H-carbazol-1-one

To a solution of tert-butyl 5,6-dichloro-1-oxo-1,2,3,4-tetrahydro-9H-carbazole-9-carboxylate (450 mg, 1.27 mmol) in dichloromethane (20 mL), trifluoroacetic acid (4 mL) was added. The reaction mixture was stirred for an hour at room temperature. After removal of solvent, the mixture was diluted with ethyl acetate, and it was washed with 10% sodium hydroxide and brine. The organic layer was dried over sodium sulfate, and it was concentrated under reduced pressure to product as a white solid (270 mg, 84%); $^1$H NMR (300 MHz) (CDCl$_3$) δ 7.90 (d, J=9 Hz, 1H), 7.47 (d, J=10 Hz, 1H), 3.33 (t, J=6 Hz, 2H), 2.64 (t, J=6 Hz, 2H), 2.24 (t, J=6 Hz, 2H).

Example 23

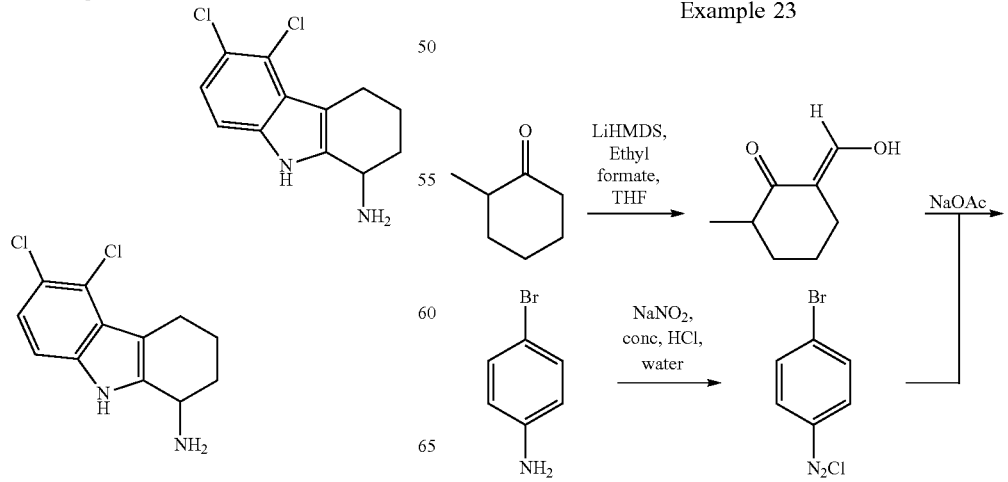

-continued

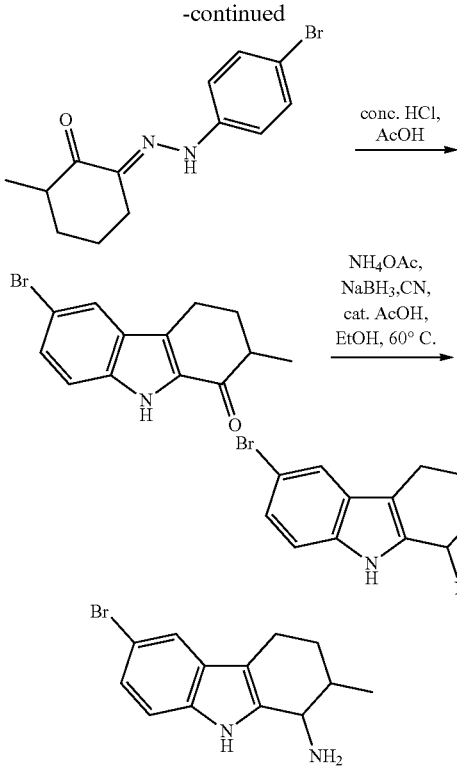

6-Bromo-2-methyl-2,3,4,9-tetrahydro-1H-carbazol-1-amine

6-Bromo-2-methyl-2,3,4,9-tetrahydro-1H-carbazol-1-one (100 mg, 0.36 mmol), ammonium acetate (277 mg, 3.60 mmol) and sodium cyanoborohydride (113 mg, 1.80 mmol) were dissolved in ethanol (10 mL). Catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (26 mg, 26%); $^1$H NMR (300 MHz) (CD$_3$OD) δ 7.49 (s, 1H), 7.20 (d, J=8 Hz, 1H), 7.12 (d, J=8 Hz, 1H), 3.99-3.64 (m, 1H), 2.76-2.57 (m, 2H), 2.10-1.98 (m, 1H), 1.79-1.78 (m, 1H), 1.68-1.56 (m, 1H), 1.27-1.09 (m, 3H); LC/MS RT=2.74 (M-H$^-$: 277/279).

The requisite intermediates were prepared as follows:
Step 1)

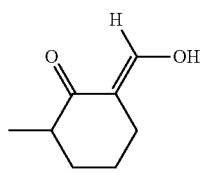

(E)-2-(Hydroxymethylene)-6-methylcyclohexan-1-one

2-Methylcylohexan-1-one (2.64 mL, 20.00 mmol) was dissolved in anhydrous tetrahydrofuran (20 mL), and it was cooled to 0° C. A solution of 1.0 M LiHMDS in tetrahydrofuran (24 mL, 24.00 mmol) was slowly added, and it was stirred for 5 minutes at the temperature. Ethyl formate (1.94 mL, 24.00 mmol) was slowly added, and it was stirred for 2 hours at the temperature. The reaction mixture was diluted with ethyl acetate, and it was washed with 6N HCl and brine. The organic layer was dried over sodium sulfate, and it was concentrated under reduced pressure. The residue was purified on an ISCO chromatograph (0-20% ethyl acetate/hexane) to give product as colorless oil (1.28 g, 46%); $^1$H NMR (300 MHz) (CDCl$_3$) δ 8.59 (d, J=4 Hz, 1H), 2.48-2.41 (m, 1H), 2.33-2.29 (m, 2H), 1.89-1.70 (m, 2H), 1.62-1.49 (m, 1H), 1.42-1.31 (m, 1H), 1.19 (d, J=7 Hz, 3H).

Step 2)

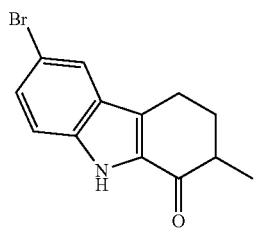 [SMILES: CC1CCc2c([nH]c3ccc(Br)cc23)C1=O]

6-Bromo-2-methyl-2,3,4,9-tetrahydro-1H-carbazol-1-one

To a solution of 4-bromoaniline (1.57 g, 9.13 mmol) in concentrated hydrochloric acid (2 mL), a solution of sodium nitrite (630 mg, 9.13 mmol) in water (4 mL) was added slowly at 0° C. The mixture was stirred for 30 minutes at the temperature. In a separate round bottom flask, (E)-2-(hydroxymethylene)-6-methylcyclohexan-1-one (1.28 g, 9.13 mmol) was dissolve in methanol (12 mL). To the mixture, a solution of sodium acetate (1.28 g, 15.58 mmol) in water (5 mL) was added slowly at 0° C. The mixture was stirred for 20 minutes at the temperature. Then, the freshly prepared diazonium salt solution was slowly added. The mixture was stirred for additional 30 minutes at the temperature. The reaction mixture was diluted with ethyl acetate, and it was washed with saturated sodium bicarbonate followed by brine. The organic layer was dried over sodium sulfate, and it was concentrated under reduced pressure to provide intermediate, (E)-2-(2-(4-bromophenyl)hydrazineylidene)-6-methylcyclohexan-1-one, as a crude material.

The crude material was dissolved in a mixture of concentrated hydrochloric acid (2 mL) and acetic acid (8 mL), and it was heated at 130° C. for 30 minutes. After it was cooled to room temperature, it was diluted with ethyl acetate. The organic layer was washed with 10% sodium hydroxide followed by brine. The organic layer was dried over sodium sulfate, and it was concentrated under reduced pressure. The residue was purified on an ISCO chromatograph (0-20% ethyl acetate/hexane) to give the product as a white solid (529 mg, 21%); $^1$H NMR (300 MHz) (CDCl$_3$) δ 8.97 (bs, 1H), 7.79 (s, 1H), 7.43 (dd, J=9 Hz, J=2 Hz, 1H), 7.30 (d, J=9 Hz, 1H), 3.07-2.89 (m, 2H), 2.73-2.67 (m, 1H), 2.36-2.29 (m, 1H), 2.05-1.95 (m, 1H), 1.30 (d, J=7 Hz, 3H).

Example 24

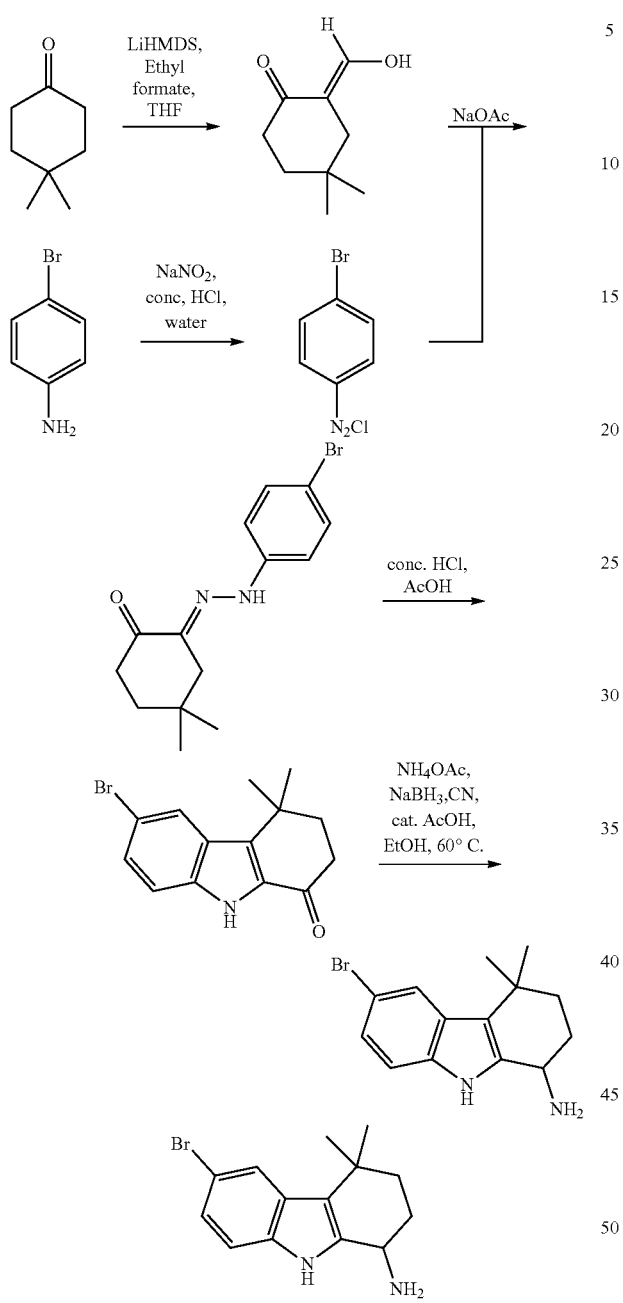

6-Bromo-4,4-dimethyl-2,3,4,9-tetrahydro-1H-carbazol-1-amine

6-Bromo-4,4-dimethyl-2,3,4,9-tetrahydro-1H-carbazol-1-one (90 mg, 0.31 mmol), ammonium acetate (239 mg, 3.10 mmol) and sodium cyanoborohydride (97 mg, 1.54 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (24 mg, 26%); $^1$H NMR (300 MHz) (CD$_3$OD) δ 7.70 (s, 1H), 7.20 (d, J=9 Hz, 1H), 7.11 (d, J=8 Hz, 1H), 4.01 (m, 1H), 2.10 (m, 1H), 1.93-1.67 (m, 3H), 1.40 (s, 3H), 1.38 (s, 3H); LC/MS RT=2.76 (M–H$^-$: 291/293).

The requisite intermediates were prepared as follows:
Step 1)

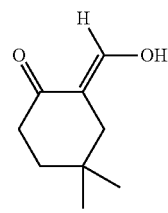

(E)-2-(Hydroxymethylene)-4,4-dimethylcyclohexan-1-one 4,4-Dimethylcyclohexan-1-one (3.39 mL, 25.00 mmol) was dissolved in anhydrous tetrahydrofuran (25 mL), and it was cooled to 0° C. A solution of 1.0 M LiHMDS in tetrahydrofuran (30 mL, 30.00 mmol) was slowly added, and it was stirred for 5 minutes at the temperature. Ethyl formate (2.42 mL, 30.00 mmol) was slowly added, and it was stirred for 2 hours at the temperature. The reaction mixture was diluted with ethyl acetate, and it was washed with 6N HCl and brine. The organic layer was dried over sodium sulfate, and it was concentrated under reduced pressure. The residue was purified on an ISCO chromatograph (0-20% ethyl acetate/hexane) to give product as colorless oil (1.78 g, 46%); $^1$H NMR (300 MHz) (CDCl$_3$) δ 8.57 (d, J=3 Hz, 1H), 2.38 (t, J=7 Hz, 2H), 2.11 (s, 2H), 1.47 (t, J=7 Hz, 2H), 0.98 (s, 6H).

Step 2)

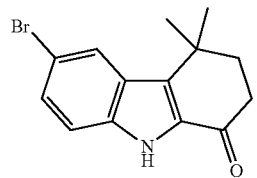 [SMILES: CC1(C)CCC(=O)c2[nH]c3ccc(Br)cc3c21]

6-Bromo-4,4-dimethyl-2,3,4,9-tetrahydro-1H-carbazol-1-one

To a solution of 4-bromoaniline (1.99 g, 11.54 mmol) in concentrated hydrochloric acid (5 mL), a solution of sodium nitrite (808 mg, 11.54 mmol) in water (10 mL) was added slowly at 0° C. The mixture was stirred for 30 minutes at the temperature. In a separate round bottom flask, (E)-2-(hydroxymethylene)-4,4-dimethylcyclohexan-1-one (1.78 g, 11.54 mmol) was dissolve in methanol (12 mL). To the mixture, a solution of sodium acetate (2.37 g, 28.85 mmol) in water (5 mL) was added slowly at 0° C. The mixture was stirred for 20 minutes at the temperature. Then, the freshly prepared diazonium salt solution was slowly added. The mixture was stirred for additional an hour at the temperature. The formed suspension was filtered to provide intermediate,

127

(E)-2-(2-(4-bromophenyl)hydrazineylidene)-4,4-dimethyl-cyclohexan-1-one, as a crude material.

The crude material was dissolved in a mixture of concentrated hydrochloric acid (2 mL) and acetic acid (8 mL), and it was heated at 130° C. for an hour. After it was cooled to room temperature, it was diluted with ethyl acetate. The organic layer was washed with 10% sodium hydroxide followed by brine. The organic layer was dried over sodium sulfate, and it was concentrated under reduced pressure. The residue was purified on an ISCO chromatograph (0-50% ethyl acetate/hexane) to give the product as a white solid (90 mg, 9%); $^1$H NMR (300 MHz) (CDCl$_3$) δ 8.69 (bs, 1H), 7.99 (s, 1H), 7.42 (dd, J=9 Hz, J=2 Hz, 1H), 7.29 (d, J=9 Hz, 1H), 2.68 (t, J=6 Hz, 2H), 2.10 (t, J=6 Hz, 2H), 1.56 (s, 3H), 1.54 (s, 3H).

Example 25

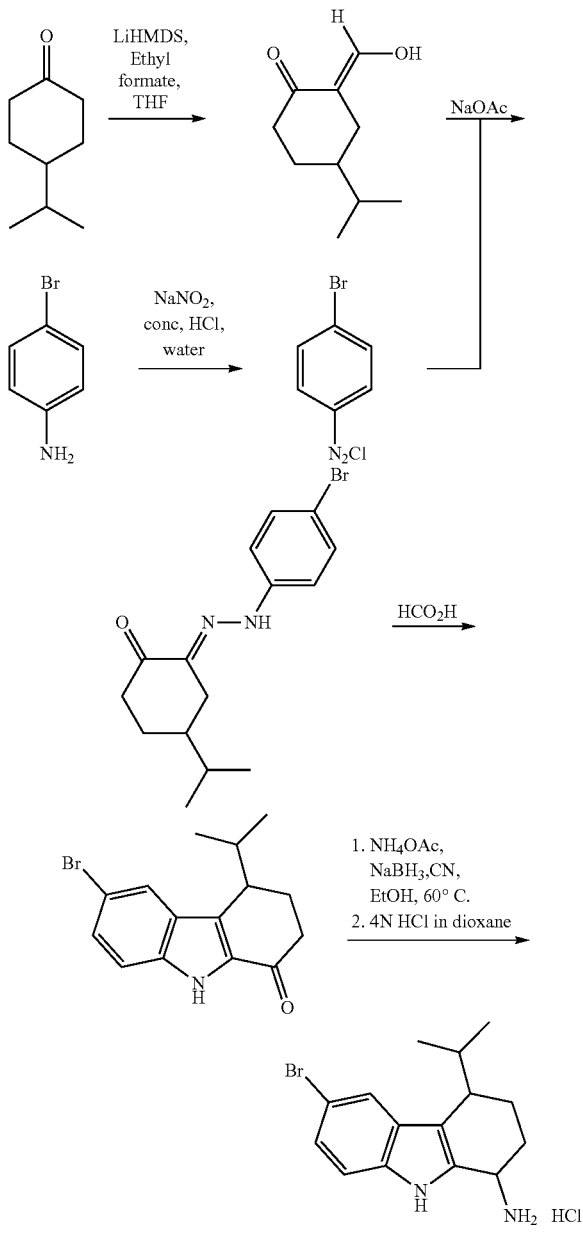

128

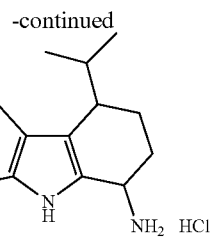

6-Bromo-4-isopropyl-2,3,4,9-tetrahydro-1H-carbazol-1-amine Hydrogen Chloride Salt 6-Bromo-4-isopropyl-2,3,4,9-tetrahydro-1H-carbazol-1-one (100 mg, 0.33 mmol), ammonium acetate (254 mg, 3.30 mmol) and sodium cyanoborohydride (104 mg, 1.65 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid. The product was suspended in 4N hydrochloric acid in dioxane, and the resulted suspension was stirred for 15 minutes at room temperature. After removal of solvent, the resulted residue was suspended in ethyl acetate. The resulted suspension was then filtered to give product of hydrochloric salt as a white solid (30 mg, 27%); $^1$H NMR (300 MHz) (CDCl$_3$) δ 8.89 (m, 1H), 7.74-7.66 (m, 1H), 7.23-7.15 (m, 2H), 6.38 (bs, 3H), 4.54 (m, 1H), 2.82 (m, 1H), 2.53-2.08 (m, 3H), 1.93-1.71 (m, 2H), 1.07-1.01 (m, 3H), 0.75-0.71 (m, 3H); LC/MS RT=2.99 (M-NH$_3^+$: 290/292).

The requisite intermediates were prepared as follows:
Step 1)

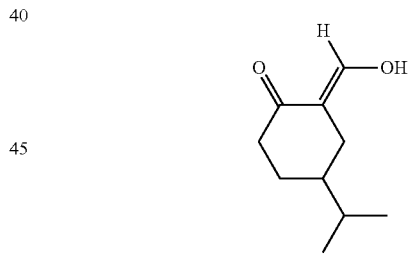

(E)-2-(Hydroxymethylene)-4-isopropylcyclohexan-1-one

4-Isopropylcyclohexan-1-one (1.10 mL, 7.13 mmol) was dissolved in anhydrous tetrahydrofuran (10 mL), and it was cooled to 0° C. A solution of 1.0 M LiHMDS in tetrahydrofuran (7.84 mL, 7.84 mmol) was slowly added, and it was stirred for 5 minutes at the temperature. Ethyl formate (0.63 mL, 7.84 mmol) was slowly added, and it was stirred for 2 hours at the temperature. The reaction mixture was diluted with ethyl acetate, and it was washed with 6N HCl and brine. The organic layer was dried over sodium sulfate, and it was concentrated under reduced pressure. The residue was purified on an ISCO chromatograph (0-20% ethyl acetate/hexane) to give product as colorless oil (667 mg, 56%); $^1$H NMR (300 MHz) (CDCl$_3$) δ 8.66 (d, J=3 Hz, 1H), 2.42-2.36

(m, 3H), 2.08-2.00 (m, 1H), 1.85-1.80 (m, 1H), 1.60-1.52 (m, 1H), 1.39-1.24 (m, 2H), 0.93 (d, J=8 Hz, 6H).
Step 2)

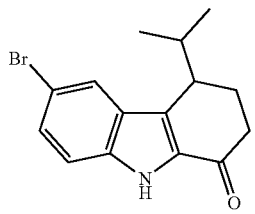 [SMILES: CC(C)C1CCC(=O)c2[nH]c3ccc(Br)cc3c21]

6-Bromo-4-isopropyl-2,3,4,9-tetrahydro-1H-carbazol-1-one

To a solution of 4-bromoaniline (677 mg, 3.96 mmol) in concentrated hydrochloric acid (1 mL), a solution of sodium nitrite (273 mg, 3.96 mmol) in water (3 mL) was added slowly at 0° C. The mixture was stirred for 30 minutes at the temperature. In a separate round bottom flask, (E)-2-(hydroxymethylene)-4-isopropylcyclohexan-1-one (667 mg, 3.96 mmol) was dissolve in methanol (6 mL). To the mixture, a solution of sodium acetate (812 mg, 9.90 mmol) in water (2.5 mL) was added slowly at 0° C. The mixture was stirred for 20 minutes at the temperature. Then, the freshly prepared diazonium salt solution was slowly added. The mixture was stirred for additional an hour at the temperature. The reaction mixture was diluted with ethyl acetate, and it was washed with saturated sodium bicarbonate followed by brine. The organic layer was dried over sodium sulfate, and it was concentrated under reduced pressure to provide intermediate, (E)-2-(2-(4-bromophenyl)hydrazineylidene)-4-isopropylcyclohexan-1-one, as a crude material.

The crude material was dissolved in formic acid (3 mL), and it was heated at 100° C. for 3 hours. After it was cooled to room temperature, it was diluted with ethyl acetate. The organic layer was washed with 10% sodium hydroxide followed by brine. The organic layer was dried over sodium sulfate, and it was concentrated under reduced pressure. The residue was purified on an ISCO chromatograph (0-10% ethyl acetate/hexane) to give the product as a white solid (100 mg, 8%); $^1$H NMR (300 MHz) (CDCl$_3$) δ 9.57 (bs, 1H), 7.86 (d, J=2 Hz, 1H), 7.42 (dd, J=9 Hz, J=2 Hz, 1H), 7.35 (d, J=9 Hz, 1H), 3.01-2.97 (m, 1H), 2.86-2.76 (m, 1H), 2.61-2.51 (m, 1H), 2.35-2.22 (m, 3H), 1.06 (d, J=7 Hz, 3H), 1.01 (d, J=7 Hz, 3H).

Example 26

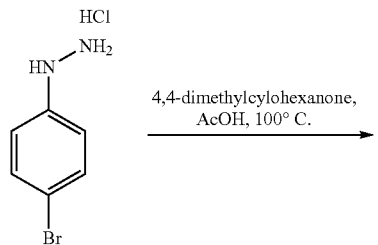

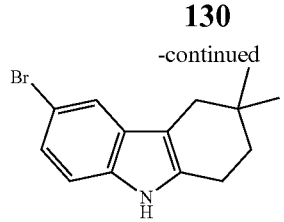

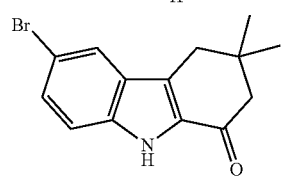

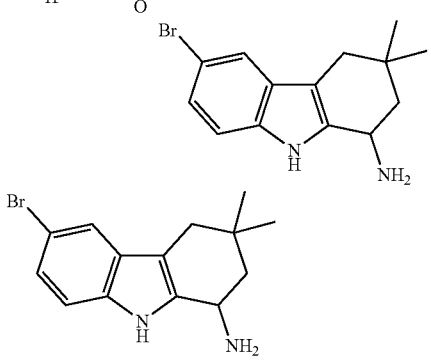

6-Bromo-3,3-dimethyl-2,3,4,9-tetrahydro-1H-carbazol-1-amine

6-Bromo-3,3-dimethyl-2,3,4,9-tetrahydro-1H-carbazol-1-one (52 mg, 0.18 mmol), ammonium acetate (139 mg, 1.80 mmol) and sodium cyanoborohydride (57 mg, 0.90 mmol) were dissolved in ethanol (10 mL). Catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (9 mg, 17%); $^1$H NMR (300 MHz) (CD$_3$OD) δ 7.54 (d, J=2 Hz, 1H), 7.27 (d, J=8 Hz, 1H), 7.18 (dd, J=8 Hz, J=2 Hz, 1H), 4.38-4.32 (m, 1H), 2.52 (s, 2H), 2.12-2.03 (m, 1H), 1.66-1.54 (m, 1H), 1.22 (s, 3H), 0.97 (s, 3H); LC/MS RT=3.11 (M-NH$_3^+$: 276/278).
The requisite intermediates were prepared as follows:
Step 1)

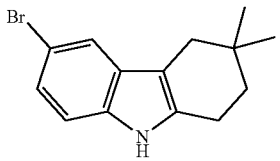 [SMILES: CC1(C)CCc2[nH]c3ccc(Br)cc3c2C1]

6-Bromo-3,3-dimethyl-2,3,4,9-tetrahydro-1H-carbazole

To a solution of 4,4-dimethylcyclohexanone (0.68 mL, 5.00 mmol) in acetic acid (10 mL), (4-bromophenyl)hydrazine hydrochloride (1.12 g, 5.00 mmol) was added. The reaction mixture was heated at 100° C. for overnight. After it was cooled to room temperature, it was diluted with ethyl acetate. The organic layer was washed with saturated sodium bicarbonate followed by brine. The organic layer was dried over sodium sulfate, and it was concentrated under reduced pressure. The residue was purified on an ISCO chromatograph (0-20% ethyl acetate/hexane) to give the product as yellow oil (1.39 g, 100%); $^1$H NMR (300 MHz) (CDCl$_3$) δ 7.74 (bs, 1H), 7.55 (s, 1H), 7.19 (dd, J=9 Hz, J=2 Hz, 1H), 7.13 (d, J=8 Hz, 1H), 2.73-2.69 (m, 1H), 2.44 (s, 2H), 2.37-2.32 (m, 1H), 1.69-1.64 (m, 2H), 1.04 (s, 6H).

Step 2)

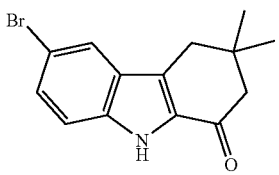 [SMILES: CC1(C)CC(=O)c2[nH]c3ccc(Br)cc3c2C1]

6-Bromo-3,3-dimethyl-2,3,4,9-tetrahydro-1H-carbazol-1-one

To a solution of 6-bromo-3,3-dimethyl-2,3,4,9-tetrahydro-1H-carbazole (300 mg, 1.08 mmol) in dioxane (10 mL), selenium dioxide (360 mg, 3.24 mmol) was added. The reaction mixture was refluxed for overnight at 100° C. After the mixture was cooled to room temperature, it was passed through Celite. The filtrate was concentrated under reduced pressure, and the residue was purified on ISCO chromatograph (0 to 20% ethyl acetate/hexane) to give the product as a yellow solid (52 mg, 16%); $^1$H NMR (300 MHz) (CDCl$_3$) δ 9.14 (bs, 1H), 7.78 (d. J=2 Hz, 1H), 7.43 (dd, J=9 Hz, J=2 Hz, 1H), 7.32 (d, J=9 Hz, 1H), 2.84 (s, 2H), 2.52 (s, 2H), 1.16 (s, 6H).

Example 27

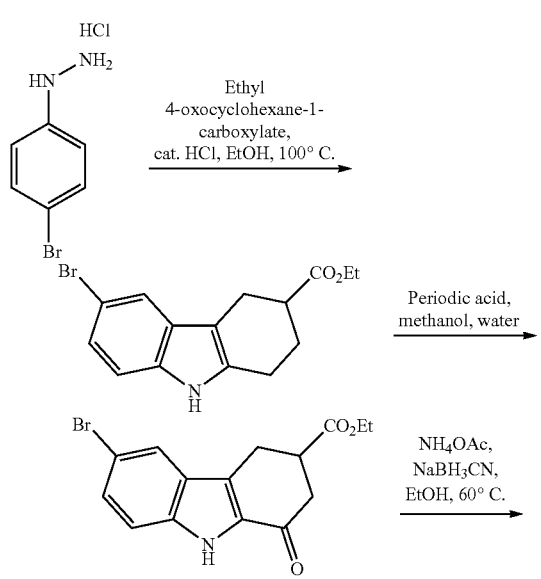

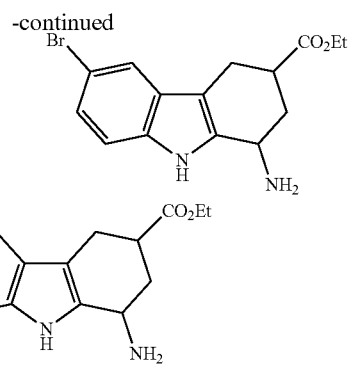

Ethyl 1-amino-6-bromo-2,3,4,9-tetrahydro-1H-carbazole-3-carboxylate

Ethyl 6-bromo-1-oxo-2,3,4,9-tetrahydro-1H-carbazole-3-carboxylate (100 mg, 0.30 mmol), ammonium acetate (231 mg, 3.00 mmol) and sodium cyanoborohydride (94 mg, 1.50 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (67 mg, 66%); $^1$H NMR (300 MHz) (DMSO-d$_6$) δ 10.87 (bs, 1H), 7.59 (s, 1H), 7.34 (d, J=9 Hz, 1H), 7.15 (d, J=8 Hz, 1H), 5.37 (bs, 2H), 4.28 (m, 1H), 4.14-4.11 (m, 2H), 2.97-2.88 (m, 2H), 2.66-2.62 (m, 2H), 1.73-1.64 (m, 1H), 1.22 (t, J=6 Hz, 3H); LC/MS RT=2.86 (M–H$^−$: 335/337).

The requisite intermediates were prepared as follows:

Step 1)

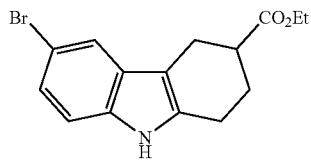 [SMILES: CCOC(=O)C1CCc2[nH]c3ccc(Br)cc3c2C1]

Ethyl 6-bromo-2,3,4,9-tetrahydro-1H-carbazole-3-carboxylate

To a solution ethyl 4-oxocyclohexane-1-carboxylate (1.59 mL, 10.00 mmol) in ethanol (20 mL), (4-bromophenyl)hydrazine hydrochloride (2.24 g, 10.00 mmol) was added. Catalytic amount of concentrated hydrochloric acid solution was added. The reaction mixture was heated at 100° C. for overnight. After it was cooled to room temperature, it was diluted with ethyl acetate. The organic layer was washed with 10% sodium hydroxide followed by brine. The organic layer was dried over sodium sulfate, and it was concentrated under reduced pressure to provide the product as a yellow solid (2.65 g, 82%); $^1$H NMR (300 MHz) (CDCl$_3$) δ 7.80 (bs, 1H), 7.58 (s, 1H), 7.20 (d, J=9 Hz, 1H), 7.13 (d, J=8 Hz, 1H), 4.19 (q, J=7 Hz, 2H), 3.02-2.82 (m, 5H), 2.32-2.28 (m, 1H), 2.10-2.02 (m, 1H), 1.29 (t, J=7 Hz, 3H).

Step 2)

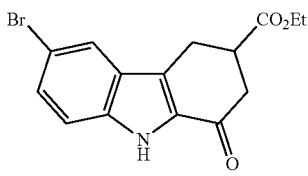 [SMILES: CCOC(=O)C1CC(=O)c2[nH]c3ccc(Br)cc3c2C1]

Ethyl 6-bromo-1-oxo-2,3,4,9-tetrahydro-1H-carbazole-3-carboxylate

To a solution of periodic acid (707 mg, 3.10 mmol) in a mixture of methanol (5 mL) and water (5 mL), a solution of ethyl 6-bromo-2,3,4,9-tetrahydro-1H-carbazole-3-carboxylate (500 mg, 1.55 mmol) in a methanol (5 mL) was added dropwise at 0° C. The reaction mixture was stirred for an hour at the temperature, and it was stirred an additional hour at room temperature. After removal of solvent, the residue was dissolved in ethyl acetate. The organic layer was washed with saturated sodium bicarbonate, 10% sodium thiosulfate and brine. The organic layer was dried over sodium sulfate, and it was concentrated under reduced pressure. The residue was suspended in methanol and the suspension was filtered to give product as a white solid (200 mg, 38%); $^1$H NMR (300 MHz) (CDCl$_3$) δ 8.88 (bs, 1H), 7.82 (s, 1H), 7.45 (d, J=9 Hz, 1H), 7.31 (d, J=9 Hz, 1H), 4.19 (q, J=7 Hz, 2H), 3.38-3.16 (m, 3H), 3.16-2.91 (m, 2H), 1.27 (t, J=7 Hz, 3H).

Example 28

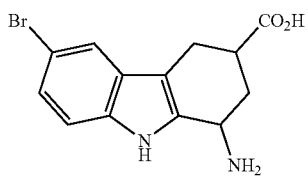 [SMILES: NC1CC(C(=O)O)Cc2c1[nH]c1ccc(Br)cc21]

1-Amino-6-bromo-2,3,4,9-tetrahydro-1H-carbazole-3-carboxylic Acid

To a solution of ethyl 1-amino-6-bromo-2,3,4,9-tetrahydro-1H-carbazole-3-carboxylate (20 mg, 0.06 mmol) in a mixture of tetrahydrofuran (1 mL) and water (0.5 mL), lithium hydroxide monohydrate (8 mg, 0.18 mmol) was added. The reaction mixture was stirred for overnight at room temperature. The mixture was diluted with ethyl acetate, and it was washed with 2N hydrochloric acid followed by brine. The organic layer was dried over sodium sulfate, and it was concentrated under reduced pressure to provide product as a white solid (7 mg, 37%); $^1$H NMR (300 MHz) (DMSO-d$_6$) δ 11.23 (bs, 1H), 7.67 (s, 1H), 7.39 (d, J=7 Hz, 1H), 7.22 (d, J=9 Hz, 1H), 4.67 (m, 1H), 3.14-1.96 (m, 5H); LC/MS RT=2.68 (M−H⁻: 307/309).

Example 29

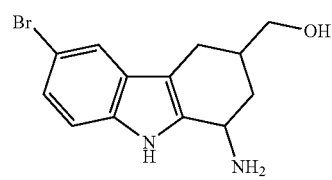 [SMILES: NC1CC(CO)Cc2c1[nH]c1ccc(Br)cc21]

(1-Amino-6-bromo-2,3,4,9-tetrahydro-1H-carbazol-3-yl)methanol

To a solution of ethyl 1-amino-6-bromo-2,3,4,9-tetrahydro-1H-carbazole-3-carboxylate (100 mg, 0.30 mmol) in a mixture of tetrahydrofuran (4 mL) and methanol (1.0 mL), lithium borohydride (20 mg, 0.90 mmol) was added at 0° C. The reaction mixture was stirred for 4 hours at room temperature, and an additional lithium borohydride (20 mg, 0.90 mmol) was added. The reaction mixture was stirred for 2 hours at room temperature. The mixture was diluted with ethyl acetate, and it was washed with water followed by brine. The organic layer was dried over sodium sulfate, and it was concentrated under reduced pressure, and the residue was purified on an ISCO chromatograph (0-10% methanol/dichloromethane+0.1% NH$_4$OH) to give the product as a white solid (67 mg, 75%); $^1$H NMR (300 MHz) (DMSO-d$_6$) δ 10.92 (bs, 1H), 7.44 (s, 1H), 7.22 (d, J=8 Hz, 1H), 7.08 (m, 1H), 4.60 (m, 1H), 3.91 (m, 1H), 2.69-2.64 (m, 1H), 2.16-1.96 (m, 4H), 1.17-1.14 (m, 1H); LC/MS RT=2.68 (M−H⁻: 293/295).

Example 30

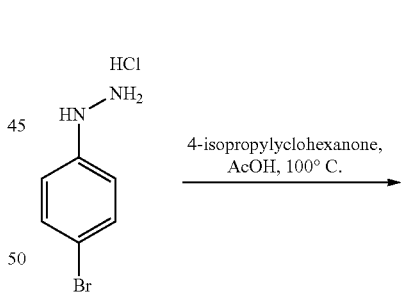

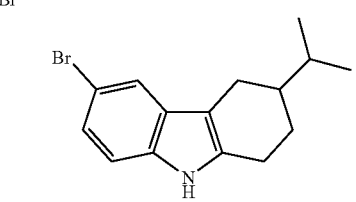

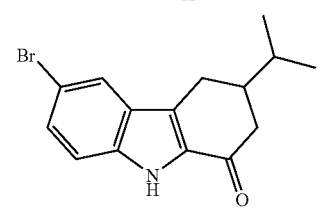

Hz, 1H), 7.13 (d, J=9 Hz, 1H), 2.77-2.70 (m, 3H), 2.37-2.29 (m, 1H), 2.05-1.99 (m, 1H), 1.72-1.52 (m, 3H), 1.00 (dd, J=7 Hz, J=2 Hz, 6H).

Step 2)

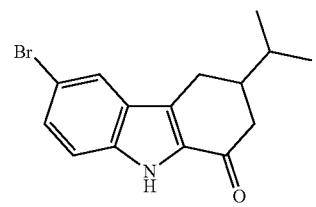

6-Bromo-3-isopropyl-2,3,4,9-tetrahydro-1H-carbazol-1-one

To a solution of 6-bromo-3-isopropyl-2,3,4,9-tetrahydro-1H-carbazole (450 mg, 1.54 mmol) in dichloromethane (25 mL), pyridinium dichromate (1.74 g, 4.62 mmol) was added. The reaction mixture was stirred for 5 hours. The formed suspension was filtered through a pad of silica gel, and the filtrated was concentrated under reduced pressure. The residue was purified on ISCO chromatograph (0 to 100% ethyl acetate/hexane) to give the product as a yellow solid (39 mg, 8%); $^1$H NMR (300 MHz) (CDCl$_3$) δ 8.93 (bs, 1H), 7.82 (s, 1H), 7.44 (d, J=7 Hz, 1H), 7.31 (d, J=9 Hz, 1H), 3.08 (dd, J=16 Hz, J=5 Hz, 1H), 2.74-2.60 (m, 2H), 2.46 (dd, J=16 Hz, J=13 Hz, 1H), 2.21-2.17 (m, 1H), 1.81-1.73 (m, 1H), 1.03 (d, J=7 Hz, 6H).

Example 31

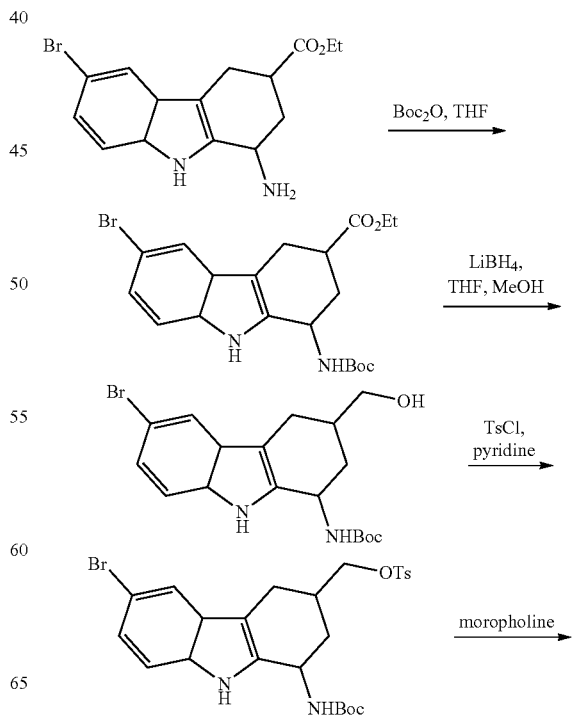

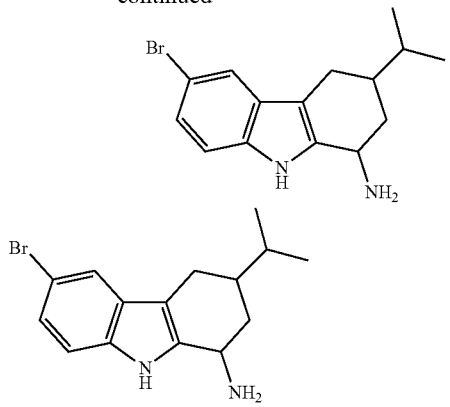

6-Bromo-3-isopropyl-2,3,4,9-tetrahydro-1H-carbazol-1-amine

6-Bromo-3-isopropyl-2,3,4,9-tetrahydro-1H-carbazol-1-one (120 mg, 0.39 mmol), ammonium acetate (301 mg, 3.90 mmol) and sodium cyanoborohydride (123 mg, 1.95 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was suspended in ethyl acetate, and the suspension was filtered to give the product as a white solid (62 mg, 52%); $^1$H NMR (300 MHz) (DMSO-d$_6$) δ 11.17 (bs, 1H), 8.53 (bs, 2H), 7.65 (s, 1H), 7.37 (dd, J=9 Hz, J=2 Hz, 1H), 7.21 (d, J=8 Hz, 1H), 4.61 (m, 1H), 2.78-2.73 (m, 2H), 2.85-2.25 (m, 2H), 1.69 (m, 2H), 0.96 (d, J=6 Hz, 6H); LC/MS RT=3.08 (M–H$^-$: 305/307).

The requisite intermediates were prepared as follows:
Step 1)

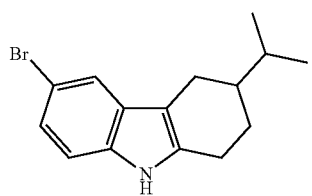 [SMILES: CC(C)C1CCc2[nH]c3ccc(Br)cc3c2C1]

6-Bromo-3-isopropyl-2,3,4,9-tetrahydro-1H-carbazole

To a solution of 4-isopropylcylcohexanone (1.53 mL, 10.00 mmol) in acetic acid (10 mL), (4-bromophenyl) hydrazine hydrochloride (2.24 g, 10.00 mmol) was added. The reaction mixture was heated at 100° C. for overnight. After it was cooled to room temperature, it was diluted with ethyl acetate. The organic layer was washed with 10% sodium hydroxide followed by brine. The organic layer was dried over sodium sulfate, and it was concentrated under reduced pressure. The residue was purified on an ISCO chromatograph (0-20% ethyl acetate/hexane) to give the product as brown oil (2.64 g, 90%); $^1$H NMR (300 MHz) (CDCl$_3$) δ 7.70 (bs, 1H), 7.58 (s, 1H). 7.18 (dd, J=8 Hz, J=2

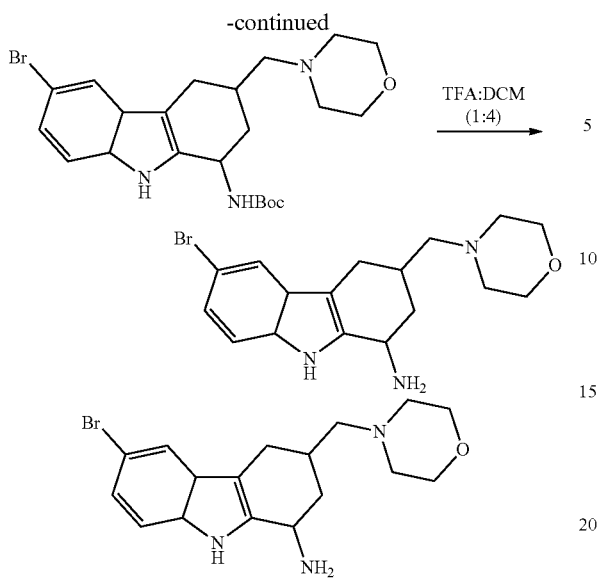

6-Bromo-3-(morpholinomethyl)-2,3,4,9-tetrahydro-1H-carbazol-1-amine

To a solution of tert-butyl (6-bromo-3-(morpholinomethyl)-2,3,4,9-tetrahydro-1H-carbazol-1-yl)carbamate (79 mg, 0.04 mmol) in dichloromethane (1 mL), trifluoroacetic acid (0.25 mL) was added. The reaction mixture was stirred for an hour at room temperature. After removal of solvent, it was diluted with ethyl acetate, and it was washed with 10% sodium hydroxide followed by brine. The organic layer was dried over sodium sulfate, and it was concentrated under reduced pressure, and the residue was purified on an ISCO chromatograph (0-10% methanol/dichloromethane+0.1% NH$_4$OH) to give the product as a white solid (46 mg, 75%); $^1$H NMR (300 MHz) (DMSO-d$_6$) δ 10.87 (bs, 1H), 7.51 (s, 1H), 7.28 (d, J=8 Hz, 1H), 7.10 (d, J=9 Hz, 1H), 4.07-3.97 (m, 1H), 3.58 (m, 4H), 2.75-2.72 (m, 1H), 2.36-2.23 (m, 8H), 2.10-2.07 (m, 1H), 1.22-1.13 (m, 1H); LC/MS RT=2.45 (M+H$^+$: 364/366).

The requisite intermediates were prepared as follows:
Step 1)

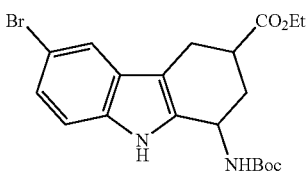 [SMILES: CCOC(=O)C1Cc2c([nH]c3ccc(Br)cc23)C(NC(=O)OC(C)(C)C)C1]

Ethyl 6-bromo-1-((tert-butoxycarbonyl)amino)-2,3,4,9-tetrahydro-1H-carbazazole-3-carboxylate To a solution of ethyl 1-amino-6-bromo-2,3,4,9-tetrahydro-1H-carbazole-3-carboxylate (100 mg, 0.30 mmol) in tetrahydrofuran (10 mL), boc anhydride (131 mg, 0.60 mmol) was added. The reaction mixture was stirred for 4 hours at room temperature, and solvent was removed under reduced pressure. The residue was purified on an ISCO chromatograph (0-20% ethyl acetate/hexane) to give product as colorless oil (131 mg, 100%); $^1$H NMR (300 MHz) (CDCl$_3$) δ 8.85 (bs, 1H), 7.59 (s, 1H), 7.24-7.13 (m, 2H), 4.93 (m, 1H), 4.20-4.07 (m, 3H), 2.95-2.82 (m, 3H), 2.51-2.48 (m, 1H), 2.04-1.97 (m, 1H), 1.49 (s, 9H), 1.30-1.20 (m, 3H).

Step 2)

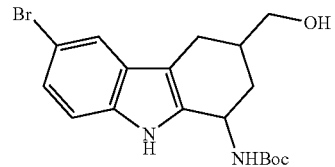 [SMILES: CC(C)(C)OC(=O)NC1CC(CO)Cc2c1[nH]c1ccc(Br)cc21]

Tert-Butyl (6-bromo-3-(hydroxymethyl)-2,3,4,9-tetrahydro-1H-carbazol-1-yl)carbamate To a solution of ethyl 6-bromo-1-((tert-butoxycarbonyl)amino)-2,3,4,9-tetrahydro-1H-carbazole-3-carboxylate (100 mg, 0.23 mmol) in a mixture of tetrahydrofuran (4 mL) and methanol (1 mL), lithium borohydride (15 mg, 0.69 mmol) was added. The reaction mixture was stirred for 5 hours at room temperature. After removal of solvent, it was diluted with ethyl acetate, and it was washed with water followed by brine. The organic layer was dried over sodium sulfate, and it was concentrated under reduced pressure, and the residue was purified on an ISCO chromatograph (0-100% ethyl acetate/hexane) to give the product as a white solid (90 mg, 100%); $^1$H NMR (300 MHz) (CDCl$_3$) δ 8.89 (bs, 1H), 7.57 (s, 1H), 7.25-7.17 (m, 2H), 5.07 (m, 1H), 4.91 (m, 1H), 3.77-3.66 (m, 3H), 2.81 (dd, J=15 Hz, J=5 Hz, 1H), 2.40-2.17 (m, 2H), 2.17 (m, 1H), 1.50 (s, 9H).

Step 3)

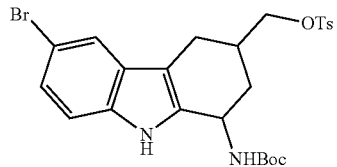 [SMILES: Cc1ccc(S(=O)(=O)OCC2Cc3c([nH]c4ccc(Br)cc34)C(NC(=O)OC(C)(C)C)C2)cc1]

(6-Bromo-1-((tert-butoxycarbonyl)amino)-2,3,4,9-tetrahydro-1H-carbazol-3-yl)methyl 4-methylbenzenesulfonate To a solution of tert-butyl (6-bromo-3-(hydroxymethyl)-2,3,4,9-tetrahydro-1H-carbazol-1-yl)carbamate (40 mg, 0.10 mmol) in pyridine (0.5 mL), p-toluenesulfonyl chloride (21 mg, 0.11 mmol) was added. The reaction mixture was stirred for 3 hours at room temperature. An additional p-toluenesulfonyl chloride (105 mg, 0.55 mmol) was added, and the reaction mixture was stirred for 2 hours at 40° C. After it was cooled to room temperature, it was diluted with ethyl acetate. The organic layer was washed with saturated ammonium chloride followed by brine. The organic layer was dried over sodium sulfate, and it was concentrated under reduced pressure. The residue was purified on an ISCO chromatograph (0-50% ethyl acetate/hexane) to give the product as colorless oil (55 mg, 100%); $^1$H NMR (300 MHz) (CDCl$_3$) δ 8.80 (bs, 1H), 7.81 (d, J=8 Hz, 2H), 7.49 (d, J=2 Hz, 1H), 7.37 (d, J=8 Hz, 2H), 7.22-7.15 (m, 2H), 4.84 (m, 2H), 4.08-4.01 (m, 2H), 2.69-2.66 (m, 1H), 2.47 (s, 3H), 2.33-2.25 (m, 3H), 1.50 (s, 9H).

Step 4)

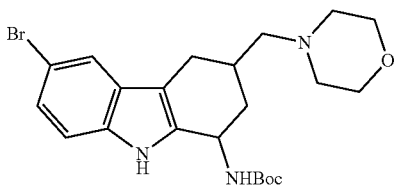 [SMILES: CC(C)(C)OC(=O)NC1CC(CN2CCOCC2)Cc2c1[nH]c1ccc(Br)cc21]

Tert-Butyl (6-bromo-3-(morpholinomethyl)-2,3,4,9-tetrahydro-1H-carbazol-1-yl)carbamate (6-Bromo-1-((tert-butoxycarbonyl)amino)-2,3,4,9-tetrahydro-1H-carbazol-3-yl)methyl 4-methylbenzenesulfonate (55 mg, 0.10 mmol) was dissolved in a neat morpholine (2 mL), and the reaction mixture was stirred for 2 hours at 50° C. After it was cooled to room temperature, it was diluted with ethyl acetate. The organic layer was washed with water followed by brine. The organic layer was dried over sodium sulfate, and it was concentrated under reduced pressure. The residue was purified on an ISCO chromatograph (0-50% ethyl acetate/hexane) to give the product as colorless oil (20 mg, 43%); $^1$H NMR (300 MHz) (CDCl$_3$) δ 9.22 (bs, 1H), 7.59 (s, 1H), 7.55 (bs, 1H), 7.22 (m, 2H), 4.71 (m, 1H), 3.78-3.69 (m, 4H), 2.84-2.79 (m, 1H), 2.52-2.12 (m, 9H), 2.00-1.96 (m, 1H), 1.43 (s, 9H).

Example 32

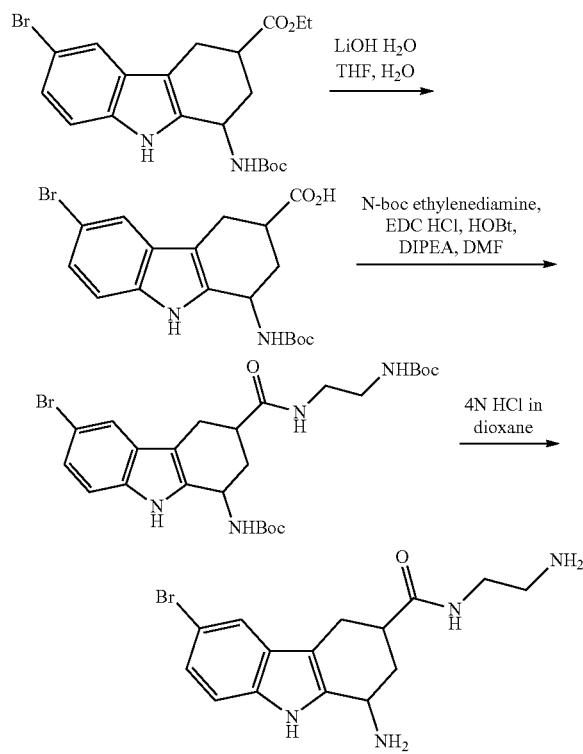

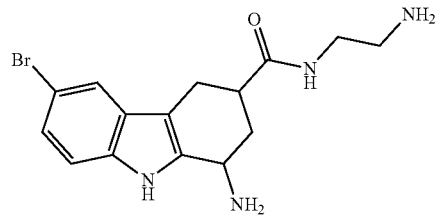 [SMILES: NCCNC(=O)C1Cc2c([nH]c3ccc(Br)cc23)C(N)C1]

1-Amino-N-(2-aminoethyl)-6-bromo-2,3,4,9-tetrahydro-1H-carbazole-3-carboxamide

A solution of tert-butyl (6-bromo-3-((2-((tert-butoxycarbonyl)amino)ethyl)carbamoyl)-2,3,4,9-tetrahydro-1H-carbazol-1-yl)carbamate (155 mg, 0.28 mmol) in 4N hydrochloric acid in dioxane (5 mL, 20 mmol) was stirred for an hour at room temperature. After removal of solvent, it was diluted with ethyl acetate, and it was washed with 10% sodium hydroxide followed by brine. The organic layer was dried over sodium sulfate, and it was concentrated under reduced pressure, and the residue was purified on an ISCO chromatograph (0-10% methanol/dichloromethane+0.1% NH$_4$OH) to give the product as a white solid (42 mg, 43%); $^1$H NMR (300 MHz) (DMSO-d$_6$) δ 11.01 (bs, 1H), 7.91 (bs, 1H), 7.50 (s, 1H), 7.24-7.10 (m, 2H), 3.94 (m, 1H), 3.07-1.07 (m, 9H); LC/MS RT=2.38 (M+H$^+$: 351/353).

The requisite intermediates were prepared as follows:

Step 1)

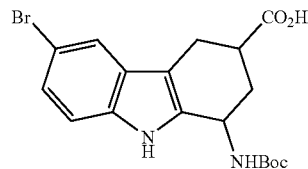 [SMILES: CC(C)(C)OC(=O)NC1CC(C(=O)O)Cc2c1[nH]c1ccc(Br)cc21]

6-Bromo-1-((tert-butoxycarbonyl)amino)-2,3,4,9-tetrahydro-1H-carbazole-3-carboxylic Acid To a solution of ethyl 6-bromo-1-((tert-butoxycarbonyl)amino)-2,3,4,9-tetrahydro-1H-carbazole-3-carboxylate (131 mg, 0.30 mmol) in a mixture of tetrahydrofuran (10 mL) and water (5 mL), lithium hydroxide monohydrate (38 mg, 0.90 mmol) was added. The reaction mixture was stirred for overnight at room temperature. The mixture was diluted with ethyl acetate, and it was washed with 2N hydrochloric acid followed by brine. The organic layer was dried over sodium sulfate, and it was concentrated under reduced pressure to provide product as a white solid (128 mg, 100%); $^1$H NMR (300 MHz) (CDCl$_3$) δ 8.88 (bs, 1H), 7.60 (d, J=2 Hz, 1H), 7.26-7.23 (m, 1H), 7.19 (d, J=8 Hz, 1H), 5.34-5.31 (m, 1H), 4.98-4.96 (m, 1H), 3.78-3.73 (m, 1H), 3.06-2.98 (m, 1H), 2.58-2.53 (m, 1H), 1.99-1.95 (m, 1H), 1.88-1.83 (m, 1H), 1.50 (s, 9H).

Step 2)

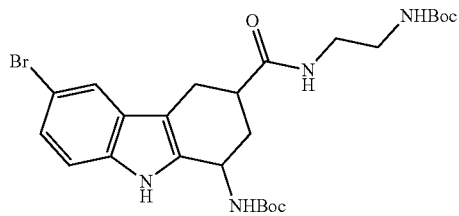 [SMILES: CC(C)(C)OC(=O)NCCNC(=O)C1Cc2c([nH]c3ccc(Br)cc23)C(NC(=O)OC(C)(C)C)C1]

Tert-Butyl (6-bromo-3-((2-((tert-butoxycarbonyl)amino)ethyl)carbamoyl)-2,3,4,9-tetrahydro-1H-carbazol-1-yl)carbamate 6-Bromo-1-((tert-butoxycarbonyl)amino)-2,3,4,9-tetrahydro-1H-carbazole-3-carboxylic acid (100 mg, 0.24 mmol), N-(3-Dimethylaminopropyl)-N'-ethylcarbodiimide hydrochloride (92 mg, 0.72 mmol), 1-hydroxybenzotriazole (32 mg, 0.24 mmol) and N,N-diisopropylethylamine (0.13 mL, 0.72 mmol) were dissolved in N,N-dimethylformamide (5 mL). After the reaction mixture was stirred for 15 minutes, N-boc ethylenediamine (0.11 mL, 0.72 mmol) was added. The reaction mixture was stirred for overnight at room temperature, and it was diluted with ethyl acetate. The organic layer was washed with 1N hydrochloric acid, 10% sodium hydroxide and brine, and it was dried over sodium sulfate. The organic layer was then concentrated under reduced pressure, and the residue was purified on an ISCO chromatograph (0-100% ethyl acetate/hexane) to give the product as colorless oil (55 mg, 42%); $^1$H NMR (300 MHz) (CDCl$_3$) δ 8.89 (bs, 1H), 7.53 (s, 1H), 0.7.25-7.18 (m, 2H), 6.79 (bs, 1H), 5.52 (bs, 1H), 4.98 (bs, 1H), 4.93-4.88 (m, 1H), 3.38-3.28 (m, 4H), 2.79-2.71 (m, 5H), 1.48 (s, 9H), 1.45 (s, 9H).

Example 33

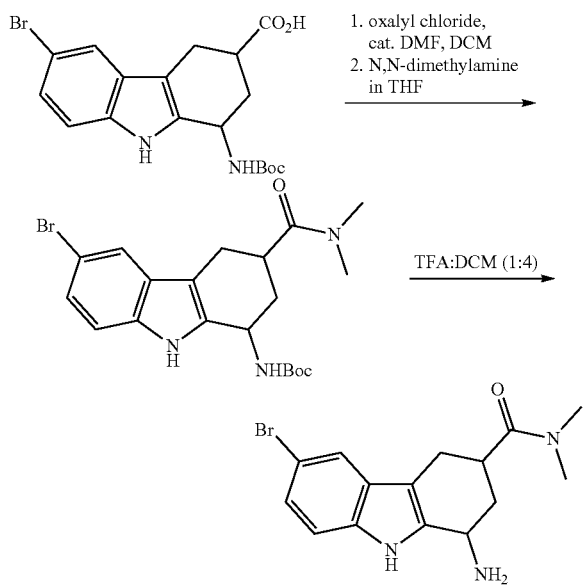

-continued

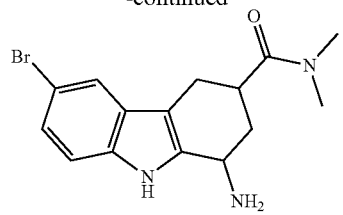

1-Amino-6-bromo-N,N-dimethyl-2,3,4,9-tetrahydro-1H-carbazole-3-carboxamide

To a solution of tert-butyl (6-bromo-3-(dimethylcarbamoyl)-2,3,4,9-tetrahydro-1H-carbazol-1-yl)carbamate (53 mg, 0.12 mmol) in dichloromethane (10 mL), trifluoroacetic acid (2.5 mL) was added. The reaction mixture was stirred for an hour at room temperature. After removal of solvent, it was diluted with ethyl acetate, and it was washed with 10% sodium hydroxide followed by brine. The organic layer was dried over sodium sulfate, and it was concentrated under reduced pressure, and the residue was purified on an ISCO chromatograph (0-10% methanol/dichloromethane+0.1% NH$_4$OH) to give the product as a white solid (26 mg, 65%); $^1$H NMR (300 MHz) (DMSO-d$_6$) δ 10.88 (bs, 1H), 7.61 (s, 1H), 7.37 (d, J=8 Hz, 1H), 7.18 (d, J=8 Hz, 1H), 6.56 (bs, 2H), 4.42 (m, 1H), 3.07 (s, 3H), 2.86 (m, 4H), 2.65-2.57 (m, 2H), 2.24-2.15 (m, 1H), 1.82-1.77 (m, 1H); LC/MS RT=2.78 (M+H$^+$: 336/338).

The requisite intermediate was prepared as follows:
Step 1)

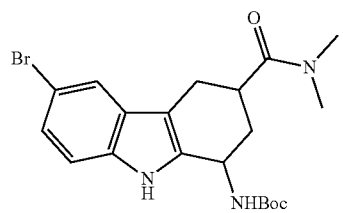 [SMILES: CN(C)C(=O)C1Cc2c([nH]c3ccc(Br)cc23)C(NC(=O)OC(C)(C)C)C1]

Tert-Butyl (6-bromo-3-(dimethylcarbamoyl)-2,3,4,9-tetrahydro-1H-carbazol-1-yl)carbamate To a solution of 6-bromo-1-((tert-butoxycarbonyl)amino)-2,3,4,9-tetrahydro-1H-carbazole-3-carboxylic acid (50 mg, 0.12 mmol) in dichloromethane (5 mL), oxalyl chloride (21 µL, 0.24 mmol) followed by catalytic amount of N,N-dimethylformamide were added at 0° C. The reaction mixture was stirred for 30 minutes at the temperature. After removal of solvent, the residue was reacted with 1 M N,N-dimethylamine in tetrahydrofuran (2 mL, 2.0 mmol). The reaction mixture was stirred for 30 minutes at room temperature, and it was diluted with ethyl acetate. The organic layer was washed with saturated ammonium chloride and brine, and it was dried over sodium sulfate. The organic layer was then concentrated under reduced pressure, and the residue was purified on an ISCO chromatograph (0-100% ethyl acetate/hexane) to give the product as a white solid (23 mg, 44%); $^1$H NMR (300 MHz) (CDCl$_3$) δ 8.84 (bs, 1H), 7.56 (s, 1H), 7.26-7.17 (m, 2H), 5.48 (bs, 1H), 4.97-4.92 (m, 1H), 3.13 (s, 3H), 3.00 (s, 3H), 2.88-2.84 (m, 2H), 2.37-2.30 (m, 1H), 2.06-1.99 (m, 1H), 1.51 (s, 9H).

Example 34

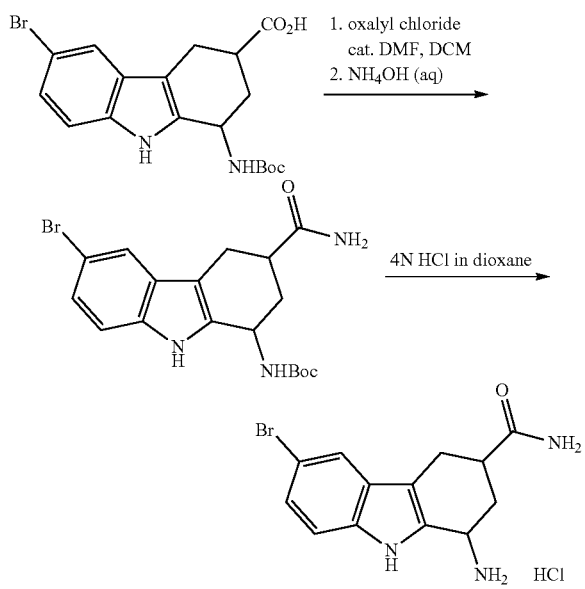

1-Amino-6-bromo-2,3,4,9-tetrahydro-1H-carbazole-3-carboxamide Hydrogen Chloride Salt tert-Butyl (6-bromo-3-carbamoyl-2,3,4,9-tetrahydro-1H-carbazol-1-yl)carbamate (42 mg, 0.10 mmol) was reacted with 4N HCl in dioxane (5 mL), and the reaction mixture was stirred for 1.5 hours at room temperature. After removal of solvent, the residue was suspended in ethyl acetate. The suspension was filtered to give product of hydrochloric salt as a white solid (34 mg, 100%); $^1$H NMR (300 MHz) (DMSO-$d_6$) δ 11.32 (bs, 1H), 8.70 (bs, 3H), 7.66 (s, 1H), 7.58 (s, 1H), 7.38 (d, J=9 Hz, 1H), 7.22 (d, J=8 Hz, 1H), 7.06 (s, 1H), 4.63 (m, 1H), 2.94-2.89 (m, 1H), 2.75-2.58 (m, 1H), 2.75-2.62 (m, 2H), 2.34-2.18 (m, 1H), 1.97-1.84 (m, 1H); LC/MS RT=2.64 (M+H$^+$: 308/310).

The requisite intermediate was prepared as follows:
Step 1)

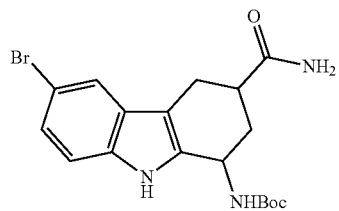 [SMILES: CC(C)(C)OC(=O)NC1CC(C(N)=O)Cc2c1[nH]c1ccc(Br)cc21]

Tert-Butyl (6-bromo-3-carbamoyl-2,3,4,9-tetrahydro-1H-carbazol-1-yl)carbamate To a solution of 6-bromo-1-((tert-butoxycarbonyl)amino)-2,3,4,9-tetrahydro-1H-carbazole-3-carboxylic acid (100 mg, 0.24 mmol) in dichloromethane (5 mL), oxalyl chloride (37 μL, 0.48 mmol) followed by catalytic amount of N,N-dimethylformamide were added at 0° C. The reaction mixture was stirred for 30 minutes at the temperature. After removal of solvent, the residue was reacted with ammonia solution (5 mL) at 0° C. The reaction mixture was stirred for 30 minutes at the temperature, and it was diluted with ethyl acetate. The organic layer was washed with 10% sodium hydroxide and brine, and it was dried over sodium sulfate. The organic layer was then concentrated under reduced pressure, and the residue was purified on an ISCO chromatograph (0-100% ethyl acetate/hexane) to give the product as a white solid (42 mg, 43%); $^1$H NMR (300 MHz) (CDCl$_3$) δ 8.86 (bs, 1H), 7.59 (s, 1H), 7.26-7.17 (m, 2H), 5.64 (bs, 1H), 5.46 (bs, 1H), 5.00-4.93 (m, 1H), 3.04-2.77 (m, 3H), 2.44-2.04 (m, 2H), 1.50 (s, 9H).

Example 35

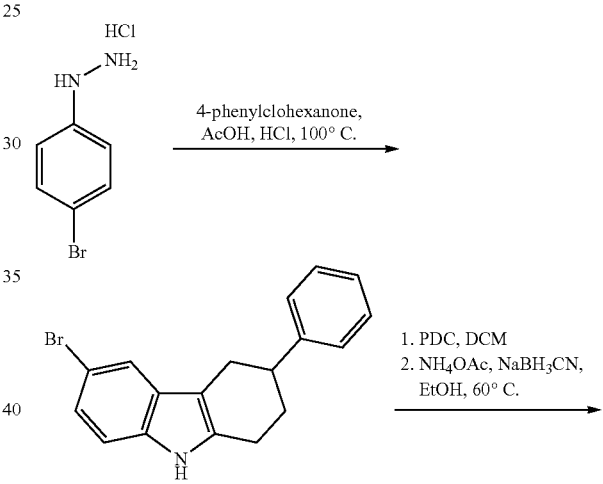

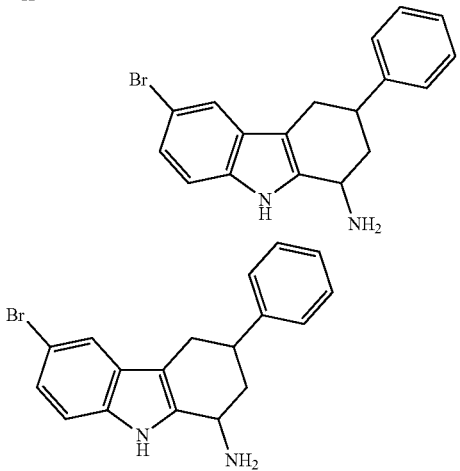

6-Bromo-3-phenyl-2,3,4,9-tetrahydro-1H-carbazol-1-amine

To a solution of 6-bromo-3-phenyl-2,3,4,9-tetrahydro-1H-carbazole (100 mg, 0.31 mmol) in dichloromethane (10 mL), pyridinium dichromate (233 mg, 0.62 mmol) was added. The reaction mixture was stirred for 5 hours. The formed suspension was filtered through a pad of silica gel, and the filtrated was concentrated under reduced pressure. The residue was purified on ISCO chromatograph (0 to 100% ethyl acetate/hexane) to give the crude product as a yellow solid.

The crude product, ammonium acetate (355 mg, 4.60 mmol) and sodium cyanoborohydride (145 mg, 2.30 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was suspended in ethyl acetate, and the suspension was filtered to give the product as colorless oil (16 mg, 15%); $^1$H NMR (300 MHz) (CDCl$_3$) δ 9.02 (bs, 1H), 7.46 (s, 1H), 7.37-7.09 (m, 7H), 6.32 (bs, 2H), 4.45 (m, 1H), 2.96-2.85 (m, 2H), 2.74-2.65 (m, 1H), 2.40 (m, 1H), 2.16-2.11 (m, 1H); LC/MS RT=3.11 (M−H$^−$: 339/341).

The requisite intermediate was prepared as follows:

Step 1)

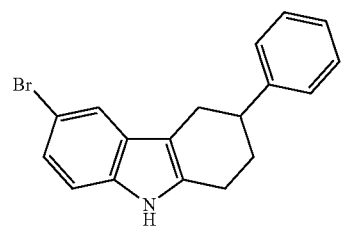 [SMILES: Brc1ccc2[nH]c3c(c2c1)CC(c1ccccc1)CC3]

6-Bromo-3-phenyl-2,3,4,9-tetrahydro-1H-carbazole

To a solution of 4-phenylcylcohexanone (1.74 g, 10.00 mmol) in acetic acid (20 mL), (4-bromophenyl)hydrazine hydrochloride (2.24 g, 10.00 mmol) was added. The reaction mixture was heated at 100° C. for overnight. After it was cooled to room temperature, it was diluted with ethyl acetate. The organic layer was washed with 10% sodium hydroxide followed by brine. The organic layer was dried over sodium sulfate, and it was concentrated under reduced pressure to give the product as brown oil (3.26 g, 100%); $^1$H NMR (300 MHz) (CDCl$_3$) δ 7.82 (bs, 1H), 7.56 (s, 1H), 7.35-7.14 (m, 7H), 3.07-2.78 (m, 7H).

Example 36

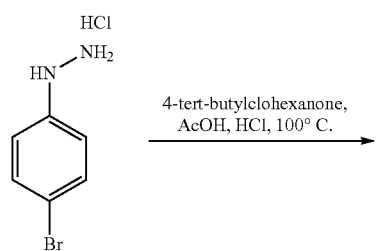

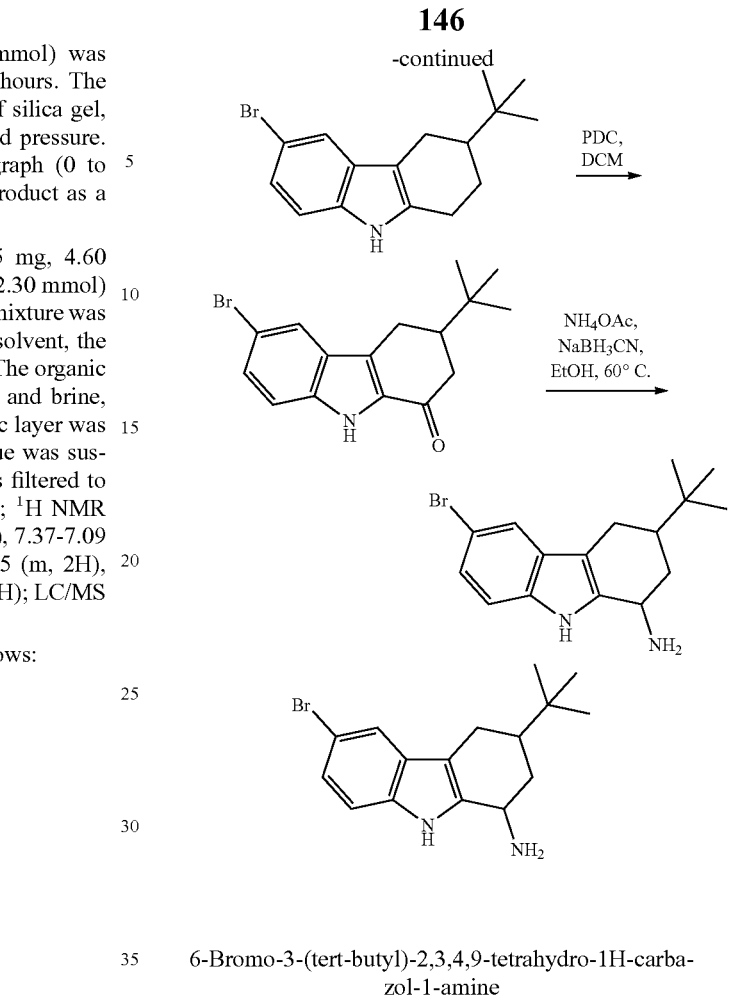

6-Bromo-3-(tert-butyl)-2,3,4,9-tetrahydro-1H-carbazol-1-amine

6-Bromo-3-(tert-butyl)-2,3,4,9-tetrahydro-1H-carbazol-1-one (155 mg, 0.48 mmol), ammonium acetate (370 mg, 4.80 mmol) and sodium cyanoborohydride (151 mg, 2.40 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was suspended in ethyl acetate, and the suspension was filtered to give the product as colorless oil (57 mg, 37%); $^1$H NMR (300 MHz) (CDCl$_3$) δ 8.59 (bs, 1H), 7.60 (s, 1H), 7.22-7.15 (m, 2H), 4.03 (m, 1H), 2.78-2.71 (m, 1H), 2.42-2.33 (m, 1H), 2.27-2.21 (m, 1H), 1.69-1.60 (m, 1H), 1.28-1.25 (m, 1H), 0.99 (s, 9H); LC/MS RT=3.09 (M−H$^−$: 319/321).

The requisite intermediates were prepared as follows:

Step 1)

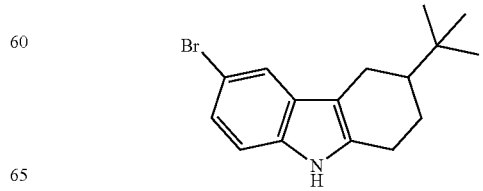

6-Bromo-3-(tert-butyl)-2,3,4,9-tetrahydro-1H-carbazole

To a solution of 4-tert-butylcylcohexanone (1.54 g, 10.00 mmol) in acetic acid (20 mL), (4-bromophenyl)hydrazine hydrochloride (2.24 g, 10.00 mmol) was added. The reaction mixture was heated at 100° C. for overnight. After it was cooled to room temperature, it was diluted with ethyl acetate. The organic layer was washed with 10% sodium hydroxide followed by brine. The organic layer was dried over sodium sulfate, and it was concentrated under reduced pressure to give the product as brown oil (3.06 g, 100%); $^1$H NMR (300 MHz) (CDCl$_3$) δ 7.83 (bs, 1H), 7.58 (d, J=2 Hz, 1H), 7.16 (dd, J=9 Hz, J=2 Hz, 1H), 7.11 (d, J=9 Hz, 1H), 2.74-2.72 (m, 2H), 2.38-2.30 (m, 1H), 2.10-2.05 (m, 2H), 1.50-1.43 (m, 2H), 0.99 (s, 9H).

Step 2)

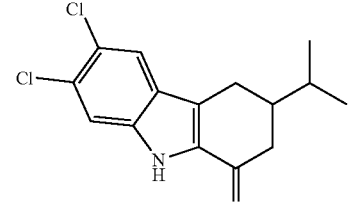

6-Bromo-3-(tert-butyl)-2,3,4,9-tetrahydro-1H-carbazol-1-one

To a solution of 6-bromo-3-(tert-butyl)-2,3,4,9-tetrahydro-1H-carbazole (3.06 g, 10.00 mmol) in dichloromethane (50 mL), pyridinium dichromate (11.29 g, 30.00 mmol) was added. The reaction mixture was stirred for overnight. The formed suspension was filtered through a pad of silica gel, and the filtrated was concentrated under reduced pressure. The residue was purified on ISCO chromatograph (0 to 50% ethyl acetate/hexane) to give the product as a white solid (155 mg, 5%); $^1$H NMR (300 MHz) (CDCl$_3$) δ 8.83 (bs, 1H), 7.82 (s, 1H), 7.44 (dd, J=9 Hz, J=2 Hz, 1H), 7.30 (d, J=9 Hz, 1H), 3.14-3.08 (m, 1H), 2.77-2.60 (m, 2H), 2.50-2.34 (m, 2H), 1.03 (s, 9H).

Example 37

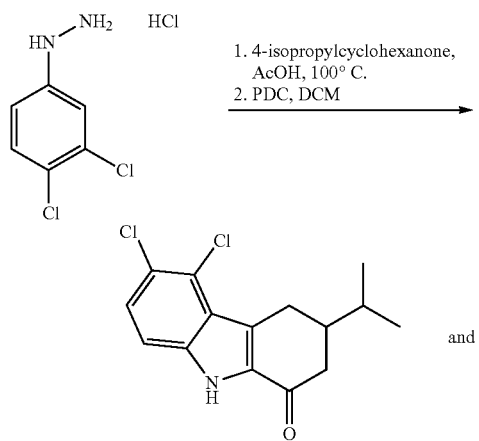

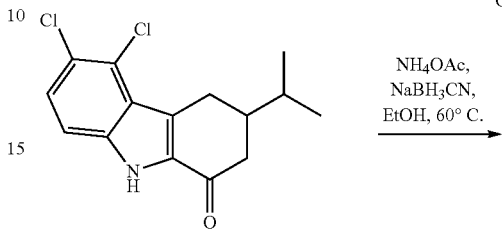

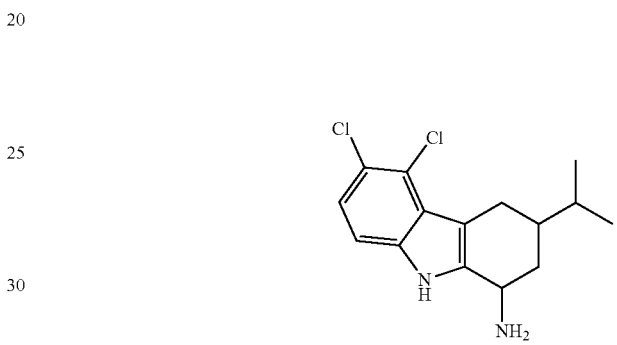

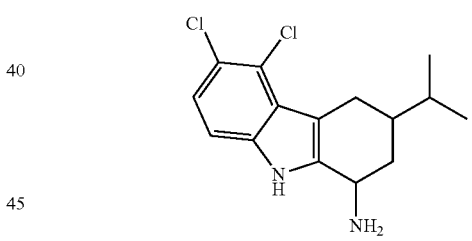

5,6-Dichloro-3-isopropyl-2,3,4,9-tetrahydro-1H-carbazol-1-amine 5,6-Dichloro-3-isopropyl-2,3,4,9-tetrahydro-1H-carbazol-1-one (124 mg, 0.42 mmol), ammonium acetate (324 mg, 4.20 mmol) and sodium cyanoborohydride (132 mg, 2.10 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was suspended in ethyl acetate, and the suspension was filtered to give the product as colorless oil (12 mg, 10%); $^1$H NMR (300 MHz) (CD$_3$OD) δ 7.49 (d, J=9 Hz, 1H), 7.15 (d, J=9 Hz, 1H), 4.35-4.30 (m, 1H), 2.63-2.55 (m, 1H), 2.31-2.01 (m, 1H), 1.78-1.67 (m, 2H), 1.48-1.40 (m, 1H), 1.05 (d, J=6 Hz, 6H); LC/MS RT=3.14 (M−H$^-$: 295/297.

The requisite intermediate was prepared as follows:
Step 1)

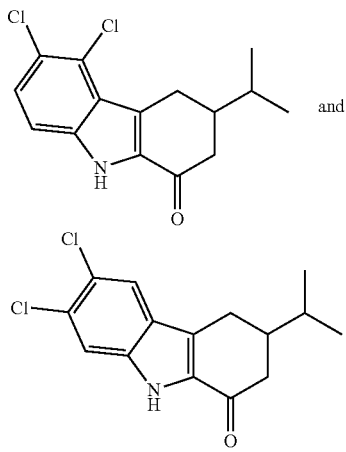

5,6-Dichloro-3-isopropyl-2,3,4,9-tetrahydro-1H-carbazol-1-one and 6,7-Dichloro-3-isopropyl-2,3,4, 9-tetrahydro-1H-carbazol-1-one To a solution of 4-isopropylcylcohexanone (1.53 mL, 10.00 mmol) in acetic acid (20 mL), (3,4-dichlorophenyl) hydrazine hydrochloride (2.13 g, 10.00 mmol) was added. The reaction mixture was heated at 100° C. for 5 hours. After it was cooled to room temperature, it was diluted with ethyl acetate. The organic layer was washed with 10% sodium hydroxide followed by brine. The organic layer was dried over sodium sulfate, and it was concentrated under reduced pressure. The residue was purified on an ISCO chromatograph (0-20% ethyl acetate/hexane) to give a mixture of two regioisomers, 5,6-dichloro-3-isopropyl-2,3,4,9-tetrahydro-1H-carbazole and 6,7-dichloro-3-isopropyl-2,3,4,9-tetrahydro-1H-carbazole, as brown oil (2.82 g, 100%).

To a solution of a mixture of two regioisomers (2.82 g, 10.00 mmol) in dichloromethane (100 mL), pyridinium dichromate (7.52 g, 20.00 mmol) was added. The reaction mixture was stirred for overnight. The formed suspension was filtered through a pad of silica gel, and the filtrated was concentrated under reduced pressure. The residue was purified on ISCO chromatograph (0 to 50% ethyl acetate/hexane) to give 5,6-dichloro-3-isopropyl-2,3,4,9-tetrahydro-1H-carbazol-1-one as a brown solid (527 mg, 18%). $^1$H NMR (300 MHz) (CDCl$_3$) δ 9.37 (bs, 1H), 7.37 (d, J=9 Hz, 1H), 7.28 (d, J=9 Hz, 1H), 3.60 (dd, J=17 Hz, J=5 Hz, 1H), 2.88 (dd, J=17 Hz, J=11 Hz, 1H), 2.69 (dd, J=17 Hz, J=4 Hz, 1H), 2.44 (dd, J=17 Hz, J=13 Hz, 1H), 2.24-2.14 (m, 1H), 1.84-1.75 (m, 1H), 1.04 (dd, J=6 Hz, J=4 Hz, 6H), along with 6,7-dichloro-3-isopropyl-2,3,4,9-tetrahydro-1H-carbazol-1-one as a brown solid (190 mg, 6%). $^1$H NMR (300 MHz) (CDCl$_3$) δ 9.13 (bs, 1H), 7.76 (s, 1H), 7.56 (s, 1H), 3.06 (dd, J=16 Hz, J=5 Hz, 1H), 2.75-2.60 (m, 2H), 2.46 (dd, J=16 Hz, J=13 Hz, 1H), 2.24-2.16 (m, 1H), 1.82-1.73 (m, 1H), 1.04 (dd, J=7 Hz, J=2 Hz, 6H).

Example 38

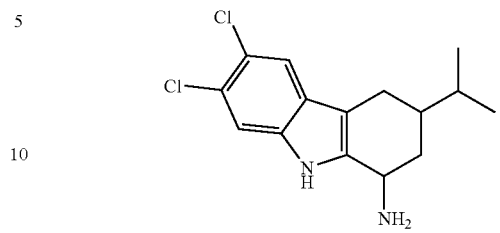

6,7-Dichloro-3-isopropyl-2,3,4,9-tetrahydro-1H-carbazol-1-amine 6,7-Dichloro-3-isopropyl-2,3,4,9-tetrahydro-1H-carbazol-1-one (65 mg, 0.22 mmol), ammonium acetate (170 mg, 2.20 mmol) and sodium cyanoborohydride (69 mg, 1.10 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was suspended in ethyl acetate, and the suspension was filtered to give the product as colorless oil (22 mg, 34%); $^1$H NMR (300 MHz) (CD$_3$OD) δ 7.47 (s, 1H), 7.41 (s, 1H), 4.05 (m, 1H), 3.34-3.30 (m, 1H), 2.71-2.66 (m, 1H), 2.33-2.21 (m 2H), 1.69-1.67 (m, 2H), 1.33-1.21 (m, 1H), 1.02 (d, J=6 Hz, 6H); LC/MS RT=3.03 (M−H$^-$: 295/297).

Example 39

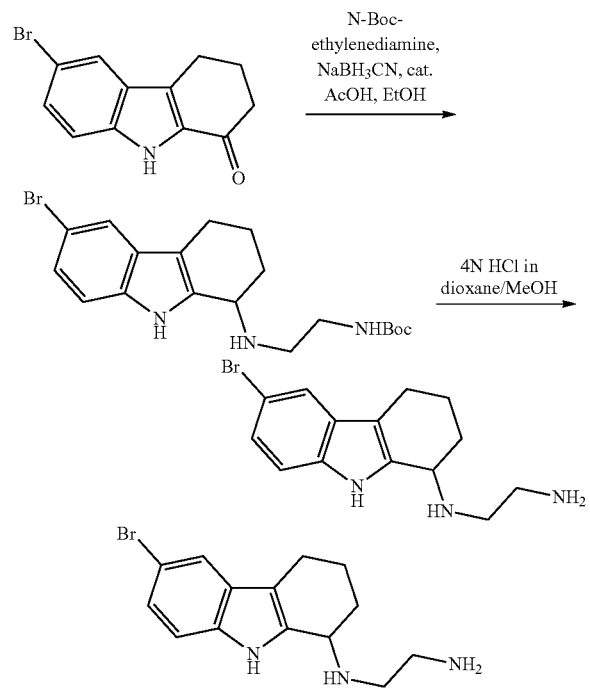

$N^1$-(6-bromo-2,3,4,9-tetrahydro-1H-carbazol-1-yl)ethane-1,2-diamine

To a solution of tert-butyl (2-((6-bromo-2,3,4,9-tetrahydro-1H-carbazol-1-yl)amino)ethyl)carbamate (952 mg, 1.60 mmol) in methanol (10 mL), 4N HCl in dioxane (10 mL, 40.00 mmol) was added. The reaction mixture was stirred for 2 hours at room temperature. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (399 mg, 55%); $^1$H NMR (300 MHz) (CD$_3$OD) δ 7.49 (d, J=2 Hz, 1H), 7.20 (d, J=8 Hz, 1H),), 7.12 (dd, J=8 Hz, J=2 Hz, 1H), 3.94-3.92 (m, 1H), 2.84-2.72 (m, 4H), 2.65-2.62 (m, 2H), 2.15-2.05 (m, 2H), 1.92-1.75 (m, 2H); LC/MS RT=2.56 (M+H$^+$: 308/310).

The requisite intermediate was prepared as follows:
Step 1)

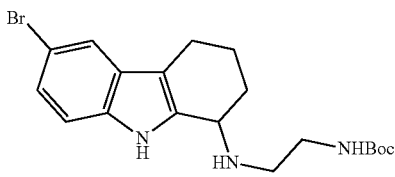 [SMILES: CC(C)(C)OC(=O)NCCNC1CCCc2c1[nH]c1ccc(Br)cc21]

Tert-Butyl (2-((6-bromo-2,3,4,9-tetrahydro-1H-carbazol-1-yl)amino)ethyl)carbamate 6-Bromo-2,3,4,9-tetrahydro-1H-carbazol-1-one (1.0 g, 3.79 mmol), N-boc ethylenediamine (1.80 mL, 11.37 mmol) and sodium cyanoborohydride (1.19 g, 18.95 mmol) were dissolved in ethanol (20 mL). Catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a yellow solid (952 mg, 61%); LC/MS RT=3.01 (M−H$^-$: 406/408).

Example 40

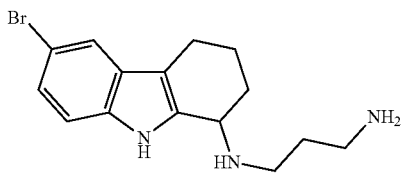 [SMILES: NCCCNC1CCCc2c1[nH]c1ccc(Br)cc21]

$N^1$-(6-Bromo-2,3,4,9-tetrahydro-1H-carbazol-1-yl)propane-1,3-diamine

To a solution of tert-butyl (3-((6-bromo-2,3,4,9-tetrahydro-1H-carbazol-1-yl)amino)propyl)carbamate (1.58 g, 3.74 mmol) in methanol (10 mL), 4N HCl in dioxane (10 mL, 40.00 mmol) was added. The reaction mixture was stirred for 2 hours at room temperature. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (850 mg, 70%); $^1$H NMR (300 MHz) (CDCl$_3$) δ 9.26 (bs, 1H), 7.57 (s, 1H), 7.21-7.15 (m, 2H), 3.96-3.91 (m, 1H), 3.78-3.63 (m, 1H), 2.92-2.58 (m, 5H), 2.23-2.16 (m, 1H), 2.05-1.99 (m, 1H), 1.85-1.44 (m, 4H); LC/MS RT=2.58 (M+H$^+$: 322/324).

The requisite intermediate was prepared as follows:
Step 1)

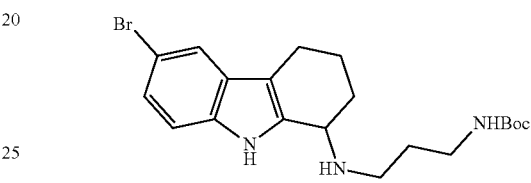

Tert-Butyl (3-((6-bromo-2,3,4,9-tetrahydro-1H-carbazol-1-yl)amino)propyl)carbamate 6-Bromo-2,3,4,9-tetrahydro-1H-carbazol-1-one (1.0 g, 3.79 mmol), N-boc propylenediamine (1.98 g, 11.37 mmol) and sodium cyanoborohydride (1.19 g, 18.95 mmol) were dissolved in ethanol (20 mL). Catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-100% ethyl acetate/hexane) to give the product as a white solid (1.58 g, 99%); $^1$H NMR (300 MHz) (CDCl$_3$) δ 9.47 (bs, 1H), 7.62 (s, 1H), 7.31-7.26 (m, 2H). 5.15 (bs, 1H), 5.02 (bs, 1H), 4.59-4.55 (m, 1H), 3.31-3.04 (m,), 2.77-2.65 (m, 4H), 2.77-2.65 (m, 2H), 2.22-1.91 (m, 6H), 1.33 (s, 9H); LC/MS RT=3.02 (M+H$^+$: 422/424).

Example 41

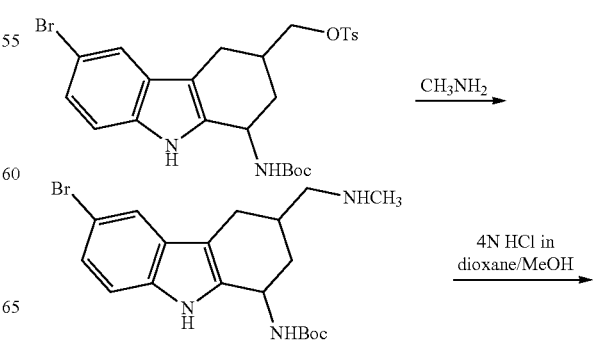

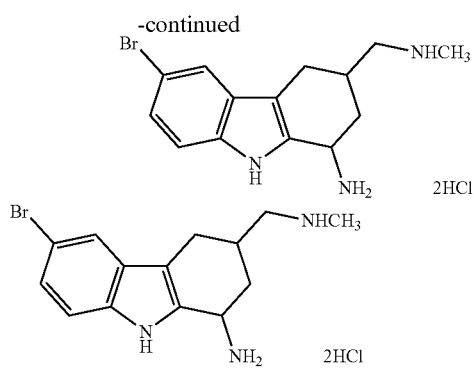

6-Bromo-3-((methylamino)methyl)-2,3,4,9-tetra-hydro-1H-carbazol-1-amine Hydrogen Chloride Salt To a solution of tert-butyl (6-bromo-3-((methylamino)methyl)-2,3,4,9-tetrahydro-1H-carbazol-1-yl)carbamate (110 mg, 0.27 mmol) in methanol (2 mL), 4N HCl in dioxane (4 mL, 16.00 mmol) was added. The reaction mixture was stirred for 2 hours at room temperature. After removal of solvent, the reaction mixture was diluted with ethyl acetate. The resulted suspension was filtered to give product of hydrochloric salt as a white solid (103 mg, 100%); $^1$H NMR (300 MHz) (DMSO-$d_6$) δ 11.69 (bs, 1H), 9.13-8.99 (bs, 5H), 7.54 (s, 1H), 7.37-7.21 (m, 2H), 4.65 (m, 1H), 3.04-2.94 (m, 4H), 2.57 (s, 3H), 2.41-2.31 (m, 3H); LC/MS RT=2.34 (M+H$^+$: 308/310).

The requisite intermediate was prepared as follows:
Step 1)

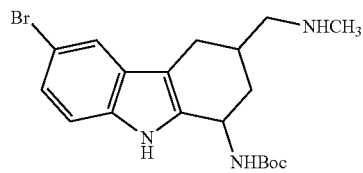 [SMILES: CNCC1Cc2c([nH]c3ccc(Br)cc23)C(NC(=O)OC(C)(C)C)C1]

Tert-Butyl (6-bromo-3-((methylamino)methyl)-2,3,4,9-tetrahydro-1H-carbazol-1-yl)carbamate (6-Bromo-1-((tert-butoxycarbonyl)amino)-2,3,4,9-tetrahydro-1H-carbazol-3-yl)methyl 4-methylbenzenesulfonate (150 mg, 0.27 mmol) was dissolved in methylamine solution (33 wt % in ethanol, 10 mL), and it was stirred for 72 hours at room temperature. After removal of solvent, it was diluted with ethyl acetate. The organic layer was washed with water followed by brine. The organic layer was dried over sodium sulfate, and it was concentrated under reduced pressure. The residue was purified on an ISCO chromatograph (0-100% ethyl acetate/hexane) to give the product as colorless oil (110 mg, 100%); $^1$H NMR (300 MHz) (CDCl$_3$) δ 9.06 (bs, 1H), 7.58 (s, 1H), 7.24-7.17 (m, 2H), 6.52 (s, 1H), 4.83-4.77 (m, 1H), 2.85-2.79 (m, 1H), 2.70-2.54 (m, 2H), 2.42 (s, 3H), 2.40-2.35 (m, 1H), 2.29-2.18 (m, 2H), 1.80-1.78 (m, 1H).

Example 42. Description of General Test Methods

Intrinsic MIC Assays
MIC assays were conducted in accordance with Clinical and Laboratory Standards Institute (CLSI) guidelines for broth microdilution. A 96-well plate containing cation-adjusted Mueller-Hinton (CAMH broth with 2-fold serial dilution of compounds was inoculated with log-phase bacterial at 5×10$^5$ CFU/mL. The final volume in each well was 100 µL. Each compound was tested in duplicate. The microtiter plates were incubated in an aerobic environment for 18 hours at 37° C. Then the bacterial growth was tested by reading the plate with a VersaMax plate reader (Molecular Devices, Inc.) at 600 nm. The MIC was defined as the lowest compound concentration that inhibited 90% of bacteria growth.

The intrinsic MIC of the experimental EPIs was tested with the method described. The 2-fold serial dilution begins with 100 µg/mL of tested compound in the first column of the 96-well plates. The following Gram-negative bacterial strains were included in these assays:
Escherichia coli ATCC 25922
Klebsiella pneumoniae ATCC 13883 and ATCC 10031
Pseudomonas aeruginosa ATCC 27853.
Pseudomonas aeruginosa PAO1
Acinetobacter baumannii ATCC 19606

MIC Assays in the Presence of a Bacterial Efflux Inhibitor
The EPI assay for the purposes of these studies represents a MIC assay in which the MIC of the antibiotic against the bacteria is tested in the presence of an experimental efflux pump inhibitor (EPI). The highest concentration of the EPI present in the assay typically is ½ of the intrinsic MIC of the compound. If the intrinsic MIC of the EPI is greater than 100 µg/mL, the EPI assay was tested with 50 µg/mL. Using serial dilutions of the EPI, its enhancement of antibiotic activity was then evaluated. The relative EPI activity was decided by comparing the MIC of the antibiotic in the presence of the EPI compound with the intrinsic MIC of the antibiotic alone. For comparative purposes, we generally used EPIs at concentration of 12.5 and 6.25 µg/ml against varying concentration of our test antibiotic.

Example 43. Pharmaceutical Forms

The following can illustrate representative pharmaceutical dosage forms, containing a compound of formula I, II, III, IV or V ('Compound X') or a pharmaceutically acceptable salt thereof, for therapeutic or prophylactic use in humans. The tablets can optionally comprise an enteric coating.

| (i) Tablet 1 | mg/tablet |
| --- | --- |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| Compound X = | 1 0.0 |
| Colloidal silicon dioxide | 1.5 |

-continued

| | |
|---|---|
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0 N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. A compound of formula I:

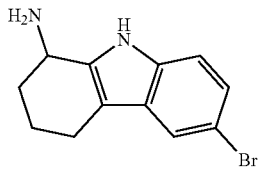

or a salt thereof, wherein:

$R^1$ is hydrogen, halo, cyano, nitro, $(C_1-C_6)$alkyl, $(C_1-C_4)$alkoxy, phenyl or heteroaryl, wherein the $(C_1-C_6)$alkyl, $(C_1-C_4)$alkoxy, phenyl or heteroaryl is optionally substituted with one or more groups selected from halo, hydroxy, $(C_1-C_4)$alkyl, $(C_1-C_4)$haloalkyl, $(C_1-C_4)$alkoxy, $(C_1-C_4)$haloalkoxy, nitro or cyano;

$R^2$ is hydrogen, halo, cyano, nitro, $(C_1-C_6)$alkyl, $(C_1-C_4)$alkoxy, phenyl or heteroaryl, wherein the $(C_1-C_6)$alkyl, $(C_1-C_4)$alkoxy, phenyl or heteroaryl is optionally substituted with one or more groups selected from halo, hydroxy, $(C_1-C_4)$alkyl, $(C_1-C_4)$haloalkyl, $(C_1-C_4)$alkoxy, $(C_1-C_4)$haloalkoxy, nitro or cyano;

$R^3$ is hydrogen, halo, cyano, nitro, $(C_1-C_6)$alkyl, $(C_1-C_4)$alkoxy, phenyl or heteroaryl, wherein the $(C_1-C_6)$alkyl, $(C_1-C_4)$alkoxy, phenyl or heteroaryl is optionally substituted with one or more groups selected from halo, hydroxy, $(C_1-C_4)$alkyl, $(C_1-C_4)$haloalkyl, $(C_1-C_4)$alkoxy, $(C_1-C_4)$haloalkoxy, nitro or cyano;

$R^4$ is hydrogen, halo, cyano, nitro, $(C_1-C_6)$alkyl, $(C_1-C_4)$alkoxy, phenyl or heteroaryl, wherein the $(C_1-C_6)$alkyl, $(C_1-C_4)$alkoxy, phenyl or heteroaryl is optionally substituted with one or more groups selected from halo, hydroxy, $(C_1-C_4)$alkyl, $(C_1-C_4)$haloalkyl, $(C_1-C_4)$alkoxy, $(C_1-C_4)$haloalkoxy, nitro or cyano;

$R^5$ is hydrogen or $(C_1-C_4)$alkyl;

$R^6$ is hydrogen, $(C_1-C_6)$alkyl, $(C_3-C_6)$cycloalkyl, —C(=O)$R^X$, or —C(=O)O$R^X$, wherein the $(C_1-C_6)$alkyl or $(C_3-C_6)$cycloalkyl is optionally substituted with one or more groups selected from halo, O$R^a$ or N$R^a R^b$;

$R^{7a}$ is hydrogen, halo, $(C_1-C_6)$alkyl, —C(=O)O$R^c$, —C(=O)N$R^d R^e$, —N$R^f R^g$, or phenyl, wherein the $(C_1-C_6)$alkyl or phenyl is optionally substituted with one or more halogen, O$R^h$, $(C_1-C_6)$alkyl, or —N$R^f R^g$;

$R^{7b}$ is hydrogen, halo, or $(C_1-C_6)$alkyl;

$R^{8a}$ is hydrogen, halo, $(C_1-C_6)$alkyl, —C(=O)O$R^c$, —C(=O)N$R^d R^e$, —N$R^f R^g$, or phenyl, wherein the $(C_1-C_6)$alkyl or phenyl is optionally substituted with one or more halogen, O$R^h$, $(C_1-C_6)$alkyl, or —N$R^f R^g$;

$R^{8b}$ is hydrogen, halo, or $(C_1-C_6)$alkyl;

$R^{9a}$ is hydrogen, halo, $(C_1-C_6)$alkyl, —C(=O)O$R^c$, —C(=O)N$R^d R^e$, —N$R^f R^g$, or phenyl, wherein the $(C_1-C_6)$alkyl or phenyl is optionally substituted with one or more halogen, O$R^h$, $(C_1-C_6)$alkyl, or —N$R^f R^g$;

$R^{9b}$ is hydrogen, halo, or $(C_1-C_6)$alkyl;

each $R^X$ is independently $(C_1-C_6)$alkyl, or $(C_3-C_6)$cycloalkyl, wherein the $(C_1-C_6)$ alkyl, or $(C_3-C_6)$ cycloalkyl, is optionally substituted with one or more groups selected from halo, O$R^a$ or N$R^a R^b$;

each $R^a$ is independently hydrogen or $(C_1-C_4)$alkyl;

each $R^b$ is independently hydrogen or $(C_1-C_4)$alkyl; or $R^a$ and $R^b$ taken together with the nitrogen to which they are attached form pyrrolidinyl, piperidinyl, piperazinyl or morpholinyl;

$R^c$ is hydrogen or $(C_1-C_4)$alkyl;

$R^d$ is hydrogen or $(C_1-C_4)$alkyl;

$R^e$ is hydrogen or $(C_1-C_4)$alkyl wherein the $(C_1-C_4)$alkyl is optionally substituted with one or more halo, $(C_1-C_4)$alkoxy, —NH$_2$, —NH$(C_1-C_4)$ alkyl or —N$((C_1-C_4)$alkyl$)_2$; or $R^d$ and $R^e$ taken together with the nitrogen to which they are attached form pyrrolidinyl, piperidinyl, piperazinyl or morpholinyl;

$R^f$ is hydrogen or $(C_1-C_4)$alkyl;

$R^g$ is hydrogen or $(C_1-C_4)$alkyl; or $R^f$ and $R^g$ taken together with the nitrogen to which they are attached form pyrrolidinyl, piperidinyl, piperazinyl or morpholinyl; and $R^h$ is hydrogen or $(C_1-C_4)$alkyl;

provided that the compound of formula I is not

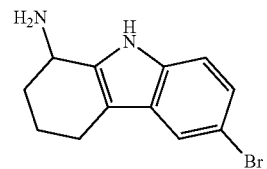 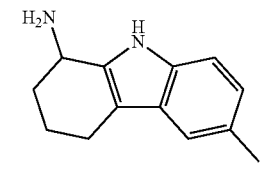

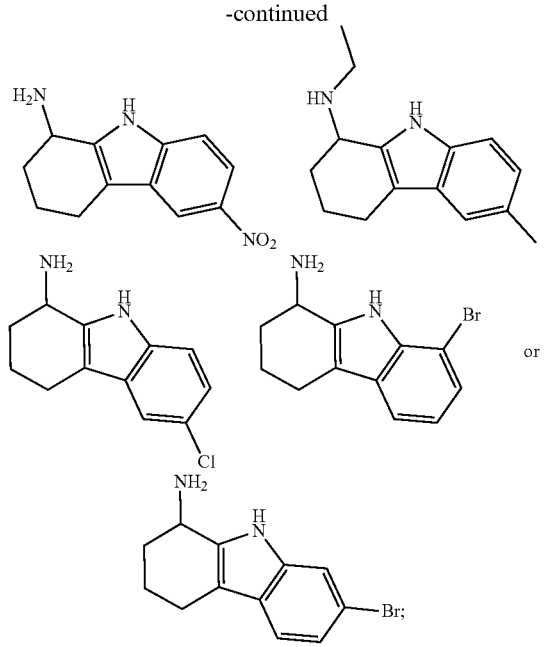
or a salt thereof.
2. The compound of claim 1 that is:
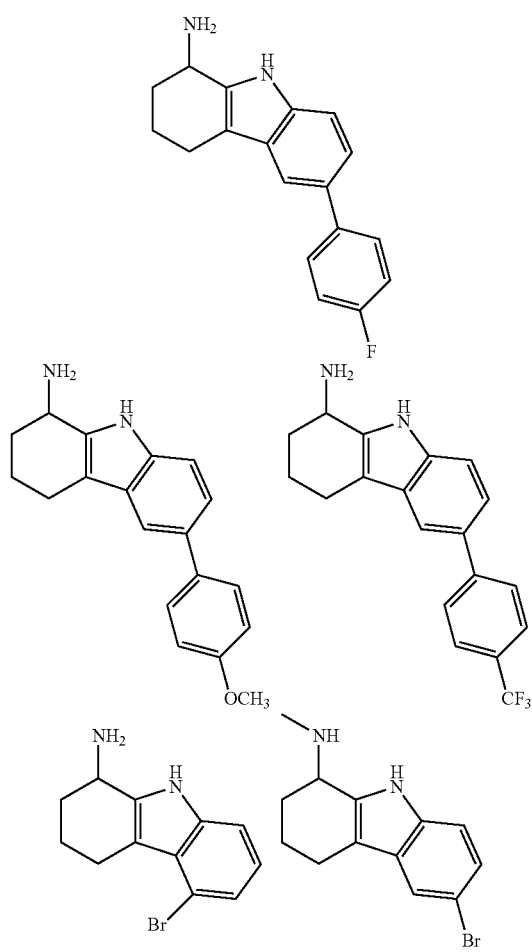
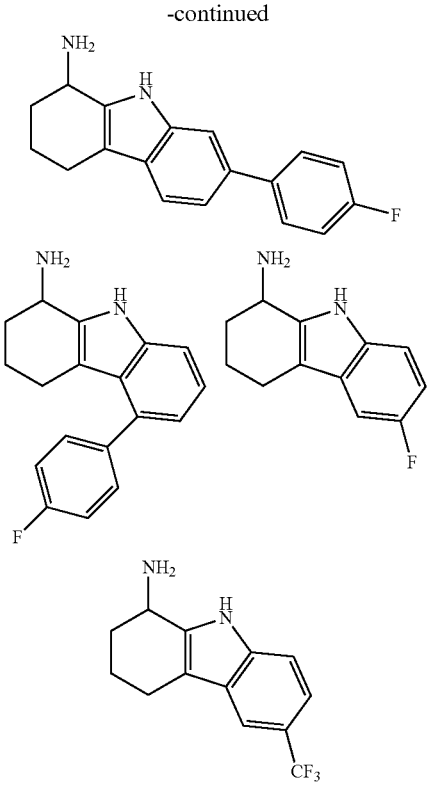
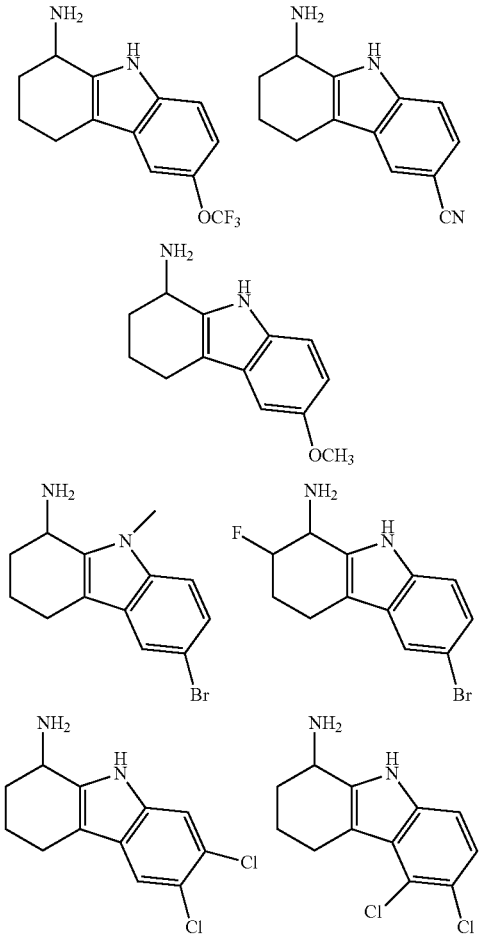

-continued
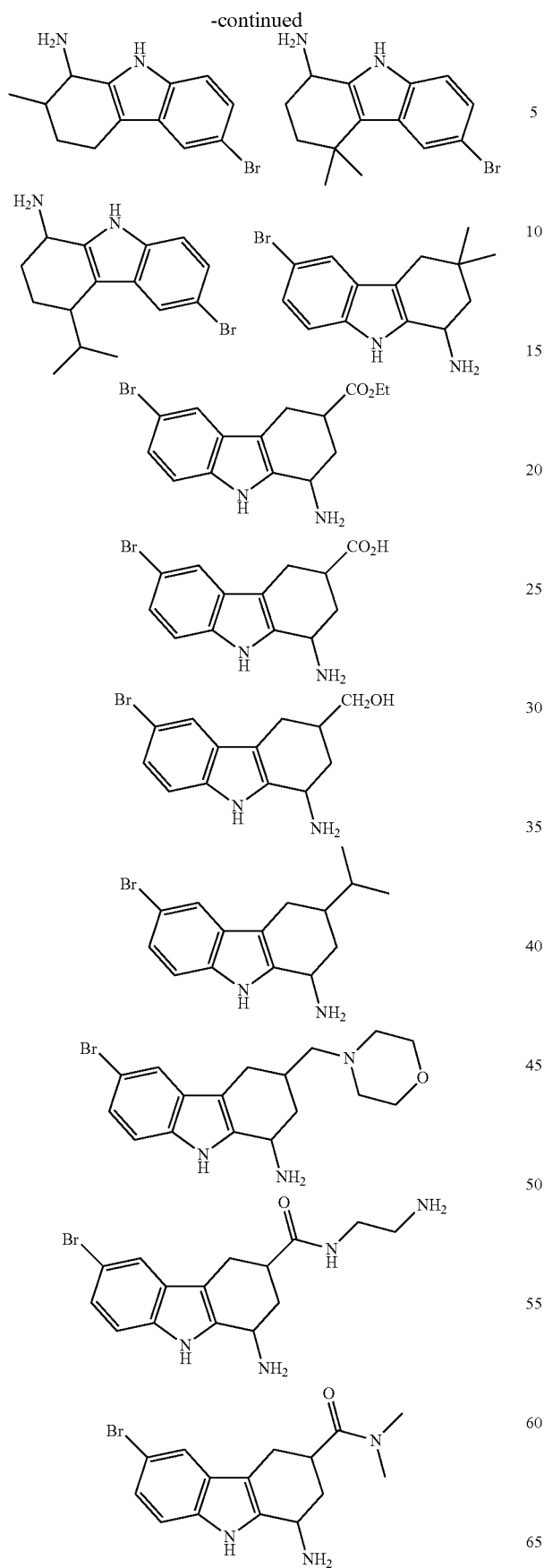
-continued
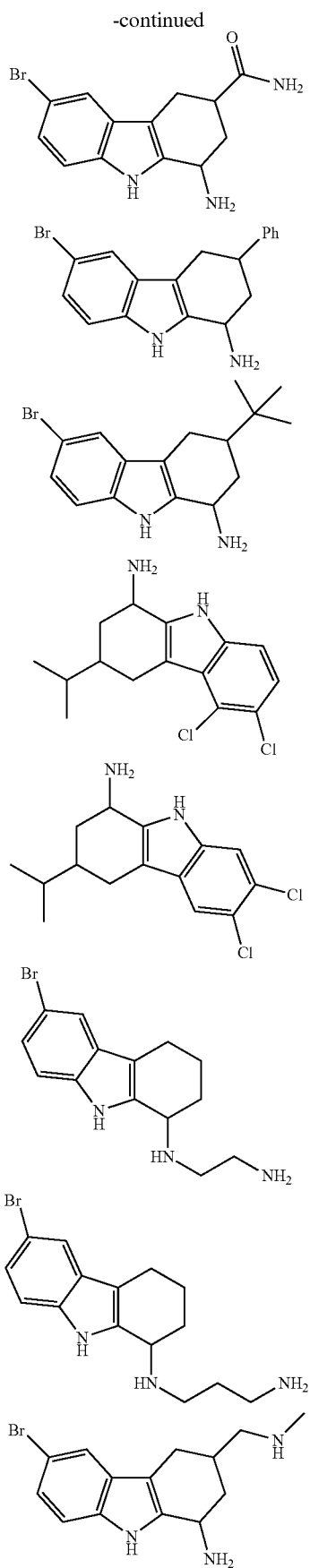

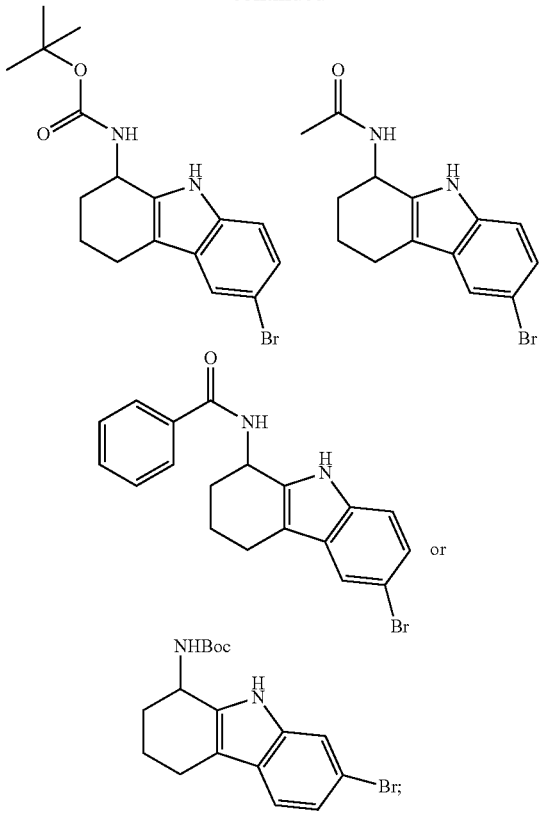

or a salt thereof.

3. A pharmaceutical composition comprising a compound of formula I as described in claim 1 or a pharmaceutically acceptable salt thereof, and a pharmaceutically acceptable vehicle.

4. The compound of claim 1, wherein $R^1$ is hydrogen.

5. The compound of claim 1, wherein $R^2$ is hydrogen, bromo, chloro or 4-fluorophenyl.

6. The compound of claim 1, wherein $R^3$ is halo, cyano, nitro, $(C_1$-$C_6)$alkyl, $(C_1$-$C_4)$alkoxy, or phenyl, wherein the $(C_1$-$C_6)$alkyl, $(C_1$-$C_4)$alkoxy, or phenyl is optionally substituted with one or more groups selected from halo, $(C_1$-$C_4)$haloalkyl, or $(C_1$-$C_4)$alkoxy.

7. The compound of claim 1, wherein $R^3$ is fluoro, bromo, chloro, —$CF_3$, —$OCF_3$, CN, —$OCH_3$, 4-fluorophenyl, 4-methoxyphenyl, or 4-trifluoromethylphenyl.

8. The compound of claim 1, wherein $R^4$ is hydrogen, bromo, or chloro.

9. The compound of claim 1, wherein at least one of $R^1$, $R^2$, $R^3$, and $R^4$ is not hydrogen.

10. The compound of claim 1, wherein $R^6$ is hydrogen, or $(C_1$-$C_6)$alkyl, wherein the $(C_1$-$C_6)$alkyl is optionally substituted with one or more groups selected from halo, $OR^3$ or $NR^3R^b$.

11. A method of treating or preventing a bacterial infection in an animal comprising administering to the animal a compound of formula I as described in claim 1 or a pharmaceutically acceptable salt thereof alone or in the presence of a bacterial efflux pump inhibitor.

12. The method of claim 11 wherein the bacterial efflux pump inhibitor when used in combination with a compound of formula I or a pharmaceutically acceptable salt thereof is a compound of formula II:

$$\underset{R^{1A}}{\overset{R^{2A}}{N}}\underset{O}{\overset{}{C}}(C(R^{3A})_2)_n\text{-Ar} \quad \text{II}$$

or a pharmaceutically acceptable salt thereof, wherein:
$R^{1A}$ is $(C_3$-$C_8)$alkyl substituted with two or more groups selected from —$NR^{b1}R^{c1}$, —$NHNH_2$, —$C(=NR^{a1})(NR^{b1}R^{c1})$, —$NR^{a1}C(=NR^{a1})(R^{d1})$ and —$NR^{a1}C(=NR^{a1})(NR^{b1}R^{c1})$;
$R^{2A}$ is hydrogen or $(C_1$-$C_3)$alkyl;
each $R^{3A}$ is independently hydrogen, halo or $(C_1$-$C_4)$alkyl;
$R^{4A}$ is hydrogen, halo, $(C_1$-$C_6)$alkyl, $(C_1$-$C_6)$haloalkyl, $(C_1$-$C_6)$alkoxy, $(C_1$-$C_4)$haloalkoxy, aryl or heteroaryl wherein the aryl or heteroaryl is optionally substituted with one or more groups independently selected from halo, $(C_1$-$C_4)$alkyl, $(C_1$-$C_4)$haloalkyl, $(C_1$-$C_4)$alkoxy and $(C_1$-$C_4)$haloalkoxy;
$R^{5A}$ is hydrogen, halo, $(C_1$-$C_6)$alkyl, $(C_1$-$C_6)$haloalkyl, $(C_1$-$C_6)$alkoxy, $(C_1$-$C_4)$haloalkoxy, aryl or heteroaryl wherein the aryl or heteroaryl is optionally substituted with one or more groups independently selected from halo, $(C_1$-$C_4)$alkyl, $(C_1$-$C_4)$haloalkyl, $(C_1$-$C_4)$alkoxy and $(C_1$-$C_4)$haloalkoxy;
$R^{6A}$ is hydrogen, halo, $(C_1$-$C_6)$alkyl, $(C_1$-$C_6)$haloalkyl, $(C_1$-$C_6)$alkoxy, $(C_1$-$C_4)$haloalkoxy, aryl or heteroaryl wherein the aryl or heteroaryl is optionally substituted with one or more groups independently selected from halo, $(C_1$-$C_4)$alkyl, $(C_1$-$C_4)$haloalkyl, $(C_1$-$C_4)$alkoxy and $(C_1$-$C_4)$haloalkoxy;
$R^{7A}$ is hydrogen, halo, $(C_1$-$C_6)$alkyl, $(C_1$-$C_6)$haloalkyl, $(C_1$-$C_6)$alkoxy, $(C_1$-$C_4)$haloalkoxy, aryl or heteroaryl wherein the aryl or heteroaryl is optionally substituted with one or more groups independently selected from halo, $(C_1$-$C_4)$alkyl, $(C_1$-$C_4)$haloalkyl, $(C_1$-$C_4)$alkoxy and $(C_1$-$C_4)$haloalkoxy;
$R^{8A}$ is hydrogen, halo, $(C_1$-$C_6)$alkyl, $(C_1$-$C_6)$haloalkyl, $(C_1$-$C_6)$alkoxy, $(C_1$-$C_4)$haloalkoxy, aryl or heteroaryl wherein the aryl or heteroaryl is optionally substituted with one or more groups independently selected from halo, $(C_1$-$C_4)$alkyl, $(C_1$-$C_4)$haloalkyl, $(C_1$-$C_4)$alkoxy and $(C_1$-$C_4)$haloalkoxy;
each $R^{a1}$ is independently hydrogen or $(C_1$-$C_4)$alkyl;
each $R^{b1}$ and $R^{c1}$ is independently hydrogen or $(C_1$-$C_4)$alkyl;
$R^{d1}$ is $(C_1$-$C_3)$alkyl; and
n is 0 or 1.

13. The method of claim 11 wherein the bacterial efflux pump inhibitor when used in combination with a compound of formula I or a pharmaceutically acceptable salt thereof is a compound of formula III:

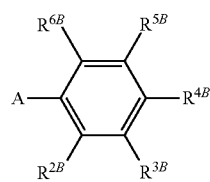

or a pharmaceutically acceptable salt thereof, wherein:

A is —C(=O)N($R^{a1}$)—$R^{1B}$, —($C_1$-$C_3$)alkyl-C(=O)N($R^{a1}$)$R^{1B}$, —($C_1$-$C_3$)alkyl-O—$R^{1B}$, —O—$R^{1B}$, —($C_1$-$C_3$)alkyl-N($R^{a1}$)—$R^{1B}$, or —N($R^{a1}$)—$R^{1B}$;

each $R^{1B}$ is independently a ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, wherein each ($C_3$-$C_7$)carbocyclyl or ($C_3$-$C_7$)carbocyclyl-($C_1$-$C_4$)alkyl- is independently substituted with one or more groups selected from the group consisting of Z and —($C_1$-$C_6$)alkyl substituted with one or more Z, and wherein each 4-7 membered monocyclic heterocyclyl or 4-7 membered monocyclic heterocyclyl-($C_1$-$C_4$)alkyl- is independently optionally substituted with one or more groups selected from the group consisting of Z and —($C_1$-$C_6$)alkyl substituted with one or more Z, wherein each Z is independently selected from the group consisting of $NR^{b2}R^{c2}$, —$NHNH_2$, —C(=$NR^{a2}$)($NR^{b2}R^{c2}$), —$NR^{a2}$C(=$NR^{a2}$)($R^{d2}$), and —$NR^{a2}$C(=$NR^{a2}$)($NR^{b2}R^{c2}$) and wherein each ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, is independently optionally substituted independently with one or more ($C_1$-$C_4$)alkyl;

$R^{2B}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_4$)alkyl, ($C_1$-$C_4$)haloalkyl, ($C_1$-$C_4$)alkoxy and ($C_1$-$C_4$)haloalkoxy;

$R^{3B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy;

$R^{4B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy;

$R^{5B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy;

$R^{6B}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_4$)alkyl, ($C_1$-$C_4$)haloalkyl, ($C_1$-$C_4$)alkoxy and ($C_1$-$C_4$)haloalkoxy;

each $R^{a1}$ is independently hydrogen, ($C_1$-$C_6$)alkyl or ($C_3$-$C_7$)carbocyclyl;

each $R^{a2}$ is independently hydrogen, ($C_1$-$C_6$)alkyl or ($C_3$-$C_7$)carbocyclyl;

each $R^{b2}$ and $R^{c2}$ is independently hydrogen, ($C_1$-$C_6$)alkyl or ($C_3$-$C_7$)carbocyclyl; and $R^{d2}$ is ($C_1$-$C_6$)alkyl or ($C_3$-$C_7$)carbocyclyl.

14. The method of claim 11 wherein the bacterial efflux pump inhibitor when used in combination with a compound of formula I or a pharmaceutically acceptable salt thereof is a compound of formula IV:

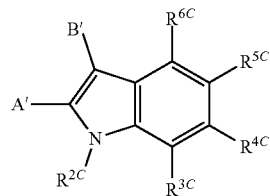

IV or a pharmaceutically acceptable salt thereof, wherein:

one of A' or B' is —C(=O)N($R^{a1}$)—$R^{1C}$, —($C_1$-$C_3$)alkyl-C(=O)N($R^{a1}$)$R^{1C}$, —($C_1$-$C_3$)alkyl-O—$R^{1C}$, —O—$R^{1C}$, —($C_1$-$C_3$)alkyl-N($R^{a1}$)—$R^{1C}$, —N($R^{a1}$)—$R^{1C}$, or $R^{1C}$ and the other of A' or B' is H, halogen, or ($C_1$-$C_4$)alkyl;

each $R^{1C}$ is independently:

(a) ($C_1$-$C_{14}$)alkyl substituted with one or more groups selected from the group consisting of —$NR^{b2}R^{c2}$, —$NHNH_2$, —C(=$NR^{a2}$)($NR^{b2}R^{c2}$), —$NR^{a2}$C(=$NR^{a2}$)($R^{d2}$), and —$NR^{a2}$C(=$NR^{a2}$)($NR^{b2}R^{c2}$); and wherein ($C_1$-$C_{14}$)alkyl is optionally substituted independently with one or more halo, ($C_1$-$C_4$)alkyl or ($C_3$-$C_7$)carbocyclyl; or (b) ($C_3$-$C_7$)carbocyclyl, ($C_3$-$C_7$)carbocyclyl-($C_1$-$C_4$)alkyl-, 4-7 membered monocyclic heterocyclyl, 4-7 membered monocyclic heterocyclyl-($C_1$-$C_4$)alkyl-, ($C_3$-$C_7$)carbocyclyl-$NR^e$—($C_1$-$C_4$)alkyl- or 4-7 membered monocyclic heterocyclyl-$NR^e$—($C_1$-$C_4$)alkyl- wherein each ($C_3$-$C_7$)carbocyclyl, ($C_3$-$C_7$)carbocyclyl-($C_1$-$C_4$)alkyl- or -, ($C_3$-$C_7$)carbocyclyl-$NR^e$—($C_1$-$C_4$)alkyl- is independently substituted with one or more $Z^1$ or $Z^2$, and wherein each 4-7 membered monocyclic heterocyclyl, 4-7 membered monocyclic heterocyclyl-($C_1$-$C_4$)alkyl- or 4-7 membered monocyclic heterocyclyl-$NR^e$—($C_1$-$C_4$)alkyl- is independently optionally substituted with one or more $Z^1$ or $Z^2$, and wherein any ($C_3$-$C_7$)carbocyclyl, ($C_3$-$C_7$)carbocyclyl-($C_1$-$C_4$)alkyl-, 4-7 membered monocyclic heterocyclyl, 4-7 membered monocyclic heterocyclyl-($C_1$-$C_4$)alkyl-, ($C_3$-$C_7$)carbocyclyl $NR^e$—($C_1$-$C_4$)alkyl- or 4-7 membered monocyclic heterocyclyl-$NR^e$—($C_1$-$C_4$)alkyl- of $R^1$ is independently optionally substituted with one or more halo, ($C_1$-$C_4$)alkyl, ($C_3$-$C_7$)carbocyclyl, —C(=O)$NH_2$, —C(=O)NH($C_1$-$C_4$)alkyl, —C(=O)N(($C_1$-$C_4$)alkyl)$_2$, —NHC(=O)($C_1$-$C_4$)alkyl-$NH_2$, or 3-7 membered monocyclic heterocyclyl wherein ($C_1$-$C_4$)alkyl, ($C_3$-$C_7$)carbocyclyl or 3-7 membered monocyclic heterocyclyl is optionally substituted with one or more halogen, ($C_1$-$C_4$)alkyl, —$NH_2$, —NH($C_1$-$C_4$)alkyl or —N(($C_1$-$C_4$)alkyl)$_2$;

$R^{2C}$ is hydrogen, ($C_1$-$C_4$)alkyl or phenyl(($C_1$-$C_3$)alkyl-, wherein the phenyl is optionally substituted with one or more ($C_1$-$C_4$)alkyl, —O($C_1$-$C_4$)alkyl, halogen, or —$NO_2$;

$R^{3C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^{4C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, heteroaryl, aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)

alkynyl-, phenoxy or heteroaryloxy, wherein the aryl, heteroaryl, aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl ($C_2$-$C_4$)alkynyl-, phenoxy or heteroaryloxy, is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, ($C_1$-$C_4$)haloalkoxy, methylenedioxy (—$OCH_2O$—), and ($C_3$-$C_7$)carbocyclyl;

$R^{5C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, heteroaryl aryl ($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)alkynyl-, phenoxy or heteroaryloxy, wherein the aryl, heteroaryl, aryl($C_1$-$C_4$)alkyl-, heteroaryl($C_1$-$C_4$)alkyl-, ($C_3$-$C_7$)carbocyclyl($C_1$-$C_4$)alkyl-, ($C_3$-$C_7$)carbocyclyl($C_2$-$C_4$)alkynyl-, phenoxy or heteroaryloxy, is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, ($C_1$-$C_4$)haloalkoxy, methylenedioxy (—$OCH_2O$—), and ($C_3$-$C_7$)carbocyclyl;

$R^{6C}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

each $Z^1$ is independently selected from the group consisting of —$NR^{b3}R^{c3}$, —$NHNH_2$, —C(=$NR^{a3}$)($NR^{b3}R^{c3}$), —$NR^{a3}$C(=$NR^{a3}$)($R^{d3}$), and —$NR^{a3}$C(=$NR^{a3}$)($NR^{b3}R^{c3}$);

each $Z^2$ is independently —($C_1$-$C_6$)alkyl substituted with one or more $Z^1$ and optionally substituted with one or more $Z^3$;

each $Z^3$ is independently halo or ($C_3$-$C_7$)carbocyclyl;

each $R^{a1}$ is independently hydrogen, ($C_1$-$C_4$)alkyl, ($C_3$-$C_7$)carbocyclyl or 3-7 membered monocyclic heterocycly optionally substituted with one or more halogen or ($C_1$-$C_4$)alkyl;

each $R^{a2}$ is independently hydrogen, ($C_1$-$C_4$)alkyl or ($C_3$-$C_7$)carbocyclyl;

each $R^{b2}$ and $R^{c2}$ is independently hydrogen, ($C_1$-$C_4$)alkyl or ($C_3$-$C_7$)carbocyclyl;

$R^{d2}$ is ($C_1$-$C_4$)alkyl or ($C_3$-$C_7$)carbocyclyl;

each $R^{a3}$ is independently hydrogen ($C_1$-$C_4$)alkyl or ($C_3$-$C_7$)carbocyclyl;

each $R^{b3}$ and $R^3$ is independently hydrogen ($C_1$-$C_4$)alkyl or ($C_3$-$C_7$)carbocyclyl;

$R^{d3}$ is ($C_1$-$C_4$)alkyl or ($C_3$-$C_7$)carbocyclyl; and each $R^e$ is independently hydrogen, ($C_1$-$C_4$)alkyl or ($C_3$-$C_7$)carbocyclyl.

15. The method of claim 11 wherein the bacterial efflux pump inhibitor when used in combination with a compound of formula I or a pharmaceutically acceptable salt thereof is a compound of formula V:

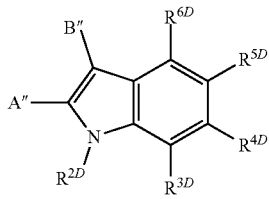

V or a pharmaceutically acceptable salt thereof, wherein:

A″ is —C(=O)N($R^{a1}$)—$R^{1D}$, —($C_1$-$C_3$)alkyl-C(=O)N($R^{a1}$)$R^{1D}$, —($C_1$-$C_3$)alkyl-O—$R^{1D}$, —O—$R^{1D}$, —($C_1$-$C_3$)alkyl-N($R^{a1}$)—$R^{1D}$, —N($R^{a1}$)—$R^{1D}$, or $R^{1D}$;

B″ is ($C_2$-$C_8$)alkenyl, ($C_2$-$C_8$)alkynyl, ($C_1$-$C_4$)haloalkyl, ($C_1$-$C_4$)alkoxy, ($C_1$-$C_4$)haloalkoxy, ($C_3$-$C_7$)carbocyclyl, ($C_3$-$C_7$)carbocyclyl-($C_1$-$C_4$)alkyl-, aryl, aryl-($C_1$-$C_4$)alkyl-, heteroaryl, heteroaryl-($C_1$-$C_4$)alkyl-, 3-7 membered-monocyclic-heterocycle, or 3-7 membered-monocyclic-heterocycle-($C_1$-$C_4$)alkyl- wherein any ($C_3$-$C_7$)carbocyclyl, ($C_3$-$C_7$)carbocyclyl-($C_1$-$C_4$)alkyl-, aryl, aryl-($C_1$-$C_4$)alkyl-, heteroaryl, heteroaryl-($C_1$-$C_4$)alkyl-, 3-7 membered-monocyclic-heterocycle, or 3-7 membered-monocyclic-heterocycle-($C_1$-$C_4$)alkyl- of B″ is optionally substituted with one or more $Z^1$ groups;

each $R^{1D}$ is independently:

(a) ($C_1$-$C_{14}$)alkyl substituted with one or more groups selected from the group consisting of —$NR^{b2}R^{c2}$, —$NHNH_2$, —C(=$NR^{a2}$)($NR^{b2}R^{c2}$), —$NR^{a2}$C(=$NR^{a2}$)($R^{d2}$), and —$NR^{a2}$C(=$NR^{a2}$)($NR^{b2}R^{c2}$) and wherein ($C_1$-$C_{14}$)alkyl is optionally substituted independently with one or more halo, ($C_1$-$C_4$)alkyl or ($C_3$-$C_7$)carbocyclyl; or (b) ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, wherein each ($C_3$-$C_7$)carbocyclyl or ($C_3$-$C_7$)carbocyclyl-($C_1$-$C_4$)alkyl- is independently substituted with one or more $Z^2$ or $Z^3$, and wherein each 4-7 membered monocyclic heterocyclyl or 4-7 membered monocyclic heterocyclyl-($C_1$-$C_4$)alkyl- is independently optionally substituted with one or more $Z^2$ or $Z^3$, and wherein any ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl- of $R^1$ is optionally substituted independently with one or more halo, ($C_1$-$C_4$)alkyl or ($C_3$-$C_7$)carbocyclyl;

$R^{2D}$ is hydrogen, ($C_1$-$C_4$)alkyl or phenyl($C_1$-$C_3$)alkyl-, wherein the phenyl is optionally substituted with one or more ($C_1$-$C_4$)alkyl, —O($C_1$-$C_4$)alkyl, halogen, or —$NO_2$;

$R^{3D}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^{4D}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^{5D}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —$NO_2$, —CN, ($C_1$-$C_4$)alkyl, ($C_1$-$C_4$)haloalkyl, ($C_1$-$C_4$)alkoxy, and ($C_1$-$C_4$)haloalkoxy;

$R^{6D}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl, or heteroaryl wherein the aryl or heteroaryl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

each $Z^1$ is independently halo, —OH, —NO$_2$, —CN, (C$_1$-C$_4$)alkyl, (C$_1$-C$_4$)haloalkyl, (C$_1$-C$_4$)alkoxy, or (C$_1$-C$_4$)haloalkoxy;

each $Z^2$ is independently selected from the group consisting of —NR$^{b3}$R$^{c3}$, —NHNH$_2$, —C(=NR$^{a3}$)(NR$^{b3}$R$^{c3}$), —NR$^{a3}$C(=NR$^{a3}$)(R$^{d3}$), and —NR$^{a3}$C(=NR$^{a3}$)(NR$^{b3}$R$^{c3}$)

each $Z^3$ is independently —(C$_1$-C$_6$)alkyl substituted with one or more $Z^2$ and optionally substituted with one or more $Z^4$;

each $Z^4$ is independently halo or (C$_3$-C$_7$)carbocyclyl;

each $R^{a1}$ is independently hydrogen, (C$_1$-C$_4$)alkyl or (C$_3$-C$_7$)carbocyclyl;

each $R^{a2}$ is independently hydrogen, (C$_1$-C$_4$)alkyl or (C$_3$-C$_7$)carbocyclyl;

each $R^{b2}$ and $R^{c2}$ is independently hydrogen, (C$_1$-C$_4$)alkyl or (C$_3$-C$_7$)carbocyclyl;

$R^{d2}$ is (C$_1$-C$_4$)alkyl or (C$_3$-C$_7$)carbocyclyl;

each $R^{a3}$ is independently hydrogen (C$_1$-C$_4$)alkyl or (C$_3$-C$_7$)carbocyclyl;

each $R^{b3}$ and $R^{c3}$ is independently hydrogen (C$_1$-C$_4$)alkyl or (C$_3$-C$_7$)carbocyclyl; and $R^{d3}$ is (C$_1$-C$_4$)alkyl or (C$_3$-C$_7$)carbocyclyl.

16. The method of claim 11 wherein the bacterial efflux pump inhibitor when used in combination with a compound of formula I or a pharmaceutically acceptable salt thereof is selected from the group consisting of:

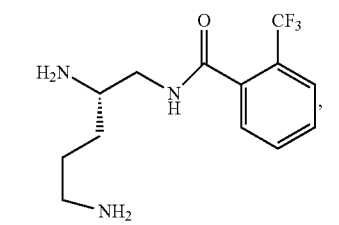

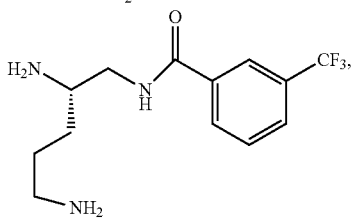

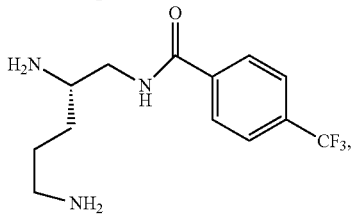

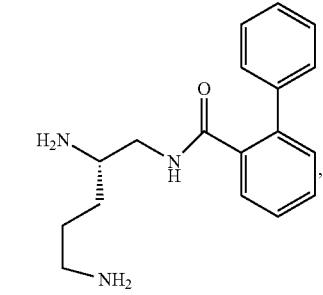

-continued

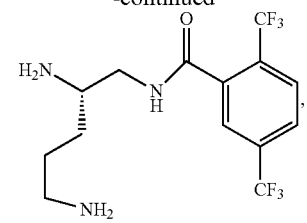

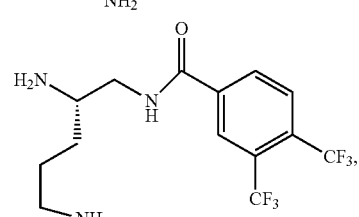

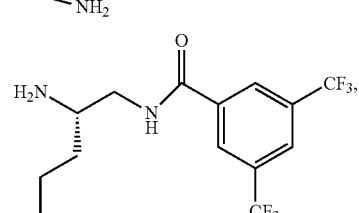

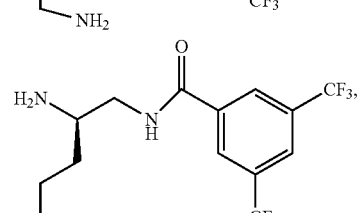

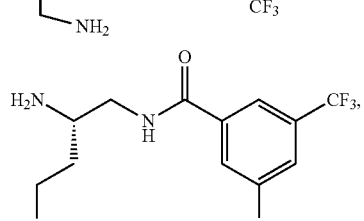

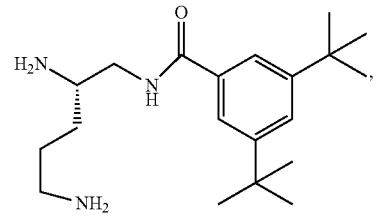

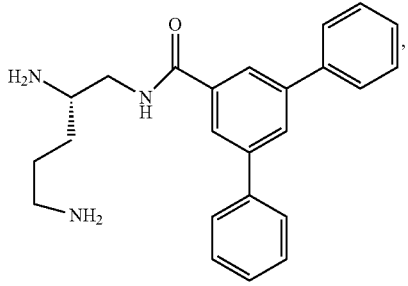

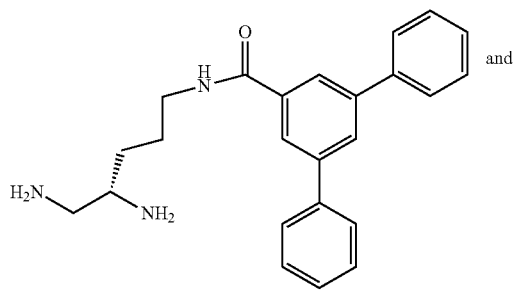
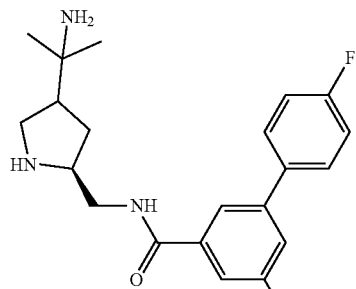
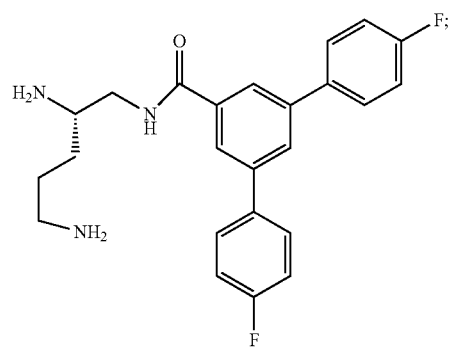
or a pharmaceutically acceptable salt thereof.
17. The method of claim 11 wherein the bacterial efflux pump inhibitor when used in combination with a compound of formula I or a pharmaceutically acceptable salt thereof is selected from the group consisting of:
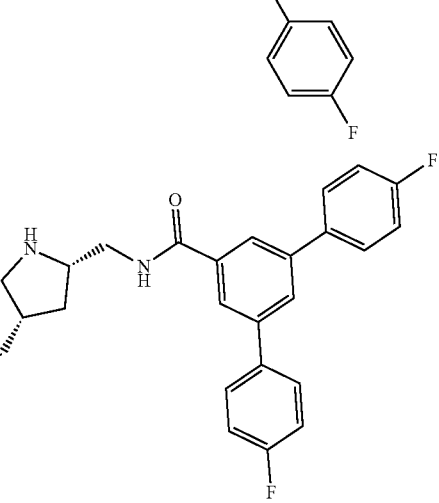
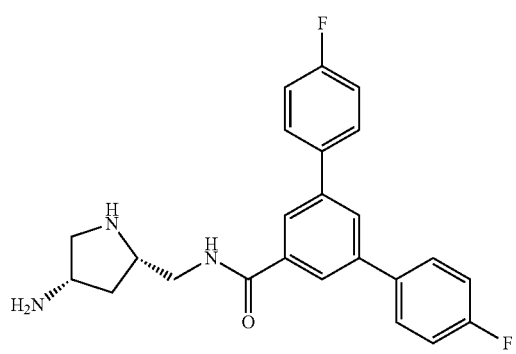
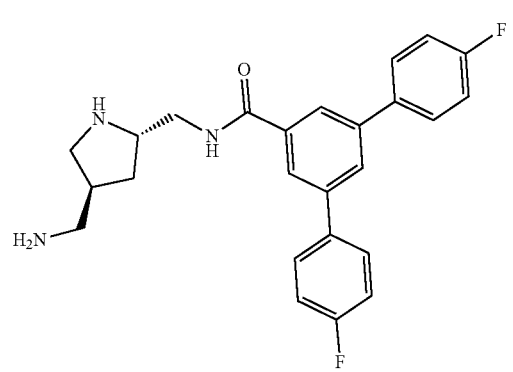
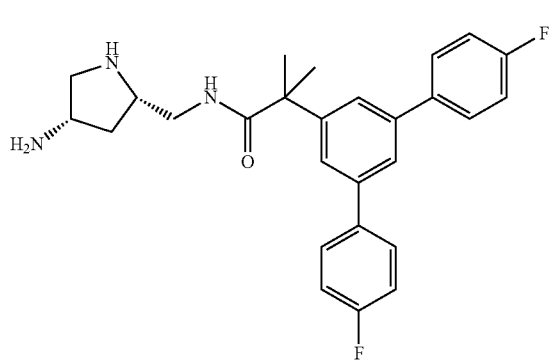
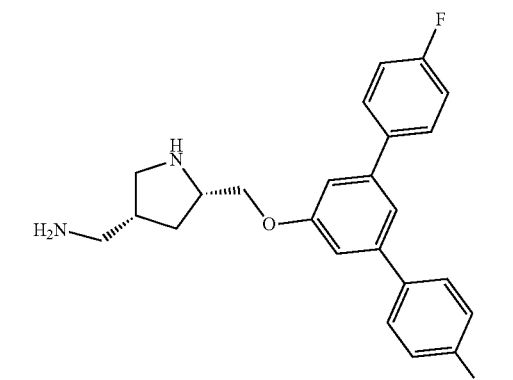

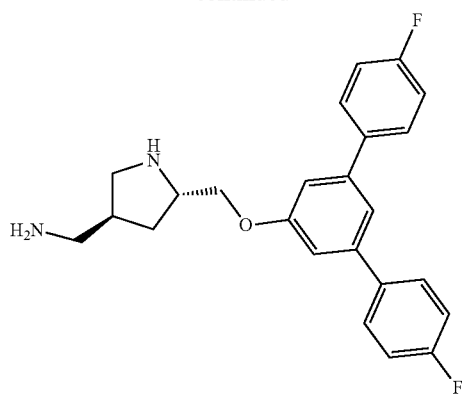
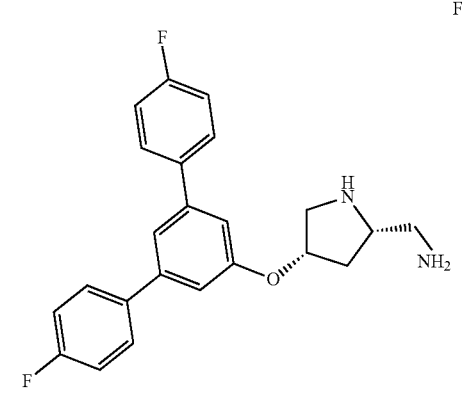
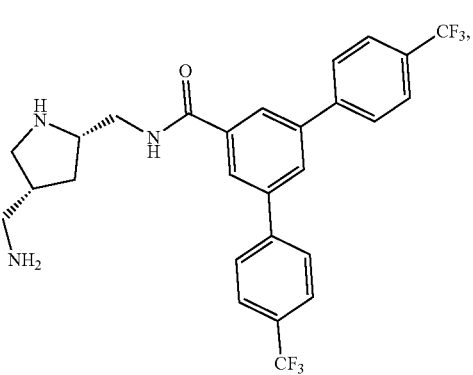
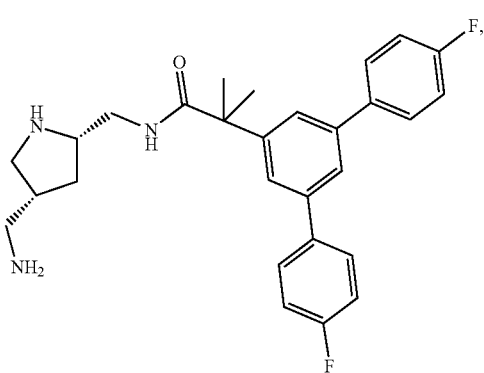
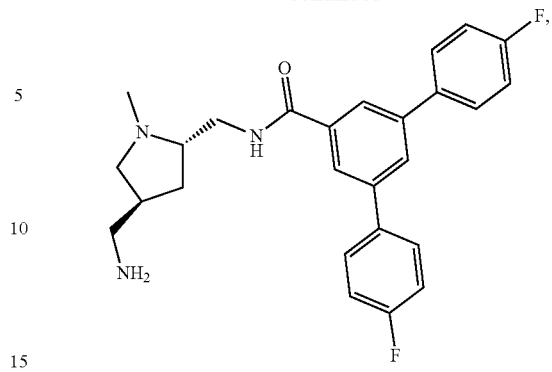
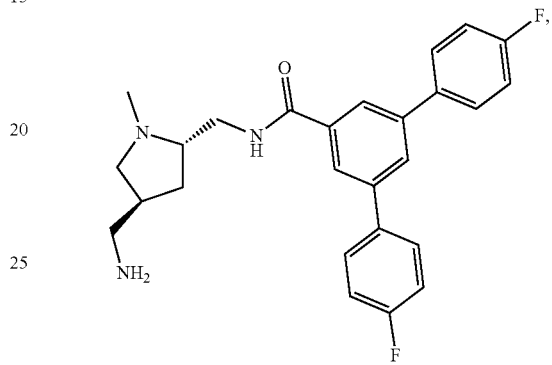
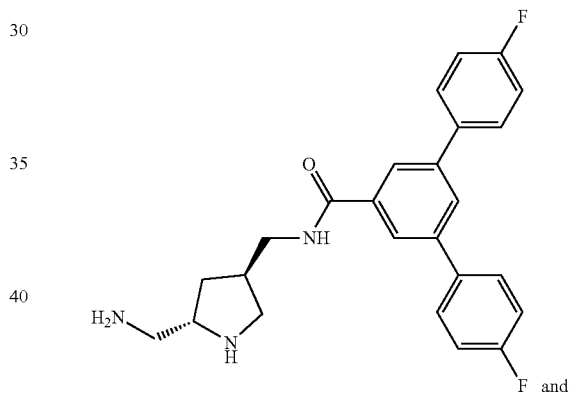
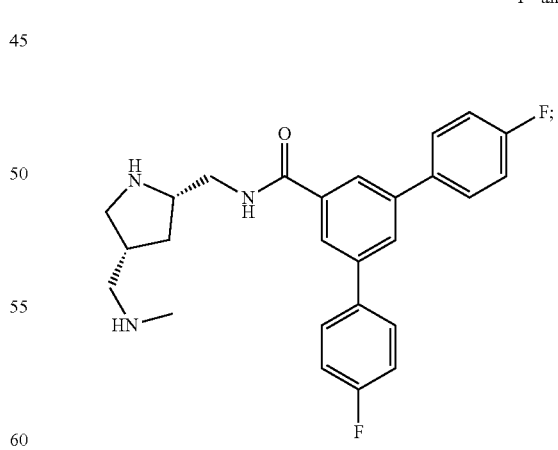
or a pharmaceutically acceptable salt thereof.
18. The method of claim 11 wherein the bacterial efflux pump inhibitor when used in combination with a compound of formula I or a pharmaceutically acceptable salt thereof is selected from the group consisting of:

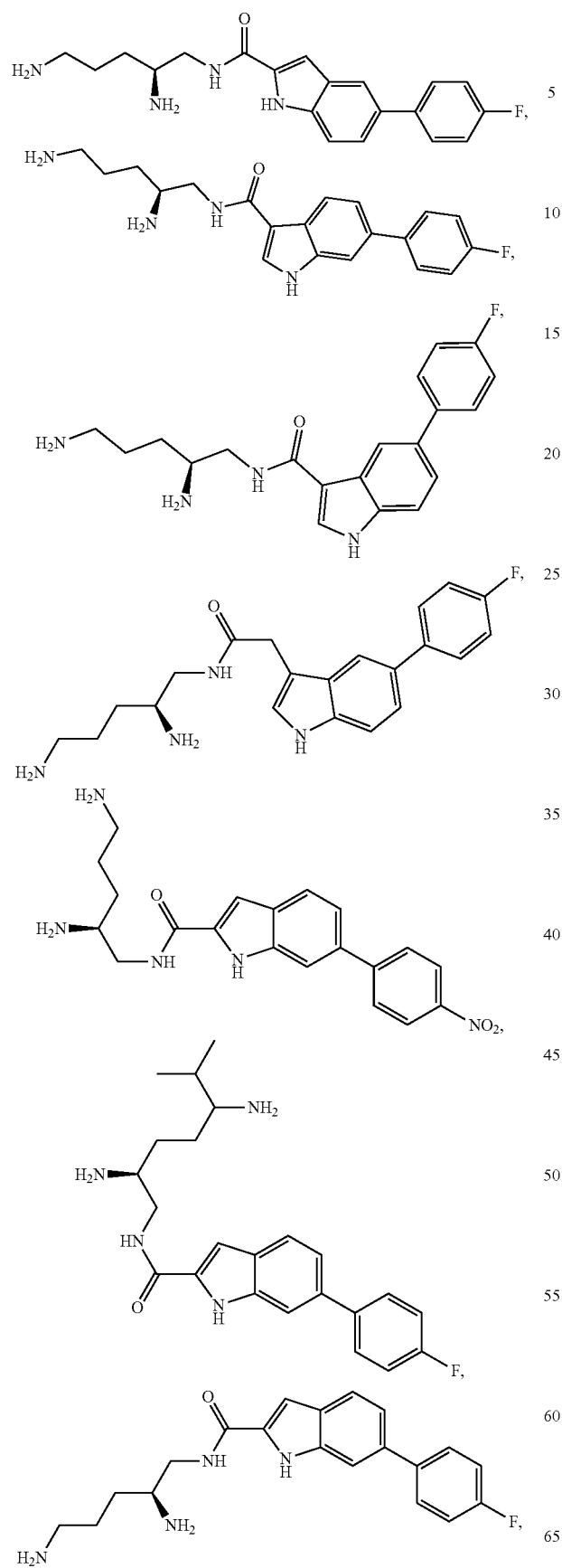
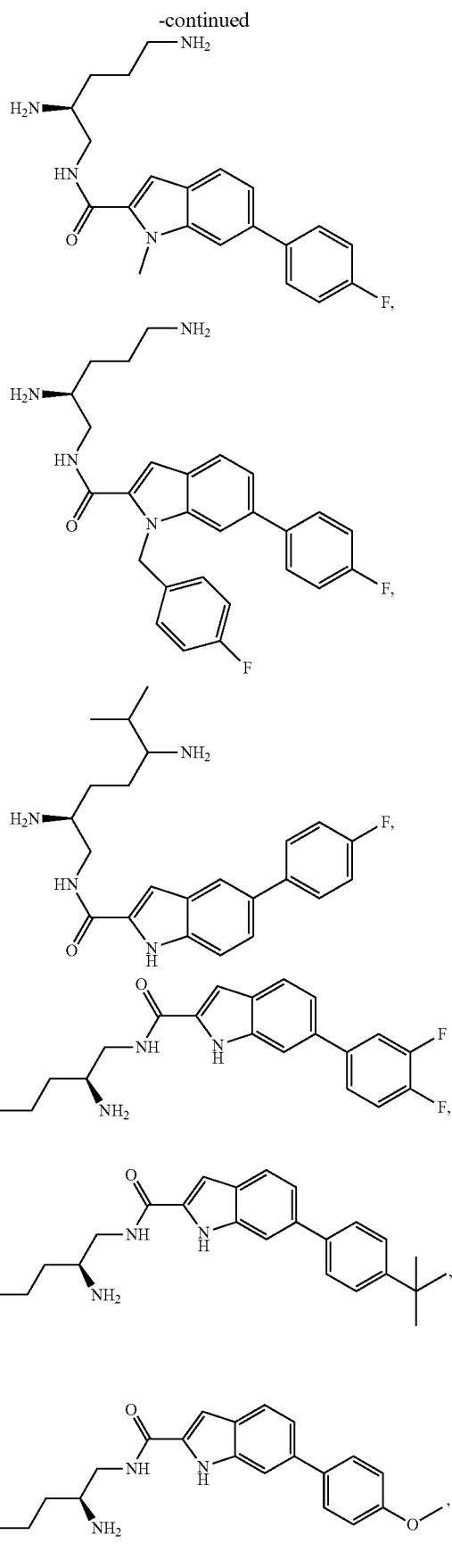

-continued
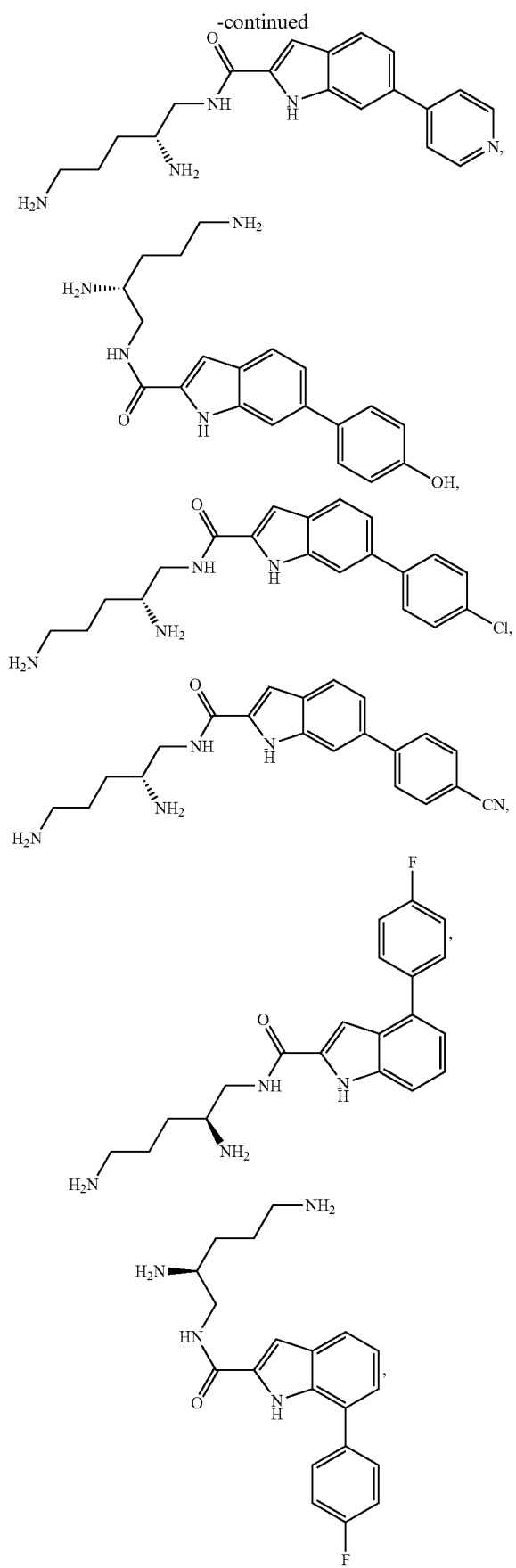
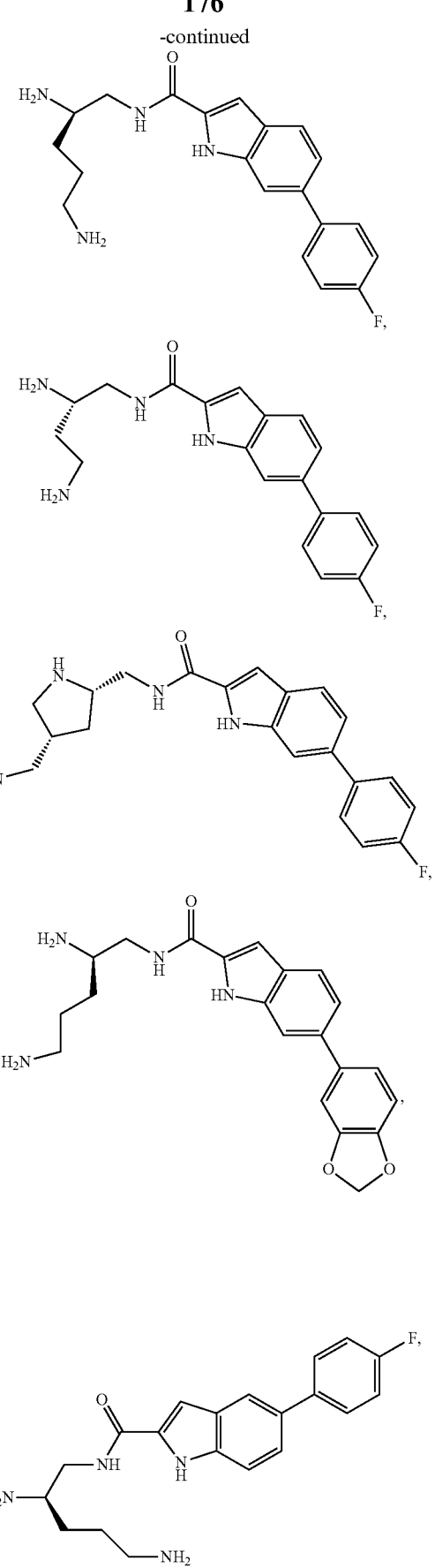

177
-continued
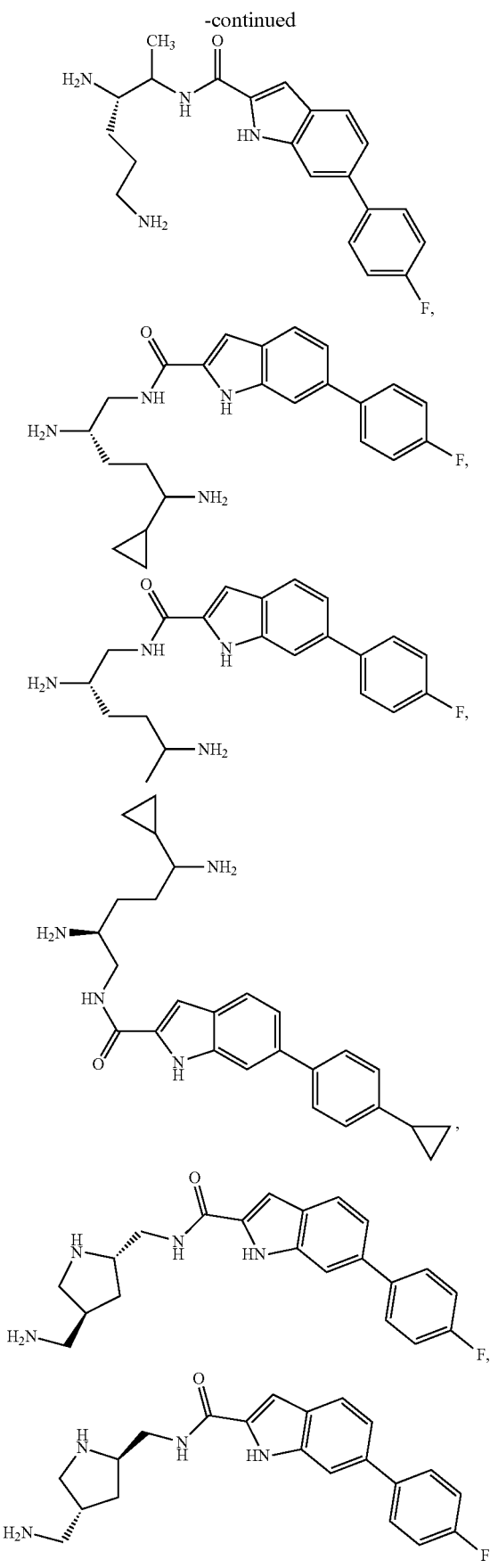
178
-continued
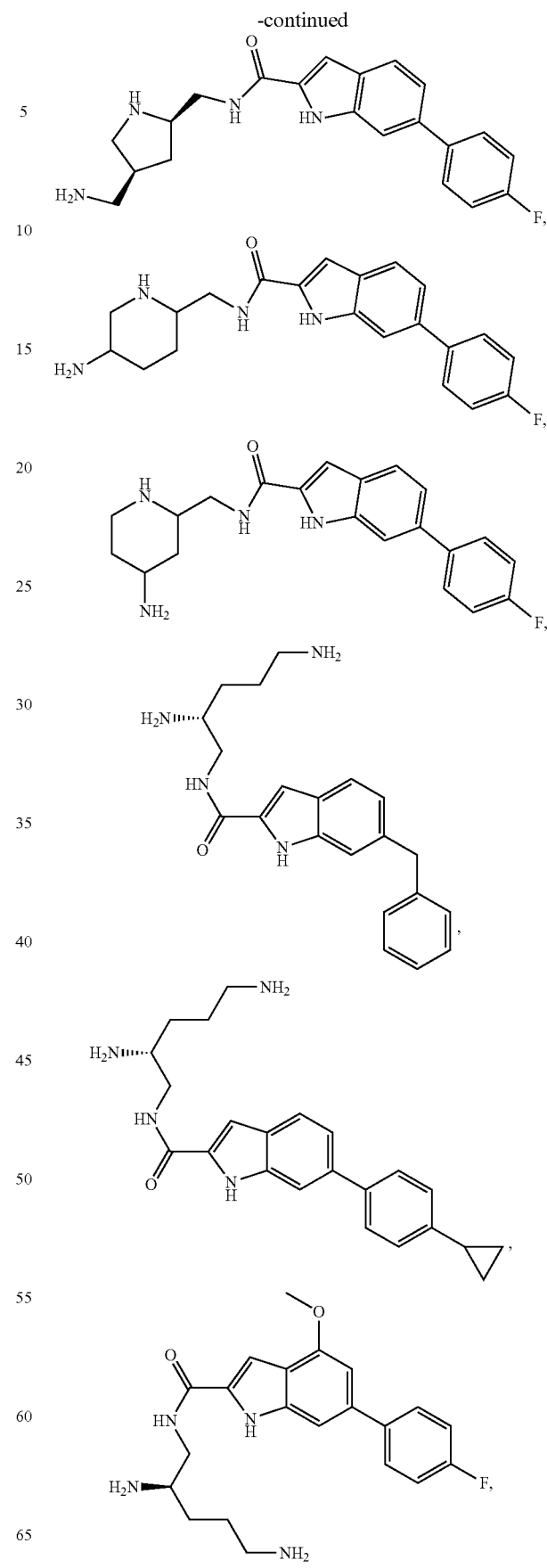

179
-continued
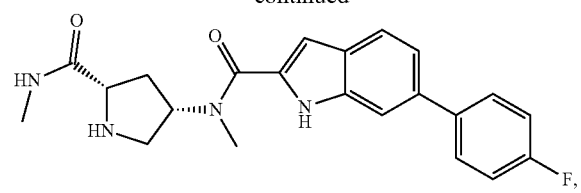
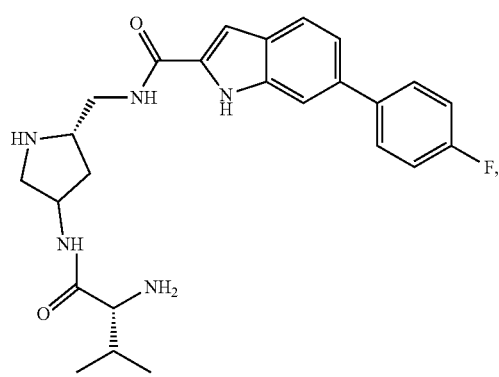
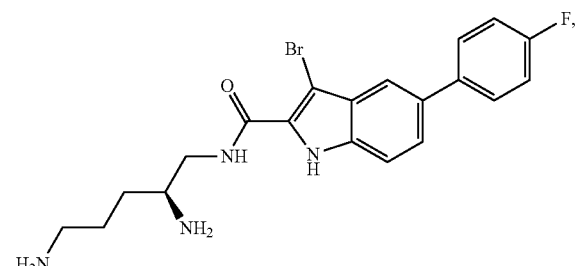
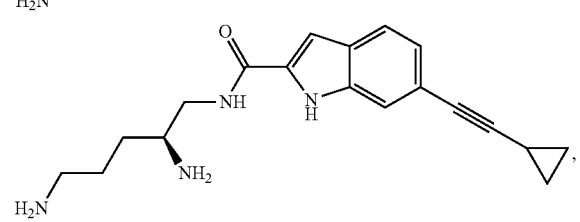
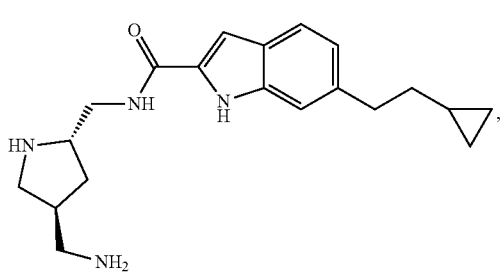
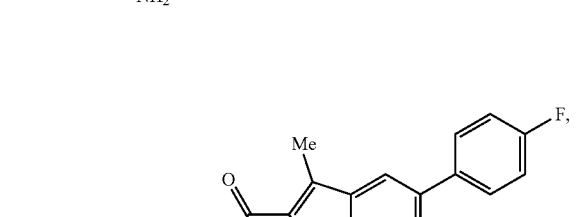
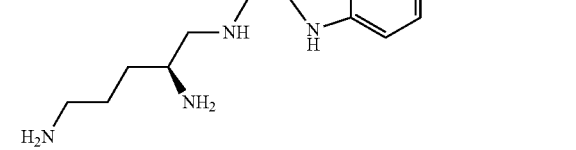
180
-continued
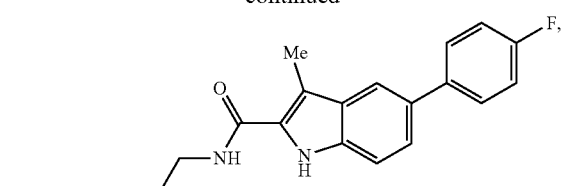
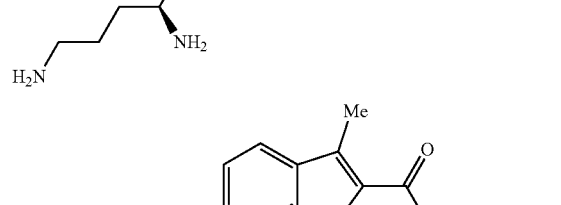
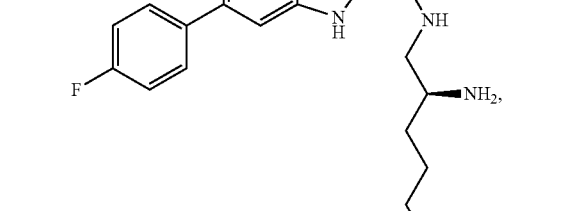
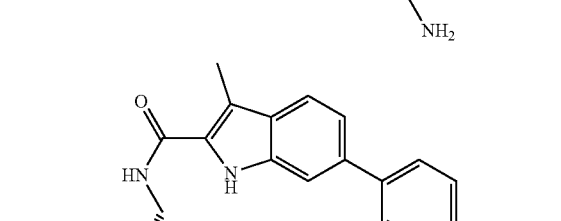
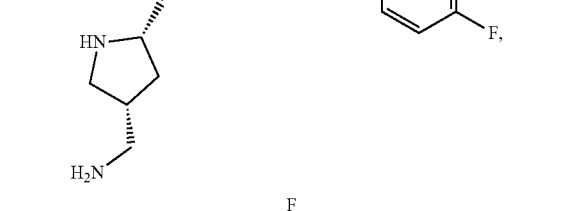
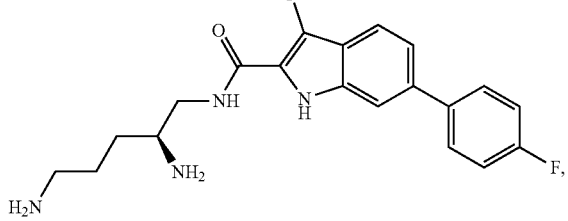
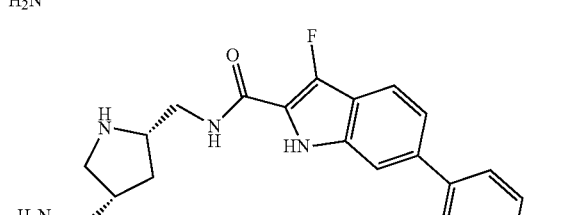

-continued
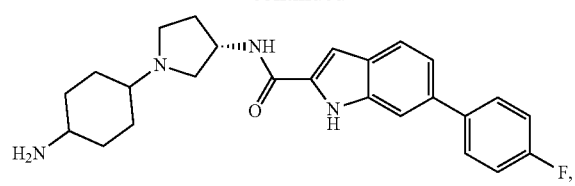
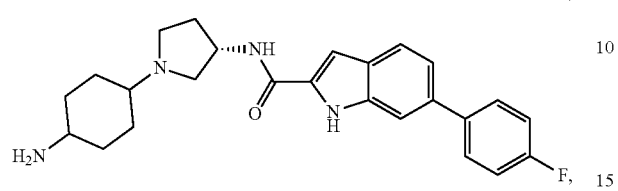
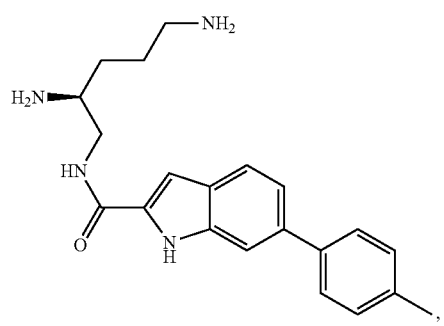
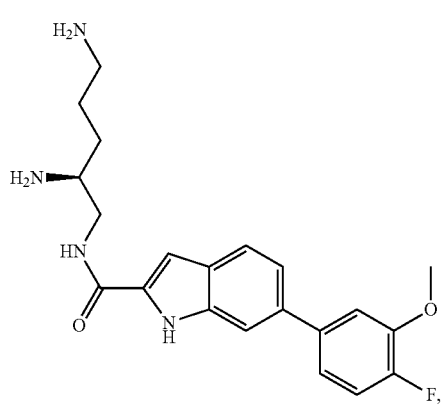
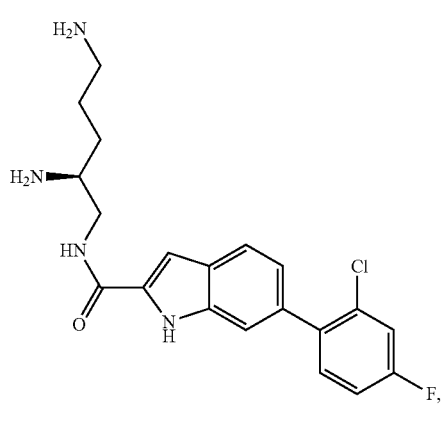
-continued
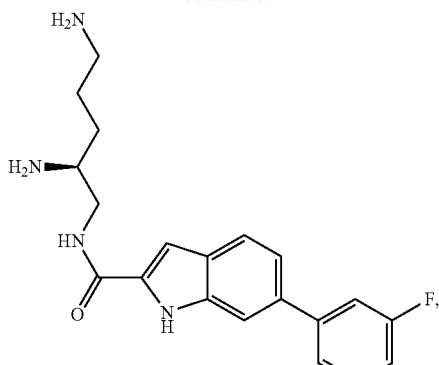
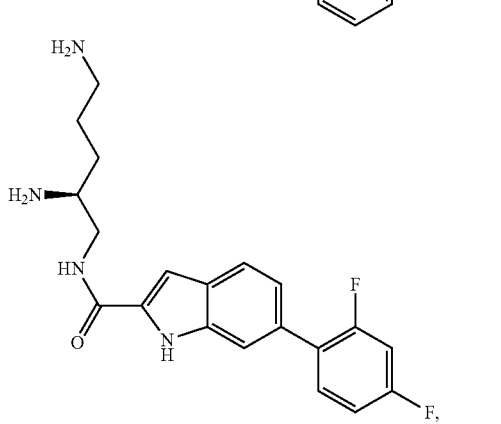
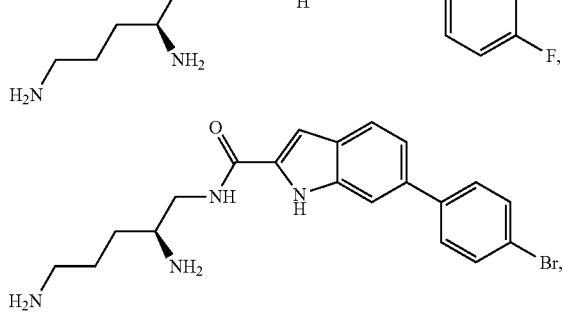
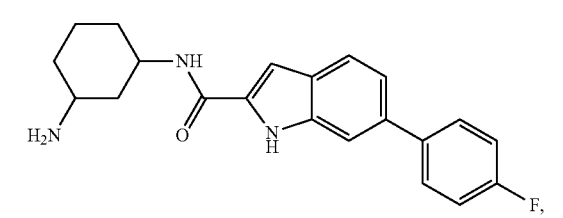
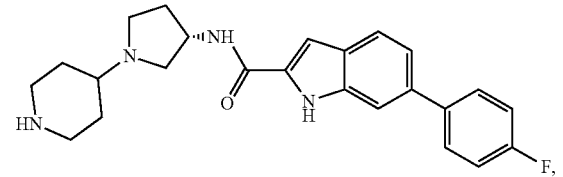

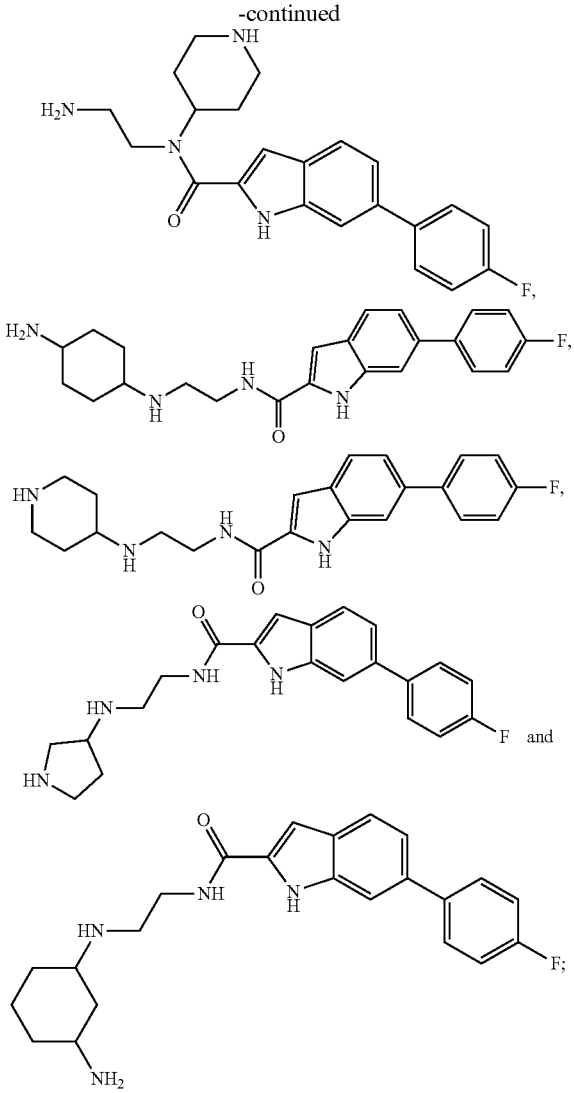
or a pharmaceutically acceptable salt thereof.
19. The method of claim 11 wherein the bacterial efflux pump inhibitor when used in combination with a compound of formula I or a pharmaceutically acceptable salt thereof is selected from the group consisting of:
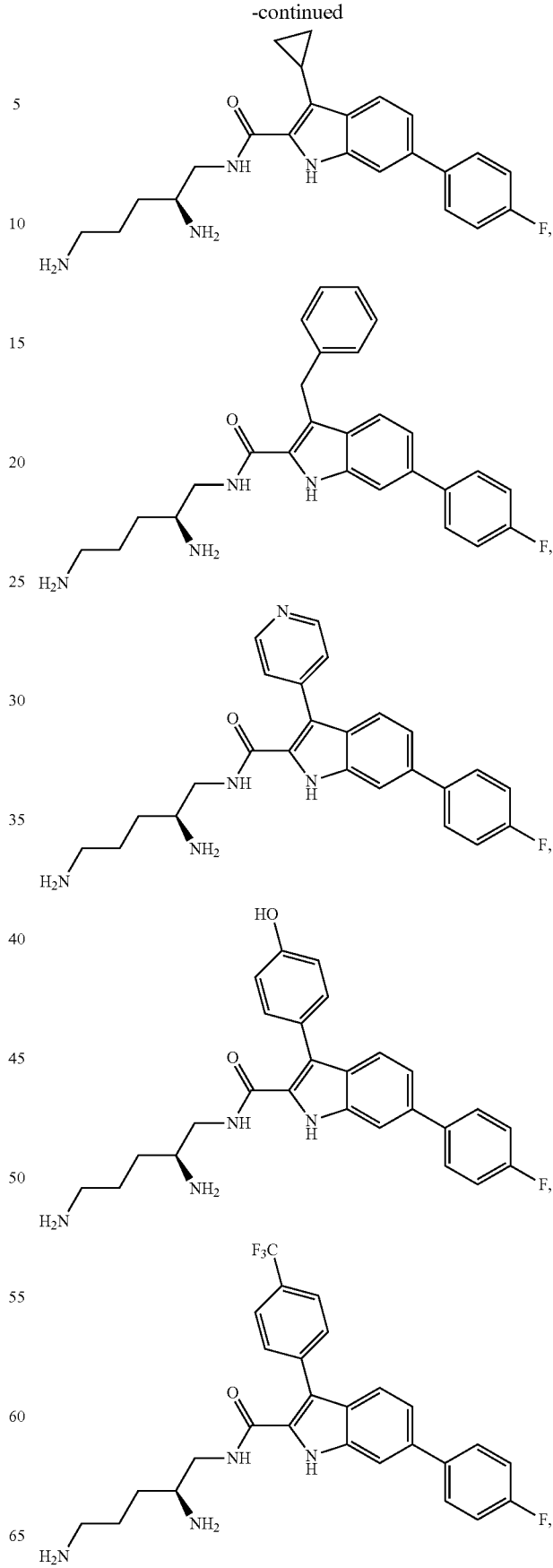

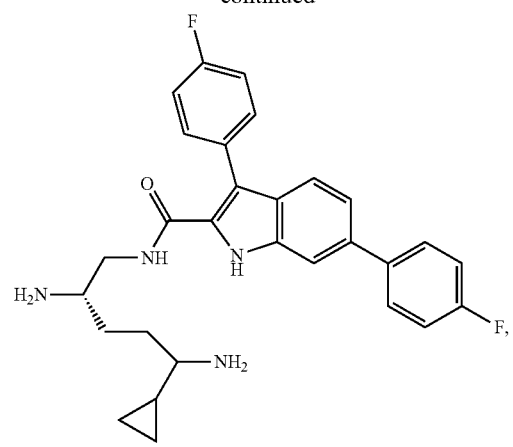
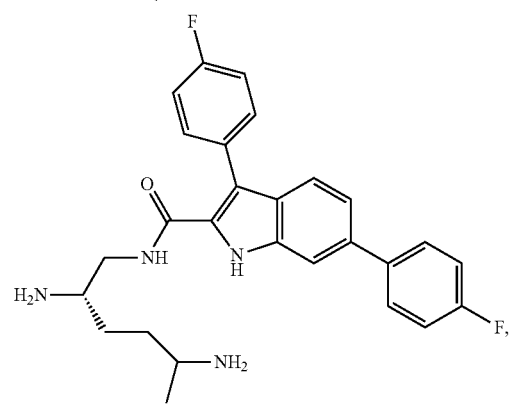
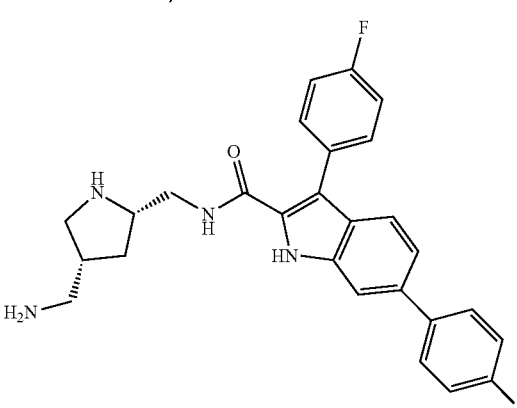
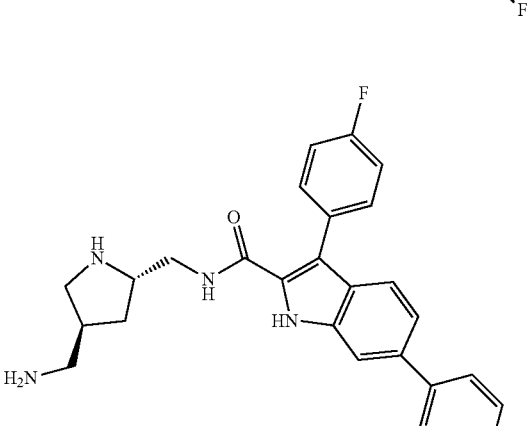
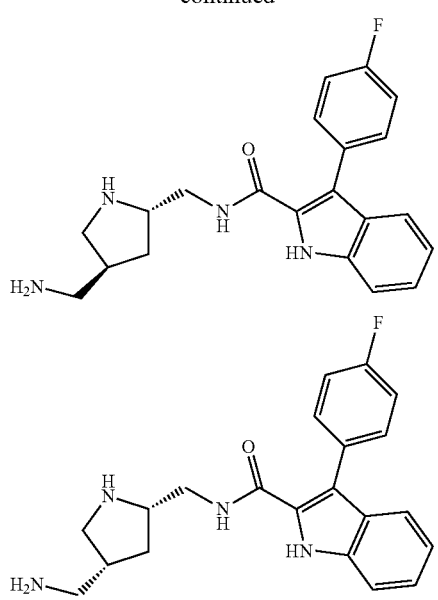
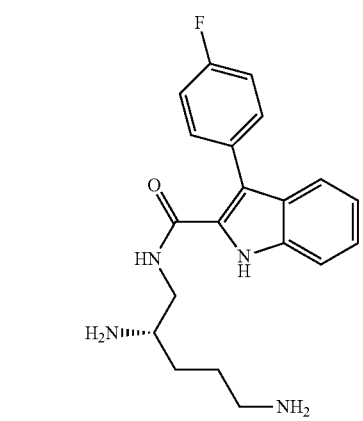
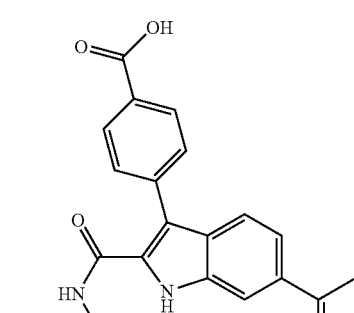

187
-continued
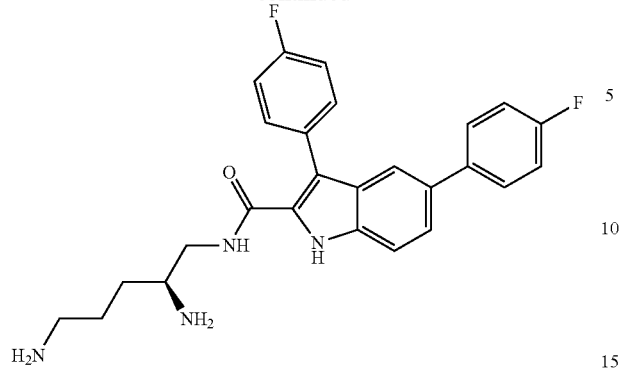
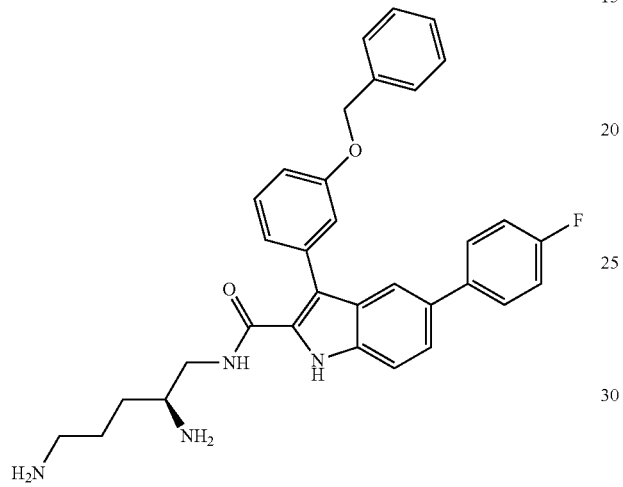
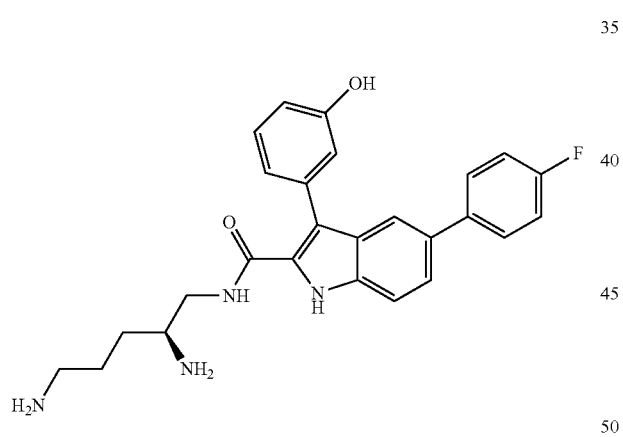
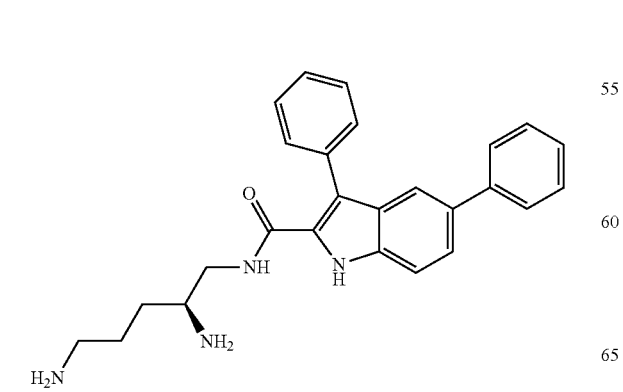
188
-continued
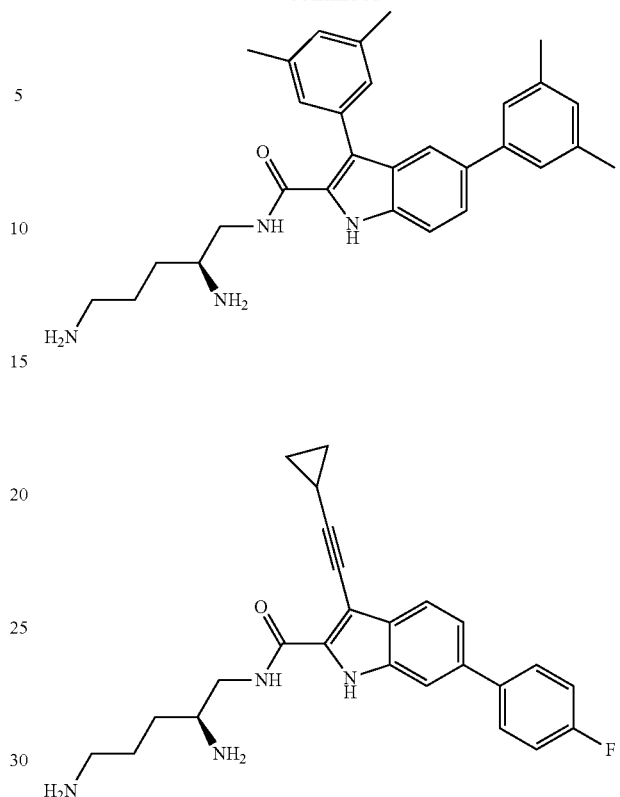
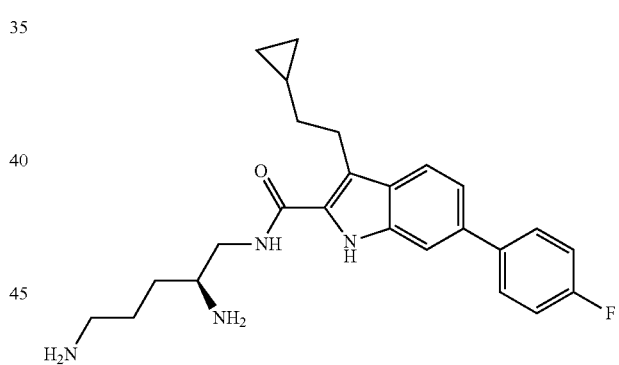
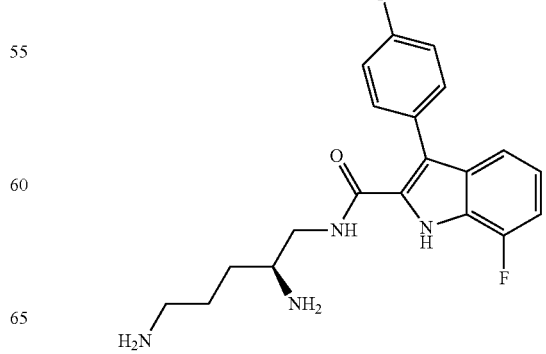

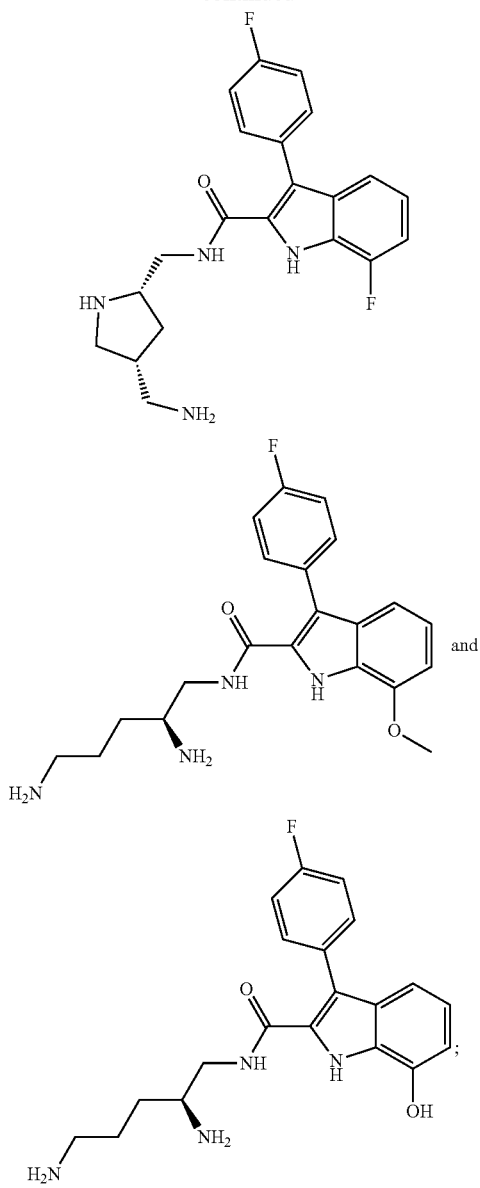
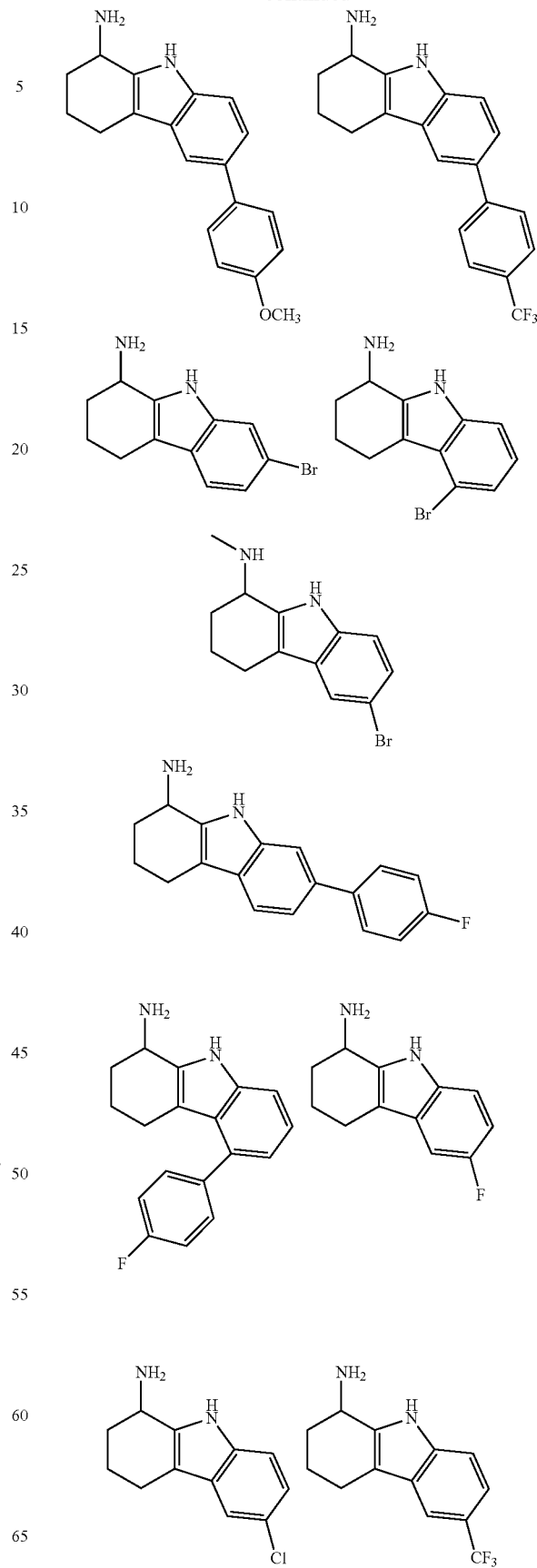
or a pharmaceutically acceptable salt thereof.
20. The method of claim 11, wherein the compound of formula I is:
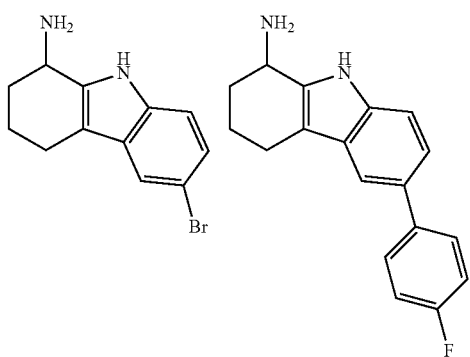

-continued
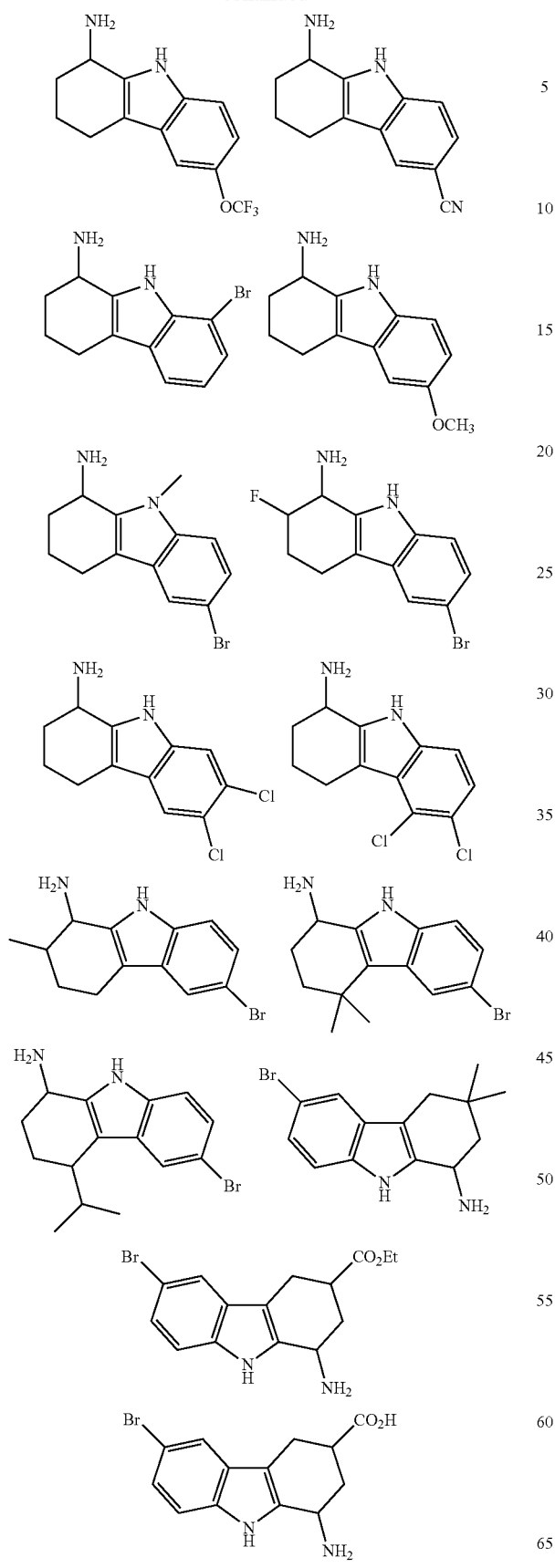
-continued
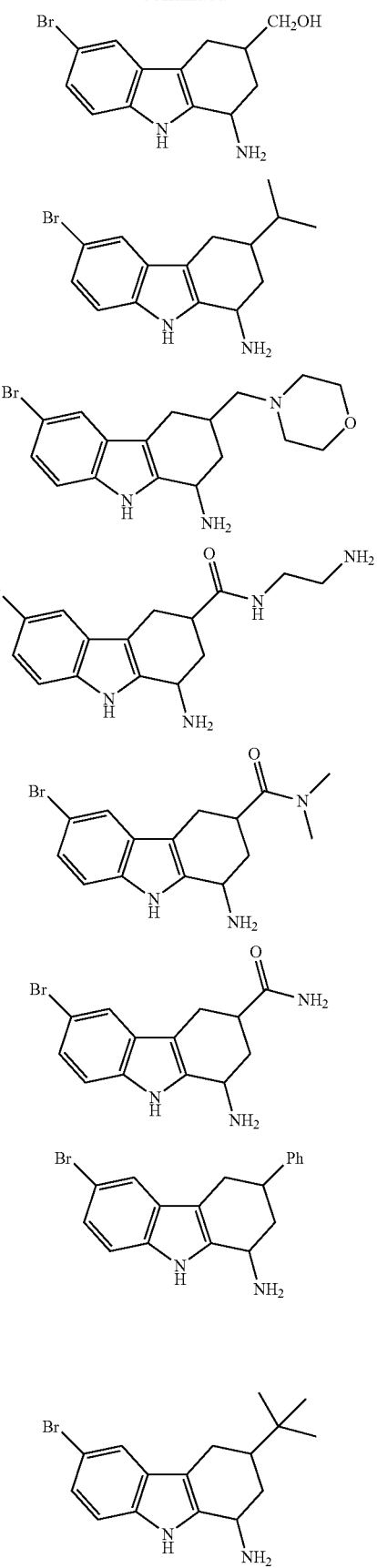

-continued
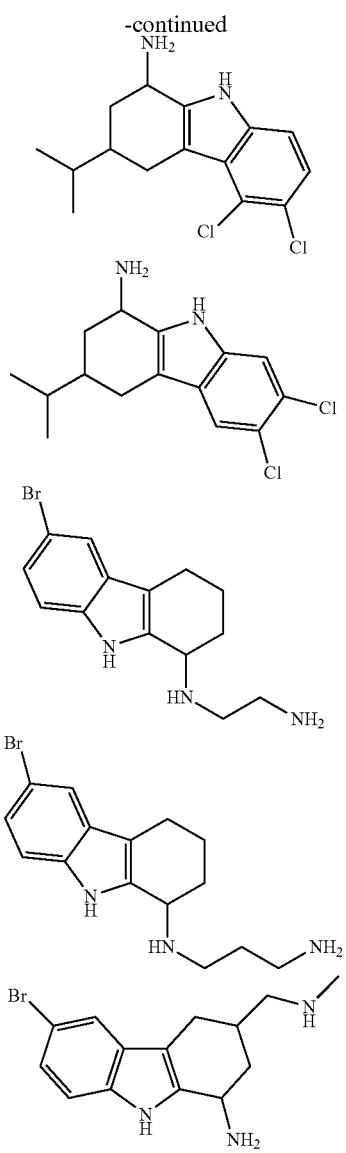
-continued
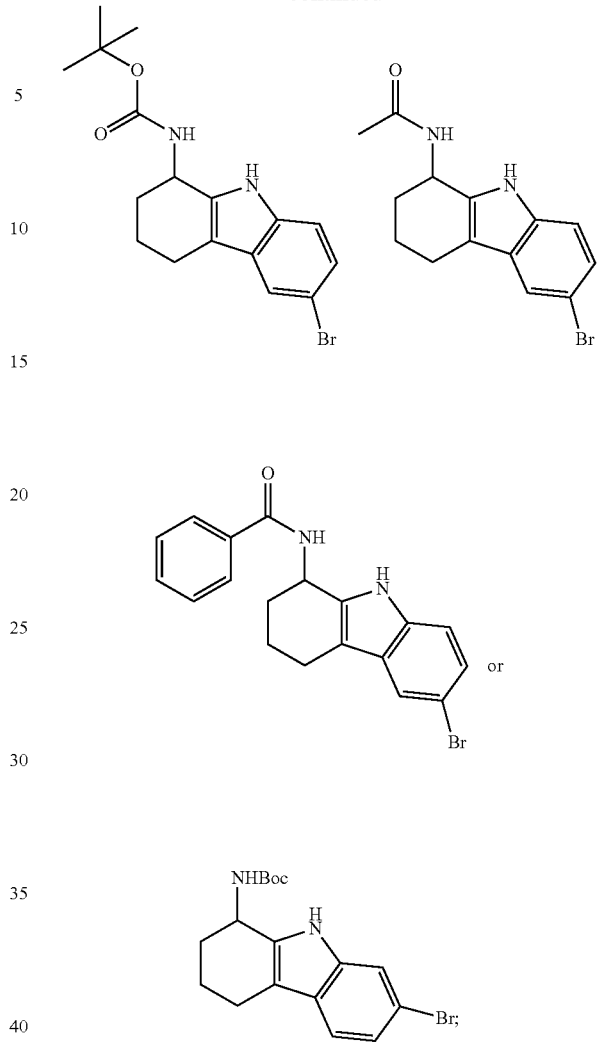
or a pharmaceutically acceptable salt thereof.
* * * * *

UNITED STATES PATENT AND TRADEMARK OFFICE
CERTIFICATE OF CORRECTION

PATENT NO. : 11,458,121 B2  
APPLICATION NO. : 16/626249  
DATED : October 4, 2022  
INVENTOR(S) : Edmond J. LaVoie, Ajit K. Parhi and Hye Yeon Sagong Page 1 of 1

It is certified that error appears in the above-identified patent and that said Letters Patent is hereby corrected as shown below:

In the Claims

Column 155, Lines 40-51 Claim 1, please delete:
"A compound of formula I:

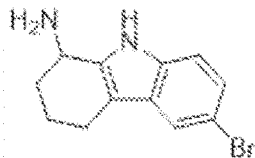

or a salt thereof, wherein:"
And insert:
-- A compound of formula I:

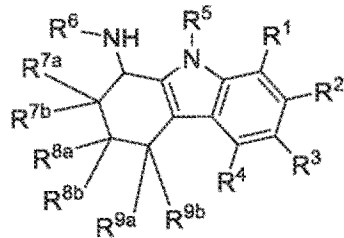

I
or a salt thereof, wherein: --; and

Column 157, Line 27 Claim 1, delete:
"or a salt thereof."
And insert:
-- or a pharmaceutically acceptable salt thereof alone or in the presence of a bacterial efflux pump inhibitor. -- therefor.

Signed and Sealed this  
Twenty-ninth Day of August, 2023

*Katherine Kelly Vidal*

Katherine Kelly Vidal  
*Director of the United States Patent and Trademark Office*